United States Patent
Simons et al.

(10) Patent No.: US 12,226,493 B2
(45) Date of Patent: Feb. 18, 2025

(54) METHODS OF TREATING NON-SYNDROMIC SENSORINEURAL HEARING LOSS

(71) Applicant: Akouos, Inc., Boston, MA (US)

(72) Inventors: Emmanuel John Simons, Brookline, MA (US); Robert Ng, Newton, MA (US)

(73) Assignee: Akouos, Inc., Boston, MA (US)

( * ) Notice: Subject to any disclaimer, the term of this patent is extended or adjusted under 35 U.S.C. 154(b) by 1046 days.

(21) Appl. No.: 17/259,661

(22) PCT Filed: Jul. 12, 2019

(86) PCT No.: PCT/US2019/041625
§ 371 (c)(1),
(2) Date: Jan. 12, 2021

(87) PCT Pub. No.: WO2020/014625
PCT Pub. Date: Jan. 16, 2020

(65) Prior Publication Data
US 2021/0330814 A1    Oct. 28, 2021

Related U.S. Application Data

(60) Provisional application No. 62/697,652, filed on Jul. 13, 2018.

(51) Int. Cl.
*A61K 48/00* (2006.01)
*C07K 14/47* (2006.01)
*C12N 9/22* (2006.01)
*C12N 15/11* (2006.01)
*C12N 15/86* (2006.01)
*C12N 15/90* (2006.01)

(52) U.S. Cl.
CPC ............ *A61K 48/005* (2013.01); *C07K 14/47* (2013.01); *C12N 9/22* (2013.01); *C12N 15/11* (2013.01); *C12N 15/86* (2013.01); *C12N 15/907* (2013.01); *C12N 2310/20* (2017.05); *C12N 2320/33* (2013.01); *C12N 2750/14143* (2013.01); *C12N 2830/50* (2013.01); *C12N 2840/007* (2013.01)

(58) Field of Classification Search
None
See application file for complete search history.

(56) References Cited

U.S. PATENT DOCUMENTS

| | | |
|---|---|---|
| 5,168,062 A | 12/1992 | Stinski |
| 5,552,157 A | 9/1996 | Yagi et al. |
| 5,565,213 A | 10/1996 | Nakamori et al. |
| 5,567,434 A | 10/1996 | Szoka, Jr. |
| 5,656,016 A | 8/1997 | Ogden |
| 5,697,899 A | 12/1997 | Hillman et al. |
| 5,738,868 A | 4/1998 | Shinkarenko |
| 5,770,219 A | 6/1998 | Chiang et al. |
| 5,779,708 A | 7/1998 | Wu |
| 5,783,208 A | 7/1998 | Venkateshwaran et al. |
| 5,795,587 A | 8/1998 | Gao et al. |
| 5,797,898 A | 8/1998 | Santini, Jr. et al. |
| 2006/0040354 A1 | 2/2006 | O'Keefe |
| 2016/0076054 A1 | 3/2016 | Auricchio et al. |
| 2022/0288236 A1 | 9/2022 | Decibel |

FOREIGN PATENT DOCUMENTS

| | | | |
|---|---|---|---|
| WO | WO-05/073384 A2 | 8/2005 | |
| WO | WO-2015/048577 A2 | 4/2015 | |
| WO | WO-2017/100791 A1 | 6/2017 | |
| WO | WO-2018039375 A1 * | 3/2018 | ......... A01K 67/0276 |
| WO | WO-2020/014625 A1 | 1/2020 | |
| WO | WO-2021/158854 A2 | 8/2021 | |
| WO | WO-2022/056440 A1 | 3/2022 | |
| WO | WO-2022/235933 A2 | 11/2022 | |
| WO | WO-2022/241302 A2 | 11/2022 | |
| WO | WO-2023/064388 A2 | 4/2023 | |
| WO | WO-2023/122719 A2 | 6/2023 | |
| WO | WO-2024/151703 A2 | 7/2024 | |

OTHER PUBLICATIONS

Vona, B., et al. "DFNB16 is a frequent cause of congenital hearing impairment: implementation of STRC mutation analysis in routine diagnostics." Clinical genetics 87.1 (2015): 49-55. (Year: 2015).*
Adachi, K. et al., Drawing a high-resolution functional map of adeno-associated virus capsid by massively parallel sequencing, Nat Commun., 5:3075 (2014).
Andersen, J. K. et al., Herpesvirus-mediated Gene Delivery Into the Rat Brain: Specificity and Efficiency of the Neuron-Specific Enolase Promoter, Cell. Mol. Neurobiol., 13:503-15 (1993).
Arbuthnot, P. B. et al., In Vitro and in Vivo Hepatoma Cell-Specific Expression of a Gene Transferred With an Adenoviral Vector, Hum. Gene Ther., 7:1503-14 (1996).
Asokan, A. et al., The AAV Vector Toolkit: Poised at the Clinical Crossroads, Mol. Ther. 20: 699-7080 (2012).
Banasik, M. B. et al., Integrase-defective lentiviral vectors: progress and applications, Gene Ther. 17:150-7 (2010).
Bartoli. M. et al., Noninvasive Monitoring of Therapeutic Gene Transfer in Animal Models of Muscular Dystrophies, Gene Ther. 13:20-28 (2006).
Basu, J. and Willard H. F., Human Artificial Chromosomes: Potential Applications and Clinical Considerations, Pediatr. Clin. North Am. 53:843-853 (2006).
Batt, D. B. and Carmichael, G. G., Characterization of the Polyomavirus Late Polyadenylation Signal, Mol. Cell Biol. (9):4783-4790, 25 (1995).

(Continued)

Primary Examiner — Emily A Cordas
(74) Attorney, Agent, or Firm — Choate, Hall & Stewart LLP; Stephanie L. Schonewald

(57) ABSTRACT

Provided herein are compositions that include at least two different nucleic acid vectors, where each of the at least two different vectors includes a coding sequence that encodes a different portion of a stereocilin protein, and the use of these compositions to treat non-syndromic sensorineural hearing loss in a subject.

15 Claims, 5 Drawing Sheets

Specification includes a Sequence Listing.

(56) References Cited

OTHER PUBLICATIONS

Bellec, J. et al., CFTR Inactivation by Lentiviral Vector-Mediated RNA Interference and CRISPR-Cas9 Genome Editing in Human Airway Epithelial Cells, Current Gene Ther., 5(5):447-59 (2015).
Boshart, M. et al., A Very Strong Enhancer is Located Upstream of an Immediate Early Gene of Human Cytomegalovirus, Cell, 41:521-530 (1985).
Bourlais, C. L. et al., Ophthalmic drug delivery systems—Recent advances, Progress in Retinal Eye Research, 17(1):33-58 (1998).
Bremer, J. et al., Antisense Oligonucleotide-mediated Exon Skipping as a Systemic Therapeutic Approach for Recessive Dystrophic Epidermolysis Bullosa, Mol. Ther. Nucleic Acids, 5(10):e379 (2016).
Chamorro, C. et al., Gene Editing for the Efficient Correction of a Recurrent COL7A1 Mutation in Recessive Dystrophic Epidermolysis Bullosa Keratinocytes, Mol. Ther. Nucleic Acids, 5(4):e307 (2016).
Chen, C. Y. A. et al., mRNA Decay Mediated by Two Distinct AU-rich Elements From C-Fos and Granulocyte-Macrophage Colony-Stimulating Factor Transcripts: Different Deadenylation Kinetics and Uncoupling From Translation, Mol. Cell. Biol., 15(10):5777-5788 (1995).
Chen, J. et al., Expression of Rat Bone Sialoprotein Promoter in Transgenic Mice, J. Bone Miner., 10 Res., 11:654-64 (1996).
Chen, Q. et al., An AU-rich element in the 3' untranslated region of the spinach chloroplast petD gene participates in sequence-specific RNA-protein complex formation, Mol Cell Biol., 15(4):2010-2018 (1995).
Chen, Z. et al., Inner Ear Drug Delivery via a Reciprocating Perfusion System in the Guinea Pig, J Controlled Rel. 110:1-19 (2005).
Choi, J.H. et al., Optimization of AAV expression cassettes to improve packaging capacity and transgene expression in neurons, Mol. Brain., 7:17 (2014).
Cong, L. et al., Multiplex genome engineering using CRISPR/Cas systems, Science, 339(6121):819-23 (2013).
Crispo, M. et al., Embryo development, fetal growth and postnatal phenotype of eGFP lambs generated by lentiviral transgenesis, Transgenic Res., 24(1):31-41 (2014).
De Felipe, P. and Izquierdo, M., Tricistronic and Tetracistronic Retroviral Vectors for Gene Transfer, Human Gene Therapy, 11:1921-1931 (2000).
De Felipe, P. et al., Use of the 2A sequence from foot-and-mouth disease virus in the generation of retroviral vectors for gene therapy, Gene Therapy, 6:198-208 (1999).
De Fougerolles, A.R., Delivery vehicles for small interfering RNA in vivo, Hum. Gene. Ther., 19(2):125-132 (2008).
Dmitriev, I. et al., An Adenovirus Vector With Genetically Modified Fibers Demonstrates Expanded Tropism via Utilization of a Coxsackievirus and Adenovirus Receptor-Independent Cell Entry Mechanism, J. Virol. 72:9706-9713 (1998).
Duan, D. et al., Expanding AAV Packaging Capacity with Trans-splicing or Overlapping Vectors: A Quantitative Comparison, Mol. Ther., 4:383-391 (2001).
Duncker, S. V. et al., toferlin Couples to Clathrin-Mediated Endocytosis in Mature Cochlear Inner Hair Cells, J Neurosci., 33(22):9508-9519 (2013).
Fisher, K. J. et al., Transduction With Recombinant Adeno-Associated Virus for Gene Therapy is Limited by Leading-Strand Synthesis, J. Virol., 70:520-532 (1996).
Francey, L.J. et al., Genome-wide SNP genotyping identifies the Stereocilin (STRC) gene as a major contributor to pediatric bilateral sensorineural hearing impairment, Am. J. Med. Genet. A., 158A(2):298-308 (2012).
Furler, S. et al., Recombinant AAV Vectors Containing the Foot and Mouth Disease Virus 2A Sequence Confer Efficient Bicistronic Gene Expression in Cultured Cells and Rat Substantia Nigra Neurons, Gene Therapy, 8:864-873 (2001).
Gao, G. et al., Clades of Adeno-associated viruses are widely disseminated in human tissues, J. Virol.. 78(12): 6381-6388 (2004).
Ghosh, A. et al., A Hybrid Vector System Expands Adeno-Associated Viral Vector Packaging Capacity in a Transgene-Independent Manner, Mol. Ther. 16:124-130 (2008).
Ghosh, A. et al., Efficient Transgene Reconstitution With Hybrid Dual AAV Vectors Carrying the Minimized Bridging Sequences, Human Gene Ther., 22:77-83 (2011).
Gossen, M. et al., Tight control of gene expression in mammalian cells by tetracycline-responsive promoters., Proc. Natl. Acad. Sci. USA, 89:5547-5551 (1992).
Gossen, M. et al., Transcriptional activation by tetracyclines in mammalian cells, Science, 268:1766-1769 (1995).
Halpin, C. et al., Self-processing 2A?polyproteins—a system for co?ordinate expression of multiple proteins in transgenic plants, The Plant Journal, 4:453-459 (1999).
Hansal, S. A. et al., Cutting Edge: Induction of Antigen-Specific Hyporesponsiveness by Transplantation of Hemopoietic Cells Containing an MHC Class I Transgene Regulated by a Lymphocyte-Specific Promoter, J. Immunol., 161:1063-8 (1998).
Harvey, D. M. and Caskey, C. T., Inducible Control of Gene Expression: Prospects for Gene Therapy, Curr. Opin. Chem. Biol., 2:512-518 (1998).
He, X. et al., Knock-in of large reporter genes in human cells via CRISPR/Cas9-induced homology-dependent and independent DNA repair, Nucleic Acids Res., 44(9):e85 (2016).
Heidel, J.D. et al., Administration in non-human primates of escalating intravenous doses of targeted nanoparticles containing ribonucleotide reductase subunit M2 siRNA, PNAS USA, 104(14):5715-5721 (2007).
Heidrych, P. et al., Otoferlin interacts with myosin VI: implications for maintenance of the basolateral synaptic structure of the inner hair cell, Hum. Mol. Genet., 18(15):2779-2790 (2009).
Heidrych, P. et al., Rab8b GTPase, a Protein Transport Regulator, is an Interacting Partner of Otoferlin, Defective in a Human Autosomal Recessive Deafness Form, Hum. Mol. Genet., 17(23):3814-3821 (2008).
Hellen, C. U. T. and Sarnow, P., Internal Ribosome Entry Sites in Eukaryotic mRNA Molecules, Genes Dev. 15(13):1593-612 (2001).
Huang, M.T. and Gorman, C.M. et al., The simian virus 40 small-t intron, present in many common expression vectors, leads to aberrant splicing, Mol. Ther. Biol., 10(4):1805-1810 (1990).
Hu-Lieskovan, S. et al., Sequence-specific knockdown of EWS-FLI1 by targeted, nonviral delivery of small interfering RNA inhibits tumor growth in a murine model of metastatic Ewing's sarcoma, Cancer Res., 65(19):8984-8992 (2005).
Ikeno, M. et al., Construction of YAC-based Mammalian Artificial Chromosomes, Nat. Biotech., 16:431-439 (1998).
Isgrig, K. et al., AAV2.7m8 is a powerful viral vector for inner ear gene therapy, Nat. Commun., 10(1):427 (2019).
Jirka, S.M.G. et al., Peptide conjugation of 2'-O-methyl phosphorothioate antisense oligonucleotides enhances cardiac uptake and exon skipping in mdx mice, Nucleic Acid Ther., 24(1):25-36 (2014).
Kanaan, N. M. et al., Rationally Engineered AAV Capsids Improve Transduction and Volumetric Spread in the CNS, Mol. Ther. Nucleic Acids, 8:184-197 (2017).
Katoh, M. et al., Construction of a Novel Human Artificial Chromosome Vector for Gene Delivery, Biochem. Biophys. Res. Commun., 321:280-290 (2004).
Kawecka, K. et al., Adeno-Associated Virus (AAV) Mediated Dystrophin Gene Transfer Studies and Exon Skipping Strategies for Duchenne Muscular Dystrophy (DMD), Curr. Gene. Ther., 15(4):395-415 (2015).
Kazuki, Y. and Oshimura, M., Human Artificial Chromosomes for Gene Delivery and the Development of Animal Models, Mol. Ther. 19(9):1591-1601 (2011).
Kazuki, Y. et al., Refined human artificial chromosome vectors for gene therapy and animal transgenesis, Gen. Ther. 18:384-393 (2011).
Klump, H et al., Retroviral vector-mediated expression of HoxB4 in hematopoietic cells using a novel coexpression strategy, Gene Therapy, 8:811-817 (2001).
Kouprina, N. et al., Human Artificial Chromosome-Based Gene Delivery Vectors for Biomedicine and Biotechnology, Expert Opin. Drug Deliv 11(4):517-535 (2014).
Kurachi, S. et al., Role of intron I in expression of the human factor IX gene, J. Biol. Chem., 270(10):5276-5281 (1995).

(56) References Cited

OTHER PUBLICATIONS

Lai, Y. et al., Efficient in vivo gene expression by trans-splicing adeno-associated viral vectors, Nat. Biotechnol., 23(11):1435-1439 (2005).
Levitt, N. el al, Definition of an efficient synthetic poly(A) site, Genes Dev. 3(7):1019-1025 (1989).
Li, W. et al., Engineering and selection of shuffled AAV genomes: a new strategy for producing targeted biological nanoparticles, Mol. Ther. 16(7):1252-1260 (2008).
Magari, S. R. et al., Pharmacologic control of a humanized gene therapy system implanted into nude mice., J. Clin. Invest., 100:2865-2872 (1997).
Maier, P. et al., Radioprotective gene therapy, Future Microbiol., 5:1507-23 (2010).
Mandelker, D. et al., Comprehensive diagnostic testing for stereocilin: an approach for analyzing medically important genes with high homology, J. Mol. Diagn., 16(6):639-647 (2014).
Matrai, I. et al., Recent Advances in Lentiviral Vector Development and Applications, Mol. Ther., 18:477-490 (2010).
Mattion, N. M. et al., Foot-and-mouth Disease Virus 2A Protease Mediates Cleavage in Attenuated Sabin 3 Poliovirus Vectors Engineered for Delivery of Foreign Antigens, J. Virology, 70(11)8124-8127 (1996).
Menchaca, A. and Rubianes, E., New treatments associated with timed artificial insemination in small ruminants, Reprod. Fertil. Dev., 16(4):403-413 (2004).
Menoret et al., Advanced protocols for Animal Transgenesis. An ISTT Manual. Heidelberg: Springer, pp. 117-136 (2011).
Merkle, F.T. et al., Efficient CRISPR-Cas9-mediated generation of knockin human pluripotent stem cells lacking undesired mutations at the targeted locus, Cell Rep., 11(6):875-883 (2015).
Milone, M. C. et al., Chimeric Receptors Containing CD137 Signal Transduction Domains Mediate Enhanced Survival of T Cells and Increased Antileukemic Efficacy In Vivo, Mol. Ther. 17(8):1453-1464 (2009).
No, D. et al., Ecdysone-inducible gene expression in mammalian cells and transgenic mice, Proc. Natl. Acad. Sci. USA, 93:3346-3351 (1996).
Orkin, S. H. et al., Thalassemia due to a mutation in the cleavage-polyadenylation signal of the human f-globin gene, EMBO J. 4(2):453-456 (1985).
Ostedgaard, L.S. et al., A shortened adeno-associated virus expression cassette for CFTR gene transfer to cystic fibrosis airway epithelia, PNAS USA, 102(8):2952-2957 (2005).
Pelletier, J. et al., Cap-independent translation of poliovirus mRNA is conferred by sequence elements within the 5' noncoding region., Mol. Cell. Biol. 8(3):1103-1112 (1988).
Piccioli, P. et al., Neuroantibodies: Ectopic Expression of a Recombinant Anti-Substance P Antibody in the Central Nervous System of Transgenic Mice, Neuron., 15:373-84 (1995).
Piccioli, P. et al., Neuroantibodies: Molecular Cloning of a Monoclonal Antibody Against Substance P for Expression in the Central Nervous System, Proc. Natl. Acad. Sci. USA, 88:5611-5 (1991).
Poulin, K. L. et al., Use of Cre/loxP recombination to swap cell binding motifs on the adenoviral capsid protein IX, J. Virol. 8:10074-10086 (2010).
Proudfoot, N. J. et al., Integrating mRNA Processing with Transcription, Cell, 108:501-512 (2002).
Pryadkina, M. et al., A Comparison of AAV Strategies Distinguishes Overlapping Vectors for Efficient Systemic Delivery of the 6.2 Kb Dysferlin Coding Sequence, Meth. Clin. Devel. 2:15009 (2015).
Reich, S. J. et al., Efficient Trans-Splicing in the Retina Expands the Utility of Adeno-Associated Virus as a Vector for Gene Therapy, Human Gene Ther. 14(1):37-44 (2003).
Ren, X. et al., Human artificial chromosome vectors meet stem cells, Stem. Cell Rev., 2(1):43-50 (2006).
Rozema, D.B. et al., Dynamic PolyConjugates for targeted in vivo delivery of siRNA to hepatocyte, PNAS USA, 104(32):12982-12987 (2007).
Ryan, A. et al., Cellular targeting for cochlear gene therapy, Adv Otorhinolaryngol., 66:99-115 (2009).
Ryan, M. D. and Drew, J., Foot-and-mouth Disease Virus 2A Oligopeptide Mediated Cleavage of an Artificial Polyprotein, EMBO, 4:928-933 (1994).
Sandig, V. et al., HBV-derived Promoters Direct Liver-Specific Expression of an Adenovirally Transduced LDL Receptor Gene, Gene Ther., 3:1002-9 (1996).
Schek, N. et al., Definition of the Upstream Efficiency Element of the Simian Virus 40 Late Polyadenylation Signal by Using in Vitro Analyses, Mol. Cell Biol., 12(12):5386-5393 (1992).
Shu, Y. et al., Identification of Adeno-Associated Viral Vectors That Target Neonatal and Adult Mammalian Inner Ear Cell Subtypes, Human Gene Therapy, 27(9): 687-699 (2016).
Stein, G. S. et al., The Osteocalcin Gene: A Model for Multiple Parameters of Skeletal-Specific Transcriptional Control, Mol. Biol. Rep., 24:185-96 (1997).
Stiller, M. et al., Direct multiplex sequencing (DMPS)—a novel method for targeted high-throughput sequencing of ancient and highly degraded DNA, Genome Res., 19(10):184-1848 (2009).
Szymanski, P. et al., Development and Validation of a Robust and Versatile One-plasmid Regulated Gene Expression System, Mol. Therapy, 15(7):1340-1347 (2007).
Tandon, V. et al. Microfabricated infuse-withdraw micropump component for an integrated inner-ear drug-delivery platform, Biomedical Microdevices, 17: Article No. 37 (2015).
Tandon, V. et al., Microfabricated Reciprocating Micropump for Intracochlear Drug Delivery With Integrated Drug/Fluid Storage and Electronically Controlled Dosing, Lab Chip, 16:829-846 (2016).
Tei, S. et al., Antisense oligonucleotide-mediated exon skipping of CHRNA1 pre-mRNA as potential therapy for Congenital Myasthenic Syndromes, Biochem. Biophys. Res. Commun., 461(3):481-486 (2015).
Thein, S. L. et al., The polyadenylation site mutation in the alpha-globin gene cluster, Blood, 71(2):313-319 (1988).
Tian, Y. et al., Creation of a transgenic mouse for hair-cell gene targeting by using a modified bacterial artificial chromosome containing Prestin, Dev Dyn., 231(1):199-203 (2004).
Trapani, I. et al., Effective Delivery of Large Genes to the Retina by Dual AAV Vectors, EMBO Mol Med, 6: 194-211 (2014).
Verma, N. et al., CRISPR/Cas-Mediated Knockin in Human Pluripotent Stem Cells, Methods Mol. Biol., 1513:119-140 (2017).
Verpy, E. et al., Stereocilin connects outer hair cell stereocilia to one another and to the tectorial membrane, J. Comp. Neurol., 519(2):194-210 (2011).
Verpy, E. et al., Stereocilin-deficient mice reveal the origin of cochlear waveform distortions, Nature, 456(7219):255-258 (2008).
Vilette, D. et al., Establishment of astrocyte cell lines from sheep genetically susceptible to scrapie, In Vitro Cell Dev Biol Anim, 36(1):45-9 (2000).
Wang, K. et al., Efficient Generation of Orthologous Point Mutations in Pigs via CRISPR-assisted ssODN-mediated Homology-directed Repair, Mol. Ther. Nucleic Acids., 5(11):e396 (2016).
Wang, Y. et al., Ligand-inducible and liver-specific target gene expression in transgenic mice, Nat. Biotech., 15:239-243 (1997).
Wang, Y. et al., Positive and negative regulation of gene expression in eukaryotic cells with an inducible transcriptional regulator, Gene Ther., 4:432-441 (1997).
Wanisch, K. and Yanez-Munoz, R. J. et al., Integration-deficient Lentiviral Vectors: A Slow Coming of Age, Mol. Ther., 17: 1316-32 (2009).
Woychik, R. P. et al., Requirement for the 3' flanking region of the bovine growth hormone gene for accurate polyadenylylation, Proc. Natl. Acad. Sci. U.S.A., 81(13):3944-3948 (1984).
Wu, Z. et al., Optimization of self-complementary AAV vectors for liver-directed expression results in sustained correction of hemophilia B at low vector dose, Mol. Ther., 16(2):280-289 (2008).
Xiao, W. et al., Gene therapy vectors based on adeno-associated virus type 1, J. Virol., 73(5):3994-4003 (1999).
Yan, Z. et al., Trans-splicing vectors expand the utility of adeno-associated virus for gene therapy, Proc.Natl. Acad. Sci. U.S.A., 97:12; 6716-6721 (2000).

(56) References Cited

OTHER PUBLICATIONS

Yew, N.S. et al., Optimization of plasmid vectors for high-level expression in lung epithelial cells, Hum. Gene. Ther., 8(5):575-584 (1997).

Zhang, Y. et al., Sensorineural deafness and male infertility: a contiguous gene deletion syndrome, J. Med. Genet., 44(4):233-240 (2007).

Brotto, D. et al., Autosomal Recessive Non-Syndromic Deafness: Is AAV Gene Therapy a Real Chance? Audiol. Res., 14(2):239-253 (2024).

NCBI GenBank Accession No. NP_714544.1, Stereocilin precursor [Homo sapiens], 3 pages, Jun. 3, 2018.

NCBI Reference Sequence: NM_153700.2, Homo sapiens stereocilin (STRC), mRNA, 7 pages, (2014).

Dyka, F. M. et al., Dual Adeno-Associated Virus Vectors Result in Efficient In Vitro and In Vivo Expression of an Oversized Gene, MYO7A, Human Gene Therapy Methods, 25(2):166-177 (2014).

International Search Report for PCT/US2019/041625 (Methods of Treating Non-Syndromic Sensorineural Hearing Loss, filed Jul. 12, 2019), received by ISA/KR, 5 pages (Oct. 29, 2019).

NCBI GenBank Accession No. NR_146078.1, Homo sapiens stereocilin pseudogene 1 (STRCP1), non-coding RNA, 3 pages, Mar. 9, 2017.

Sloan-Higgin, C. M. et al., Comprehensive Genetic Testing in the Clinical Evaluation of 1119 Patients with Hearing Loss, Human Genetics, 135(4):441-450 (2016).

Verpy, E. et al., Mutations in a new gene encoding a protein of the hair bundle cause non-syndromic deafness at the DFNB16 locus, Nature Genetics, 29:345-349 (2001).

Written Opinion for PCT/US2019/041625 (Methods of Treating Non-Syndromic Sensorineural Hearing Loss, filed Jul. 12, 2019), received by ISA/KR, 11 pages (Oct. 29, 2019).

Zhang, W. et al., Cochlear Gene Therapy for Sensorineural Hearing Loss: Current Status and Major Remaining Hurdles for Translational Success, Frontiers in Molecular Neuroscience, 11:1-15 (2018).

\* cited by examiner

SEQUENCE LISTING

```
<160> NUMBER OF SEQ ID NOS: 38

<210> SEQ ID NO 1
<211> LENGTH: 1810
<212> TYPE: PRT
<213> ORGANISM: Homo sapiens

<400> SEQUENCE: 1

Met Ala Leu Ser Leu Trp Pro Leu Leu Leu Leu Leu Leu Leu Leu Leu
1               5                   10                  15

Leu Leu Ser Phe Ala Val Thr Leu Ala Pro Thr Gly Pro His Ser Leu
            20                  25                  30

Asp Pro Gly Leu Ser Phe Leu Lys Ser Leu Leu Ser Thr Leu Asp Gln
        35                  40                  45

Ala Pro Gln Gly Ser Leu Ser Arg Ser Arg Phe Phe Thr Phe Leu Ala
    50                  55                  60

Asn Ile Ser Ser Ser Phe Glu Pro Gly Arg Met Gly Glu Gly Pro Val
65                  70                  75                  80

Gly Glu Pro Pro Pro Leu Gln Pro Pro Ala Leu Arg Leu His Asp Phe
                85                  90                  95

Leu Val Thr Leu Arg Gly Ser Pro Asp Trp Glu Pro Met Leu Gly Leu
            100                 105                 110

Leu Gly Asp Met Leu Ala Leu Leu Gly Gln Glu Gln Thr Pro Arg Asp
        115                 120                 125

Phe Leu Val His Gln Ala Gly Val Leu Gly Gly Leu Val Glu Val Leu
    130                 135                 140

Leu Gly Ala Leu Val Pro Gly Gly Pro Thr Pro Thr Arg Pro Pro
145                 150                 155                 160
```

-continued

```
Cys Thr Arg Asp Gly Pro Ser Asp Cys Val Leu Ala Ala Asp Trp Leu
                165                 170                 175
Pro Ser Leu Leu Leu Leu Glu Gly Thr Arg Trp Gln Ala Leu Val
            180                 185                 190
Gln Val Gln Pro Ser Val Asp Pro Thr Asn Ala Thr Gly Leu Asp Gly
            195                 200                 205
Arg Glu Ala Ala Pro His Phe Leu Gln Gly Leu Leu Gly Leu Leu Thr
        210                 215                 220
Pro Thr Gly Glu Leu Gly Ser Lys Glu Ala Leu Trp Gly Gly Leu Leu
225                 230                 235                 240
Arg Thr Val Gly Ala Pro Leu Tyr Ala Ala Phe Gln Glu Gly Leu Leu
                245                 250                 255
Arg Val Thr His Ser Leu Gln Asp Glu Val Phe Ser Ile Leu Gly Gln
            260                 265                 270
Pro Glu Pro Asp Thr Asn Gly Gln Cys Gln Gly Val Phe Phe Leu Thr
            275                 280                 285
Leu Ser Leu Leu Gly Asn Leu Gln Gln Leu Leu Leu Trp Gly Val Arg
        290                 295                 300
His Asn Leu Ser Trp Asp Val Gln Ala Leu Gly Phe Leu Ser Gly Ser
305                 310                 315                 320
Pro Pro Pro Pro Ala Leu Leu His Cys Leu Ser Thr Gly Val Pro
                325                 330                 335
Leu Pro Arg Ala Ser Gln Pro Ser Ala His Ile Ser Pro Arg Gln Arg
            340                 345                 350
Arg Ala Ile Thr Val Glu Ala Leu Cys Glu Asn His Leu Gly Pro Ala
            355                 360                 365
Pro Pro Tyr Ser Ile Ser Asn Phe Ser Ile His Leu Leu Cys Gln His
        370                 375                 380
Thr Lys Pro Ala Thr Pro Gln Pro His Pro Ser Thr Thr Ala Ile Cys
385                 390                 395                 400
Gln Thr Ala Val Trp Tyr Ala Val Ser Trp Ala Pro Gly Ala Gln Gly
                405                 410                 415
Trp Leu Gln Ala Cys His Asp Gln Phe Pro Asp Glu Phe Leu Asp Ala
            420                 425                 430
Ile Cys Ser Asn Leu Ser Phe Ser Ala Leu Ser Gly Ser Asn Arg Arg
        435                 440                 445
Leu Val Lys Arg Leu Cys Ala Gly Leu Leu Pro Pro Pro Thr Ser Cys
    450                 455                 460
Pro Glu Gly Leu Pro Pro Val Pro Leu Thr Pro Asp Ile Phe Trp Gly
465                 470                 475                 480
Cys Phe Leu Glu Asn Glu Thr Leu Trp Ala Glu Arg Leu Cys Gly Glu
                485                 490                 495
Ala Ser Leu Gln Ala Val Pro Pro Ser Asn Gln Ala Trp Val Gln His
            500                 505                 510
Val Cys Gln Gly Pro Thr Pro Asp Val Thr Ala Ser Pro Pro Cys His
        515                 520                 525
Ile Gly Pro Cys Gly Glu Arg Cys Pro Asp Gly Gly Ser Phe Leu Val
        530                 535                 540
Met Val Cys Ala Asn Asp Thr Met Tyr Glu Val Leu Val Pro Phe Trp
545                 550                 555                 560
Pro Trp Leu Ala Gly Gln Cys Arg Ile Ser Arg Gly Gly Asn Asp Thr
                565                 570                 575
```

```
Cys Phe Leu Glu Gly Leu Leu Gly Pro Leu Pro Ser Leu Pro Pro
                580                 585                 590

Leu Gly Pro Ser Pro Leu Cys Leu Thr Pro Gly Pro Phe Leu Leu Gly
        595                 600                 605

Met Leu Ser Gln Leu Pro Arg Cys Gln Ser Ser Val Pro Ala Leu Ala
610                 615                 620

His Pro Thr Arg Leu His Tyr Leu Leu Arg Leu Leu Thr Phe Leu Leu
625                 630                 635                 640

Gly Pro Gly Ala Gly Ala Glu Ala Gln Gly Met Leu Gly Arg Ala
                645                 650                 655

Leu Leu Leu Ser Ser Leu Pro Asp Asn Cys Ser Phe Trp Asp Ala Phe
            660                 665                 670

Arg Pro Glu Gly Arg Arg Ser Val Leu Arg Thr Ile Gly Glu Tyr Leu
        675                 680                 685

Glu Gln Asp Glu Glu Gln Pro Thr Pro Ser Gly Phe Glu Pro Thr Val
690                 695                 700

Asn Pro Ser Ser Gly Ile Ser Lys Met Glu Leu Leu Ala Cys Phe Ser
705                 710                 715                 720

Pro Val Leu Trp Asp Leu Leu Gln Arg Glu Lys Ser Val Trp Ala Leu
            725                 730                 735

Gln Ile Leu Val Gln Ala Tyr Leu His Met Pro Pro Glu Asn Leu Gln
            740                 745                 750

Gln Leu Val Leu Ser Ala Glu Arg Glu Ala Ala Gln Gly Phe Leu Thr
        755                 760                 765

Leu Met Leu Gln Gly Lys Leu Gln Gly Lys Leu Gln Val Pro Pro Ser
770                 775                 780

Glu Glu Gln Ala Leu Gly Arg Leu Thr Ala Leu Leu Gln Arg Tyr
785                 790                 795                 800

Pro Arg Leu Thr Ser Gln Leu Phe Ile Asp Leu Ser Pro Leu Ile Pro
            805                 810                 815

Phe Leu Ala Val Ser Asp Leu Met Arg Phe Pro Pro Ser Leu Leu Ala
                820                 825                 830

Asn Asp Ser Val Gln Gln Gly Tyr Arg Gly Ser Glu Glu Asn Ser Leu
        835                 840                 845

Glu Glu Asp Lys Gly Leu Arg Pro Met Thr Pro Arg Ser Leu Ala Ala
850                 855                 860

Ile Arg Asp Tyr Ser Pro Gly Met Arg Pro Glu Gln Lys Glu Ala Leu
865                 870                 875                 880

Ala Lys Arg Leu Leu Ala Pro Glu Leu Phe Gly Glu Val Pro Ala Trp
                885                 890                 895

Pro Gln Glu Leu Leu Trp Ala Val Leu Pro Leu Leu Pro His Leu Pro
        900                 905                 910

Leu Glu Asn Phe Leu Gln Leu Ser Pro His Gln Ile Gln Ala Leu Glu
    915                 920                 925

Asp Ser Trp Pro Ala Ala Gly Leu Gly Pro Gly His Ala Arg His Val
930                 935                 940

Leu Arg Ser Leu Val Asn Gln Ser Val Gln Asp Gly Glu Glu Gln Val
945                 950                 955                 960

Arg Arg Leu Gly Pro Leu Ala Cys Phe Leu Ser Pro Glu Glu Leu Gln
                965                 970                 975

Ser Leu Val Pro Leu Ser Asp Pro Thr Gly Pro Val Glu Arg Gly Leu
            980                 985                 990

Leu Glu Cys Ala Ala Asn Gly Thr  Leu Ser Pro Glu Gly  Arg Val Ala
```

-continued

```
          995                1000               1005
Tyr Glu Leu Leu Gly Val Leu Arg Ser Ser Gly Gly Ala Val Leu
    1010                1015               1020

Ser Pro Arg Glu Leu Arg Val Trp Ala Pro Leu Phe Ser Gln Leu
    1025                1030               1035

Gly Leu Arg Phe Leu Gln Glu Leu Ser Glu Pro Gln Leu Arg Ala
    1040                1045               1050

Met Leu Pro Val Leu Gln Gly Thr Ser Val Thr Pro Ala Gln Ala
    1055                1060               1065

Val Leu Leu Leu Gly Arg Leu Leu Pro Arg His Asp Leu Ser Leu
    1070                1075               1080

Glu Glu Leu Cys Ser Leu His Leu Leu Leu Pro Gly Leu Ser Pro
    1085                1090               1095

Gln Thr Leu Gln Ala Ile Pro Arg Arg Val Leu Val Gly Ala Cys
    1100                1105               1110

Ser Cys Leu Ala Pro Glu Leu Ser Arg Leu Ser Ala Cys Gln Thr
    1115                1120               1125

Ala Ala Leu Leu Gln Thr Phe Arg Val Lys Asp Gly Val Lys Asn
    1130                1135               1140

Met Gly Thr Thr Gly Ala Gly Pro Ala Val Cys Ile Pro Gly Gln
    1145                1150               1155

Gln Pro Ile Pro Thr Thr Trp Pro Asp Cys Leu Leu Pro Leu Leu
    1160                1165               1170

Pro Leu Lys Leu Leu Gln Leu Asp Ser Leu Ala Leu Leu Ala Asn
    1175                1180               1185

Arg Arg Arg Tyr Trp Glu Leu Pro Trp Ser Glu Gln Gln Ala Gln
    1190                1195               1200

Phe Leu Trp Lys Lys Met Gln Val Pro Thr Asn Leu Thr Leu Arg
    1205                1210               1215

Asn Leu Gln Ala Leu Gly Thr Leu Ala Gly Gly Met Ser Cys Glu
    1220                1225               1230

Phe Leu Gln Gln Ile Asn Ser Met Val Asp Phe Leu Glu Val Val
    1235                1240               1245

His Met Ile Tyr Gln Leu Pro Thr Arg Val Arg Gly Ser Leu Arg
    1250                1255               1260

Ala Cys Ile Trp Ala Glu Leu Gln Arg Arg Met Ala Met Pro Glu
    1265                1270               1275

Pro Glu Trp Thr Thr Val Gly Pro Glu Leu Asn Gly Leu Asp Ser
    1280                1285               1290

Lys Leu Leu Leu Asp Leu Pro Ile Gln Leu Met Asp Arg Leu Ser
    1295                1300               1305

Asn Glu Ser Ile Met Leu Val Val Glu Leu Val Gln Arg Ala Pro
    1310                1315               1320

Glu Gln Leu Leu Ala Leu Thr Pro Leu His Gln Ala Ala Leu Ala
    1325                1330               1335

Glu Arg Ala Leu Gln Asn Leu Ala Pro Lys Glu Thr Pro Val Ser
    1340                1345               1350

Gly Glu Val Leu Glu Thr Leu Gly Pro Leu Val Gly Phe Leu Gly
    1355                1360               1365

Thr Glu Ser Thr Arg Gln Ile Pro Leu Gln Ile Leu Leu Ser His
    1370                1375               1380

Leu Ser Gln Leu Gln Gly Phe Cys Leu Gly Glu Thr Phe Ala Thr
    1385                1390               1395
```

-continued

```
Glu Leu Gly Trp Leu Leu Leu Gln Glu Ser Val Leu Gly Lys Pro
    1400                1405                1410

Glu Leu Trp Ser Gln Asp Glu Val Glu Gln Ala Gly Arg Leu Val
    1415                1420                1425

Phe Thr Leu Ser Thr Glu Ala Ile Ser Leu Ile Pro Arg Glu Ala
    1430                1435                1440

Leu Gly Pro Glu Thr Leu Glu Arg Leu Leu Glu Lys Gln Gln Ser
    1445                1450                1455

Trp Glu Gln Ser Arg Val Gly Gln Leu Cys Arg Glu Pro Gln Leu
    1460                1465                1470

Ala Ala Lys Lys Ala Ala Leu Val Ala Gly Val Val Arg Pro Ala
    1475                1480                1485

Ala Glu Asp Leu Pro Glu Pro Val Pro Asn Cys Ala Asp Val Arg
    1490                1495                1500

Gly Thr Phe Pro Ala Ala Trp Ser Ala Thr Gln Ile Ala Glu Met
    1505                1510                1515

Glu Leu Ser Asp Phe Glu Asp Cys Leu Thr Leu Phe Ala Gly Asp
    1520                1525                1530

Pro Gly Leu Gly Pro Glu Glu Leu Arg Ala Ala Met Gly Lys Ala
    1535                1540                1545

Lys Gln Leu Trp Gly Pro Pro Arg Gly Phe Arg Pro Glu Gln Ile
    1550                1555                1560

Leu Gln Leu Gly Arg Leu Leu Ile Gly Leu Gly Asp Arg Glu Leu
    1565                1570                1575

Gln Glu Leu Ile Leu Val Asp Trp Gly Val Leu Ser Thr Leu Gly
    1580                1585                1590

Gln Ile Asp Gly Trp Ser Thr Thr Gln Leu Arg Ile Val Val Ser
    1595                1600                1605

Ser Phe Leu Arg Gln Ser Gly Arg His Val Ser His Leu Asp Phe
    1610                1615                1620

Val His Leu Thr Ala Leu Gly Tyr Thr Leu Cys Gly Leu Arg Pro
    1625                1630                1635

Glu Glu Leu Gln His Ile Ser Ser Trp Glu Phe Ser Gln Ala Ala
    1640                1645                1650

Leu Phe Leu Gly Thr Leu His Leu Gln Cys Ser Glu Glu Gln Leu
    1655                1660                1665

Glu Val Leu Ala His Leu Leu Val Leu Pro Gly Gly Phe Gly Pro
    1670                1675                1680

Ile Ser Asn Trp Gly Pro Glu Ile Phe Thr Glu Ile Gly Thr Ile
    1685                1690                1695

Ala Ala Gly Ile Pro Asp Leu Ala Leu Ser Ala Leu Leu Arg Gly
    1700                1705                1710

Gln Ile Gln Gly Val Thr Pro Leu Ala Ile Ser Val Ile Pro Pro
    1715                1720                1725

Pro Lys Phe Ala Val Val Phe Ser Pro Ile Gln Leu Ser Ser Leu
    1730                1735                1740

Thr Ser Ala Gln Ala Val Ala Val Thr Pro Glu Gln Met Ala Phe
    1745                1750                1755

Leu Ser Pro Glu Gln Arg Arg Ala Val Ala Trp Ala Gln His Glu
    1760                1765                1770

Gly Lys Glu Ser Pro Glu Gln Gln Gly Arg Ser Thr Ala Trp Gly
    1775                1780                1785
```

```
Leu Gln Asp Trp Ser Arg Pro Ser Trp Ser Leu Val Leu Thr Ile
   1790                1795                1800

Ser Phe Leu Gly His Leu Leu
   1805                1810

<210> SEQ ID NO 2
<211> LENGTH: 5433
<212> TYPE: DNA
<213> ORGANISM: Homo sapiens

<400> SEQUENCE: 2
atggctctca gcctctggcc cctgctgctg ctgctgctgc tgctgctgct gctgtccttt      60
gcagtgactc tggcccctac tgggcctcat tccctggacc tggtctctc cttcctgaag      120 tcattgctct ccactctgga ccaggctccc cagggctccc tgagccgctc acggttcttt      180
acattcctgg ccaacatttc ttcttccttt gagcctggga gaatggggga aggaccagta      240
ggagagcccc cacctctcca gccgcctgct ctgcggctcc atgattttct agtgacactg      300
agaggtagcc ccgactggga gccaatgcta gggctgctag ggatatgct ggcactgctg      360 ggacaggagc agactccccg agatttcctg gtgcaccagg caggggtgct gggtggactt      420
gtggaggtgc tgctgggagc cttagttcct ggggccccc ctaccccaac tcggccccca      480
tgcacccgtg atgggccgtc tgactgtgtc ctggctgctg actggttgcc ttctctgctg      540
ctgttgttag agggcacacg ctggcaagct ctggtgcagg tgcagcccag tgtggacccc      600
accaatgcca caggcctcga tgggagggag gcagctcctc acttttttgca gggtctgttg      660 ggtttgctta ccccaacagg ggagctaggc tccaaggagg ctcttttggg cggtctgcta      720
cgcacagtgg gggcccccct ctatgctgcc tttcaggagg ggctgctccg tgtcactcac      780
tccctgcagg atgaggtctt ctccattttg gggcagccag agcctgatac caatgggcag      840
tgccagggag ttttcttcct tactctttcc ctcctaggta accttcaaca gctgctctta      900
tggggcgtcc ggcacaacct ttcctgggat gtccaggcgc tgggctttct gtctggatca      960 ccaccccac cccctgccct ccttcactgc ctgagcacgg gcgtgcctct gcccagagct      1020
tctcagccgt cagcccacat cagcccacgc caacggcgag ccatcactgt ggaggccctc      1080
tgtgagaacc acttaggccc agcaccaccc tacagcattt ccaacttctc catccacttg      1140
ctctgccagc acaccaagcc tgccactcca cagccccatc ccagcaccac tgccatctgc      1200
cagacagctg tgtggtatgc agtgtcctgg gcaccaggtg cccaaggctg gctacaggcc      1260
tgccacgacc agtttcctga tgagttttg gatgcgatct gcagtaacct ctccttttca      1320
gccctgtctg gctccaaccg ccgcctggtg aagcggctct gtgctggcct gctcccaccc      1380
cctaccagct gccctgaagg cctgccccct gttcccctca cccagacat cttttgggc      1440 tgcttcttgg agaatgagac tctgtgggct gagcgactgt gtgggaggc aagtctacag      1500 gctgtgcccc cagcaacca ggcttgggtc agcatgtgt gccagggccc cacccagat      1560 gtcactgcct ccccaccatg ccacattgga ccctgtgggg aacgctgccc ggatgggggc      1620
agcttcctgg tgatggtctg tgccaatgac accatgtatg aggtcctggt gcccttctgg      1680
ccttggctag caggccaatg caggataagt cgtggggca atgacacttg cttcctagaa      1740
gggctgctgg gccccttct gcctctctg ccaccactgg accatccccc actctgtctg      1800
acccctggcc ccttcctcct tggcatgcta tcccagttgc cacgctgtca gtcctctgtc      1860
ccagctcttc ctcaccccac acgcctacac tatctcctcc gctgctgac cttcctcttg      1920 ggtccagggg ctggggggcgc tgaggcccag gggatgctgg gtcgggccct actgctctcc      1980
```

```
agtctcccag acaactgctc cttctgggat gcctttcgcc cagagggccg gcgcagtgtg    2040
ctacggacga ttggggaata cctggaacaa gatgaggagc agccaacccc atcaggcttt    2100
gaacccactg tcaaccccag ctctggtata agcaagatgg agctgctggc ctgctttagt    2160
cctgtgctgt gggatctgct ccagagggaa aagagtgttt gggccctgca gattctagtg    2220
caggcgtacc tgcatatgcc cccagaaaac ctccagcagc tggtgctttc agcagagagg    2280
gaggctgcac agggcttcct gacactcatg ctgcagggga agctgcaggg gaagctgcag    2340
gtaccaccat ccgaggagca ggccctgggt cgcctgacag ccctgctgct ccagcggtac    2400
ccacgcctca cctcccagct cttcattgac ctgtcaccac tcatcccttt cttggctgtc    2460
tctgacctga tgcgcttccc accatccctg ttagccaacg acagtgtaca gcagggctac    2520
agagggtcag aggaaaacag tttggaggaa gacaaagggt taagacccat gactcctcgc    2580
agcctggctg ccatccggga ttacagccca ggaatgaggc ctgaacagaa ggaggctctg    2640
gcaaagcgac tgctggcccc tgaactgttt ggggaagtgc ctgcctggcc ccaggagctg    2700
ctgtgggcag tgctgcccct gctcccccac ctccctctgg agaacttttt gcagctcagc    2760
cctcaccaga tccaggccct ggaggatagc tggccagcag caggtctggg gccagggcat    2820
gcccgccatg tgctgcgcag cctggtaaac cagagtgtcc aggatggtga ggagcaggta    2880
cgcaggcttg gcccctcgc ctgtttcctg agccctgagg agctgcagag cctagtgccc    2940
ctgagtgatc aacggggcc agtagaacgg gggctgctgg aatgtgcagc caatgggacc    3000
ctcagcccag aaggacgggt ggcatatgaa cttctgggtg tgttgcgctc atctggagga    3060
gcggtgctga gccccggga gctgcgggtc tgggcccctc tcttctctca gctgggcctc    3120
cgcttccttc aggagctgtc agagcccag cttagagcca tgcttcctgt cctgcaggga    3180
actagtgtta cacctgctca ggctgtcctg ctgcttggac ggctccttcc taggcacgat    3240
ctatccctgg aggaactctg ctccttgcac cttctgctac caggcctcag cccccagaca    3300
ctccaggcca tccctaggcg agtcctggtc ggggcttgtt cctgcctggc ccctgaactg    3360
tcacgcctct cagcctgcca gaccgcagca ctgctgcaga cctttcgggt taaagatggt    3420
gttaaaaata tgggtacaac aggtgctggt ccagctgtgt gtatccctgg tcagcagcct    3480
attcccacca cctggccaga ctgcctgctt cccctgctcc cattaaagct gctacaactg    3540
gattccttgg ctcttctggc aaatcgaaga cgctactggg agctgccctg gtctgagcag    3600
caggcacagt ttctctggaa gaagatgcaa gtacccacca accttaccct caggaatctg    3660
caggctctgg gcaccctggc aggaggcatg tcctgtgagt ttctgcagca gatcaactcc    3720
atggtagact tccttgaagt ggtgcacatg atctatcagc tgcccactag agttcgaggg    3780
agcctgaggg cctgtatctg ggcagagcta cagcggagga tggcaatgcc agaaccagaa    3840
tggacaactg tagggccaga actgaacggg ctggatagca agctactcct ggacttaccg    3900
atccagttga tggacagact atccaatgaa tccattatgt tggtggtgga gctggtgcaa    3960
agagctccag agcagctgct ggcactgacc cccctccacc aggcagccct ggcagagagg    4020
gcactacaaa acctggctcc aaaggagact ccagtctcag gggaagtgct ggagaccttta   4080
ggcccttttgg ttggattcct ggggacagag agcacacgac agatcccct acagatcctg    4140
ctgtcccatc tcagtcagct gcaaggcttc tgcctaggag agacatttgc cacagagctg    4200
ggatggctgc tattgcagga gtctgttctt gggaaaccag agttgtggag ccaggatgaa    4260
gtagagcaag ctggacgcct agtattcact ctgtctactg aggcaatttc cttgatcccc    4320
```

-continued

```
agggaggcct tgggtccaga gaccctggag cggcttctag aaaagcagca gagctgggag     4380
cagagcagag ttggacagct gtgtagggag ccacagcttg ctgccaagaa agcagccctg     4440
gtagcagggg tggtgcgacc agctgctgag gatcttccag aacctgtgcc aaattgtgca     4500
gatgtacgag ggacattccc agcagcctgg tctgcaaccc agattgcaga gatggagctc     4560
tcagactttg aggactgcct gacattattt gcaggagacc caggacttgg gcctgaggaa     4620
ctgcgggcag ccatgggcaa agcaaaacag ttgtggggtc cccccgggg atttcgtcct     4680
gagcagatcc tgcagcttgg taggctctta ataggtctag gagatcggga actacaggag     4740
ctgatcctag tggactgggg agtgctgagc accctgggc agatagatgg ctggagcacc     4800
actcagctcc gcattgtggt ctccagtttc ctacggcaga gtggtcggca tgtgagccac     4860
ctggacttcg ttcatctgac agcgctgggt tatactctct gtggactgcg gccagaggag     4920
ctccagcaca tcagcagttg ggagttcagc caagcagctc tcttcctcgg caccctgcat     4980
ctccagtgct ctgaggaaca actggaggtt ctggcccacc tacttgtact gcctggtggg     5040
tttgcccaa tcagtaactg ggggcctgag atcttcactg aaattggcac catagcagct     5100
gggatcccag acctggctct ttcagcactg ctgcggggac agatccaggg cgttactcct     5160
cttgccattt ctgtcatccc tcctcctaaa tttgctgtgg tgtttagtcc catccaacta     5220
tctagtctca ccagtgctca ggctgtggct gtcactcctg agcaaatggc ctttctgagt     5280
cctgagcagc gacgagcagt tgcatgggcc aacatgagg gaaaggagag cccagaacag     5340
caaggtcgaa gtacagcctg ggcctccag gactggtcac gaccttcctg gtccctggta     5400
ttgactatca gcttccttgg ccacctgcta tga                                 5433
```

<210> SEQ ID NO 3
<211> LENGTH: 5433
<212> TYPE: DNA
<213> ORGANISM: Artificial Sequence
<220> FEATURE:
<223> OTHER INFORMATION: Codon optimized human Stereocilin cDNA

<400> SEQUENCE: 3

```
atggctctgt ctctgtggcc tctgctgctg ctcctgttgc tgcttctgct gctcagcttc       60
gccgtgacac tggctccaac aggaccccac tctctggatc ctggcctgag ctttctgaag      120
tccctgctga gcaccctgga tcaggctcct cagggcagcc tgagcagatc cagattcttc      180
accttcctgg ccaacatcag cagcagcttc gagcctggca gaatgggaga aggacctgtg      240
ggagaacctc ctccactgca acctccagct ctgcggctgc acgattttct ggtcacactg      300
agaggcagcc ccgactggga acctatgctg ggactgctgg gagatatgct ggccctgctc      360
ggacaagagc agacccctag agatttcctg gtgcatcagg ctggcgtgct cggaggactg      420
gttgaagttc tgcttggagc actggtgcct ggcggaccctc ctacacctac aagacctcca      480
tgcaccagag atggcccag cgattgtgtg ctggctgctg attggctgcc tagcctgctc      540
ctgcttctgg aaggcacaag atggcaggcc tggtgcagg ttcagccttc tgtggatcct      600
accaatgcca ccggcctgga tggaagagaa gccgctccac actttctgca gggactgctt      660
ggactgctca cacctactgg cgagctgggc tctaaagaag ccctttgggg aggcctgctg      720
agaacagttg gagcccctct gtacgccgcc tttaagagg gactcctgag agtgacacac      780
agcctgcagg acgaggtgtt cagcatcctg ggacagccag agcctgacac caatggacag      840
tgtcagggcg tgttcttcct gacctgagc ctgctgggca acctgcagca actgcttctg      900
tggggcgtca gacacaacct gagctgggat gtgcaggcac tgggctttct gtctggaagc      960
```

```
cctccacctc caccagcact gctgcattgt ctgtctactg gcgtgccact gcctagagcc   1020
tctcagccta gcgctcacat cagccccaga cagagaaggg ccatcaccgt ggaagctctg   1080
tgcgagaatc acctgggacc tgctcctcca tacagcatca gcaacttctc catccatctg   1140
ctgtgtcagc acaccaagcc tgccacacct cagcctcatc ctagcaccac agccatctgt   1200
cagaccgccg tttggtacgc cgtttcttgg gctcctggtg ctcaaggatg gctgcaggcc   1260
tgtcacgatc agttccccga cgagttcctg gacgccatct gcagcaatct gagcttctct   1320
gccctgtccg gcagcaatcg gagactggtc aaaagactgt gcgccggact gctgcctcct   1380
ccaacatctt gtcctgaggg actgcctcct gtgcctctga ctcccgatat cttttggggc   1440
tgcttcctgg aaaacgagac actgtgggcc gagagactgt gtggcgaagc ctctctgcaa   1500
gccgtgcctc catctaatca ggcctgggtg cagcacgttt gtcagggccc tacacctgac   1560
gtgacagcct ctcctccttg tcacatcgga ccttgcggcg agagatgtcc tgatggcggc   1620
agctttctcg tgatggtctg cgccaacgac actatgtacg aggtgctggt gcccttctgg   1680
ccttggctgg ctggccagtg tagaatctcc agaggcggca acgatacctg tttcctggaa   1740
ggactcctgg gaccactgct tccatctctg cctccgcttg gaccctctcc tctgtgtctt   1800 accccctggac ctttcctgct ggggatgctg tctcagctgc tagatgcca gtctagcgtg   1860 ccagctctgg cccatccaac cagactgcac tatctgttgc ggctgctgac cttcctcctt   1920
ggacctggcg ctggcggagc tgaagctcaa ggcatgcttg gcagagccct gctgctgtca   1980
tccctgcctg acaactgcag cttctgggac gccttcagac ctgaaggacg cagaagcgtg   2040
ctgaggacca tcggcgagta cctggaacag gatgaggaac agcctacacc aagcggcttc   2100
gaacccaccg tgaatcctag cagcggcatc tccaagatgg aactgctggc ctgcttcagc   2160
cccgtgctgt gggatctgct gcagagggaa aaaagcgtgt gggccctgca gatcctggtc   2220
caggcctatc tgcacatgcc tccagagaac ctgcaacagc tggtgctgtc tgccgagaga   2280
gaagctgccc aggattcct gactctgatg ctgcagggaa agctgcaggg caaactccag   2340
gtgccaccta gcgaagaaca ggcccttggc agactgacag cactcctgct ccagagatac   2400
cccagactga cctctcagct gtttatcgat ctgagccctc tgatcccatt cctggccgtg   2460
tccgacctga tgagattccc tcctagtctg ctggccaacg actccgtgca gcagggatac   2520
agaggcagcg aggaaaacag cctggaagag gacaaaggcc tgcggcctat gacacctaga   2580
tctctggccg ccatccggga ttacagcccc ggaatgaggc ccgagcagaa agaggccctg   2640
gctaagagac tgctggctcc cgagctgttt ggcgaagttc cagcctggcc tcaagaactg   2700
ctgtgggctg ttctgccct gctgccacat ctgcctctgg aaaacttcct gcagctgagc   2760
ccacaccaga ttcaggccct cgaggattct tggcctgccg ctggactcgg acctggacat   2820
gctagacacg tgctgagaag cctggtcaac cagagcgttc aggacggcga ggaacaagtg   2880
cggagacttg gaccctggc ctgttttctg agccccgagg aactgcagag tctggtgcct   2940
ctgtctgacc ctacaggccc tgttgaaagg gcctgctgg aatgtgccgc caatggaaca   3000
ctgagccctg agggcagagt ggcctatgaa cttctgggag tgctgagatc tagcggcgga   3060
gccgttctgt cccctaggga acttagagtg tgggcacccc tgtttagcca gctgggcctg   3120
agattcctgc aagagctgtc tgagccacag ctgagggcta tgctgcctgt gctccagggc   3180
acatctgtga caccagctca agccgtcctg ctgttgggca gactgctccc tagacacgat   3240
ctgtccctgg aagaactgtg cagcctgcac ttgctgctgc ctggactgtc tcctcagaca   3300
```

```
ctgcaggcca ttcctcggag agtgcttgtg ggagcctgta gctgtctggc ccctgagctg    3360
tctagactga gcgcctgtca aacagccgct ctcctgcaga ccttcagagt gaaggatggc    3420
gtgaagaaca tgggcaccac aggcgctgga cctgccgtgt gtattcctgg acagcagccc    3480
attcctacca cctggccaga ttgtctgctc ccactgctgc ccctgaaact gctgcagctg    3540
gattctctgg ctctgctggc taaccggcgg agatattggg aactgccttg agcgaacag    3600 caggcacagt tcctgtggaa gaagatgcag gtccccacca atctgacact gcggaatctg    3660
caggctctcg gcacacttgc tggcggaatg agctgcgagt cctccagca gatcaacagc    3720 atggtggact ttctggaagt ggtgcacatg atctaccagc tgccaaccag agtgcgggga    3780
agcctgagag cttgtatttg ggctgaactg cagcggcgga tggccatgcc tgaacctgaa    3840
tggacaacag tgggccccga gctgaacggc ctggactcta acttctgct ggatctcccc     3900 atccagctga tggacagact gagcaacgag agcatcatgc tggtggtgga actggtgcag    3960
agagccccag aacagctgct ggcactgaca cctctgcatc aagctgctct ggccgaacgg    4020
gcccttcaga atctggctcc caaagaaacc cctgtgtccg gggaagtgct ggaaacactg    4080
ggacctcttg tgggcttcct gggcaccgag tctaccagac agattcctct ccagatcctg    4140
ctgtcccacc tgagccagct ccaggggattt tgtctgggcg acattcgc caccgaactc     4200 ggatggttgc tgctccaaga gagcgtgctg ggaaagcccg aactgtggtc acaggacgaa    4260
gtggaacagg ccggcagact ggtgtttacc ctgtctaccg aggccatcag tctgatcccc    4320
agagaagcac tgggccctga aacactcgag aggctgctgg aaaagcagca gtcttgggaa    4380
cagagcagag tgggccagct gtgtagagaa cctcagctgg ccgctaaaaa ggccgcactg    4440
gttgctggcg ttgtcagacc tgctgccgag gatctgccag agccagtgcc taattgtgcc    4500
gatgtgcggg gcacatttcc tgccgcttgg agcgctacac agatcgccga aatgaactg     4560 agcgacttcg aggactgtct gactctgttt gccggcgatc ctggactggg accagaagaa    4620
ctgagagccg ccatgggcaa agccaagcaa cttggggac ctccaagagg cttcagaccc     4680
gaacagattc tgcagctcgg ccgcctgctt atcggactgg gcgatagaga gctgcaagaa    4740
ctgatcctgg tggactgggg cgtgctgtct actctgggca aaatcgacgg ctggtccacc    4800
acacagctgc ggattgtggt gtccagcttc ctgaggcagt ctggcagaca tgtgtctcac    4860
ctggacttcg tgcacctgac tgccctgggc tacacactgt gtggactgcg gcctgaggaa    4920
cttcagcaca tcagctcttg ggagttcagc caggcagccc tgtttctggg aaccctgcat    4980
ctgcagtgct ccgaagaaca actggaagtg ctcgcccatc tgctcgtgct gccaggcgga    5040
tttggcccca tctctaattg gggacccgag atcttcaccg agatcggcac cattgccgct    5100
ggcatccctg atctggccct gtctgcactg ctgagaggac agatccaggg cgtgacacca    5160
ctggccatta gcgtgatccc tccaccaaag ttcgccgtgg tgtttagccc cattcagctg    5220
tccagcctga catctgccca agccgtggct gtgaccctg aacagatggc atttctgtct     5280
cccgagcagc ggagagctgt tgcttgggct caacacgagg gcaaagagag tcctgagcaa    5340
cagggaagaa gcaccgcttg gggactgcag gattggtcca gaccttcttg gtcactggtg    5400
ctgaccatca gctttctggg ccacctcctg tga                                 5433
```

<210> SEQ ID NO 4
<211> LENGTH: 19238
<212> TYPE: DNA
<213> ORGANISM: Homo sapiens

<400> SEQUENCE: 4

```
gccctgccct cacctggcta tcccacacag gtgagaataa ccagaactca cctccggtac      60
cagtgttcac ttggaaacat ggctctcagc ctctggcccc tgctgctgct gctgctgctg     120
ctgctgctgc tgtcctttgc aggtaagaag aacagtgagc agaactgggg atgaggagga     180
gggtggctgg aaaaagactt taagaatatg gaggtgaacc tgttagatag aaggacaaag     240
gagagaggca gagacttgtg caaaagggaa aaatgagggt taagaaaagc aggccaagac     300
ttactgtagg ccagtgaaag gggttcagct caccatcccc tcacctcatc tttagatcca     360
ggtagggaac tgtgctcagg ggcagggttg agtttgggct ctgtgttcct ctccttcagt     420
gacctctggt ttctctcctt acagtgactc tgggccctac tgggcctcat ccctggacc      480
ctggtctctc cttcctgaag tcattgctct ccactctgga ccaggctccc cagggctccc     540
tgagccgctc acggttcttt acattcctgg ccaacatttc ttcttccttt gagcctggga     600
gaatggggga aggaccagta ggagagcccc cacctctcca gccgcctgct ctgcggctcc     660
atgattttct agtgacactg agaggtagcc ccgactggga gccaatgcta gggctgctag     720
gggatatgct ggcactgctg gacaggagc agactccccg agatttcctg gtgcaccagg     780
cagggggtgct gggtggactt gtggaggtgc tgctgggagc cttagttcct gggggccccc     840
ctaccccaac tcggccccca tgcacccgtg atgggccgtc tgactgtgtc ctggctgctg     900
actggttgcc ttctctgctg ctgttgttag agggcacacg ctggcaagct ctggtgcagg     960
tgcagcccag tgtggacccc accaatgcca caggcctcga tgggagggag gcagctcctc    1020
acttttgca gggtctgttg ggtttgctta ccccaacagg ggagctaggc tccaaggagg    1080
ctctttgggg cggtctgcta cgcacagtgg gggcccccct ctatgctgcc tttcaggagg    1140
ggctgctccg tgtcactcac tccctgcagg atgaggtctt ctccattttg gggcagccag    1200
agcctgatac caatgggcag tgccagggag gtgagtgtgg ccagggctgg gactgggatg    1260
tggcagggca aggaaagtga aattggggta gttttcttcc ttactctttc cctcctaggt    1320
aaccttcaac agctgctctt atggtaagta acaggagacc agttctgagg gattgggcct    1380
ggaaaatctg gaggtgaaga gctgaagacc tcagcctcta gagaggaaaa ctgatgggag    1440
gagtgtagtt tagtggtttt ggggtgtgac tgtctgggtt ggtgtcccag ctccacctct    1500
tcctagccat atgaccttga gcaggttaca tagtctttct atacctcagt ttccccattt    1560
ataaaatgag aatgataata ttagttacca cagagttgtt gcacccggtt aaatgagttg    1620
atactgtgta tgcaaacgac ttaaaaccgt gctggcacat agcgcttaat aatgttagct    1680
agtaaagatg ggatttggaa aataaggaca cagctggatt cctctacccc cttactactt    1740
cagtacaaca atgccagaca gtagttagac atattgagtt gctgagcaga tttcctaaca    1800
tgaggcccgc tgagggttgt gtttaagcta tctaaaagca tacgaagaaa ggagacagaa    1860
gggggccagg tggacagaaa gaattccaac tggggcttct cctaggtgat tttggacctt    1920
ggcagggcag ctttctcttt tttgccccgt tgcagcattt caaccagtaa cgcctaaact    1980
ctcagggacc tcgcttgtag aaaagcctat gcttgccatg ccccttgagg gctctgagtc    2040
agggtcagaa tcttcagctg gaggaaatgt gaactgacca gatcctgcct gctcctccct    2100
ctgcacccag gggcgtccgg cacaacccttt cctgggatgt ccaggcgctg gcttctctgt    2160
ctggatcacc accccccaccc cctgccctcc ttcactgcct gagcacgggc gtgcctctgc    2220
ccagagcttc tcagccgtca gcccacatca gcccacgcca acggcgagcc atcactgtgg    2280
aggccctctg tgagaaccac ttaggcccag caccacccta cagcatttcc aacttctcca    2340
```

```
tccacttgct ctgccagcac accaagcctg ccactccaca gccccatccc agcaccactg    2400
ccatctgcca gacagctgtg tggtatgcag tgtcctgggc accaggtgcc caaggctggc    2460
tacaggcctg ccacgaccag tttcctgatg agttttggga tgcgatctgc agtaacctct    2520
ccttttcagc cctgtctggc tccaaccgcc gcctggtgaa gcggctctgt gctggcctgc    2580
tcccacccCC taccagctgc cctgaaggcc tgccccctgt tcccctcacc ccagacatct    2640 tttgggctg cttcttggag aatgagactc tgtgggctga gcgactgtgt ggggaggcaa     2700
gtctacaggc tgtgcccccc agcaaccagg cttgggtcca gcatgtgtgc cagggcccca    2760
ccccagatgt cactgcctcc ccaccatgcc acattggacc ctgtggggaa cgctgcccgg    2820
atgggggcag cttcctggtg atggtctgtg ccaatgacac catgtatgag gtcctggtgc    2880
ccttctggcc ttggctagca ggccaatgca ggataagtcg tgggggcaat gacacttgct    2940
tcctagaagg gctgctgggc cccttctgc cctctctgcc accactggga ccatcccac     3000 tctgtctgac ccctgccccc ttcctccttg gcatgctatc ccagttgcca cgctgtcagt    3060
cctctgtccc agctcttgct caccccacac gcctacacta tctcctccgc ctgctgacct    3120
tcctcttggg tccaggggct gggggcgctg aggcccaggg gatgctgggt cgggccctac    3180
tgctctccag tctcccagac aactgctcct tctgggatgc ctttcgccca gagggccggc    3240
gcagtgtgct acggacgatt ggggaatacc tggaacaaga tgaggagcag ccaaccccat    3300
caggctttga acccactgtc aaccccagct ctggtataag caagatggag ctgctggcct    3360
gctttagtgt gagtgctctg ccagagggaa agctcctaga acagtgagaa ggccctccag    3420
gggaattcct cgaatactca gaggcagtag tgtggggtag tagttgaagc acacagctct    3480
agagtcagac aggcttggat tcatatcttg gttctgtgac cagccttgaa tgagttattt    3540
aacttctctg agcaatattt ttctcgtctc atttataaac tagggatgat aatggtatat    3600
gagataatac atgctgtggg cttagcacag tgcatgatac acaaacatgc aataaatatt    3660
accttgttat tcttttgggc tctttgactc tctcactttc tgcaccagaa agaaaaagga    3720
tcaagttaga ggactctaaa ttttttcccct agagagtgag aattggaggc tggcagaata    3780
caggaagata aggtaggaat gagaaagatt cagggacact accaatcaga agactttggt    3840
tctaggttca actgtgccac aaattagtgt gatcttaggc aagcaatttc atttagtttt    3900
tctgggcttc agtttttagt ctgtagaatg gaggggtgag aatatgttaa acaccataat    3960
taattcactg agtgcctatt atatgcaagg cactttgcta ggttctgtag gatatataaa    4020
gatttcttac tccatgttgg ggccaccttt ttcaaacccct gggcccagta aaatggaatt    4080
agatagtctc atagtatttg gttcaggtct acaagtatta attgagccaa ctatggacct    4140
ggcatgggag agggtacaag agaaattaga gatatgatcc cggacctaaa agagcttaat    4200
atctgaagaa tcacacttga gatgatggac aagcatccca gcaagtggag ctggaatgcc    4260
tgggggagct gcaggagaga cagagaagac agctctgttg gcatattgtc tttcttccca    4320
ccagcctgtg ctgtgggatc tgctccagag ggaaaagagt gtttgggccc tgcagattct    4380
agtgcaggta acaggtggag ggcacatggg tgggctgggt gacagccatg gctggaggtc    4440
cctgccccgt gaggtgaggc catacccacc atgacctcct attcgcaggc gtacctgcat    4500
atgcccccag aaaacctcca gcagctggtg ctttcagcag agagggaggc tgcacagggc    4560
ttcctgacac tcatgctgca ggggaagctg caggggaagc tgcaggtgag cactgagaaa    4620
ggggagcaag gcaccctgga gcctagtgtt cagagggctt gctttagtgg gaggaggaac    4680
tccagagagg aaatggcagg gatactgagc atctccagag gcagaatcca ttcctgtgcc    4740
```

```
cctacaggta ccaccatccg aggagcaggc cctgggtcgc ctgacagccc tgctgctcca    4800
gcggtaccca cgcctcacct cccagctctt cattgacctg tcaccactca tcccttcctt    4860
ggctgtctct gacctgatgc gcttcccacc atccctgtta gccaacgaca gtgtgtaagg    4920
ttcttgcact actcctcctg ctcctgtcac ggtcaggcca accgcatcca cctggagcag    4980 cccctccgg agctcctctc tgttttttc tttcatgcca gataggcaat gtgccaacat     5040
cgtagcaagg tttgagagag gcacatctca cgcctgagtg tgaaaaccca atcattatgc    5100
taatgaacta caaaaggatc agagagctcc tctctattaa aaccagggag aggatgggcg    5160
tggtggctca tgcctgtaat cccagcacgt gggagcccg aggcaggtgg atcactaggt     5220
ccgcctagtg agttcgagac cagcctggcc aatatggtga acccccgtct ctattaaact    5280
acaaaaatta gccaggcatg gtggtgggcg cttgtagtcc cagttactct ggaggctgag    5340
gcaggaggat agcttgaacc tgggaggcag aggttgcagt gaaccaagat cgtgccactg    5400
cactccagcc tgggtgacag agcgagactc cgtcttaaaa aaacaaaaa acaaaacaaa     5460 acaaaaaac agggagagtc tccttcctat ctagacagca gggctacaga gggtcagagg    5520
aaaacagttt ggaggaagac aaagggttaa gacccatgac tcctcgcagc ctggctgcca    5580
tccgggatta cagcccagga atgaggcctg aacagaagga ggctctggca aagcgactgc    5640
tggcccctga actgtttggg gaagtgcctg cctggcccca ggagctgctg tgggcagtgc    5700
tgcccctgct cccccacctc cctctggaga acttttttgca gctcagccct caccaggtat    5760
gagaatcatc ttctttactt gactggccca tcttctgcta gtggggacaa agagtcaatg    5820
gcatgtctct cagtggcccc tccctgcaag aaccctatag tgaccccagt gcgagctaac    5880
cttccccatc tcagatccag gccctggagg atagctggcc agcagcaggt ctggggccag    5940
ggcatgcccg ccatgtgctg cgcagcctgg taaaccagag tgtccaggat ggtgaggagc    6000
aggtacgcag gtgagttgtt gtgggatcag taaccaaggc aagagtggaa gaggtagaga    6060
gaggaaggca cagctgtcac gctgggtcgg tgttctagga agaaaggggc aagagagtag    6120
gcagtggcct caggcagcat agagttccag gagagaggtc tatagatggt gcccctgtgt    6180
agtggtgtag tgtcagagtg cccagtgtat gtacccatac catctgctgc caggcctgcc    6240
ttagtgctag tcttggggac cacacaaagg tcagcttcat gccctcctca ggcttgggcc    6300
cctcgcctgt ttcctgagcc ctgaggagct gcagagccta gtgcccctga gtgatccaac    6360
ggggccagta aacgggggc tgctggaatg tgcagccaat gggaccctca gcccagaagg     6420
acgggtgagc ccctcagcac aagcctacaa gactttaggc ttcccctggg tctgtgtgga    6480
tggctttccc attgtgtcaa cttgagcaca gtggtgccag ccccatccc acttttgcaa     6540 cctccattcc ttactccatg gccattctta cctgttacca cctcttcctg gcccttctct    6600
atctggtctg tagcacccca aacatacct ttgccatttt gaacctaatc tactccagtc     6660
caatccctag ttccaaaccc tagcccaggc cctgggaaat tcagatgtgg gattagagag    6720
gaagttcaag gttcatctgt cttttctctc cagtcctaaa ccttctttgg ttacaggtgg    6780
catatgaact tctgggtgtg ttgcgctcat ctggaggagc ggtgctgagc ccccgggagc    6840
tgcgggtctg ggcccctctc ttctctcagc tgggcctccg cttccttcag gagctgtcag    6900
agccccagct tagagccatg cttcctgtcc tgcagggaac tagtgttaca cctgctcagg    6960
tttgcctgtc tcactccctg gcatgtaccc tccatccccg cttgagcccc agtcaagaga    7020
atcccattca gggataaaag cagcccctcc tttccctggg tgaacagtag aggtaaactc    7080
```

-continued

| | |
|---|---|
| tgtctgcagg aggacgcctt cattcccttt cctcagatca agaagggacc tgagtcactg | 7140 |
| aggatggtta ctagggatgg ttaagaggca gcgggaagtt ttggagggtt tgccttagga | 7200 |
| acccacttag gacctggctg ctgggtcctg agagctgttg ttttcggtcc catcccaaca | 7260 |
| caggctgtcc tgctgcttgg acggctcctt cctaggcacg atgtgagtag cagcaacttc | 7320 |
| tcagcctccc gccagaggtc tctatcctct tttaacctgg ctcctgcatc tgcccctcct | 7380 |
| ctctctccgc tcccctcata cttactgcct tgctgcattg tgattgttgt cttccccaac | 7440 |
| acccttccct tcttcttcag gcctcttgtc tctcttgctc tttagctatc cctggaggaa | 7500 |
| ctctgctcct tgcaccttct gctaccaggc ctcagccccc agacactcca ggccatccct | 7560 |
| aggcgagtcc tggtcggggc ttgttcctgc ctggcccctg aactgtcacg cctctcagcc | 7620 |
| tgccagaccg cagcactgct gcagaccttt cgggtatgag agtggcaagg aggatgagat | 7680 |
| aatcagggat accggctctt tctggttggg aggaaggcat cttccctgag gccagggaag | 7740 |
| gcctttcata cctccccact tacacacaca cacacacaca cacacacaca cacacacaca | 7800 |
| accaattctc atgcaggtta aagatggtgt taaaaatatg ggtacaacag gtgctggtcc | 7860 |
| agctgtgtgt atccctggtc aggtaagtgt gagatctccc aactgagctc ctctccccat | 7920 |
| tctggggcag tttcatatgg ctggtgctac ctcccacact accctgcagt ggccctgaga | 7980 |
| gttctggtta gctctgtgcc cattagcagc cctccccagt gccagatgca ggacagcatg | 8040 |
| atccactcac attgtcctag actaatgtca aagctggaag ggcctgagaa tcttccagg | 8100 |
| ccacccaccc tgctttcaga tgaaaagacc aaggctggga gaagctaagg gactttgttt | 8160 |
| gcctggtgcc taactagcag caacacttga ccacagcagc ctgcagtgtg aggctcttag | 8220 |
| gcgtttattg ctacagtggc aaatgccatt ccacttctgt cctagctttg gtcccttcc | 8280 |
| acccccatgg ttcctttct ctgagtgcta agtacagact ctctcaccta tcactacact | 8340 |
| gctataccca tcaccgccag cagcctattc ccaccacctg gccagactgc ctgcttcccc | 8400 |
| tgctcccatt aaagctgcta caactggatt ccttggctct tctggcaaat cgaagacgct | 8460 |
| actgggagct gccctggtct gagcagcagg taattctccc cacttaattt cagaacttcc | 8520 |
| tccctcaatg tagtctacct tctttaccta tcccttagcc ctatttggcc agcttatccc | 8580 |
| tactatcctt tatttgattg tttgagatac agtctcactc tgttgcccag gctgcagtgc | 8640 |
| agtggcatga tcagagttcg ctgtaacctc aaactcctga gctcaggcaa tcttctgcc | 8700 |
| tcagcctcct gaatagctag gacgacaggt ggttaccacc atgcctggct aattttaaa | 8760 |
| tttttttttt gttttttgag atgaagtctt gctctgtcac ccaggcttga gtacagtggc | 8820 |
| acaagcttgg ctcactgcaa cctctgtctc ccgggttcaa gcgattctcc tgcctcagcc | 8880 |
| tcccgagtag ctgggactac aggcactccc acaatgcct ggctaatttt ttttttgttt | 8940 |
| tagtagagac agggtttcac catattggcc aggctggtct cgaactgctg accttgtgat | 9000 |
| ctgcctgcct ctgcctctca aagtgctggg attacaggtg tgagccacca tgcccggcca | 9060 |
| atttttaaat tttttgtaga gacagacaat acaaaaatgt ggacactatg tggagacact | 9120 |
| atgttgaggt actatgctgt ccagattggt cttgaactcc tggcctcaag caatcctcct | 9180 |
| gccttggcct cccaaagtgc tgggattaca gacctgagcc actgcaccca gccccctagt | 9240 |
| atctcttata atgtgacttg cttttcttt tctttctcct tcccttttct ttcatttctt | 9300 |
| tctcactctc gagagaagag tgggcatctg ggagagtggg aggctggtgg gtcccacaga | 9360 |
| gtgaggaggc aggactgggt ccaaggcagt cctgcctctc cactctaggg ggtatccttg | 9420 |
| gacagtgtct cttctgggaa ggggctcgtc tttctttctc ttgtaggcac agtttctctg | 9480 |

-continued

```
gaagaagatg caagtaccca ccaaccttac cctcaggaat ctgcagtgag taacttgtgt   9540
tgagcagtgc gctgaattcg accaacattt ttttgagtgc ttactatgtg ccaggcacca   9600
tgtgatatgg aatgggggat atagggatga atgatgcata gtccctgcct cgtggacgtt   9660
ctcctagcac ctcccttgc cctccttcc ttcacagtg ccatgcctat cctgactaga    9720
gccaaaggac tcagaaaacc tggattcagg ttccagtcct gtcacctact tgtcctcttg   9780
ggcaagtcat ttaacgtccc tgtgtcagtt ttcccttctt taaatgagaa ttacaatggc   9840
accagcctca taggtagtta ctgtgaagat taaatgaggt aggtcatgta agatatttaa   9900
cacagtgttt ggtccattgt aaagtcccag tagtcatttg ctactgttag tttacttcag   9960
gatgacttca gaggcactgg ccaagcaaga ataaatagga ataagaaggt atcacttac   10020 ttacacccac attagaagaa caatgggctt cagaatcttt tttttttttt tttttcgag   10080 acagtcttgc tctgttgccc aggctggagt gcagtggcgc gatttcggct cactgcaacc   10140
tctgcctccc aggttcaagc gattctcctg tctcagcctc tggagtagct gggattacag   10200
gaatgtgcca ccatacccag ctaattttg tatttttagt agagatgggg tttcaccatt   10260
ttggccaggc tggtctcaaa ctcctgacct caggtgatcc acccgcctca gcctcccaag   10320
ggcttcagaa tctaagacat ggctctagtt tcagtttacc acatttctag cagaatgatg   10380
ttgggaatgt cacctgactt ccataaatcc ttatttctc ctctgataaa cagcagtgat   10440
gttatgggga gctgatgaga tatctatgta aaaacatttc tcaaaccata aattacggtg   10500
gatgaacatc tgtacttgtg ttgagagtac tgatatcaag gagcaaacag gctgttgtat   10560
gtgttgaatg agcctctccc cactcacaca cccacagggc tctgggcacc ctggcaggag   10620
gcatgtcctg tgagtttctg cagcagatca actccatggt agacttcctt gaagtggtgc   10680
acatgatcta tcagctgccc actagagttc gagggagcct ggtgagaggg ggtgcctgga   10740
ctttagtggg agcagggagg ctgggaccct aggtatagaa cccagctcct atgttctgct   10800
ctggcctcac actgcttccc tacagagggc ctgtatctgg gcagagctac agcggaggat   10860
ggcaatgcca gaaccagaat ggacaactgt agggccagaa ctgaacgggc tggatagcaa   10920
gctactcctg gacttaccgt aagtactgca gctagagata ttggcccctc agaaagctca   10980
atctggggtg aagatctgcc cttagggaat gccctggagg aggtagtttt tctgtctggt   11040
agttccctga cataatttat agcccaaagc agaggatttt attcaaagtt gctctatgta   11100
ttgactggtt cccagaatat gctccagcac agggcagctg agggtggcaa cactgtattg   11160
aagcctgcca agtaatctta caataaccta gtccacatta attgagattg agacagagca   11220
tctgaagtga gggaggcaat gctccaaatc tgccccagag gattgtagtt gctcagggc   11280 actgtgttct tagtgcattc agaggagtag atcgagagaa aaatatatga aaaatgtgat   11340 aaatacctc aaatacctga ggggctatca agtagaaatt agattgtcat atttatgagt   11400
ggccccattg ggcaagacta agagtagtta acggagatca gatttttaca tagtataaga   11460
aaaactaagg tagtgagttc ctggtccttg gagctgttcg agcctaagcc agatggcccc   11520
atggcaggaa tgttgtagag cacgttcata tacaggttgt gggaagaaaa ggctatagga   11580
acccaaggct cctccctacc catggagaaa tttattagta tgttactcat atgctgcttt   11640 tctcattta cccctaccac cacccgttg ccatccgcac tgtaagtcag gataggaaaa   11700
tgctggtgtt acagtcttcc tggggaatat ggagctgaag tggagtaaaa gcagttgact   11760
tcattcctac tttttctttt ttttcttt tttttttttt tgagacagag ttttgctgtg   11820
```

```
tcaccaaggc tggagtgcag tgacgtgatc tcggctcact gcaacctcca tcttccaggt   11880
tcaagcaatt ctcctgcctc agtctcccga gtagctggga ctgtaggtgt gcaccaccat   11940
gccaggctaa ttttttgtatt tgttgtaggg acgagctttc accatgttgg ccaggctggt   12000
cttgaactcc tggcttcaag tgatctgccc acctcggctt cccaacattc ttatatttt    12060 ataggccttt ccacagattt cagctcttgt atgacttagc ccagttccag aactggtaat   12120
cctaggtagg gtacaggtta tcacctctga tttcgggtaa aagggattta tttatttatt   12180
tgtttattta tttatatttt tgagacagag tctcgctctg tcacccaggc tggagtgcaa   12240
tggtgccatc tcggctcact gcaacctctc cctctgggt  tcaagcaatt ctcctgcctc    12300
agcctgctga gtagctggga ttacaggcgc gtgccaccac acccggctaa tttttgcatt   12360
tttagtagag acggggtttc accatgttgc tcagggtggt ctcgaatttc tgaccctgtg   12420
atctgcctgc ctcggcctcc caaagtgctg ggattacagg catgagccac tgcgtccggc   12480 ctgttttac ttttttttaa tgccattcag atctgtttaa atatgtgggt tctgtgagat     12540
aatttagaat cccaaggtta cagatgaggt gaaagatcct agaccatgca tcaaaaaact   12600
tgagtttctc atttgtgaaa gaaggataag agaaacacct attttgtctg ggtgcagtgg   12660
ctcatgccta taatcccagc atttgggag gccaaggtgg gtggatcacg gaggtcaggt    12720
gttcaagacc agactggcca acatggcaaa acaccatctc tactaaaat  acaaaagtta   12780 gctgggcgtg gtggcacgtg cgtgtaattc cagctattcg ggaggctgag gcacgagaat   12840
tgcttgaacc tgggaggtgc gggttgcagt gaactgagat cgcagcacca ctgtgctcca   12900
gcctgagtga tggagtgagg ccaggtcttg ttgtaggatc aaatgagata acacctgaaa   12960
gaactttgta aattgtatag cacgtacaaa caagaaggga cctcttcaca agcagaggaa   13020
gggtggtcct gtggaaaaaa acgggaattg ggagtgagag acctcaacat ttgatctctg   13080
tgaacctcag ttttttaatc tataaaatgg ggaaatgtta atggtactta atatttggag   13140
cttttgagtc cattagatca ggtaggattg ttcgttattt tttttttta  ggaagactag   13200 aaatatgttg ctccctttt  ctcccccact caagcttgat ggtgggaatt ggccctggag   13260
ctgtttacta tcagttcctg tccagcttca ctaaatttgg tctggggtca catcttagct   13320
gcggactgtg gggttttgtg gtcccttctc gacttggccc agctccacct gaatcctgtt   13380
gttgtcaaat tgctgtaata ggatccagtt gatggacaga ctatccaatg aatccattat   13440
gttggtggtg gagctggtgc aaagagctcc agagcagctg ctggcactga ccccctcca    13500 ccaggcagcc ctggcagaga gggcactaca aaacctggta agagtccacc ctaccagact   13560
cagatttgct gccctgggca attcttgctc ctcagacaat gctctctgac tgtccccaa    13620 ccctctactt cttgctttct tgctgccaaa cagattcctg tctacaaggc ctggcccctg   13680
ttttgcctct gggttctgtt ccttgataat atgcttcacg ttacttgtcc atacctcttg   13740
gagtccgaga aatctcttgg agtccacctc tcagtctttc tgcctgctcc tatctgggct   13800
cattgcttaa ggaagtgaac aaaggtagtg agcatcatag ggtgctgagc tgggagcagg   13860
agggagggaa ggttagggg  cttggtgtct tgatcaaggt gtctggtatt ctgagtcaga   13920
agtgcattgt ccaagttctg atgctcttct ccaggctcca aaggagactc cagtctcagg   13980
ggaagtgctg gagaccttag gcccttttggt tggattcctg gggacagaga gcacacgaca   14040 gatccccta cagatcctgc tgtcccatct cagtcgctg  caaggcttct gcctaggaga    14100
gacatttgcc acagagctgg gatggctgct attgcaggag tctgttcttg ggtatgacc    14160 ttcgagaact tcagattcta actcattcta tacccagtcc ctcagccacc atcatcagtg   14220
```

```
gcagcctgtt ccatattctt aaggtccccct ggagccctgt gtccgaaatc ctagcatgtc    14280
ctcttttccc cttcctttttc ctcacagttc cctcagctcc ccagccccg attttcttcc    14340 tgtccccagg aaaccagagt tgtggagcca ggatgaagta gagcaagctg gacgcctagt    14400
attcactctg tctactgagg caatttcctt gatccccagg gtgagatgaa ggaagaaggg    14460
aagggagtaa atgcatagag gggactggtg agctggttat ggggacccgt ggccaaagag    14520
ggcaaaggat atgaagccta gatctggggg gagactgcaa aacagagaca ggactttgga    14580
cttagagcta tagcagcagg tcctgatctg tccagatctc cccactctcc ttctaccttc    14640
tcatgcagga ggccttgggt ccagagaccc tggagcggct tctagaaaag cagcagagct    14700
gggagcagag cagagttgga cagctgtgta gggagccaca gcttgctgcc aagaaagcag    14760
ccctggtagc aggggtggtg cgaccagctg ctgaggatct tccaggtgaa actacccaaa    14820
tacttatatg tccagcagga tgtacaggga gtatcaaacg gtctgggttc tacatgtgct    14880
cttccctggg actgggtttt ctaatttata aagcaaagag tttagaggga tgatcttcaa    14940
gcctcttgta gttctagaat tctgtagttc tgggagtttg taaactatta agttttcttt    15000
tagcccagaa cttccatttt cctgctctct cgtgtctgct ctagactcag ctctagctcg    15060
gctaagtgtg gagctctctg ctggggagat ccctagaagc tttgaaggag acattgtgag    15120
gctggagaac tgggttcaaa ttcagtgcta ccattaaatc tctgaataac atcctcagtc    15180
ttccatctat aaaagtcttg gcatctccaa tcacttcttg ttctattatc tcctaagccc    15240
tatacatatt actctgtaat actcctttga tccctatttc tcacagtgct ctatcctcca    15300
aaggttggaa gactcactct atctacagat atctctctgg gcatattta ttactgcgct    15360 gacctcctgg ccctgccttc cccttcaga acctgtgcca aattgtgcag atgtacgagg    15420
gacattccca gcagcctggt ctgcaaccca gattgcagag atggagctct cagactttga    15480
ggactgcctg acattatttg caggagaccc aggacttggg cctgaggaac tgcgggcagc    15540
catgggcaaa gcaaaacagg ttagggatgg agagccaact ggggttggcc atgaggaagc    15600
tatttgggtg tgatgtagga cacaaagaga atggagagtt ggatgagagg tggggaagc    15660 aagagataga agagttagaa gatttgggtc acaagtagga ggtgaaggga gataaatatt    15720
gaggaaagag agctagtata atgaatagag ggacgaaagc agtggttacc aaatttaat    15780 gcatatcacg atcatcaagg gaacagattt ttttcttat ttttttttct ttcttaaaaa    15840
aataatggca tgcttcggct gggtgcagcg gctcacgcct ataatctcag aactttggga    15900
ggccaaggcg gcagatcac gaggtcagga gatcaagacc atcctgtcta acacggcgaa    15960
acacggtctc tactaaaaat acaaaaaagt tagccgggca tggtggtgca cacttgttgt    16020
cccagctact tgggaggctg aggcaggaga atggcgtgaa cctgggaggg ggagcttgca    16080
gtgagccgaa gtcaagccaa tgcactccat cctgggtgac agagcaagac tccatctcaa    16140
aaaaaaaaaa aaaaaaaaa ggcatgcttc atgaatttgc gtgttatcct tgcacaggcg    16200
ccatgcaaat ctctgtatca ttccaatttt ttggggtatg tgctgctgaa ctgagcatgg    16260
gaacagtgcc agtgccagat taccatgctt cactgactta ataaaaacct ttggggaggc    16320
tgggcgcagt gactcatgcc tgtaatcaca gcactttggg aggcggaggc aggtggattg    16380
cttgagccca ggagttagag accagactgg gcaacatggt gaaaccctgt ctctactaaa    16440
aatagaaaaa acattagctg ggtgtggcgg cacatgcctg taatcccagc tactcaggag    16500
gctggggtag gagaatccca tgagtgcagg aggtggaggg tgcaatgtgc caagatcgca    16560
```

```
ccactgccct ccagcctggg tgtcagagca agaccctgtc tcataaatta aaaaataagc    16620
ctctggggga aagagtctag acatctgcat ctccttttt tttttttttt tttttttttg     16680
agacagagtc tcactctgtc acccagcatc caggctggag tgcagtggtg tgatcttggc    16740
tcactgtaac ctctacatcc tgggttcaaa cgatcctcct gcctcagcct ctcaagtagc    16800
tgggactaca ggtgcaccac acctggctaa tttttgtatc tttggtagag atggggtttc    16860
actatgttgc ccaggatggt ctcgaacttc tgggctcaag caatcctccc acctcagcct    16920
cccaaagtgc tgggattaca gctgttagcc actgtgctgg ccctaggca tctgttttaa     16980 taagcgtctc tgtgtctgat gcacataaaa gtgtggaact catggactag agttagtttg    17040
ctcttctttt ccactgattg taatgtcttt caaaacacct tagaggaact gtaaggcaac    17100
ggtctcattt tatagtggag gaaactaaag aaaaggcaaa tgatttacct agagttatac    17160
agctaagggc agaggcaaga cttaaaaccc agcagtatga ctcccaatcc actgcttttc    17220
cactcacatt gttcctgtct ttctcctagt tgtggggtcc cccccgggga tttcgtcctg    17280
agcagatcct gcagcttggt aggctcttaa taggtctagg agatcgggaa ctacaggagc    17340
tgatcctagt ggactgggga gtgctgagca ccctggggca gatagatggc tggagcacca    17400
ctcaggtaac acttttcctc ctccctacgg cttcccaaac acccatccca cagacccagc    17460
cctatagatc atctaaagcc caaggaattt ttttcctgtg accctacctg gtccttcttt    17520
ctatcttttg ttgatacccc atactagtga ccttcaggac tctgatttat tcactctgag    17580
gccctggaca cataatactg tctcctacct cttttcctgg aggcttcctc ttttctttc     17640 cttttctttt ctgagtcctc agccttcccc atgactcctt aggtcttaat agtaacagaa    17700
tataacccag taacacctat cacttccctg tccattaatt ctccataact ttcctccttc    17760
ccctcttctc ccacccccca ccccagctcc gcattgtggt ctccagtttc ctacggcaga    17820
gtggtcggca tgtgagccac ctggacttcg ttcatctgac agcgctgggt tatactctct    17880
gtggactgcg gccagaggag ctccagcaca tcagcagttg ggagttcagg tcatttgtga    17940
aggggctgag ggtggtggtg ctgaggtaaa ggtggactta ctggggaaag aaggatcatg    18000
aaggtctggt cccatggagg aagggaactc atttgaagcc atctcttcct ttgtctcatg    18060
accacagccc ctttcactga agccgaattc ttcttccttc cttcctactg ttctacagcc    18120
aagcagctct cttcctcggc accctgcatc tccagtgctc tgaggaacaa ctggaggttc    18180
tggcccacct acttgtactg cctggtgggt ttggcccaat cagtaactgg gggcctgaga    18240
tcttcactga aattggcacc atagcaggtg gggagctggg ccactgctgg tgcaagttgg    18300
tttggtttct ataccatggg tggactggat ggaagactgc cctgcaattc ttaaggtggg    18360
ggcctgaggt tgtttaaata aggggctaga gacatattgg ggaaggtcta tgatagggca    18420
ctttgggagt agttagagaa ggtctatagg tttgaagaga gggaaggtca gtctaagaca    18480
atgtttggat gccacttgct tcaacagctg ggatcccaga cctggctctt tcagcactgc    18540 tgcgggggaca gatccagggc gttactcctc ttgccatttc tgtcatccct cctcctaaat    18600
ttgctgtaag tattaatgga ctggggtgac cacaggagag ccagggccca atgggtacta    18660
catgcatgca ctgattccta cccctgccct caggtggtgt ttagtcccat ccaactatct    18720
agtctcacca gtgctcaggc tgtggctgtc actcctgagc aaatggcctt tctgagtcct    18780
gagcagcgac gagcagttgc atgggcccaa catgagggaa aggagagccc agaacagcaa    18840
ggtgagttcc cagctgcaca gcttgatcct ccatctcctg acccagaatc aaaccctaa     18900 tttggtgctg tctggctctt agagtgcacc cagggagatc cctggagtga aggagtctac    18960
```

```
aggcagagcg ctaatttcca agtatcaatg ctcctggaga gctgagttgt gatattactc    19020
ccattccctg tctattatag gtcgaagtac agcctggggc ctccaggact ggtcacgacc    19080
ttcctggtcc ctggtattga ctatcagctt ccttggccac ctgctatgag cctgtctcta    19140
cagtagaagg agattgtggg gagagaaatc ttaagtcata atgaataaag tgcaaacaga    19200
agtgcatcct gattattttc agaagctgat gaggaata                            19238
```

<210> SEQ ID NO 5
<211> LENGTH: 18884
<212> TYPE: DNA
<213> ORGANISM: Homo sapiens

<400> SEQUENCE: 5

```
gccctgccct cacctggcta tcccacacag gtgagaataa ccagaactca cctccggtac      60
cagtgttcac ttggaaacat ggctctcagc ctctggcccc tgctgctgct gctgctgctg     120
ctgctgctgc tgtcctttgc aggtaagaag aacagtgagc agaactgggg atgaggagga     180
gggtggctgg aaaaagactt taagaatatg gaggtgaacc tgttagatag aaggacaaag     240
gagagaggca gagacttgtg caaaagggaa aaatgagggt taagaaaagc aggccaagac     300
ttactgtagg ccagtgaaag gggttcagct caccatcccc tcacctcatc tttagatcca     360
ggtagggaac tgtgctcagg ggcagggttg agtttgggct ctgtgttcct ctccttcagt     420
gacctctggt ttctctcctt acagtgactc tggcccctac tgggcctcat tccctggacc     480
ctggtctctc cttcctgaag tcattgctct ccactctgga ccaggctccc cagggctccc     540
tgagccgctc acggttcttt acattcctgg ccaacatttc ttcttccttt gagcctggga     600
gaatggggga aggaccagta ggagagcccc cacctctcca gccgcctgct ctgcggctcc     660
atgattttct agtgacactg agaggtagcc ccgactggga gccaatgcta gggctgctag     720
gggatatgct ggcactgctg ggacaggagc agactcccg agatttcctg gtgcaccagg     780 cagggggtgct gggtggactt gtggaggtgc tgctgggagc cttagttcct gggggccccc     840
ctaccccaac tcagccccca tgcacccgtg atgggccgtc tgactgtgtc ctggctgctg     900
actggttgcc ttctctgctg ctgttgttag agggcacacg ctggcaagct ctggtgcagg     960
tgcagcccag tgtggacccc accaatgcca caggcctcga tgggagggag gcagctcctc    1020 acttttttgca gggtctgttg ggtttgctta ccccaacagg ggagctaggc tccaaggagg    1080
ctctttgggg cggtctgcta cgcacagtgg gggcccccct ctatgctgcc tttcaggagg    1140
ggctgctccg tgtcactcac tccctgcagg atgaggtctt ctccattttg gggcagccag    1200
agcctgatac caatgggcag tgccagggag gtgagtgtgg ccagggctgg gactgggatg    1260
tggcagggca aggaaagtga aattgggta gttttcttcc ttactctttc cctcctaggt    1320
aaccttcaac agctgctctt atggtaagta acaggagacc agttctgagg gattgggcct    1380
ggaaaatctg gaggtgaaga gctgaagacc tcagcctcta gagaggaaaa ctgatgggag    1440
gagtgtagtt tagtggtttt ggggtgtgac tgtctgggtt ggtgtcccag ctccacctct    1500
tcctagccat atgaccttga gcaggttaca tagtctttct atacctcagt ttccccattt    1560
ataaaatgag aatgataata ttagttacca cagagttgtt gcacccggtt aaatgagttg    1620
atactgtgta tgcaaacgac ttaaaaccgt gctggcacat agcgcttaat aatgttagct    1680
agtaaagatg ggatttggaa aataaggaca cagctggatt cctctacccc cttactactt    1740
cagtacaaca atgccagaca gtagttagac atattgagtt gctgagcaga tttcctaaca    1800
```

```
tgaggcccgc tgagggttgt gtttaagcta tctaaaagca tatgaagaaa ggagacagaa    1860
gggggccagg tggacagaaa gaattccaac tggggcttct cctaggtgat tttggacctt    1920
ggcagggcag ctttctcttt tttgccccgt tgcagcattt caaccagtaa cgcctaaact    1980
ctcagggacc tcgcttgtag aaaagcctat gcttgccatg ccccttgagg gctctgagtc    2040
agggtcagaa tcttcagctg gaggaaatgt gaactgacca gatcctgcct gctcctccct    2100
ctgcacccag gggcgtccgg cacaacctttt cctgggatgt ccaggcgctg ggctttctgt    2160
ctggatcacc accccaccc cctgccctcc ttcactgcct gagcacgggc gtgcctctgc    2220
ccagagcttc tcagccgtca gcccacatca gcccacgcca acggcgagcc atcactgtgg    2280
aggccctctg tgagaaccac ttaggcccag caccacccta cagcatttcc aacttctcca    2340
tccacttgct ctgccagcac accaagcctg ccactccaca gccccatccc agcaccactg    2400
ccatctgcca gacagctgtg tggtatgcag tgtcctgggc accaggtgcc caaggctggc    2460
tacaggcctg ccacgaccag tttcctgatg agttttgga tgcgatctgc agtaacctct    2520
ccttttcagc cctgtctggc tccaaccgcc gcctggtgaa gcggctctgt gctggcctgc    2580 tcccacccc taccagctgc cctgaaggcc tgccccctgt tccctcacc ccagacatct    2640 tttgggctg cttcttggag aatgagactc tgtgggctga gcgactgtgt ggggaggcaa    2700
gtctacaggc tgtgcccccc agcaaccagg cttgggtcca gcatgtgtgc cagggcccca    2760
ccccagatgt cactgcctcc ccaccatgcc acattggacc ctgtggggaa cgctgcccgg    2820
atgggggcag cttcctggtg atggtctgtg ccaatgacac catgtatgag gtcctggtgc    2880
ccttctgggc ttggctagca ggccaatgca ggataagtcg tgggggcaat gacacttgct    2940
tcctagaagg gctgctgggc cccttctgc cctctctgcc accactggga ccatccccac    3000
tctgtctgac ccctggcccc ttcctccttg gcatgctatc ccagttgcca cgctgtcagt    3060
cctctgtccc agctcttgct caccccacac gcctacacta tctcctccgc ctgctgacct    3120
tcctcttggg tccaggggct gggggcgctg aggcccaggg gatgctgggt cgggccctac    3180
tgctctccag tctcccagac aactgctcct tctgggatgc cttcgccca gagggccggc    3240 gcagtgtgct acgacgatt ggggaatacc tggaacaaga tgaggagcag ccaaccccat    3300
caggctttga acccactgtc aaccccagct ctggtataag caagatggag ctgctggcct    3360
gctttagtgt gagtgctctg ccagagggaa agctcctaga acagtgagaa ggccctccag    3420
gggaattcct cgaatactca gaggcagtag tgtggggtag tagttgaagc acacagctct    3480
agagtcagac aggcttggat tcatatcttg gttctgtgac cagccttgaa tgagttattt    3540
aacttctctg agcaatattt ttctcgtctc atttataaac tagggatgat aatggtatat    3600
gagataatac atgctgtggg cttagcacag tgcatgatac acaaacatgc aataaatatt    3660
accttgttat tctttgggc tctttgactc tctcactttc tgcaccagaa agaaaaagga    3720
tcaagttaga ggactctaaa ttttccct agagagtgag aattggaggc tggcagaata    3780
caggaagata aggtaggaat gagaaagatt cagggacact accaatcaga agactttggt    3840
tctaggttca actgtgccac aaattagtgt gatcttaggc aagcaatttc atttagtttt    3900
tctgggcttc agtttttagt ctgtagaatg gaggggtgag aatatgttaa acaccataat    3960
taattcactg agtgcctatt atatgcaagg cactttgcta ggttctgtag gatatataaa    4020
gatttcttac tccatgttgg ggccaccttt ttcaaaccct gggcccagta aaatggaatt    4080
agatagtctc atagtatttg gttcaggtct acaagtatta attgagccaa ctatggacct    4140
ggcatgggag agggtacaag agaaattaga gatatgatcc cggacctaaa agagcttaat    4200
```

```
atctgaagaa tcacacttga gatgatggac aagcatccca gcaagtgag  ttggaatgcc    4260
tgggggagct gcaggagaga cagagaagac agctctgttg gcatattgtc tttcttccca    4320
ccagcctgtg ctgtgggatc tgctccagag ggaaaagagt gtttgggccc tgcagattct    4380
agtgcaggta acaggtggag ggcacatggg tgggctgggt gacagccatg gctggaggtc    4440
cctgccccgt gaggtgaggc catacccacc atgacctcct attcgcaggc gtacctgcat    4500
atgccccag  aaaacctcca gcagctggtg ctttcagcag agaggaggc  tgcacagggc    4560
ttcctgacac tcatgctgca ggggaagctg caggggaagc tgcaggtgag cactgagaaa    4620
ggggagcaag gcacctgga  gcctagtgtt cagagggctt gctttagtgg gaggaggaac    4680
tccagagagg aaatggcagg gatactgagc atctccagag gcagaatcca ttcctgtgcc    4740
cctacaggta ccaccatccg aggagcaggc cctgggtcgc ctgacagccc tgctgctcca    4800
gcggtaccca cgcctcacct cccagctctt cattgacctg tcaccactca tccctttctt    4860
ggctgtctct gacctgatgc gcttcccacc atccctgtta gccaacgaca gtgtgtaagg    4920
ttcttgcact actcctcctg ctcctgtcac ggtcaggcca accgcatcca cctggagcag    4980
cccttccgg  agctcctctc tgttttttc  tttcatgcca gataggcaat gtgccaacat    5040
cgtagcaagg tttgagagag gcacatctca cgcctgagtg tgaaaaccca atcattatgc    5100
taatgaacta caaaaggatc agagagctcc tctctattaa aaccaggag  aggatgggcg    5160
tggtggctca tgcctgtaat cccagcacgt gggagcccg  aggcaggtgg atcactaggt    5220
ccgcctagtg agttcgagac cagcctggcc aatatggtga accctgtct  ctattaaact    5280
acaaaaatta gccaggcatg gtggtgggcg cttgtagtcc cagttactct ggaggctgag    5340
gcaggaggat agcttgaacc tgggaggcag aggttgcagt gagccaagat cgtgccactg    5400
cactccagcc tgggtgacag agcgagactc cgtcttaaaa aaacaaaaa  acaaaacaaa    5460
acaaaaaaac agggagagtc tccttcctat ctagacagca gggctacaga gggtcagagg    5520
aaaacagttt ggaggaagac aaagggttaa gacccatgac tcctcgcagc ctggctgcca    5580
tccgggatta cagcccagga atgaggcctg aacagaagga ggctctggca aagcgactgc    5640
tggcccctga actgtttggg gaagtgcctg cctggcccca ggagctgctg tgggcagtgc    5700
tgcccctgct cccccacctc cctctggaga actttttgca gctcagccct caccaggtat    5760
gagaatcatc ttctttactt gactggccca tcttctgcta gtggggacaa agagtcaatg    5820
gcatgtctct cagtggcccc tccctgcaag aaccctatag tgaccccagt gcgagctaac    5880
cttccccatc tcagatccag gccctggagg atagctggcc agcagcaggt ctggggccag    5940
ggcatgcccg ccatgtgctg cgcagcctgg taaaccagag tgtccaggat ggtgaggagc    6000
aggtacgcag gtgagttgtt gtgggatcag taaccaaggc aagagtggaa gaggtagaga    6060
gaggaaggca cagctgtcac gctgggtcgg tgttctagga agaaaggggc aagagagtag    6120
gcagtggcct caggcagcat agagttccag gagagaggtc tatagatggt gccctgtgt    6180
agtggtgtag tgtcagagtg cccagtgtat gtacccatac catctgctgc caggcctgcc    6240
ttagtgctag tcttggggac cacacaaagg tcagcttcat gccctcctca ggcttgggcc    6300
cctcgcctgt ttcctgagcc ctgaggagct gcagagccta gtgcccctga gtgatccaac    6360
ggggccagta gaacgggggc tgctggaatg tgcagccaat gggaccctca gcccagaagg    6420
acgggtgagc ccctcagcac aagcctacaa gactttaggc ttcccctggg tctgtgtgga    6480
tggctttccc attgtgtcaa cttgagcaca gtggtgccag ccccatccc  acttttgcaa    6540
```

```
cctccattcc ttactccatg gccattctta cctgttacca cctcttcctg gcccttctct    6600
atctggtctg tagcacccca aacataccct ttgccatttt gaacctaatc tactccagtc    6660
caatccctag ttccaaaccc tagcccaggc cctgggaaat tcagatgtgg gattagagag    6720
gaagttcaag gttcatctgt cttttctctc cagtcctaaa ccttctttgg ttacaggtgg    6780
catatgaact tctgggtgtg ttgcgctcat ctggaggagc ggtgctgagc ccccgggagc    6840
tgcgggtctg ggcccctctc ttctctcagc tgggcctccg cttccttcag gagctgtcag    6900
agccccagct tagagccatg cttcctgtcc tgcagggaac tagtgttaca cctgctcagg    6960
tttgcctgtc tcactccctg gcatgtaccc tccatcccg cttgagcccc agtcaagaga    7020
atcccattca gggataaaag cagcccctcc tttccctggg tgaacagtag aggtaaactc    7080
tgtctgcagg aggacgcctt cattcccttt cctcagatca agaagggacc tgagtcactg    7140
aggatggtta ctggggatgg ttaagaggca gcgggaagtt ttggagggtt tgccttagga    7200
acccacttag gacctggctg ctgggtcctg agagctgttg ttttcggtcc catcccaaca    7260
caggctgtcc tgctgcttgg acggctcctt cctaggcacg atgtgagtag cagcaacttc    7320
tcagcctccc gccagaggtc tctatcctct tttaacctgg ctcctgcatc tgcccctcct    7380
ctctctccgc tcccctcata cttactgcct tgctgcattg tgattgttgt cttccccaac    7440
acccttccct tcttcttcag gcctcttgtc tctcttgctc tttagctatc cctggaggaa    7500
ctctgctcct tgcaccttct gctaccaggc ctcagccccc agacactcca ggccatccct    7560
aggcgagtcc tggtcgggc ttgttcctgc ctggcccctg aactgtcacg cctctcagcc    7620
tgccagaccg cagcactgct gcagaccttt cgggtatgag agtggcaagg aggatgagat    7680
aatcagggat accggctctt tctggttggg aggaaggcat cttccctgag gccagggaag    7740
gcctttcata cctcccact tacacacaca cacacacaca cacacacaca accaattctc    7800
atgcaggtta aagatggtgt taaaaatatg ggtacaacag gtgctggtcc agctgtgtgc    7860
atccctggtc aggtaagtgt gagatctccc aactgagctc ctctccccat tctggggcag    7920
tttcatatgg ctggtgctac ctcccacact accctgcagt ggccctgaga gttctggtta    7980
gctctgtgcc cattagcagc cctccccagt gccagatgca ggacagcatg atccactcac    8040
attgtcctag actaatgtca aagctggaag ggcctgagaa atcttccagg ccacccaccc    8100
tgctttcaga tgaaaagacc aaggctggga gaagctaagg gactttgttt gcctggtgcc    8160
taactagcag caacacttga ccacagcagc ctgcagtgtg aggctcttag gcgtttattg    8220
ctacagtggc aaatgccatt ccacttctgt cctagctttg gtccctttcc accccatgg    8280
ttccttttct ctgagtgcta agtacagact ctctcaccta tcactacact gctatacca    8340
tcaccgccag cagcctattc ccaccacctg gccagactgc ctgcttcccc tgctcccatt    8400
aaagctgcta caactggatt ccttggctct tctggcaaat cgaagacgct actgggagct    8460
gccctggtct gagcagcagg taattctccc cacttaattt cagaacttcc tccctcaatg    8520
tagtctacct tctttaccta tcccttagcc ctatttggcc agcttatccc tactatcctt    8580
tatttgattg tttgagatac agtctcactc tgttgcccag gctgcagtgc agtggcatga    8640
tcagagttcg ctgtaacctc aaactcatga gctcaggcaa tctttctgcc tcagcctcct    8700
gaatagctag gatgacaggt ggttaccacc atgcctggct aatttttaaa ttttttttt    8760
gtttttgag atgaagtctt gctctgtcac ccaggcttga gtacagtggc acaagcttgg    8820
ctcactgcaa cctctgtctc ccgggttcaa gcgattctcc tgcctcagcc tcccgagtag    8880
ctgggactac aggcactccc cacaatgccc ggctaatttt tttttgttt tagtagagac    8940
```

-continued

```
agggtttcac catattggcc aggctggtct cgaactgctg accttgtgat ctgcctgcct    9000
ctgcctctca aagtgctggg attacaggtg tgagccacca tgcccggcca attttaaat    9060
ttttgtaga dacagacaat acaaaaatgt ggacactatg tggagacact atgttgaggt    9120
actatgctgt ccagattggt cttgaactcc tggcctcaag caatcctcct gccttggcct    9180
cccaaagtgc tgggattaca gacctgagcc actgcaccca gcccctagt atcccttata    9240
atgtgacttg ctttctttt tctttctcct tcccttttct ttcatttctt tctcactctc    9300
gagagaagag tgggcatctg ggagagtggg aggctggtgg gtcccacaga gtgaggaggc    9360
aggactgggt ccaaggcagt cctgcctctc cactctaggg ggtatccttg gacagtgtct    9420
cttctgggaa ggggctcgtc tttctttctc ttgtaggcac agtttctctg gaagaagatg    9480
caagtaccca ccaacctgac cctcaggaat ctacagtgag taacttgtgt tgagcagtgc    9540
gctgaattcg accaacattt ttttgagtgc ttactatgtg ccaggcacca tatgatatgg    9600
aatgggggat atagggatga atgatgcata gtccctgcct cgtggacgtt ctcctagcac    9660
ctcccttgc cctcctttcc ttccacagtg ccatgcctat cctgactaga gccaaaggac    9720
tcagaaaacc tggattcagg ttccagtcct gtcacctact tgtcctcttg ggcaagtcat    9780
ttaacgtccc tgtgtcagtt ttcccttctt taaatgagaa ttacaatggc accagcctca    9840
taggtagtta ctgtgaagat taaatgaggt aggtcatgta agatatttaa cacagtgttt    9900
ggtccattgt aaagttccag tagtcatttg ctactgttag tttacttcag gatgacttca    9960
gaggcactgg ccaagcaaga ataaatagga ataagaaggt atcactttac ttatacccac   10020
attagaagaa caatgggctt cagaatcttt ttttttttt ttttcgagac agtccttgctc   10080
tgttgcccag gctggagtgc agtggcgcga tttcggctca ctgcaacctc tgcctcccag   10140
gttcaagcga ttctcctgtc tcagcctctg gagtagctgg gattacagga atgtgccacc   10200
atacccagct aattttgta ttttagtag agatgggggtt tcaccatttt ggccaggctg   10260
gtctcaaact cctgacctca ggtgatccac ccgcctcagc ctcccaaggg cttcagaatc   10320
taagacatgt ctctagtttc agtttaccac atttctagca gaatgatgtt gggaatgtca   10380
cctgacttcc ataaatcctt attttctcct ctgataaaca gcagtgatgt tatggggagc   10440
tgatgagata tctatgtaaa aacatttctc aaaccataaa ttacggtgga tgaacatctg   10500
tacttgtgtt gagagtactg atatcaagga gcaaacaggc tgttgtatgt gttgaatgag   10560
cctctcccca ctcacacacc cacagggctc tgggcaccct ggcaggaggc atgtcctgtg   10620
agtttctgca gcagatcaac tccatggtag acttccttga agtggtgcac atgatctatc   10680
agctgcccac tagagttcga gggagcctgg tgagagggga tgcctggact ttagtgggag   10740
cagggaggct gggaccctag gtatagaacc cagctcctat gttctgctct ggcctcactc   10800
tgcttcccta cagagggcct gtatctgggc agagctacag cggaggatgg caatgccaga   10860
accagaatgg acaactgtag ggccagaact gaacgggctg gatagcaagc tactcctgga   10920
cttaccgtaa gtactgcagc tagagatatt ggcccctcag aaagctcaat ctggggtgaa   10980
gatctgccct tagggaatgc cctggaggag gtagtttttc tgtctggtag ttccctgaca   11040
taatttatag cccaaagcag aggatttat tcaaagttgc tctatgtatt gactggttcc   11100
cagaatatgc tccagcacag ggcagctgag ggtggcaaca ctgtattgaa gcctgccaag   11160
taatcttaca ataacctagt ccacattaat tgagattgag acagagcatc tgaagtgagg   11220
gaggcaatgc tccaaatctg ccccagagga ttgtagtttg ctcagggcac tgtgttctta   11280
```

```
gtgcattcag aggagtggat cgagagaaaa atatatgaaa aatgtgataa ataccttcaa    11340
atacctgagg ggctatcaag tagaaattag attgtcatat ttatgagtgg ccccattggg    11400
caagactaag agtagttaac ggagatcaga tttttacata gtataagaaa aactaaggta    11460
gtgagttcct ggtccttgga gctgttcgag cctaagccag atggccccat ggcaggaatg    11520
ttgtagagca cgttcatata caggttgtgg gaagaaaagg ctataggaac ccaaggctcc    11580
tccctaccca tggagaaatt tattagtatg ttactcatat gctgcttttc tcattttacc    11640
cctaccacca ccccgttgcc atccgcactg taagtcagga taggaaaatg ctggtgttac    11700
agtcttcctg gggaatatgg agctgaagtg gagtaaaagc agttgacttc attcttactt    11760 ttttctttt ctttttttt ttttttttga gacagagttt tgctgtgtca ccaaggctgg    11820
agtgcagtga cgtgatctcg gctcactgca acctccatct tccaggttca agcaattctc    11880
ctgcctcagt ctcccgagta gctgggactg taggtgtgca ccaccatgcc aggctaattt    11940
ttgtatttgt tgtagggacg agctttcacc atgttggcca ggctggtctt gaactcctgg    12000
cttcaagtga tctgcccacc tcggcttccc aacattctta tatttttata ggcctttcca    12060
cagatttcag ctcttgtatg acttagccca gttccagaac tggtaatcct aggtagggta    12120
caggttatca cctctgattt cgggtaaaag ggatttattt atttatttgt ttatttattt    12180
atatttttga gacagagtct cgctctgtca cccaggctgg agtgcaatgg tgccatctcg    12240
gctcactgca acctctccct ctggggttca agcacttctg cctcagcctc ctgagtagct    12300
gggattacag gcgcgtgcca ccacacccgg ctaattttg cattttagt agagacgggg    12360 tttcaccatg ttgctcaggg tggtctcgaa tttctgaccc tgtgatctgc ctgcctcggc    12420
ctcccaaagt gctgggatta caggcatgag ccactgcgtc cggcctgttt ttactttttt    12480
ttaatgccat tcagatctgt ttaaatatgt gggttctgtg agataattta gaatcccaag    12540
gttacagatg aggtgaaaga tcctagacca tgcatcaaaa aacttgagtt tctcatttgt    12600
gaaagaagga taagagaaac acctattttg tctgggtgca gtggctcatg cctataatcc    12660
cagcatttgg ggaggccaag gtgggtggat cacggaggtc aggtgttcaa gaccagactg    12720
gccaacatgc aaaacacca tctctactaa aaatacaaaa gttagctggg cgtggtggca    12780
cgtgcgtgta attccagcta ttcgggaggc tgaggcacga gaattgcttg aacctgggag    12840
gtgcgggttg cagtgaactg agatcgcagc accactgtgc tccagcctga gtgatggagt    12900
gaggccaggt cttgttgtag gatcaaatga gataacacct gaaagaactt tgtaaattgt    12960
atagcacgta caaacaagaa gggacctctt cacaagcaga ggaagggtgg tcctgtggaa    13020
aaaaacggga attgggagtg agagacctca acatttgatc tctgtgaacc tcagtttttt    13080
aatctataaa atgggaaat gttaatggta cttaatattt ggagcttttg agtccattag    13140
atcaggtagg attgttcgtt attttttttt tttaggaaga ctagaaatat gttgctccct    13200
ttttctcccc cactcaagct tgatggtggg aattggccct ggagctgttt actgtcagtt    13260
cctgtccagc ttcactaaat ttggtctggg gtcacatctt agctgggac tgtggggttc    13320 tgtggtccct tctcgacttg gcccagctcc acttgaatga tattgttgtc aaattgctat    13380
aatagaatcc agttgatgga cagactatcc aatgaatcca ttatgttggt ggtggagctg    13440
gtgcaaagag ctccagagca gctgctggca ctgacccccc tccaccaggc agccctggca    13500
gagagggcac tacaaaacct ggtaagagtc caccctacca gactcagatt tgctgccctg    13560
ggcaattctt gctcctcaga caatgctctc tgactgtcct ccaaccctct acttcttgct    13620
ttcttgctgc caaacaggtt cctgtctaca aggcctggcc cgttttgcct ctgggttctg    13680
```

```
ttccttgata atatgcttca cgttacttgt ccatacctct tggagtccga gaaatctctt   13740
ggagtccacc tctcagtctt tctgcctgct cctatctggt ctcattgctt aagaaagtga   13800
acaaaggtag tgagcatcat agggtgctga gttgggagca ggagggaggg aaggtcaggg   13860
ggcttggtgt cttgatcaag gtgtctggta ttctgagtca gaagtgcatt gtccaagttc   13920
tgatgctctt ctccaggctc caaaggagac tccagtctca ggggaagtgc tggagacctt   13980 aggcccttg gttggattcc tggggacaga gagcacacga cagatccccc tacagatcct   14040
gctgtcccat ctcagtcagc tgtaaggctt ctgcctagga gagacatttg ccacagagct   14100
gggatggctg ctattgcagg agtctgttct tgggtatgga tcttcgagaa cttcagattc   14160
taactcattc tatacccagt ccctcagcca ccatcatcag tggcagcctg ttccatattc   14220
ctaagggccc ttggagccct gtgtccgaaa tcctagcatg tcctcttttc cccttccttt   14280
tcctcacagt tccctcagct ccccagcccc cgattttctt cctgtcccca ggaaaccaga   14340
gttgtggagc caggatgaag tagagcaagc tggacgccta gtattcactc tgtctactga   14400
ggcaatttcc ttgatcccca gggtgagatg aaggaagaag ggaagggagt aaatgcatag   14460
aggggactgg tgagctggtt atggggaccc gtggccaacg agggcaaagg atatgaagcc   14520
tagatctggg gggatactgc gaaacagaga caggactttg gacttatagc tatagcagca   14580
ggtcctgatc tgtccagatc tccccactct ccttctacct tctcatgcag gaggccttgg   14640
gtccagagac cctggagcgg cttctagaaa agcagcagag ctgggagcag agcagagttg   14700
gacagctgtg taggggggcca cagcttgctg ccaagaaagc agccctggta gcaggggtgg   14760
tgcgaccagc tgctgaggat cttccaggtg aaactaccca aatacttata tgtccagcag   14820
gatgtacagg gagtatcaaa cggtctgggt tctacatgtg cttttctctg ggactgggtt   14880 ttctaatta taaagcaaag agtttagagg gatgatcttc aagtctcgtc tagttctaaa   14940
attctatagc tctgggagtg tgtaaactat taagttttcc tttagcccag aacttccatt   15000
ttcctgctgt cttgtctctt taaacagctg actcagctct agctcggcta agtgtggagc   15060
tctctgctgg ggagatccct cgaaggagac attgtgaggc tagagaactg gtttcaaatt   15120
cagctctgcc atgaaatccc tgaccaacat cctcagtctt ccatctataa aatgagggac   15180
ttggcatctc caatcacttc ttgttcaatt cacttctaag ccctatacat cttaacctgt   15240
aatactccct cgatccctac ttcccacagt gctccatcct ccaaaggttg gaagagtcat   15300
tccatctaca gatacctcct ggccctgcct tccccttca gaacctgtgc caaattgtgc   15360
agatgtacga gggacattcc cagcagcctg ctctgcaacc cagattgctg agatggagct   15420
ctcagacttt aaggactgcc tgacactatt tgcaggagac ccaggacttg gcctgagga   15480 accacgggca gccatgggca aagcaaaatg ggtcagggac ggagagccaa ctgaggttgg   15540
ccatgaggaa gctgtgtggg tgtgatgtag dacacgaaga gaatagagag ttggatgaga   15600
ggtgggggaa gcagaagata aaagagttag aagatttggg tcacaagtag aaggtgagga   15660
gagataaata ttgaggaaag agagctacta taatgaatag agggactaaa gcagtgatta   15720
ccaaatttta atgcatatca caatcatcaa gggaacagat tttttcttt tttctttttt   15780 tttctttctt aaaaaataat ggcatacttc atgaatttgt gtgttatcct tgcgcaggcg   15840
ccatgctaat ctctgtatca ttccaatttt tttttgtata tgtgctgctg aaccgagcac   15900
gggaacagtg ccaatgctgg attaccatgc tagactgact taataaaaac ctttgcggag   15960
gctggacgga gtggctcgtg cctgtaatca cagcactttg ggaggctgag gcaggtggat   16020
```

```
tgcttgagcc caggagtttg agaccagact gggcaacatg gtgaagccct gtctctacta    16080
aaaatagaaa aaaattagc tgggtgtggc ggcacatgcc tgtaatccca gctactcagg     16140
aggctggggt aggagaatcc cctgagcgca ggaggtggag ggtgcaatga gccaagatca    16200
caccactgca ctccagcctg ggtgtcagag caagaccctg tctcataaat taaaaaataa    16260
gcctctggga gaaagtctag acatctgcat ctgctttttt tttttttttt tttttgaga    16320
cacagtctca ctctgtcacc cagcatccag gctggagtgc ggtggtgtga tcttggctca    16380
ctgtaacctc tacatcctgg gctcaaacga tcctcctgcc tcagcctctc gagaagctgg    16440
gactacaggt gcacaccact acacctggct aattttgta tttttggtag agatgaggtt     16500
tcgctgtgtt gcccaggatg gtcttgaact cctgggctca agcattcctc ccacctcagc    16560
ctcccaaagt gctgggatta cagctgtgag ccactgtgct gggccccagg catctgcatt    16620
ttaataagcg tctctgtgtc tgatgcacat aaaagtgtgg aactcatgga ctagagttag    16680
tttgctcttc ttttccactg attgtaatgt ctttcaaaac accttagagg aactgtaagg    16740
caacggtctc attttatagt ggaggaaacc aaagaaaagg caagtgactt gcctagagtt    16800
atacagctaa ggtcagaggc aagacttaaa acccagcatt ctgactccca atctactggt    16860
tttccactca cattgttcct ctcttttctcc tagttgtggg gtccccccg gggatttggt    16920
cctgagcaga tcctgcagct cggtagactc ttaataggtc tgggagatca ggaactacag    16980
gagctgatcc tagtggactg gggagtgctg agcaccctgg ggcagataga tggctggagc    17040
tccactcagg taacactttt actcctccct accgcttccc aaacacccat cccacagacc    17100
cagccctata gatcatctaa agcccaagga attttttcct gtgaccctac ctggtcattc    17160
tttctgtctt ttgttaatat cccatactag tgaccttcag gactcttgat ttattcactc    17220
tgaggccctg gacacataat actgtctcct acctcttttc ctggaggctt cctcttttc     17280
tttccttttc ttttctgagt cctcagcctt ccccatgact ccttaggtct taatagtaac    17340
agaatataac ccagtaacac ctatcacttc cctgtccatt aattctccat aactttcctc    17400
cttcccctct tctcccaccc cccaccccag ctccgcattg tggtctccag tttcctacgg    17460
cagagtggtc ggcatgtgag ccacctggac ttcgttcatc tgacagcgct gggttatact    17520
ctctgtggac tgcggccaga ggagctccag cacatcagca gttgggagtt taggtcattt    17580
gtgaagggc tgagggtggt cgtgttcagg taaaggtgga cttgctgggg aaaggaggat    17640
catgaagtta tagtcccatg gaggaaggga actcatttga agccatctct tcctttgtct    17700
catgaccaca gtcccttca ctgaagccga attcttcttc cttccttccc actgttctac     17760
agccaagcag ctctcttcct gggcaccctg catctgcagt gctctgagga acaactggag    17820
tttctggccc acctctttgt actgcctggt gggtttggcc caatcagtaa ctgggggcct    17880
gagatcttca ctgaaattgg caccatagca ggtggggagc tgggccactg ctggtgcaag    17940
ttggtttggt ttctataccca tgggtggact ggatggaaga ctgccctgca attcttcagg   18000
tgtgggcctg agagggtgtt taaataaggg gctagagaca tattgtggaa ggtctatgat    18060
agggcacttt gggagtagtt agagaaggtc tataggtttg aagagaggga aggtcagtct    18120
aagacaatgt ttggatgcca cttgcttcaa cagctgggat cccagacctg gctcttcag    18180
cactgctgcg gggacagatc cagggcgtta ctcctcttgc catttctgtc atccctcctc    18240
ctaaatttgc tgtaagtatt aatggactgg ggtgaccaca ggagagccag ggcccaatgg    18300
ggactacatg catgcactga ttcctacccc tgccctcagg tggtgtttag tcccatccaa    18360
ctatctagtc tcgccagtgc tcaggctgtg gctgtcactc ctgagcaaat ggccttctg    18420
```
agtcctgagc agcgacgagc agttgcatgg gcccaacatg agggaaagga gagcccagaa 18480
cagcaaggtg agttcccagc tgcacagctt gatcctccat ctcctgaccc agaatcaaac 18540
ccctaatttg gtgctgtctg gctcttagag tgcacccagg gagatccctg gagtgaagga 18600
gtctacaggc agagcgctaa tttccaagta tcaatgctcc tggagagctg agttgtgata 18660
ttactcccat tccctgtcta ttataggtcg aagtacagcc tggggcctcc aggactggtc 18720
acgaccttcc tggtccctgg tattgactat cagcttcctt ggccacctgc tatgagcctg 18780
tctctacagt agaaggagat tgtggggaga gaaatcttaa gtcataatga ataaagtgca 18840
aacagaagtg catcctgatt attttcagaa gctgatgagg aata 18884

<210> SEQ ID NO 6
<211> LENGTH: 82
<212> TYPE: DNA
<213> ORGANISM: Artificial Sequence
<220> FEATURE:
<223> OTHER INFORMATION: Splicing donor signal

<400> SEQUENCE: 6
gtaagtatca aggttacaag acaggtttaa ggagaccaat agaaactggg cttgtcgaga 60
cagagaagac tcttgcgttt ct 82

<210> SEQ ID NO 7
<211> LENGTH: 51
<212> TYPE: DNA
<213> ORGANISM: Artificial Sequence
<220> FEATURE:
<223> OTHER INFORMATION: Splicing accepting signal

<400> SEQUENCE: 7
gataggcacc tattggtctt actgacatcc actttgcctt tctctccaca g 51

<210> SEQ ID NO 8
<211> LENGTH: 1809
<212> TYPE: PRT
<213> ORGANISM: Mus musculus

<400> SEQUENCE: 8

Met Ala Leu Ser Leu Gln Pro Gln Leu Leu Leu Leu Ser Leu Leu
1               5                   10                  15

Pro Gln Glu Val Thr Ser Ala Pro Thr Gly Pro Gln Ser Leu Asp Ala
            20                  25                  30

Gly Leu Ser Leu Leu Lys Ser Phe Val Ala Thr Leu Asp Gln Ala Pro
        35                  40                  45

Gln Arg Ser Leu Ser Gln Ser Arg Phe Ser Ala Phe Leu Ala Asn Ile
    50                  55                  60

Ser Ser Ser Phe Gln Leu Gly Arg Met Gly Glu Gly Pro Val Gly Glu
65                  70                  75                  80

Pro Pro Pro Leu Gln Pro Pro Ala Leu Arg Leu His Asp Phe Leu Val
                85                  90                  95

Thr Leu Arg Gly Ser Pro Asp Trp Glu Pro Met Leu Gly Leu Leu Gly
            100                 105                 110

Asp Val Leu Ala Leu Leu Gly Gln Glu Gln Thr Pro Arg Asp Phe Leu
        115                 120                 125

Val His Gln Ala Gly Val Leu Gly Gly Leu Val Glu Ala Leu Leu Gly
    130                 135                 140

Ala Leu Val Pro Gly Gly Pro Pro Ala Pro Thr Arg Pro Pro Cys Thr

-continued

```
                145                 150                 155                 160
            Arg Asp Gly Pro Ser Asp Cys Val Leu Ala Ala Asp Trp Leu Pro Ser
                            165                 170                 175
            Leu Met Leu Leu Leu Glu Gly Thr Arg Trp Gln Ala Leu Val Gln Leu
                        180                 185                 190
            Gln Pro Ser Val Asp Pro Thr Asn Ala Thr Gly Leu Asp Gly Arg Glu
                        195                 200                 205
            Pro Ala Pro His Phe Leu Gln Gly Leu Gly Leu Leu Thr Pro Ala
                    210                 215                 220
            Gly Glu Leu Gly Ser Glu Glu Ala Leu Trp Gly Gly Leu Leu Arg Thr
            225                 230                 235                 240
            Val Gly Ala Pro Leu Tyr Ala Ala Phe Gln Glu Gly Leu Leu Arg Val
                            245                 250                 255
            Thr His Ser Leu Gln Asp Glu Val Phe Ser Ile Met Gly Gln Pro Glu
                        260                 265                 270
            Pro Asp Ala Ser Gly Gln Cys Gln Gly Gly Asn Leu Gln Gln Leu Leu
                        275                 280                 285
            Leu Trp Gly Met Arg Asn Asn Leu Ser Trp Asp Ala Arg Ala Leu Gly
                    290                 295                 300
            Phe Leu Ser Gly Ser Pro Pro Pro Ala Leu Leu His Cys Leu
            305                 310                 315                 320
            Ser Arg Gly Val Pro Leu Pro Arg Ala Ser Gln Pro Ala His Ile
                            325                 330                 335
            Ser Pro Arg Gln Arg Arg Ala Ile Ser Val Glu Ala Leu Cys Glu Asn
                        340                 345                 350
            His Ser Gly Pro Glu Pro Pro Tyr Ser Ile Ser Asn Phe Ser Ile Tyr
                    355                 360                 365
            Leu Leu Cys Gln His Ile Lys Pro Ala Thr Pro Arg Pro Pro Thr
                    370                 375                 380
            Thr Pro Arg Pro Pro Thr Thr Pro Gln Pro Pro Thr Thr Thr
            385                 390                 395                 400
            Gln Pro Ile Pro Asp Thr Thr Gln Pro Pro Val Thr Pro Arg Pro
                            405                 410                 415
            Pro Pro Thr Thr Pro Gln Pro Pro Ser Thr Ala Val Ile Cys Gln
                        420                 425                 430
            Thr Ala Val Trp Tyr Ala Val Ser Trp Ala Pro Gly Ala Arg Gly Trp
                        435                 440                 445
            Leu Gln Ala Cys His Asp Gln Phe Pro Asp Gln Phe Leu Asp Met Ile
                    450                 455                 460
            Cys Gly Asn Leu Ser Phe Ser Ala Leu Ser Gly Pro Asn Arg Arg Leu
            465                 470                 475                 480
            Val Lys Gln Leu Cys Ala Gly Leu Leu Pro Pro Thr Ser Cys Pro
                            485                 490                 495
            Pro Gly Leu Ile Pro Val Pro Leu Thr Pro Glu Ile Phe Trp Gly Cys
                        500                 505                 510
            Phe Leu Glu Asn Glu Thr Leu Trp Ala Glu Arg Leu Cys Val Glu Asp
                        515                 520                 525
            Ser Leu Gln Ala Val Pro Pro Arg Asn Gln Ala Trp Val Gln His Val
                    530                 535                 540
            Cys Arg Gly Pro Thr Leu Asp Ala Thr Asp Phe Pro Cys Arg Val
            545                 550                 555                 560
            Gly Pro Cys Gly Glu Arg Cys Pro Asp Gly Gly Ser Phe Leu Leu Met
                            565                 570                 575
```

```
Val Cys Ala Asn Asp Thr Leu Tyr Glu Ala Leu Val Pro Phe Trp Ala
            580                 585                 590

Trp Leu Ala Gly Gln Cys Arg Ile Ser Arg Gly Asn Asp Thr Cys
        595                 600                 605

Phe Leu Glu Gly Met Leu Gly Pro Leu Pro Ser Leu Leu Pro Leu
    610                 615                 620

Gly Pro Ser Pro Leu Cys Leu Ala Pro Gly Pro Phe Leu Leu Gly Met
625                 630                 635                 640

Leu Ser Gln Leu Pro Arg Cys Gln Ser Ser Val Pro Ala Leu Ala His
                645                 650                 655

Pro Thr Arg Leu His Tyr Leu Leu Arg Leu Leu Thr Phe Leu Leu Gly
            660                 665                 670

Pro Gly Thr Gly Gly Ala Glu Thr Gln Gly Met Leu Gly Gln Ala Leu
            675                 680                 685

Leu Leu Ser Ser Leu Pro Asp Asn Cys Ser Phe Trp Asp Ala Phe Arg
        690                 695                 700

Pro Glu Gly Arg Arg Ser Val Leu Arg Thr Val Gly Glu Tyr Leu Gln
705                 710                 715                 720

Arg Glu Glu Pro Thr Pro Pro Gly Leu Asp Ser Ser Leu Ser Leu Gly
                725                 730                 735

Ser Gly Met Ser Lys Met Glu Leu Leu Ser Cys Phe Ser Pro Val Leu
            740                 745                 750

Trp Asp Leu Leu Gln Arg Glu Lys Ser Val Trp Ala Leu Arg Thr Leu
        755                 760                 765

Val Lys Ala Tyr Leu Arg Met Pro Pro Glu Asp Leu Gln Gln Leu Val
    770                 775                 780

Leu Ser Ala Glu Met Glu Ala Ala Gln Gly Phe Leu Thr Leu Met Leu
785                 790                 795                 800

Arg Ser Trp Ala Lys Leu Lys Val Gln Pro Ser Glu Glu Gln Ala Met
                805                 810                 815

Gly Arg Leu Thr Ala Leu Leu Leu Gln Arg Tyr Pro Arg Leu Thr Ser
            820                 825                 830

Gln Leu Phe Ile Asp Met Ser Pro Leu Ile Pro Phe Leu Ala Val Pro
        835                 840                 845

Asp Leu Met Arg Phe Pro Pro Ser Leu Leu Ala Asn Asp Ser Val Leu
    850                 855                 860

Ala Ala Ile Arg Asp His Ser Ser Gly Met Lys Pro Glu Gln Lys Glu
865                 870                 875                 880

Ala Leu Ala Lys Arg Leu Leu Ala Pro Glu Leu Phe Gly Glu Val Pro
                885                 890                 895

Asp Trp Pro Gln Glu Leu Leu Trp Ala Ala Leu Pro Leu Leu Pro His
            900                 905                 910

Leu Pro Leu Glu Ser Phe Leu Gln Leu Ser Pro His Gln Ile Gln Ala
        915                 920                 925

Leu Glu Asp Ser Trp Pro Val Ala Gly Leu Gly Pro Gly His Ala Arg
    930                 935                 940

His Val Leu Arg Ser Leu Val Asn Gln Ser Met Glu Asp Gly Glu Glu
945                 950                 955                 960

Gln Val Leu Arg Leu Gly Ser Leu Ala Cys Phe Leu Ser Pro Glu Glu
                965                 970                 975

Leu Gln Ser Leu Val Pro Leu Ser Asp Pro Met Gly Pro Val Glu Gln
            980                 985                 990
```

```
Gly Leu Leu Glu Cys Ala Ala Asn  Gly Thr Leu Ser Pro  Glu Gly Arg
        995                 1000                 1005

Val Ala Tyr Glu Leu Leu Gly Val  Leu Arg Ser Ser  Gly Gly Thr
1010                1015                 1020

Val Leu Ser Pro Arg Glu Leu Arg  Val Trp Ala Pro  Leu Phe Pro
1025                1030                 1035

Gln Leu Gly Leu Arg Phe Leu Gln  Glu Leu Ser Glu  Thr Gln Leu
1040                1045                 1050

Arg Ala Met Leu Pro Ala Leu Gln  Gly Ala Ser Val  Thr Pro Ala
1055                1060                 1065

Gln Ala Val Leu Leu Phe Gly Arg  Leu Leu Pro Lys  His Asp Leu
1070                1075                 1080

Ser Leu Glu Glu Leu Cys Ser Leu  His Pro Leu  Pro Gly Leu
1085                1090                 1095

Ser Pro Gln Thr Leu Gln Ala Ile  Pro Lys Arg Val  Leu Val Gly
1100                1105                 1110

Ala Cys Ser Cys Leu Gly Pro Glu  Leu Ser Arg Leu  Ser Ala Cys
1115                1120                 1125

Gln Ile Ala Ala Leu Leu Gln Thr  Phe Arg Val Lys  Asp Gly Val
1130                1135                 1140

Lys Asn Met Gly Ala Ala Gly Ala  Gly Ser Ala Val  Cys Ile Pro
1145                1150                 1155

Gly Gln Pro Thr Thr Trp Pro Asp  Cys Leu Leu Pro  Leu Leu Pro
1160                1165                 1170

Leu Lys Leu Leu Gln Leu Asp Ala  Ala Ala Leu Leu  Ala Asn Arg
1175                1180                 1185

Arg Leu Tyr Arg Gln Leu Pro Trp  Ser Glu Gln Ala  Gln Phe
1190                1195                 1200

Leu Trp Lys Lys Met Gln Val Pro  Thr Asn Leu Ser  Leu Arg Asn
1205                1210                 1215

Leu Gln Ala Leu Gly Asn Leu Ala  Gly Gly Met Thr  Cys Glu Phe
1220                1225                 1230

Leu Gln Gln Ile Ser Ser Met Val  Asp Phe Leu Asp  Val Val His
1235                1240                 1245

Met Leu Tyr Gln Leu Pro Thr Gly  Val Arg Glu Ser  Leu Arg Ala
1250                1255                 1260

Cys Ile Trp Thr Glu Leu Gln Arg  Arg Met Thr Met  Pro Glu Pro
1265                1270                 1275

Glu Leu Thr Thr Leu Gly Pro Glu  Leu Ser Glu Leu  Asp Thr Lys
1280                1285                 1290

Leu Leu Leu Asp Leu Pro Ile Gln  Leu Met Asp Arg  Leu Ser Asn
1295                1300                 1305

Asp Ser Ile Met Leu Val Val Glu  Met Val Gln Gly  Ala Pro Glu
1310                1315                 1320

Gln Leu Leu Ala Leu Thr Pro Leu  His Gln Thr Ala  Leu Ala Glu
1325                1330                 1335

Arg Ala Leu Lys Asn Leu Ala Pro  Lys Glu Thr Pro  Ile Ser Lys
1340                1345                 1350

Glu Val Leu Glu Thr Leu Gly Pro  Leu Val Gly Phe  Leu Gly Ile
1355                1360                 1365

Glu Ser Thr Arg Arg Ile Pro Leu  Pro Ile Leu Leu  Ser His Leu
1370                1375                 1380

Ser Gln Leu Gln Gly Phe Cys Leu  Gly Glu Thr Phe  Ala Thr Glu
```

-continued

```
                1385                1390                1395
Leu Gly Trp Leu Leu Leu Gln Glu Pro Val Leu Gly Lys Pro Glu
    1400                1405                1410
Leu Trp Ser Gln Asp Glu Ile Glu Gln Ala Gly Arg Leu Val Phe
    1415                1420                1425
Thr Leu Ser Ala Glu Ala Ile Ser Ser Ile Pro Arg Glu Ala Leu
    1430                1435                1440
Gly Pro Glu Thr Leu Glu Arg Leu Leu Gly Lys His Gln Ser Trp
    1445                1450                1455
Glu Gln Ser Arg Val Gly His Leu Cys Gly Ser Gln Leu Ala
    1460                1465                1470
His Lys Lys Ala Ala Leu Val Ala Gly Ile Val His Pro Ala Ala
    1475                1480                1485
Glu Gly Leu Gln Glu Pro Val Pro Asn Cys Ala Asp Ile Arg Gly
    1490                1495                1500
Thr Phe Pro Ala Ala Trp Ser Ala Thr Gln Ile Ser Glu Met Glu
    1505                1510                1515
Leu Ser Asp Phe Glu Asp Cys Leu Ser Leu Phe Ala Gly Asp Pro
    1520                1525                1530
Gly Leu Gly Pro Glu Glu Leu Arg Ala Ala Met Gly Lys Ala Lys
    1535                1540                1545
Gln Leu Trp Gly Pro Pro Arg Gly Phe Arg Pro Glu Gln Ile Leu
    1550                1555                1560
Gln Leu Gly Arg Leu Leu Ile Gly Leu Gly Glu Arg Glu Leu Gln
    1565                1570                1575
Glu Leu Thr Leu Val Asp Trp Gly Val Leu Ser Ser Leu Gly Gln
    1580                1585                1590
Ile Asp Gly Trp Ser Ser Met Gln Leu Arg Ala Val Val Ser Ser
    1595                1600                1605
Phe Leu Arg Gln Ser Gly Arg His Val Ser His Leu Asp Phe Ile
    1610                1615                1620
Tyr Leu Thr Ala Leu Gly Tyr Thr Leu Cys Gly Leu Arg Pro Glu
    1625                1630                1635
Glu Leu Gln His Ile Ser Ser Trp Glu Phe Ser Gln Ala Ala Leu
    1640                1645                1650
Phe Leu Gly Ser Leu His Leu Pro Cys Ser Glu Glu Gln Leu Glu
    1655                1660                1665
Val Leu Ala Tyr Leu Leu Val Leu Pro Gly Gly Phe Gly Pro Val
    1670                1675                1680
Ser Asn Trp Gly Pro Glu Ile Phe Thr Glu Ile Gly Thr Ile Ala
    1685                1690                1695
Ala Gly Ile Pro Asp Leu Ala Leu Ser Ala Leu Leu Arg Gly Gln
    1700                1705                1710
Ile Gln Gly Leu Thr Pro Leu Ala Ile Ser Val Ile Pro Ala Pro
    1715                1720                1725
Lys Phe Ala Val Val Phe Asn Pro Ile Gln Leu Ser Ser Leu Thr
    1730                1735                1740
Arg Gly Gln Ala Val Ala Val Thr Pro Glu Gln Leu Ala Tyr Leu
    1745                1750                1755
Ser Pro Glu Gln Arg Arg Ala Val Ala Trp Ala Gln His Glu Gly
    1760                1765                1770
Lys Glu Ile Pro Glu Gln Leu Gly Arg Asn Ser Ala Trp Gly Leu
    1775                1780                1785
```

Tyr Asp Trp Phe Gln Ala Ser Trp Ala Leu Ala Leu Pro Val Ser
    1790                1795                1800

Ile Phe Gly His Leu Leu
    1805

<210> SEQ ID NO 9
<211> LENGTH: 1767
<212> TYPE: PRT
<213> ORGANISM: Canis lupus familiaris

<400> SEQUENCE: 9

Met Ala Leu Ser Leu Trp Pro Val Leu Leu Leu Thr Cys Ala Ala
1               5                   10                  15

Thr Leu Val Ser Ser Gly Ile Gln Ser Leu Asp Pro Asp Leu Ser Leu
            20                  25                  30

Leu Lys Ser Leu Leu Ser Thr Met Asp Gln Ala Pro Gln Gly Ser Leu
        35                  40                  45

Ser Arg Ser Gln Phe Ser Ala Phe Leu Ala Asn Ile Ser Ser Ser Phe
    50                  55                  60

Glu Ser Gly Arg Met Gly Glu Gly Pro Val Gly Glu Pro Pro Leu
65                  70                  75                  80

Gln Ser Pro Ala Leu Arg Leu His Asp Phe Leu Val Thr Leu Arg Gly
                85                  90                  95

Ser Pro Asp Trp Glu Pro Met Leu Gly Leu Leu Gly Asp Val Leu Ala
            100                 105                 110

Leu Leu Gly Gln Glu Gln Thr Pro Arg Asp Phe Leu Gly His Gln Ala
        115                 120                 125

Gly Val Leu Gly Gly Leu Ala Glu Val Leu Leu Gly Ala Leu Val Pro
    130                 135                 140

Ile Gly Pro Pro Thr Pro Thr Arg Pro Pro Cys Ile Arg Asp Gly Pro
145                 150                 155                 160

Ser Asp Cys Val Leu Val Ala Asp Trp Leu Pro Ser Leu Leu Leu Leu
                165                 170                 175

Leu Glu Gly Thr Arg Trp Gln Ala Leu Val Gln Val Gln Pro Ser Val
            180                 185                 190

Asp Pro Thr Asn Ala Thr Gly Leu Asp Gly Arg Glu Pro Ala Pro His
        195                 200                 205

Phe Leu Gln Gly Leu Leu Gly Leu Leu Thr Pro Val Gly Glu Leu Gly
    210                 215                 220

Ser Glu Glu Ala Leu Trp Gly Gly Leu Leu Arg Thr Val Gly Ala Pro
225                 230                 235                 240

Leu Tyr Ala Ala Phe Gln Glu Gly Leu Leu Arg Val Thr Asp Ser Leu
                245                 250                 255

Arg Asn Glu Val Phe Ser Ile Leu Gly Gln Pro Glu Pro Asp Ala Asn
            260                 265                 270

Gly Gln Cys Gln Gly Gly Asn Leu Arg Gln Leu Leu Leu Trp Gly Ile
        275                 280                 285

Arg His Asn Leu Ser Trp Asp Val Gln Ala Leu Gly Phe Leu Ser Gly
    290                 295                 300

Ser Pro Pro Pro Pro Ala Leu Leu His Cys Leu Ser Thr Gly Val
305                 310                 315                 320

Pro Leu Pro Arg Ala Ser Gln Pro Ser Ala His Ile Asn Pro Arg Gln
                325                 330                 335

Arg Arg Ala Ile Ser Val Glu Ala Leu Cys Glu Asn His Ser Gly Pro

-continued

```
            340             345             350
Ala Pro Pro Tyr Ser Ile Ser Asn Phe Ser Ile His Leu Leu Cys Gln
        355             360             365

His Ala Gln Pro Ala Thr Pro Gln Pro Pro Ser Thr Ala Ala Val
    370             375             380

Cys Gln Thr Ala Met Trp Tyr Ala Val Ser Trp Ala Pro Gly Ala Gln
385             390             395             400

Gly Trp Leu Gln Ala Cys His Asp Gln Phe Pro Asp Gln Phe Leu Glu
                405             410             415

Ala Ile Cys Ser Asn Leu Ser Phe Ser Ala Leu Ser Gly Pro Asn Arg
            420             425             430

Arg Leu Val Lys Gln Leu Cys Ala Gly Leu Leu Pro Pro Thr Asn
        435             440             445

Cys Pro Glu Gly Leu Pro Pro Ala Pro Leu Thr Pro Glu Val Phe Trp
    450             455             460

Gly Cys Phe Leu Glu Asn Glu Thr Leu Trp Ala Glu Arg Leu Cys Gly
465             470             475             480

Glu Ala Gly Leu Gln Ala Val Pro Pro Ser Asn Gln Ala Trp Val Gln
                485             490             495

His Val Cys Gln Gly Pro Thr Pro Asp Val Thr Ala Phe Pro Pro Cys
            500             505             510

His Val Gly Pro Cys Gly Glu Arg Cys Pro Asp Gly Gly Ser Phe Leu
        515             520             525

Met Met Val Cys Ala Asn Asp Thr Met Tyr Glu Ala Leu Val Pro Phe
    530             535             540

Trp Pro Trp Leu Ala Gly Gln Cys Arg Ile Ser Arg Gly Gly Asn Asp
545             550             555             560

Thr Cys Phe Leu Glu Gly Leu Leu Gly Pro Leu Pro Ser Leu Pro
                565             570             575

Pro Leu Gly Pro Ser Pro Leu Cys Leu Ala Pro Ala Pro Phe Leu Leu
            580             585             590

Gly Met Leu Ser Gln Leu Pro Arg Cys Gln Ser Ser Val Pro Ala Leu
        595             600             605

Ala His Ser Thr Arg Leu His Tyr Leu Leu Arg Leu Leu Thr Phe Leu
    610             615             620

Leu Gly Pro Gly Ala Gly Gly Thr Glu Ala Gln Gly Met Leu Gly Gln
625             630             635             640

Ala Leu Met Leu Ser Ser Leu Pro Asp Asn Cys Ser Phe Trp Asp Ala
                645             650             655

Phe Arg Pro Glu Gly Arg Arg Ser Val Leu Arg Thr Val Gly Glu Tyr
            660             665             670

Leu Glu Arg Glu Glu Gln Leu Thr Pro Pro Gly Phe Glu Pro Thr Ala
        675             680             685

Ser Pro Ser Ser Gly Ile Thr Lys Met Glu Leu Leu Ala Cys Phe Ser
    690             695             700

Pro Val Leu Trp Asp Leu Leu Gln Arg Glu Lys Ser Val Trp Ala Leu
705             710             715             720

Gln Ile Leu Val Gln Ala Tyr Leu His Met Pro Pro Glu Asn Leu Gln
                725             730             735

Gln Leu Val Leu Ser Ala Glu Arg Glu Ala Ala Gln Gly Phe Leu Thr
            740             745             750

Leu Met His Arg Ser Trp Ala Gln Leu Gln Val Pro Pro Ser Glu Glu
        755             760             765
```

-continued

```
Gln Ala Leu Gly Arg Leu Thr Ala Leu Leu Leu Gln Arg Tyr Pro Arg
            770                 775                 780
Leu Thr Ser Gln Leu Phe Ile Asp Leu Ser Pro Leu Ile Pro Phe Leu
785                 790                 795                 800
Ala Val Ser Asp Leu Met Arg Phe Pro Pro Ser Leu Leu Ala Asn Asp
                805                 810                 815
Ser Val Leu Ala Ala Ile Arg Asp Tyr Ser Pro Gly Met Arg Pro Glu
            820                 825                 830
Gln Lys Glu Ala Leu Ala Lys Arg Leu Leu Ala Pro Glu Leu Phe Gly
            835                 840                 845
Glu Val Pro Ala Trp Ser Gln Glu Leu Leu Trp Ala Val Leu Pro Leu
            850                 855                 860
Leu Pro His Leu Pro Leu Glu Asn Phe Leu Gln Leu Ser Pro His Gln
865                 870                 875                 880
Ile Gln Ala Leu Glu Asp Ser Trp Pro Ala Ala Gly Leu Gly Pro Gly
                885                 890                 895
His Ala Arg His Val Leu Arg Ser Leu Val Asn Gln Ser Val Gln Asp
            900                 905                 910
Gly Glu Glu Gln Val Arg Arg Leu Gly Pro Leu Ala Cys Phe Leu Ser
            915                 920                 925
Pro Glu Glu Leu Gln Ser Leu Val Pro Leu Ser Asp Pro Met Gly Pro
            930                 935                 940
Val Glu Arg Gly Leu Leu Glu Cys Ala Ala Asn Gly Thr Leu Ser Pro
945                 950                 955                 960
Gln Gly Arg Val Ala Tyr Glu Leu Leu Gly Val Leu Arg Ser Ser Gly
                965                 970                 975
Gly Ala Val Leu Ser Pro Leu Glu Leu Arg Val Trp Ala Pro Leu Phe
            980                 985                 990
Pro Gln Leu Gly Leu Arg Phe Leu Gln Glu Leu Ser Glu Pro Gln Leu
            995                 1000                1005
Arg Ala Met Leu Pro Ala Leu Gln Gly Thr Ser Val Thr Pro Ala
            1010                1015                1020
Gln Ala Val Leu Leu Leu Gly Arg Leu Leu Pro Arg His Asp Leu
            1025                1030                1035
Ser Leu Glu Glu Leu Cys Ser Leu His Pro Leu Leu Pro Gly Leu
            1040                1045                1050
Ser Ser Gln Thr Leu Gln Ala Ile Pro Arg Arg Val Leu Ile Gly
            1055                1060                1065
Ala Cys Ser Cys Leu Ala Pro Glu Leu Ser Arg Leu Ser Ala Cys
            1070                1075                1080
Gln Thr Ala Ala Leu Leu Gln Thr Phe Arg Val Lys Asp Gly Val
            1085                1090                1095
Lys Asn Ile Gly Thr Thr Gly Ala Ser Ala Ala Val Cys Ile Pro
            1100                1105                1110
Gly Gln Gln Pro Ile Pro Thr Thr Trp Pro Asp Cys Leu Leu Pro
            1115                1120                1125
Leu Leu Pro Leu Lys Leu Leu Gln Leu Asp Ser Ala Ala Leu Leu
            1130                1135                1140
Ala Asn Arg Arg Arg Tyr Arg Asp Leu Pro Trp Ser Glu Gln Gln
            1145                1150                1155
Ala Gln Phe Leu Trp Lys Lys Met Gln Val Pro Thr Asn Leu Thr
            1160                1165                1170
```

```
Leu Arg Asn Leu Gln Ala Leu Gly Thr Leu Ala Gly Gly Met Ser
1175                1180                1185

Cys Glu Phe Leu Gln Gln Ile Asn Leu Met Ala Asp Phe Leu Glu
1190                1195                1200

Val Val His Met Ile Tyr Gln Leu Pro Thr Gly Val Arg Gly Ser
1205                1210                1215

Leu Arg Ala Cys Ile Trp Ala Glu Leu Gln Arg Lys Met Thr Met
1220                1225                1230

Pro Glu Pro Glu Leu Ala Thr Leu Gly Ser Glu Leu Ser Gly Leu
1235                1240                1245

Asp Thr Lys Leu Leu Leu Asp Ser Pro Ile Tyr Leu Met Asp Arg
1250                1255                1260

Leu Ser Asn Glu Ser Ile Met Leu Met Val Glu Leu Val Arg Arg
1265                1270                1275

Ala Pro Glu Gln Leu Leu Ala Leu Thr Pro Leu His Arg Val Ala
1280                1285                1290

Leu Ala Glu Arg Ala Leu Gln Asn Leu Ala Pro Lys Glu Thr Thr
1295                1300                1305

Val Ser Arg Glu Val Leu Glu Thr Leu Gly Pro Leu Val Gly Phe
1310                1315                1320

Leu Gly Ile Glu Ser Thr Arg Arg Ile Pro Leu Pro Ile Leu Leu
1325                1330                1335

Ala His Leu Asn Gln Leu Gln Gly Phe Cys Leu Gly Glu Pro Phe
1340                1345                1350

Ala Thr Glu Leu Gly Trp Leu Leu Ser Gln Glu Pro Ile Leu Gly
1355                1360                1365

Lys Pro Glu Leu Trp Ser Glu Gly Glu Val Glu Gln Ala Gly Arg
1370                1375                1380

Leu Val Leu Thr Leu Ser Thr Glu Ala Ile Ser Leu Ile Pro Arg
1385                1390                1395

Glu Ala Leu Gly Pro Glu Thr Leu Glu Arg Leu Leu Glu Lys Gln
1400                1405                1410

Gln Ser Trp Glu Gln Ser Arg Val Gly Gln Leu Cys Gly Thr Pro
1415                1420                1425

Gln Leu Ala Pro Lys Lys Ala Ala Leu Val Ala Gly Val Val Arg
1430                1435                1440

Pro Thr Ala Glu Asp Leu Ser Glu Pro Val Pro Asn Cys Ala Asp
1445                1450                1455

Val Arg Gly Thr Phe Pro Ala Ala Trp Ser Ala Thr Gln Ile Ala
1460                1465                1470

Glu Met Glu Leu Ser Asp Phe Glu Asp Cys Leu Ala Leu Phe Ala
1475                1480                1485

Gly Asp Pro Gly Leu Gly Pro Glu Glu Leu Arg Ala Ala Met Gly
1490                1495                1500

Lys Ala Lys Gln Leu Trp Gly Pro Pro Arg Gly Phe Arg Pro Glu
1505                1510                1515

Gln Ile Leu Gln Leu Ser Arg Leu Leu Ile Gly Leu Gly Glu Arg
1520                1525                1530

Glu Leu Gln Glu Leu Ile Leu Val Asp Trp Gly Val Leu Ser Thr
1535                1540                1545

Leu Gly Gln Ile Asp Gly Trp Ser Ser Ile Gln Leu Arg Val Val
1550                1555                1560

Val Ser Ser Phe Leu Arg Gln Ser Gly Arg His Val Ser His Leu
```

```
                    1565                1570                1575

Asp Phe Leu His Leu Thr Ala Leu Gly Tyr Thr Leu Cys Gly Leu
            1580                1585                1590

Arg Pro Glu Glu Leu Gln His Ile Ser Ser Trp Glu Phe Ser Gln
        1595                1600                1605

Ala Ala Leu Phe Leu Gly Asn Leu His Leu Gln Cys Ser Glu Glu
    1610                1615                1620

Gln Leu Glu Val Leu Ala Gln Leu Leu Val Leu Pro Gly Gly Phe
1625                1630                1635

Gly Pro Val Ser Asn Trp Gly Pro Glu Ile Phe Thr Glu Ile Gly
    1640                1645                1650

Thr Ile Ala Ala Gly Ile Pro Asp Leu Ala Leu Ser Ala Leu Leu
    1655                1660                1665

Gln Glu Gln Ile Gln Gly Leu Thr Pro Leu Ala Ile Ser Val Ile
    1670                1675                1680

Pro Ala Pro Lys Phe Ala Val Val Phe Ser Pro Thr Gln Leu Ser
    1685                1690                1695

Ser Leu Thr Ser Val Gln Ala Met Ala Val Thr Pro Glu Gln Met
    1700                1705                1710

Ala Phe Leu Ser Pro Glu Gln Arg Arg Ala Val Trp Ala Gln
    1715                1720                1725

His Glu Gly Lys Glu Ser Pro Glu Gln Gln Gly Arg Ser Thr Ala
    1730                1735                1740

Trp Gly Leu Gln Asp Trp Ser Gln Pro Ser Trp Ala Met Ala Leu
    1745                1750                1755

Thr Ile Cys Phe Leu Gly Asn Leu Ile
    1760                1765

<210> SEQ ID NO 10
<211> LENGTH: 22
<212> TYPE: PRT
<213> ORGANISM: Homo sapiens

<400> SEQUENCE: 10

Met Ala Leu Ser Leu Trp Pro Leu Leu Leu Leu Leu Leu Leu Leu
1               5                   10                  15

Leu Leu Ser Phe Ala Val
            20

<210> SEQ ID NO 11
<211> LENGTH: 1775
<212> TYPE: PRT
<213> ORGANISM: Homo sapiens

<400> SEQUENCE: 11

Met Ala Leu Ser Leu Trp Pro Leu Leu Leu Leu Leu Leu Leu Leu
1               5                   10                  15

Leu Leu Ser Phe Ala Val Thr Leu Ala Pro Thr Gly Pro His Ser Leu
            20                  25                  30

Asp Pro Gly Leu Ser Phe Leu Lys Ser Leu Leu Ser Thr Leu Asp Gln
        35                  40                  45

Ala Pro Gln Gly Ser Leu Ser Arg Ser Arg Phe Phe Thr Phe Leu Ala
    50                  55                  60

Asn Ile Ser Ser Ser Phe Glu Pro Gly Arg Met Gly Glu Gly Pro Val
65                  70                  75                  80

Gly Glu Pro Pro Pro Leu Gln Pro Pro Ala Leu Arg Leu His Asp Phe
```

-continued

```
                    85                  90                  95
Leu Val Thr Leu Arg Gly Ser Pro Asp Trp Glu Pro Met Leu Gly Leu
                    100                 105                 110
Leu Gly Asp Met Leu Ala Leu Leu Gly Gln Glu Gln Thr Pro Arg Asp
                115                 120                 125
Phe Leu Val His Gln Ala Gly Val Leu Gly Gly Leu Val Glu Val Leu
130                 135                 140
Leu Gly Ala Leu Val Pro Gly Pro Pro Thr Pro Thr Arg Pro Pro
145                 150                 155                 160
Cys Thr Arg Asp Gly Pro Ser Asp Cys Val Leu Ala Ala Asp Trp Leu
                165                 170                 175
Pro Ser Leu Leu Leu Leu Glu Gly Thr Arg Trp Gln Ala Leu Val
                180                 185                 190
Gln Val Gln Pro Ser Val Asp Pro Thr Asn Ala Thr Gly Leu Asp Gly
                195                 200                 205
Arg Glu Ala Ala Pro His Phe Leu Gln Gly Leu Leu Gly Leu Leu Thr
                210                 215                 220
Pro Thr Gly Glu Leu Gly Ser Lys Glu Ala Leu Trp Gly Gly Leu Leu
225                 230                 235                 240
Arg Thr Val Gly Ala Pro Leu Tyr Ala Ala Phe Gln Glu Gly Leu Leu
                245                 250                 255
Arg Val Thr His Ser Leu Gln Asp Glu Val Phe Ser Ile Leu Gly Gln
                260                 265                 270
Pro Glu Pro Asp Thr Asn Gly Gln Cys Gln Gly Gly Asn Leu Gln Gln
                275                 280                 285
Leu Leu Leu Trp Gly Val Arg His Asn Leu Ser Trp Asp Val Gln Ala
290                 295                 300
Leu Gly Phe Leu Ser Gly Ser Pro Pro Pro Pro Ala Leu Leu His
305                 310                 315                 320
Cys Leu Ser Thr Gly Val Pro Leu Pro Arg Ala Ser Gln Pro Ser Ala
                325                 330                 335
His Ile Ser Pro Arg Gln Arg Arg Ala Ile Thr Val Glu Ala Leu Cys
                340                 345                 350
Glu Asn His Leu Gly Pro Ala Pro Pro Tyr Ser Ile Ser Asn Phe Ser
                355                 360                 365
Ile His Leu Leu Cys Gln His Thr Lys Pro Ala Thr Pro Gln Pro His
                370                 375                 380
Pro Ser Thr Thr Ala Ile Cys Gln Thr Ala Val Trp Tyr Ala Val Ser
385                 390                 395                 400
Trp Ala Pro Gly Ala Gln Gly Trp Leu Gln Ala Cys His Asp Gln Phe
                405                 410                 415
Pro Asp Glu Phe Leu Asp Ala Ile Cys Ser Asn Leu Ser Phe Ser Ala
                420                 425                 430
Leu Ser Gly Ser Asn Arg Arg Leu Val Lys Arg Leu Cys Ala Gly Leu
                435                 440                 445
Leu Pro Pro Pro Thr Ser Cys Pro Glu Gly Leu Pro Pro Val Pro Leu
                450                 455                 460
Thr Pro Asp Ile Phe Trp Gly Cys Phe Leu Glu Asn Glu Thr Leu Trp
465                 470                 475                 480
Ala Glu Arg Leu Cys Gly Glu Ala Ser Leu Gln Ala Val Pro Pro Ser
                485                 490                 495
Asn Gln Ala Trp Val Gln His Val Cys Gln Gly Pro Thr Pro Asp Val
                500                 505                 510
```

```
Thr Ala Ser Pro Pro Cys His Ile Gly Pro Cys Gly Glu Arg Cys Pro
        515                 520                 525

Asp Gly Gly Ser Phe Leu Val Met Val Cys Ala Asn Asp Thr Met Tyr
    530                 535                 540

Glu Val Leu Val Pro Phe Trp Pro Trp Leu Ala Gly Gln Cys Arg Ile
545                 550                 555                 560

Ser Arg Gly Gly Asn Asp Thr Cys Phe Leu Glu Gly Leu Leu Gly Pro
                565                 570                 575

Leu Leu Pro Ser Leu Pro Pro Leu Gly Pro Ser Pro Leu Cys Leu Thr
            580                 585                 590

Pro Gly Pro Phe Leu Leu Gly Met Leu Ser Gln Leu Pro Arg Cys Gln
        595                 600                 605

Ser Ser Val Pro Ala Leu Ala His Pro Thr Arg Leu His Tyr Leu Leu
    610                 615                 620

Arg Leu Leu Thr Phe Leu Leu Gly Pro Gly Ala Gly Gly Ala Glu Ala
625                 630                 635                 640

Gln Gly Met Leu Gly Arg Ala Leu Leu Leu Ser Ser Leu Pro Asp Asn
                645                 650                 655

Cys Ser Phe Trp Asp Ala Phe Arg Pro Glu Gly Arg Arg Ser Val Leu
            660                 665                 670

Arg Thr Ile Gly Glu Tyr Leu Glu Gln Asp Glu Glu Gln Pro Thr Pro
        675                 680                 685

Ser Gly Phe Glu Pro Thr Val Asn Pro Ser Ser Gly Ile Ser Lys Met
    690                 695                 700

Glu Leu Leu Ala Cys Phe Ser Pro Val Leu Trp Asp Leu Leu Gln Arg
705                 710                 715                 720

Glu Lys Ser Val Trp Ala Leu Gln Ile Leu Val Gln Ala Tyr Leu His
                725                 730                 735

Met Pro Pro Glu Asn Leu Gln Gln Leu Val Leu Ser Ala Glu Arg Glu
            740                 745                 750

Ala Ala Gln Gly Phe Leu Thr Leu Met Leu Gln Gly Lys Leu Gln Gly
        755                 760                 765

Lys Leu Gln Val Pro Pro Ser Glu Glu Gln Ala Leu Gly Arg Leu Thr
    770                 775                 780

Ala Leu Leu Leu Gln Arg Tyr Pro Arg Leu Thr Ser Gln Leu Phe Ile
785                 790                 795                 800

Asp Leu Ser Pro Leu Ile Pro Phe Leu Ala Val Ser Asp Leu Met Arg
                805                 810                 815

Phe Pro Pro Ser Leu Leu Ala Asn Asp Ser Val Leu Ala Ala Ile Arg
            820                 825                 830

Asp Tyr Ser Pro Gly Met Arg Pro Glu Gln Lys Glu Ala Leu Ala Lys
        835                 840                 845

Arg Leu Leu Ala Pro Glu Leu Phe Gly Glu Val Pro Ala Trp Pro Gln
    850                 855                 860

Glu Leu Leu Trp Ala Val Leu Pro Leu Leu Pro His Leu Pro Leu Glu
865                 870                 875                 880

Asn Phe Leu Gln Leu Ser Pro His Gln Ile Gln Ala Leu Glu Asp Ser
                885                 890                 895

Trp Pro Ala Ala Gly Leu Gly Pro Gly His Ala Arg His Val Leu Arg
            900                 905                 910

Ser Leu Val Asn Gln Ser Val Gln Asp Gly Glu Glu Gln Val Arg Arg
        915                 920                 925
```

```
Leu Gly Pro Leu Ala Cys Phe Leu Ser Pro Glu Glu Leu Gln Ser Leu
    930                 935                 940

Val Pro Leu Ser Asp Pro Thr Gly Pro Val Glu Arg Gly Leu Leu Glu
945                 950                 955                 960

Cys Ala Ala Asn Gly Thr Leu Ser Pro Glu Gly Arg Val Ala Tyr Glu
                965                 970                 975

Leu Leu Gly Val Leu Arg Ser Ser Gly Gly Ala Val Leu Ser Pro Arg
            980                 985                 990

Glu Leu Arg Val Trp Ala Pro Leu Phe Ser Gln Leu Gly Leu Arg Phe
        995                 1000                1005

Leu Gln Glu Leu Ser Glu Pro Gln Leu Arg Ala Met Leu Pro Val
    1010                1015                1020

Leu Gln Gly Thr Ser Val Thr Pro Ala Gln Ala Val Leu Leu Leu
    1025                1030                1035

Gly Arg Leu Leu Pro Arg His Asp Leu Ser Leu Glu Glu Leu Cys
    1040                1045                1050

Ser Leu His Leu Leu Leu Pro Gly Leu Ser Pro Gln Thr Leu Gln
    1055                1060                1065

Ala Ile Pro Arg Arg Val Leu Val Gly Ala Cys Ser Cys Leu Ala
    1070                1075                1080

Pro Glu Leu Ser Arg Leu Ser Ala Cys Gln Thr Ala Ala Leu Leu
    1085                1090                1095

Gln Thr Phe Arg Val Lys Asp Gly Val Lys Asn Met Gly Thr Thr
    1100                1105                1110

Gly Ala Gly Pro Ala Val Cys Ile Pro Gly Gln Pro Ile Pro Thr
    1115                1120                1125

Thr Trp Pro Asp Cys Leu Leu Pro Leu Leu Pro Leu Lys Leu Leu
    1130                1135                1140

Gln Leu Asp Ser Leu Ala Leu Leu Ala Asn Arg Arg Arg Tyr Trp
    1145                1150                1155

Glu Leu Pro Trp Ser Glu Gln Gln Ala Gln Phe Leu Trp Lys Lys
    1160                1165                1170

Met Gln Val Pro Thr Asn Leu Thr Leu Arg Asn Leu Gln Ala Leu
    1175                1180                1185

Gly Thr Leu Ala Gly Gly Met Ser Cys Glu Phe Leu Gln Gln Ile
    1190                1195                1200

Asn Ser Met Val Asp Phe Leu Glu Val Val His Met Ile Tyr Gln
    1205                1210                1215

Leu Pro Thr Arg Val Arg Gly Ser Leu Arg Ala Cys Ile Trp Ala
    1220                1225                1230

Glu Leu Gln Arg Arg Met Ala Met Pro Glu Pro Glu Trp Thr Thr
    1235                1240                1245

Val Gly Pro Glu Leu Asn Gly Leu Asp Ser Lys Leu Leu Leu Asp
    1250                1255                1260

Leu Pro Ile Gln Leu Met Asp Arg Leu Ser Asn Glu Ser Ile Met
    1265                1270                1275

Leu Val Val Glu Leu Val Gln Arg Ala Pro Glu Gln Leu Leu Ala
    1280                1285                1290

Leu Thr Pro Leu His Gln Ala Ala Leu Ala Glu Arg Ala Leu Gln
    1295                1300                1305

Asn Leu Ala Pro Lys Glu Thr Pro Val Ser Gly Glu Val Leu Glu
    1310                1315                1320

Thr Leu Gly Pro Leu Val Gly Phe Leu Gly Thr Glu Ser Thr Arg
```

-continued

```
            1325                1330                1335

Gln Ile Pro Leu Gln Ile Leu Leu Ser His Leu Ser Gln Leu Gln
            1340                1345                1350

Gly Phe Cys Leu Gly Glu Thr Phe Ala Thr Glu Leu Gly Trp Leu
            1355                1360                1365

Leu Leu Gln Glu Ser Val Leu Gly Lys Pro Glu Leu Trp Ser Gln
            1370                1375                1380

Asp Glu Val Glu Gln Ala Gly Arg Leu Val Phe Thr Leu Ser Thr
            1385                1390                1395

Glu Ala Ile Ser Leu Ile Pro Arg Glu Ala Leu Gly Pro Glu Thr
            1400                1405                1410

Leu Glu Arg Leu Leu Glu Lys Gln Gln Ser Trp Glu Gln Ser Arg
            1415                1420                1425

Val Gly Gln Leu Cys Arg Glu Pro Gln Leu Ala Ala Lys Lys Ala
            1430                1435                1440

Ala Leu Val Ala Gly Val Val Arg Pro Ala Ala Glu Asp Leu Pro
            1445                1450                1455

Glu Pro Val Pro Asn Cys Ala Asp Val Arg Gly Thr Phe Pro Ala
            1460                1465                1470

Ala Trp Ser Ala Thr Gln Ile Ala Glu Met Glu Leu Ser Asp Phe
            1475                1480                1485

Glu Asp Cys Leu Thr Leu Phe Ala Gly Asp Pro Gly Leu Gly Pro
            1490                1495                1500

Glu Glu Leu Arg Ala Ala Met Gly Lys Ala Lys Gln Leu Trp Gly
            1505                1510                1515

Pro Pro Arg Gly Phe Arg Pro Glu Gln Ile Leu Gln Leu Gly Arg
            1520                1525                1530

Leu Leu Ile Gly Leu Gly Asp Arg Glu Leu Gln Glu Leu Ile Leu
            1535                1540                1545

Val Asp Trp Gly Val Leu Ser Thr Leu Gly Gln Ile Asp Gly Trp
            1550                1555                1560

Ser Thr Thr Gln Leu Arg Ile Val Val Ser Ser Phe Leu Arg Gln
            1565                1570                1575

Ser Gly Arg His Val Ser His Leu Asp Phe Val His Leu Thr Ala
            1580                1585                1590

Leu Gly Tyr Thr Leu Cys Gly Leu Arg Pro Glu Glu Leu Gln His
            1595                1600                1605

Ile Ser Ser Trp Glu Phe Ser Gln Ala Ala Leu Phe Leu Gly Thr
            1610                1615                1620

Leu His Leu Gln Cys Ser Glu Glu Gln Leu Glu Val Leu Ala His
            1625                1630                1635

Leu Leu Val Leu Pro Gly Gly Phe Gly Pro Ile Ser Asn Trp Gly
            1640                1645                1650

Pro Glu Ile Phe Thr Glu Ile Gly Thr Ile Ala Ala Gly Ile Pro
            1655                1660                1665

Asp Leu Ala Leu Ser Ala Leu Leu Arg Gly Gln Ile Gln Gly Val
            1670                1675                1680

Thr Pro Leu Ala Ile Ser Val Ile Pro Pro Lys Phe Ala Val
            1685                1690                1695

Val Phe Ser Pro Ile Gln Leu Ser Ser Leu Thr Ser Ala Gln Ala
            1700                1705                1710

Val Ala Val Thr Pro Glu Gln Met Ala Phe Leu Ser Pro Glu Gln
            1715                1720                1725
```

```
Arg Arg Ala Val Ala Trp Ala Gln His Glu Gly Lys Glu Ser Pro
    1730            1735                1740
Glu Gln Gln Gly Arg Ser Thr Ala Trp Gly Leu Gln Asp Trp Ser
    1745                1750                1755
Arg Pro Ser Trp Ser Leu Val Leu Thr Ile Ser Phe Leu Gly His
    1760                1765                1770
Leu Leu
    1775

<210> SEQ ID NO 12
<211> LENGTH: 4324
<212> TYPE: DNA
<213> ORGANISM: Artificial Sequence
<220> FEATURE:
<223> OTHER INFORMATION: pITR-201

<400> SEQUENCE: 12
cctgcaggca gctgcgcgct cgctcgctca ctgaggccgc ccgggcgtcg ggcgaccttt        60
ggtcgcccgg cctcagtgag cgagcgagcg cgcagagagg gagtggccaa ctccatcact       120
aggggttcct gcggccgcac gcgtagactt gcccaaaaac tctggcaaag ttgaattgct       180
tccaaaagtt caactttatc agaaggacct attccctacg gaaactagct gaaggtctcc       240
tggcactctg gatctcgtgg aagggagcct tcttcaggga acagagggag cgattaagtg       300
gtgaaaagca acagacctg aaaagttcc ctttctgaga gtagcaacag aaagctctgc       360
aaagactccc tccaagctat tggatcctct tgcttgggat aaccacttga gtactcagat       420
accaaaagaa gagtggaaat cccaagagaa gtcaccagaa aaaacagctt ttaagaaaaa       480
ggatacactt ttgtccctga acgcttgtga aagcaatctg acaatagcag caattgaaaa       540
gggacaaaat aagcccgaaa tagaagtcac ctgggcaaag caaggtagga ctgaaaggct       600
gtgctctcaa aacccaccag tcttgaaacg cactcaacgg gtgaaagtag taggaaaggg       660
tgaatttaca aaggacgtag gactcaaaga gtgagttttt ccaagcagca gaaacctatt       720
tcttactaac ttggataatt tactgaaaaa taatacacac aatcaagaaa aaaaaattca       780
ggaagaaata gaaaagaagg aaaacttaat ccaagagtga atagttttgc ctcagataac       840
tacagtgact ggcactaaga atttctgaaa gaaccttttc ttactgagca ctaggctgaa       900
aatagaaggt tacttgaacg gggacttgac tccagtactt caagatttta ggtactttga       960
aaattcaaca aatagaacaa agaaacacac agctactttc tcaaaaaaag gggaggaaga      1020
aaacttggaa ggcttgggaa atcaaaccaa gcaaattgta gagaaattga ctgacaccac      1080
aaggatatct cctaatacaa gccagcagaa ttttgtcacg caacgtagta agagagcttt      1140
gaaactagat cccatatatg gagttccgcg ttacataact tacggtaaat ggcccgcctg      1200
gctgaccgcc caacgacccc cgcccattga cgtcaataat gacgtatgtt cccatagtaa      1260
cgccaatagg gactttccat tgacgtcaat gggtggagta tttacggtaa actgcccact      1320
tggcagtaca tcaagtgtat catatgccaa gtacgccccc tattgacgtc aatgacggta      1380
aatggcccgc ctggcattat gcccagtaca tgaccttatg ggactttcct acttggcagt      1440
acatctacgt attagtcatc gctattacca tggtgatgcg gttttggtga tgcggttttg      1500
gcagtacatc aatgggcgtg gatagcggtt tgactcacgg ggatttccaa gtctccaccc      1560
cattgacgtc aatgggagtt tgttttggca ccaaaatcaa cgggactttc caaaatgtcg      1620
taacaactcc gccccattga cgcaaatggg cggtaggcgt gtacggtggg aggtctatat      1680
```

-continued

```
aagcagagct cgtttagtga accgtcaccg gtggtgccct gccctcacct ggctatccca    1740
cacaggtgag aataaccaga actcacctcc ggtaccagtg ttcacttggc caccatggct    1800
ctcagcctct ggcccctgct gctgctgctg ctgctgctgc tgctgctgtc ctttgcagtg    1860
actctggccc ctactgggcc tcattccctg gaccctggtc tctccttcct gaagtcattg    1920
ctctccactc tggaccaggc tccccagggc tccctgagcc gctcacggtt ctttacattc    1980
ctggccaaca tttcttcttc ctttgagcct gggagaatgg gggaaggacc agtaggagag    2040
cccccacctc tccagccgcc tgctctgcgg ctccatgatt ttctagtgac actgagaggt    2100
agccccgact gggagccaat gctagggctg ctaggggata tgctggcact gctgggacag    2160
gagcagactc cccgagattt cctggtgcac caggcagggg tgctgggtgg acttgtggag    2220
gtgctgctgg gagccttagt tcctgggggc cccctaccc caactcggcc ccatgcacc     2280
cgtgatgggc cgtctgactg tgtcctggct gctgactggt tgccttctct gctgctgttg    2340
ttagagggca cacgctggca agctctggtg caggtgcagc ccagtgtgga ccccaccaat    2400
gccacaggcc tcgatgggag ggaggcagct cctcactttt gcagggtct gttgggtttg     2460
cttaccccaa caggggagct aggctccaag gaggctcttt ggggcggtct gctacgcaca    2520
gtgggggccc cctctatgc tgcctttcag gaggggctgc tccgtgtcac tcactccttg     2580
caggatgagg tcttctccat tttggggcag ccagagcctg ataccaatgg gcagtgccag    2640
ggaggtaacc ttcaacagct gctcttatgg ggcgtccggc acaacctttc ctgggatgtc    2700
caggcgctgg gctttctgtc tggatcacca ccccacccc ctgccctcct tcactgcctg     2760
agcacgggcg tgcctctgcc cagagcttct cagccgtcag cccacatcag cccacgccaa    2820
cggcgagcca tcactgtgga ggccctctgt gagaaccact taggcccagc accaccctac    2880
agcatttcca acttctccat ccacttgctc tgccagcaca ccaagcctgc cactccacag    2940
ccccatccca gcaccactgc catctgccag acagctgtgt ggtatgcagt gtcctgggca    3000
ccaggtgccc aaggctggct acaggcctgc cacgaccagt ttcctgatga gttttggat     3060
gcgatctgca gtaacctctc cttttcagcc ctgtctggct ccaaccgccg cctggtgaag    3120
cggctctgtg ctggcctgct cccacccct accagctgcc ctgaaggcct gcccctgtt     3180
cccctcaccc cagacatctt ttggggctgc ttcttggaga atgagactct gtgggctgag    3240
cgactgtgtg gggaggcaag tctacaggct gtgccccca gcaaccaggc ttgggtccag    3300
catgtgtgcc agggccccac cccagatgtc actgcctccc caccatgcca cattggaccc    3360
tgtggggaac gctgcccgga tggggcagc ttcctggtga tggtctgtgc caatgacacc     3420
atgtatgagg tcctggtgcc cttctggcct tggctagcag gccaatgcag gataagtcgt    3480
gggggcaatg acacttgctt cctagaaggg ctgctgggcc ccttctgcc ctctctgcca     3540
ccactgggac catccccact ctgtctgacc cctggccct tcctccttgg catgctatcc     3600
cagttgccac gctgtcagtc ctctgtccca gctcttgctc accccacacg cctacactat    3660
ctcctccgcc tgctgacctt cctcttgggt ccaggggctg ggggcgctga ggcccagggg    3720
atgctgggtc gggccctact gctctccagt ctcccagaca actgctcctt ctgggatgcc    3780
tttcgcccag agggccggcg cagtgtgcta cggacgattg ggaatacct ggaacaagat     3840
gaggagcagc caacccatc aggctttgaa cccactgtca accccagctc tggtataagc     3900
aagatggagc tgctggcctg ctttagtcct gtgctgtggg atctgctcca gagggaaaag    3960
agtgtttggg ccctgcagat tctagtgcag gtaagtatca aggttacaag acaggtttaa    4020
ggagaccaat agaaactggg cttgtcgaga cagagaagac tcttgcgttt ctgggatttt    4080
```

-continued

```
gccgatttcg gcctattggt taaaaaatga gctgatttaa caaaaattta acgcgaattt    4140
taacaaaata agcttgaatt cagctgacgt gcctcggacc gctaggaacc cctagtgatg    4200
gagttggcca ctccctctct gcgcgctcgc tcgctcactg aggccgggcg accaaaggtc    4260
gcccgacgcc cgggctttgc ccgggcggcc tcagtgagcg agcgagcgcg cagctgcctg    4320
cagg                                                                 4324
```

<210> SEQ ID NO 13
<211> LENGTH: 4434
<212> TYPE: DNA
<213> ORGANISM: Artificial Sequence
<220> FEATURE:
<223> OTHER INFORMATION: pITR-202

<400> SEQUENCE: 13

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggccgcac gcgtgggatt ttgccgattt cggcctattg gttaaaaaat     180
gagctgattt aacaaaaatt taacgcgaat tttaacaaaa tgataggcac ctattggtct     240
tactgacatc cactttgcct ttctctccac aggcgtacct gcatatgccc cagaaaacc      300 tccagcagct ggtgctttca gcagagaggg aggctgcaca gggcttcctg acactcatgc     360
tgcaggggaa gctgcagggg aagctgcagg taccaccatc cgaggagcag gccctgggtc     420
gcctgacagc cctgctgctc cagcggtacc cacgcctcac ctcccagctc ttcattgacc     480
tgtcaccact catcccttc ttggctgtct ctgacctgat gcgcttccca ccatccctgt      540
tagccaacga cagtgtcctg gctgccatcc gggattacag cccaggaatg aggcctgaac     600
agaaggaggc tctggcaaag cgactgctgg cccctgaact gtttgggaa gtgcctgcct      660 ggcccccagga gctgctgtgg gcagtgctgc cctgctccc ccacctccct ctggagaact     720
ttttgcagct cagccctcac cagatccagg ccctggagga tagctggcca gcagcaggtc     780
tggggccagg gcatgcccgc catgtgctgc gcagcctggt aaaccagagt gtccaggatg     840
gtgaggagca ggtacgcagg cttgggcccc tcgcctgttt cctgagccct gaggagctgc     900
agagcctagt gccctgagt gatccaacgg ggccagtaga acgggggctg ctggaatgtg      960
cagccaatgg gaccctcagc ccagaaggac gggtggcata tgaacttctg ggtgtgttgc     1020
gctcatctgg aggagcggtg ctgagccccc gggagctgcg ggtctgggcc cctctcttct    1080
ctcagctggg cctccgcttc cttcaggagc tgtcagagcc cagcttaga gccatgcttc     1140 ctgtcctcca gggaactagt gttacacctg ctcaggctgt cctgctgctt ggacggctcc    1200
ttcctaggca cgatctatcc ctggaggaac tctgctcctt gcaccttctg ctaccaggcc    1260 tcagcccca gacactccag gccatcccta ggcgagtcct ggtcggggct tgttcctgcc     1320
tggcccctga actgtcacgc ctctcagcct gccagaccgc agcactgctg cagacctttc    1380
gggttaaaga tggtgttaaa aatatgggta caacaggtgc tggtccagct gtgtgtatcc    1440
ctggtcagcc tattcccacc acctggccag actgcctgct tccctgctc ccattaaagc     1500 tgctacaact ggattccttg gctcttctgg caaatcgaag acgctactgg gagctgccct    1560
ggtctgagca gcaggcacag tttctctgga agaagatgca agtacccacc aaccttaccc    1620
tcaggaatct gcaggctctg ggcaccctgg caggaggcat gtcctgtgag tttctgcagc    1680
agatcaactc catggtagac ttccttgaag tggtgcacat gatctatcag ctgcccacta    1740
```

```
gagttcgagg gagcctgagg gcctgtatct gggcagagct acagcggagg atggcaatgc    1800
cagaaccaga atggacaact gtagggccag aactgaacgg gctggatagc aagctactcc    1860
tggacttacc gatccagttg atggacagac tatccaatga atccattatg ttggtggtgg    1920
agctggtgca aagagctcca gagcagctgc tggcactgac cccctccac caggcagccc     1980 tggcagagag ggcactacaa aacctggctc caaaggagac tccagtctca ggggaagtgc    2040
tggagacctt aggcccttttg gttggattcc tggggacaga gagcacacga cagatccccc   2100
tacagatcct gctgtcccat ctcagtcagc tgcaaggctt ctgcctagga gagacatttg    2160
ccacagagct gggatggctg ctattgcagg agtctgttct tgggaaacca gagttgtgga    2220
gccaggatga agtagagcaa gctggacgcc tagtattcac tctgtctact gaggcaattt    2280
ccttgatccc cagggaggcc ttgggtccag agaccctgga gcggcttcta gaaaagcagc    2340
agagctggga gcagagcaga gttggacagc tgtgtaggga gccacagctt gctgccaaga    2400
aagcagccct ggtagcaggg gtggtgcgac cagctgctga ggatcttcca gaacctgtgc    2460
caaattgtgc agatgtacga gggacattcc cagcagcctg gtctgcaacc cagattgcag    2520
agatggagct ctcagacttt gaggactgcc tgacattatt tgcaggagac ccaggacttg    2580
ggcctgagga actgcgggca gccatgggca agcaaaaca gttgtggggt ccccccccggg    2640 gatttcgtcc tgagcagatc ctgcagcttg gtaggctctt aataggtcta ggagatcggg    2700
aactacagga gctgatccta gtggactggg gagtgctgag caccctgggg cagatagatg    2760
gctggagcac cactcagctc cgcattgtgg tctccagttt cctacggcag agtggtcggc    2820
atgtgagcca cctggacttc gttcatctga cagcgctggg ttatactctc tgtggactgc    2880
ggccagagga gctccagcac atcagcagtt gggagttcag ccaagcagct ctcttcctcg    2940
gcaccctgca tctccagtgc tctgaggaac aactggaggt tctggcccac ctacttgtac    3000
tgcctggtgg gtttggccca atcagtaact gggggcctga gatcttcact gaaattggca    3060
ccatagcagc tgggatccca gacctggctc tttcagcact gctgcgggga cagatccagg    3120
gcgttactcc tcttgccatt tctgtcatcc ctcctcctaa atttgctgtg gtgtttagtc    3180
ccatccaact atctagtctc accagtgctc aggctgtggc tgtcactcct gagcaaatgg    3240
cctttctgag tcctgagcag cgacgagcag ttgcatgggc ccaacatgag ggaaaggaga    3300
gcccagaaca gcaaggtcga agtacagcct ggggcctcca ggactggtca cgaccttcct    3360
ggtccctggt attgactatc agcttccttg gccacctgct atgagcctgt ctctacagta    3420
gaaggagatt gtggggagag aaatcttaag tcataatgaa taaagtgcaa acagaagtgc    3480
atcctgatta ttttcagaag ctgatgagga ataactagtg ctgatcagcc tcgactgtgc    3540
cttctagttg ccagccatct gttgtttgcc cctcccccgt gccttccttg acctggaag     3600 gtgccactcc cactgtcctt tcctaataaa atgaggaaat tgcatcgcat tgtctgagta    3660
ggtgtcattc tattctgggg ggtggggtgg ggcaggacag caaggggag gattgggaag     3720 acaatagcag gcatgctggg gatgcggtgg gctctatggc aattcagact cccactagaa    3780
gaaacagaac ttgaaaaaag gataattgtg gtgaacacct caacccagtg gtccaaaaac    3840
tgaaaaactt tgaccccgag caccctcaca cagatagact actgaaagaa ggagaaaggg    3900
gcacttactc agtctcccct atcagattgc cttacgagga gtactagact ccctcaagca    3960
aatagatctc acttaccact tgcaaaggta tactactttc actctattag acctatatat    4020
ctgaccaggg tcctattcca agacaactct tctactcttc cagcagactc ttatagaaag    4080
aaagattctg gggtccaaga aagcagtact ttcttacaag gagccaaaaa aaataacctt    4140
```

```
tctttagcac ttctaacctt ggagtgaact ggtgatcaaa gagaggttgg ctccctgggg    4200
acaagtgcca caaattcagt caactacaag aaagttgaga acactgttct cccgaaacca    4260
agcttgaatt cagctgacgt gcctcggacc gctaggaacc cctagtgatg gagttggcca    4320
ctccctctct gcgcgctcgc tcgctcactg aggccgggcg accaaaggtc gcccgacgcc    4380
cgggctttgc ccgggcggcc tcagtgagcg agcgagcgcg cagctgcctg cagg          4434
```

<210> SEQ ID NO 14
<211> LENGTH: 4693
<212> TYPE: DNA
<213> ORGANISM: Artificial Sequence
<220> FEATURE:
<223> OTHER INFORMATION: pITR-202GFP

<400> SEQUENCE: 14

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggccgcac gcgtgggatt ttgccgattt cggcctattg gttaaaaaat    180
gagctgattt aacaaaaatt taacgcgaat tttaacaaaa tgataggcac ctattggtct    240
tactgacatc cactttgcct ttctctccac aggcgtacct gcatatgccc ccagaaaacc    300
tccagcagct ggtgctttca gcagagaggg aggctgcaca gggcttcctg acactcatgc    360
tgcaggggaa gctgcagggg aagctgcagg taccaccatc cgaggagcag gccctgggtc    420
gcctgacagc cctgctgctc cagcggtacc cacgcctcac ctcccagctc ttcattgacc    480
tgtcaccact catccctttc ttggctgtct ctgacctgat gcgcttccca ccatccctgt    540
tagccaacga cagtgtcctg gctgccatcc gggattacag cccaggaatg aggcctgaac    600
agaaggaggc tctggcaaag cgactgctgg cccctgaact gtttgggaa gtgcctgcct     660 ggcccccagga gctgctgtgg gcagtgctgc cctgctccc ccacctccct ctggagaact    720
ttttgcagct cagccctcac cagatccagg ccctggagga tagctggcca gcagcaggtc    780
tggggccagg gcatgccgc catgtgctgc gcagcctggt aaaccagagt gtccaggatg    840
gtgaggagca ggtacgcagg cttgggcccc tcgcctgttt cctgagccct gaggagctgc    900
agagcctagt gccctgagt gatccaacgg ggccagtaga acgggggctg ctggaatgtg     960
cagccaatgg gaccctcagc ccagaaggac gggtggcata tgaacttctg ggtgtgttgc    1020
gctcatctgg aggagcggtg ctgagccccc gggagctgcg ggtctgggcc cctctcttct    1080
ctcagctggg cctccgcttc cttcaggagc tgtcagagcc ccagcttaga gccatgcttc    1140
ctgtcctcca gggaactagt gttacacctg ctcaggctgt cctgctgctt ggacggctcc    1200
ttcctaggca cgatctatcc ctggaggaac tctgctcctt gcaccttctg ctaccaggcc    1260 tcagcccca gacactccag gccatcccta ggcgagtcct ggtcggggct tgttcctgcc    1320
tggcccctga actgtcacgc ctctcagcct gccagaccgc agcactgctg cagacctttc    1380
gggttaaaga tggtgttaaa aatatgggta caacaggtgc tggtccagct gtgtgtatcc    1440
ctggtcagcc tattcccacc acctggccag actgcctgct tccctgctc ccattaaagc    1500 tgctacaact ggattccttg gctcttctgg caaatcgaag acgctactgg gagctgccct    1560
ggtctgagca gcaggcacag tttctctgga agaagatgca agtacccacc aaccttaccc    1620
tcaggaatct gcaggctctg gcaccctgg caggaggcat gtcctgtgag tttctgcagc    1680
agatcaactc catggtagac ttccttgaag tggtgcacat gatctatcag ctgcccacta    1740
```

```
gagttcgagg gagcctgagg gcctgtatct gggcagagct acagcggagg atggcaatgc   1800
cagaaccaga atggacaact gtagggccag aactgaacgg gctggatagc aagctactcc   1860
tggacttacc gatccagttg atggacagac tatccaatga atccattatg ttggtggtgg   1920
agctggtgca aagagctcca gagcagctgc tggcactgac cccctccac caggcagccc    1980 tggcagagag ggcactacaa aacctggctc caaaggagac tccagtctca ggggaagtgc   2040
tggagacctt aggcccttrg gttggattcc tggggacaga gagcacacga cagatccccc   2100
tacagatcct gctgtcccat ctcagtcagc tgcaaggctt ctgcctagga gagacatttg   2160
ccacagagct gggatggctg ctattgcagg agtctgttct tgggaaacca gagttgtgga   2220
gccaggatga agtagagcaa gctggacgcc tagtattcac tctgtctact gaggcaattt   2280
ccttgatccc cagggaggcc ttgggtccag agaccctgga gcggcttcta gaaaagcagc   2340
agagctggga gcagagcaga gttggacagc tgtgtaggga gccacagctt gctgccaaga   2400
aagcagccct ggtagcaggg gtggtgcgac cagctgctga ggatcttcca gaacctgtgc   2460
caaattgtgc agatgtacga gggacattcc cagcagcctg gtctgcaacc cagattgcag   2520
agatggagct ctcagacttt gaggactgcc tgacattatt tgcaggagac ccaggacttg   2580
ggcctgagga actgcgggca gccatgggca aagcaaaaca gttgtggggt cccccccggg   2640
gatttcgtcc tgagcagatc ctgcagcttg gtaggctctt aataggtcta ggagatcggg   2700
aactacagga gctgatccta gtggactggg gagtgctgag caccctgggg cagatagatg   2760
gctggagcac cactcagctc cgcattgtgg tctccagttt cctacggcag agtggtcggc   2820
atgtgagcca cctggacttc gttcatctga cagcgctggg ttatactctc tgtggactgc   2880
ggccagagga gctccagcac atcagcagtt gggagttcag ccaagcagct ctcttcctcg   2940
gcaccctgca tctccagtgc tctgaggaac aactggaggt tctggcccac ctacttgtac   3000
tgcctggtgg gtttggccca atcagtaact gggggcctga gatcttcact gaaattggca   3060
ccatagcagc tgggatccca gacctggctc tttcagcact gctgcgggga cagatccagg   3120
gcgttactcc tcttgccatt tctgtcatcc ctcctcctaa atttgctgtg gtgtttagtc   3180
ccatccaact atctagtctc accagtgctc aggctgtggc tgtcactcct gagcaaatgg   3240
cctttctgag tcctgagcag cgacgagcag ttgcatgggc ccaacatgag ggaaaggaga   3300
gcccagaaca gcaaggtcga agtacagcct ggggcctcca ggactggtca cgaccttcct   3360
ggtccctggt attgactatc agcttccttg gccacctgct aggctccgga gagggcagag   3420
gaagtctgct aacatgcggt gacgtcgagg agaatcctgg cccaatggag agcgacgaga   3480
gcggcctgcc cgccatggag atcgagtgcc gcatcaccgg caccctgaac ggcgtggagt   3540
tcgagctggt gggcggcgga gagggcaccc ccgagcaggg ccgcatgacc aacaagatga   3600
agagcaccaa aggcgccctg accttcagcc cctacctgct gagccacgtg atgggctacg   3660
gcttctacca cttcggcacc taccccagcg gctacgagaa ccccttcctg cacgccatca   3720
acaacggcgg ctacaccaac acccgcatcg agaagtacga ggacggcggc gtgctgcacg   3780
tgagcttcag ctaccgctac gaggccggcc gcgtgatcgg cgacttcaag gtgatgggca   3840
ccggcttccc cgaggacagc gtgatcttca ccgacaagat catccgcagc aacgccaccg   3900
tggagcacct gcacccatg ggcgataacg atctggatgg cagcttcacc cgcacctrca   3960
gcctgcgcga cggcggctac tacagctccg tggtggacag ccacatgcac ttcaagagcg   4020
ccatccaccc cagcatcctg cagaacgggg gccccatgtt cgccttccgc cgcgtggagg   4080
aggatcacag caacaccgag ctgggcatcg tggagtacca gcacgccttc aagacccccgg  4140
```

-continued

| | |
|---|---|
| atgcagatgc cggtgaagaa taagcctgtc tctacagtag aaggagattg tggggagaga | 4200 |
| aatcttaagt cataatgaat aaagtgcaaa cagaagtgca tcctgattat tttcagaagc | 4260 |
| tgatgaggaa taactagtgc tgatcagcct cgactgtgcc ttctagttgc cagccatctg | 4320 |
| ttgtttgccc ctcccccgtg ccttccttga ccctggaagg tgccactccc actgtccttt | 4380 |
| cctaataaaa tgaggaaatt gcatcgcatt gtctgagtag gtgtcattct attctggggg | 4440 |
| gtggggtggg gcaggacagc aaggggagg attgggaaga caatagcagg catgctgggg | 4500 |
| atgcggtggg ctctatggaa gcttgaattc agctgacgtg cctcggaccg ctaggaaccc | 4560 |
| ctagtgatga gttggccac tccctctctg cgcgctcgct cgctcactga ggccgggcga | 4620 |
| ccaaaggtcg cccgacgccc gggctttgcc cgggcggcct cagtgagcga gcgagcgcgc | 4680 |
| agctgcctgc agg | 4693 |

<210> SEQ ID NO 15
<211> LENGTH: 4619
<212> TYPE: DNA
<213> ORGANISM: Artificial Sequence
<220> FEATURE:
<223> OTHER INFORMATION: pITR-203

<400> SEQUENCE: 15

| | |
|---|---|
| cctgcaggca gctgcgcgct cgctcgctca ctgaggccgc ccgggcgtcg ggcgaccttt | 60 |
| ggtcgcccgg cctcagtgag cgagcgagcg cgcagagagg gagtggccaa ctccatcact | 120 |
| aggggttcct gcggccgcac gcgtagactt gcccaaaaac tctggcaaag ttgaattgct | 180 |
| tccaaaagtt caactttatc agaaggacct attccctacg gaaactagct gaaggtctcc | 240 |
| tggcactctg gatctcgtgg aagggagcct tcttcaggga acagagggag cgattaagtg | 300 |
| gtgaaaagca aacagacctg gaaaagttcc cttttctgaga gtagcaacag aaagctctgc | 360 |
| aaagactccc tccaagctat tggatcctct tgcttgggat aaccacttga gtactcagat | 420 |
| accaaaagaa gagtggaaat cccaagagaa gtcaccagaa aaacagctt ttaagaaaaa | 480 |
| ggatacactt ttgtccctga acgcttgtga aagcaatctg acaatagcag caattgaaaa | 540 |
| gggacaaaat aagcccgaaa tagaagtcac ctgggcaaag caaggtagga ctgaaaggct | 600 |
| gtgctctcaa aacccaccag tcttgaaacg cactcaacgg gtgactagat cccatatatg | 660 |
| gagttccgcg ttacataact tacggtaaat ggcccgcctg gctgaccgcc caacgacccc | 720 |
| cgcccattga cgtcaataat gacgtatgtt cccatagtaa cgccaatagg gactttccat | 780 |
| tgacgtcaat gggtggagta tttacggtaa actgcccact tggcagtaca tcaagtgtat | 840 |
| catatgccaa gtacgccccc tattgacgtc aatgacggta atggcccgc ctggcattat | 900 |
| gcccagtaca tgaccttatg ggactttcct acttggcagt acatctacgt attagtcatc | 960 |
| gctattacca tggtgatgcg gttttggtga tgcggttttg gcagtacatc aatgggcgtg | 1020 |
| gatagcggtt tgactcacgg ggatttccaa gtctccaccc cattgacgtc aatgggagtt | 1080 |
| tgttttggca ccaaaatcaa cgggactttc caaaatgtcg taacaactcc gccccattga | 1140 |
| cgcaaatggg cggtaggcgt gtacggtggg aggtctatat aagcagagct cgtttagtga | 1200 |
| accgtcaccg tggtgccct gccctcacct ggctatccca cacaggtgag aataaccaga | 1260 |
| actcacctcc ggtaccagtg ttcacttggc caccatggct ctcagcctct ggcccctgct | 1320 |
| gctgctgctg ctgctgctgc tgctgctgtc ctttgcagtg actctggccc ctactgggcc | 1380 |
| tcattccctg gaccctggtc tctccttcct gaagtcattg ctctccactc tggaccaggc | 1440 |

```
tccccagggc tccctgagcc gctcacggtt ctttacattc ctggccaaca tttcttcttc    1500
ctttgagcct gggagaatgg gggaaggacc agtaggagag cccccacctc tccagccgcc    1560
tgctctgcgg ctccatgatt ttctagtgac actgagaggt agccccgact gggagccaat    1620
gctagggctg ctaggggata tgctggcact gctgggacag gagcagactc cccgagattt    1680
cctggtgcac caggcagggg tgctgggtgg acttgtggag gtgctgctgg gagccttagt    1740
tcctgggggc cccctaccc caactcggcc cccatgcacc cgtgatgggc cgtctgactg    1800
tgtcctggct gctgactggt tgccttctct gctgctgttg ttagagggca cacgctggca    1860
agctctggtg caggtgcagc ccagtgtgga ccccaccaat gccacaggcc tcgatgggag    1920
ggaggcagct cctcactttt tgcagggtct gttgggtttg cttaccccaa caggggagct    1980
aggctccaag gaggctcttt ggggcggtct gctacgcaca gtgggggccc ccctctatgc    2040
tgcctttcag gaggggctgc tccgtgtcac tcactccttg caggatgagg tcttctccat    2100
tttggggcag ccagagcctg ataccaatgg gcagtgccag ggaggtaacc ttcaacagct    2160
gctcttatgg ggcgtccggc acaacctttc ctggatgtc caggcgctgg gctttctgtc    2220
tggatcacca cccccacccc ctgccctcct tcactgcctg agcacgggcg tgcctctgcc    2280
cagagcttct cagccgtcag cccacatcag cccacgccaa cggcgagcca tcactgtgga    2340
ggccctctgt gagaaccact taggcccagc accaccctac agcatttcca acttctccat    2400
ccacttgctc tgccagcaca ccaagcctgc cactccacag ccccatccca gcaccactgc    2460
catctgccag acagctgtgt ggtatgcagt gtcctgggca ccaggtgccc aaggctggct    2520
acaggcctgc cacgaccagt ttcctgatga gttttggat gcgatctgca gtaacctctc    2580
cttttcagcc ctgtctggct ccaaccgccg cctggtgaag cggctctgtg ctggcctgct    2640
cccacccccct accagctgcc ctgaaggcct gccccctgtt cccctcaccc cagacatctt    2700
ttggggctgc ttcttggaga atgagactct gtgggctgag cgactgtgtg gggaggcaag    2760
tctacaggct gtgcccccca gcaaccaggc ttgggtccag catgtgtgcc agggccccac    2820
cccagatgtc actgcctccc caccatgcca cattggaccc tgtggggaac gctgcccgga    2880
tgggggcagc ttcctggtga tggtctgtgc caatgacacc atgtatgagg tcctggtgcc    2940
cttctggcct tggctagcag gccaatgcag gataagtcgt gggggcaatg acacttgctt    3000
cctagaaggg ctgctgggcc cccttctgcc ctctctgcca ccactgggac catcccccact    3060
ctgtctgacc cctggccccct tcctccttgg catgctatcc cagttgccac gctgtcagtc    3120
ctctgtccca gctcttgctc accccacacg cctacactat ctcctccgcc tgctgacctt    3180
cctcttgggt ccaggggctg ggggcgctga ggcccagggg atgctgggtc gggccctact    3240
gctctccagt ctcccagaca actgctcctt ctgggatgcc tttcgcccag agggccggcg    3300
cagtgtgcta cggacgattg gggaataccct ggaacaagat gaggagcagc caaccccatc    3360
aggctttgaa cccactgtca accccagctc tggtataagc aagatggagc tgctggcctg    3420
ctttagtcct gtgctgtggg atctgctcca gagggaaaag agtgtttggg ccctgcagat    3480
tctagtgcag gtaagtatca aggttacaag acaggtttaa ggagaccaat agaaactggg    3540
cttgtcgaga cagagaagac tcttgcgttt ctctaggtgg aggccgaaag tacatgtttc    3600
gcatgggaac cccagaccct gagtacccag atgactacag ccaaggtggg accaggctgg    3660
acgggaagaa tctggtgcag gaatggctgg cgaagcgcca gggtgcccgg tatgtgtgga    3720
accgcactga gctcatgcag gcttccctgg accgtctgt gacccatctc atgggtctct    3780
ttgagcctgg agacatgaaa tacgagatcc accgagactc cacactggac ccctccctga    3840
```

```
tggagatgac agaggctgcc ctgcgcctgc tgagcaggaa cccccgcggc ttcttcctct    3900
tcgtggaggg tggtcgcatc gaccatggtc atcatgaaag cagggcttac cgggcactga    3960
ctgagacgat catgttcgac gacgccattg agagggcggg ccagctcacc agcgaggagg    4020
acacgctgag cctcgtcact gccgaccact cccacgtctt ctccttcgga ggctacccc     4080 tgcgagggag ctccatcttc gggctggccc ctggcaaggc ccgggacagg aaggcctaca    4140
cggtcctcct atacggaaac ggtccaggct atgtgctcaa ggacggcgcc cggccggatg    4200
ttaccgagag cgagagcggg agccccgagt atcggcagca gtcagcagtg ccctggacg     4260 aagagaccca cgcaggcgag gacgtggcgg tgttcgcgcg cggcccgcag gcgcacctgg    4320
ttcacggcgt gcaggagcag accttcatag cgcacgtcat ggccttcgcc gcctgcctgg    4380
agccctacac cgcctgcgac ctggcgcccc ccgccggcac caccgacgcc gcgcacccgg    4440
ggcgaagctt gaattcagct gacgtgcctc ggaccgctag gaaccccctag tgatggagtt   4500 ggccactccc tctctgcgcg ctcgctcgct cactgaggcc gggcgaccaa aggtcgcccg    4560
acgcccgggc tttgcccggg cggcctcagt gagcgagcga gcgcgcagct gcctgcagg     4619
```

<210> SEQ ID NO 16
<211> LENGTH: 4729
<212> TYPE: DNA
<213> ORGANISM: Artificial Sequence
<220> FEATURE:
<223> OTHER INFORMATION: pITR-204

<400> SEQUENCE: 16

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggccgcac gcgtctaggt ggaggccgaa agtacatgtt tcgcatggga    180
accccagacc ctgagtaccc agatgactac agccaaggtg ggaccaggct ggacgggaag    240
aatctggtgc aggaatggct ggcgaagcgc cagggtgccc ggtatgtgtg aaccgcact     300 gagctcatgc aggcttccct ggacccgtct gtgacccatc tcatgggtct ctttgagcct    360
ggagacatga aatacgagat ccaccgagac tccacactgg acccctccct gatggagatg    420
acagaggctg ccctgcgcct gctgagcagg aaccccgcg  gcttcttcct cttcgtggag    480
ggtggtcgca tcgaccatgg tcatcatgaa gcagggctt  accgggcact gactgagacg    540
atcatgttcg acgacgccat tgagagggcg ggccagctca ccagcgagga ggacacgctg    600
agcctcgtca ctgccgacca ctcccacgtc ttctccttcg gaggctaccc cctgcgaggg    660
agctccatct tcgggctggc ccctggcaag gcccgggaca ggaaggccta cacggtcctc    720
ctatacggaa acgtccagg  ctatgtgctc aaggacggcg cccggccgga tgttaccgag    780
agcgagagcg ggagccccga gtatcggcag cagtcagcag tgcccctgga cgaagagacc    840
cacgcaggcg aggacgtggc ggtgttcgcg cgcggcccgc aggcgcacct ggttcacggc    900
gtgcaggagc agaccttcat agcgcacgtc atggccttcg ccgcctgcct ggagccctac    960
accgcctgcg acctggcgcc cccgccggc  accaccgacg ccgcgcaccc ggggcggata    1020
ggcacctatt ggtcttactg acatccactt tgcctttctc tccacaggcg tacctgcata    1080 tgccccaga  aaacctccag cagctggtgc tttcagcaga gagggaggct gcacagggct    1140
tcctgacact catgctgcag gggaagctg  agggaagct  gcaggtacca ccatccgagg    1200
agcaggccct gggtcgcctg acagccctgc tgctccagcg gtacccacgc ctcacctccc    1260
```

```
agctcttcat tgacctgtca ccactcatcc ctttcttggc tgtctctgac ctgatgcgct    1320
tcccaccatc cctgttagcc aacgacagtg tcctggctgc catccgggat tacagcccag    1380
gaatgaggcc tgaacagaag gaggctctgg caaagcgact gctggcccct gaactgtttg    1440
gggaagtgcc tgcctggccc caggagctgc tgtgggcagt gctgcccctg ctcccccacc    1500
tccctctgga aacttttttg cagctcagcc ctcaccagat ccaggccctg aggatagct     1560 ggccagcagc aggtctgggg ccagggcatg cccgccatgt gctgcgcagc ctggtaaacc    1620
agagtgtcca ggatggtgag gagcaggtac gcaggcttgg gccctcgcc tgtttcctga     1680 gccctgagga gctgcagagc ctagtgcccc tgagtgatcc aacggggcca gtagaacggg    1740
ggctgctgga atgtgcagcc aatgggaccc tcagcccaga aggacgggtg gcatatgaac    1800
ttctgggtgt gttgcgctca tctggaggag cggtgctgag cccccgggag ctgcgggtct    1860
gggcccctct cttctctcag ctgggcctcc gcttccttca ggagctgtca gagccccagc    1920
ttagagccat gcttcctgtc ctccagggaa ctagtgttac acctgctcag gctgtcctgc    1980
tgcttggacg gctccttcct aggcacgatc tatccctgga ggaactctgc tccttgcacc    2040
ttctgctacc aggcctcagc ccccagacac tccaggccat ccctaggcga gtcctggtcg    2100
gggcttgttc ctgcctggcc cctgaactgt cacgcctctc agcctgccag accgcagcac    2160
tgctgcagac ctttcgggtt aaagatggtg ttaaaaatat gggtacaaca ggtgctggtc    2220
cagctgtgtg tatccctggt cagcctattc ccaccacctg gccagactgc ctgcttcccc    2280
tgctcccatt aaagctgcta caactggatt ccttggctct tctggcaaat cgaagacgct    2340
actgggagct gccctggtct gagcagcagg cacagtttct ctggaagaag atgcaagtac    2400
ccaccaacct taccctcagg aatctgcagg ctctgggcac cctggcagga ggcatgtcct    2460
gtgagtttct gcagcagatc aactccatgg tagacttcct tgaagtggtg cacatgatct    2520
atcagctgcc cactagagtt cgagggagcc tgagggcctg tatctgggca gagctacagc    2580
ggaggatggc aatgccagaa ccagaatgga caactgtagg gccagaactg aacgggctgg    2640
atagcaagct actcctggac ttaccgatcc agttgatgga cagactatcc aatgaatcca    2700
ttatgttggt ggtggagctg gtgcaaagag ctccagagca gctgctggca ctgaccccccc   2760 tccaccaggc agccctggca gagagggcac tacaaaacct ggctccaaag gagactccag    2820
tctcagggga agtgctggag accttaggcc ctttggttgg attcctgggg acagagagca    2880
cacgacagat cccccctacag atcctgctgt cccatctcag tcagctgcaa ggcttctgcc    2940
taggagagac atttgccaca gagctgggat ggctgctatt gcaggagtct gttcttggga    3000
aaccagagtt gtggagccag gatgaagtag agcaagctgg acgcctagta ttcactctgt    3060
ctactgagcg aatttccttg atccccaggg aggccttggg tccagagacc ctggagcggc    3120
ttctagaaaa gcagcagagc tgggagcaga gcagagttgg acagctgtgt agggagccac    3180
agcttgctgc caagaaagca gccctggtag caggggtggt gcgaccagct gctgaggatc    3240
ttccagaacc tgtgccaaat tgtgcagatg tacgagggac attcccagca gcctggtctg    3300
caacccagat tgcagagatg gagctctcag actttgagga ctgcctgaca ttatttgcag    3360
gagacccagg acttgggcct gaggaactgc gggcagccat gggcaaagca aaacagttgt    3420
ggggtccccc ccggggattt cgtcctgagc agatcctgca gcttggtagg ctcttaatag    3480
gtctaggaga tcgggaacta caggagctga tcctagtgga ctgggagtg ctgagcaccc     3540 tggggcagat agatgctgg agcaccactc agctccgcat tgtggtctcc agtttcctac     3600
ggcagagtgg tcggcatgtg agccacctgg acttcgttca tctgacagcg ctgggttata   3660
```

```
ctctctgtgg actgcggcca gaggagctcc agcacatcag cagttgggag ttcagccaag    3720
cagctctctt cctcggcacc ctgcatctcc agtgctctga ggaacaactg gaggttctgg    3780
cccacctact tgtactgcct ggtgggtttg gcccaatcag taactggggg cctgagatct    3840
tcactgaaat tggcaccata gcagctggga tcccagacct ggctctttca gcactgctgc    3900
ggggacagat ccagggcgtt actcctcttg ccatttctgt catccctcct cctaaatttg    3960
ctgtggtgtt tagtcccatc caactatcta gtctcaccag tgctcaggct gtggctgtca    4020
ctcctgagca aatggccttt ctgagtcctg agcagcgacg agcagttgca tgggcccaac    4080
atgagggaaa ggagagccca gaacagcaag gtcgaagtac agcctggggc ctccaggact    4140
ggtcacgacc ttcctggtcc ctggtattga ctatcagctt ccttggccac tgctatgag     4200 cctgtctcta cagtagaagg agattgtggg gagagaaatc ttaagtcata atgaataaag    4260
tgcaaacaga agtgcatcct gattattttc agaagctgat gaggaataac tagtgctgat    4320
cagcctcgac tgtgccttct agttgccagc catctgttgt ttgcccctcc ccgtgccttt    4380
ccttgaccct ggaaggtgcc actcccactg tcctttccta ataaaatgag gaaattgcat    4440
cgcattgtct gagtaggtgt cattctattc tggggggtgg ggtggggcag gacagcaagg    4500
gggaggattg ggaagacaat agcaggcatg ctggggatgc ggtgggctct atggaagctt    4560
gaattcagct gacgtgcctc ggaccgctag gaacccctag tgatggagtt ggccactccc    4620
tctctgcgcg ctcgctcgct cactgaggcc gggcgaccaa aggtcgcccg acgcccgggc    4680
tttgcccggg cggcctcagt gagcgagcga gcgcgcagct gcctgcagg              4729

<210> SEQ ID NO 17
<211> LENGTH: 4460
<212> TYPE: DNA
<213> ORGANISM: Artificial Sequence
<220> FEATURE:
<223> OTHER INFORMATION: pITR-205

<400> SEQUENCE: 17
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggccgcac gcgtgacatt gattattgac tagttattaa tagtaatcaa     180
ttacggggtc attagttcat agcccatata tggagttccg cgttacataa cttacggtaa     240
atggcccgcc tggctgaccg cccaacgacc cccgcccatt gacgtcaata atgacgtatg     300
ttcccatagt aacgccaata gggactttcc attgacgtca atgggtggac tatttacggt     360
aaactgccca cttggcagta catcaagtgt atcatatgcc aagtacgccc cctattgacg     420
tcaatgacgg taaatggccc gcctggcatt atgcccagta catgacctta tgggactttc     480
ctacttggca gtacatctac gtattagtca tcgctattac catgggtcga ggtgagcccc     540
acgttctgct tcactctccc catctccccc cctccccac cccaatttt gtatttattt      600 atttttaat tattttgtgc agcgatgggg gcgggggggg ggggggcgcg cgccaggcgg     660
ggcggggcgg ggcgagggc ggggcgggc gaggcggaga ggtgcggcgg cagccaatca      720
gagcggcgcg ctccgaaagt ttcctttat ggcgaggcg cggcggcggc ggccctataa      780
aaagcgaagc gcgcggcggg cgggagtcgc tgcgttgcct tcgccccgtg cccgctccg      840 cgccgcctcg cgccgcccgc cccggctctg actgaccgcg ttactcccac aggtgagcgg     900
gcgggacggc ccttctcctc cgggctgtaa ttagcgcttg gtttaatgac ggctcgtttc      960
```

```
tttctgtgg ctgcgtgaaa gccttaaagg gctccgggag ggccctttgt gcggggggga      1020
gcggctcggg gggtgcgtgc gtgtgtgtgt gcgtggggag cgccgcgtgc ggcccgcgct      1080
gcccggcggc tgtgagcgct gcgggcgcgg cgcggggctt tgtgcgctcc gcgtgtgcgc      1140
gaggggagcg cggccggggg cggtgccccg cggtgcgggg gggctgcgag gggaacaaag      1200
gctgcgtgcg gggtgtgtgc gtgggggggt gagcagggggg tgtgggcgcg gcggtcgggc     1260
tgtaaccccc ccctgcaccc ccctccccga gttgctgagc acggcccggc ttcgggtgcg      1320
gggctccgtg cggggcgtgg cgcggggctc gccgtgccgg gcgggggggtg gcggcaggtg    1380 ggggtgccgg gcggggcggg gccgcctcgg gccggggagg gctcggggga ggggcgcggc      1440 ggccccccgga gcgccggcgg ctgtcgaggc gcggcgagcc gcagccattg ccttttatgg    1500
taatcgtgcg agagggcgca gggacttcct ttgtcccaaa tctgtgcgga gccgaaatct      1560
gggaggcgcc gccgcacccc ctctagcggg cgcggggcga agcggtgcgg cgccggcagg     1620
aaggaaatgg gcggggaggg ccttcgtgcg tcgccgcgcc gccgtcccct tctccctctc     1680
cagcctcggg gctgtccgcg gggggacggc tgccttcggg ggggacgggg cagggcgggg    1740
ttcggcttct ggcgtgtgac cggcggctct agagcctctg ctaaccatgt tcatgccttc     1800 ttcttttttcc tacagctcct gggcaacgtg ctggttattg tgaccggtgg tgccctgccc    1860
tcacctggct atcccacaca ggtgagaata accagaactc acctccggta ccagtgttca     1920
cttggccacc atggctctca gcctctggcc cctgctgctg ctgctgctgc tgctgctgct     1980
gctgtccttt gcagtgactc tggcccctac tgggcctcat tccctggacc ctggtctctc     2040
cttcctgaag tcattgctct ccactctgga ccaggctccc cagggctccc tgagccgctc     2100
acggttcttt acattcctgg ccaacatttc ttcttccttt gagcctggga gaatggggga     2160
aggaccagta ggagagcccc cacctctcca gccgcctgct ctgcggctcc atgattttct     2220
agtgacactg agaggtagcc ccgactggga gccaatgcta gggctgctag gggatatgct     2280
ggcactgctg ggacaggagc agactccccg agatttcctg gtgcaccagg caggggtgct     2340
gggtggactt gtggaggtgc tgctgggagc cttagttcct gggggccccc ctaccccaac     2400
tcggccccca tgcacccgtg atgggccgtc tgactgtgtc ctggctgctg actggttgcc     2460
ttctctgctg ctgttgttag agggcacacg ctggcaagct ctggtgcagg tgcagcccag     2520
tgtggacccc accaatgcca caggcctcga tgggagggag gcagctcctc acttttttgca    2580 gggtctgttg ggtttgctta ccccaacagg ggagctaggc tccaaggagg ctctttgggg    2640
cggtctgcta cgcacagtgg gggccccccct ctatgctgcc tttcaggagg ggctgctccg    2700
tgtcactcac tccttgcagg atgaggtctt ctccattttg gggcagccag agcctgatac     2760
caatgggcag tgccagggag gtaaccttca acagctgctc ttatgggcg tccggcacaa     2820 cctttcctgg gatgtccagg cgctgggctt tctgtctgga tcaccacccc caccccctgc    2880
cctccttcac tgcctgagca cgggcgtgcc tctgcccaga gcttctcagc cgtcagccca     2940
catcagccca cgccaacggc gagccatcac tgtggaggcc ctctgtgaga accacttagg   3000
cccagcacca ccctacagca tttccaactt ctccatccac ttgctctgcc agcacaccaa     3060
gcctgccact ccacagcccc atcccagcac cactgccatc tgccagacag ctgtgtggta     3120
tgcagtgtcc tgggcaccag gtgcccaagg ctggctacag gctgccacg accagtttcc    3180 tgatgagttt ttggatgcga tctgcagtaa cctctccttt tcagccctgt ctggctccaa     3240
ccgccgcctg gtgaagcggc tctgtgctgg cctgctccca cccctacca gctgccctga    3300 aggcctgccc cctgttcccc tcaccccaga catctttttgg ggctgcttct tggagaatga    3360
```

```
gactctgtgg gctgagcgac tgtgtgggga ggcaagtcta caggctgtgc ccccagcaa   3420 ccaggcttgg gtccagcatg tgtgccaggg ccccacccca gatgtcactg cctccccacc   3480
atgccacatt ggaccctgtg gggaacgctg cccggatggg ggcagcttcc tggtgatggt   3540
ctgtgccaat gacaccatgt atgaggtcct ggtgccttc tggccttggc tagcaggcca    3600
atgcaggata agtcgtgggg gcaatgacac ttgcttccta aagggctgc tgggcccct    3660 tctgccctct ctgccaccac tgggaccatc cccactctgt ctgaccctg gcccttcct    3720 ccttggcatg ctatcccagt tgccacgctg tcagtcctct gtcccagctc ttgctcaccc   3780
cacacgccta cactatctcc tccgcctgct gaccttcctc ttgggtccag gggctggggg   3840
cgctgaggcc caggggatgc tgggtcgggc cctactgctc tccagtctcc cagacaactg   3900
ctccttctgg gatgcctttc gcccagaggg ccggcgcagt gtgctacgga cgattgggga   3960
atacctggaa caagatgagg agcagccaac cccatcaggc tttgaaccca ctgtcaaccc   4020
cagctctggt ataagcaaga tggagctgct ggcctgcttt agtcctgtgc tgtgggatct   4080
gctccagagg gaaaagagtg tttgggccct gcagattcta gtgcaggtaa gtatcaaggt   4140
tacaagacag gtttaaggag accaatagaa actgggcttg tcgagacaga gaagactctt   4200
gcgtttctgg gattttgccg atttcggcct attggttaaa aaatgagctg atttaacaaa   4260
aatttaacgc gaattttaac aaaataagct tgaattcagc tgacgtgcct cggaccgcta   4320 ggaacccccta gtgatggagt tggccactcc ctctctgcgc gctcgctcgc tcactgaggc   4380
cgggcgacca aggtcgccc gacgcccggg ctttgcccgg cggcctcag tgagcgagcg   4440 agcgcgcagc tgcctgcagg                                               4460

<210> SEQ ID NO 18
<211> LENGTH: 130
<212> TYPE: DNA
<213> ORGANISM: Artificial Sequence
<220> FEATURE:
<223> OTHER INFORMATION: 5' ITR

<400> SEQUENCE: 18
cctgcaggca gctgcgcgct cgctcgctca ctgaggccgc ccgggcgtcg gcgacctttt    60
ggtcgcccgg cctcagtgag cgagcgagcg cgcagagagg gagtggccaa ctccatcact   120
aggggttcct                                                          130

<210> SEQ ID NO 19
<211> LENGTH: 1000
<212> TYPE: DNA
<213> ORGANISM: Artificial Sequence
<220> FEATURE:
<223> OTHER INFORMATION: 5' FVIII stuffer_1000

<400> SEQUENCE: 19
agacttgccc aaaaactctg gcaaagttga attgcttcca aaagttcaac tttatcagaa    60
ggacctattc cctacggaaa ctagctgaag gtctcctggc actctggatc tcgtggaagg   120
gagccttctt cagggaacag agggagcgat taagtggtga aaagcaaaca gacctggaaa   180
agttcccttt ctgagagtag caacagaaag ctctgcaaag actccctcca agctattgga   240
tcctcttgct tgggataacc acttgagtac tcagatacca aagaagagt ggaaatccca    300 agagaagtca ccagaaaaaa cagctttta gaaaaaggat acacttttgt ccctgaacgc   360
ttgtgaaagc aatctgacaa tagcagcaat tgaaagggga caaataagc ccgaaataga   420
```

```
agtcacctgg gcaaagcaag gtaggactga aaggctgtgc tctcaaaacc caccagtctt        480
gaaacgcact caacgggtga aagtagtagg aaagggtgaa tttacaaagg acgtaggact        540
caaagagtga gttttccaa gcagcagaaa cctatttctt actaacttgg ataatttact         600 gaaaataat acacacaatc aagaaaaaaa aattcaggaa gaaatagaaa agaaggaaaa         660
cttaatccaa gagtgaatag ttttgcctca gataactaca gtgactggca ctaagaattt        720
ctgaaagaac cttttcttac tgagcactag gctgaaaata gaaggttact tgaacgggga        780
cttgactcca gtacttcaag attttaggta ctttgaaaat tcaacaaata gaacaaagaa        840
acacacagct actttctcaa aaaaaggggga ggaagaaaac ttggaaggct tgggaaatca      900
aaccaagcaa attgtagaga aattgactga caccacaagg atatctccta atacaagcca       960
gcagaatttt gtcacgcaac gtagtaagag agctttgaaa                            1000

<210> SEQ ID NO 20
<211> LENGTH: 342
<212> TYPE: DNA
<213> ORGANISM: Artificial Sequence
<220> FEATURE:
<223> OTHER INFORMATION: CMV enhancer

<400> SEQUENCE: 20
ctagatccca tatatggagt tccgcgttac ataacttacg gtaaatggcc cgcctggctg         60
accgcccaac gacccccgcc cattgacgtc aataatgacg tatgttccca tagtaacgcc       120
aatagggact ttccattgac gtcaatgggt ggagtattta cggtaaactg cccacttggc       180
agtacatcaa gtgtatcata tgccaagtac gccccctatt gacgtcaatg acggtaaatg       240
gcccgcctgg cattatgccc agtacatgac cttatgggac tttcctactt ggcagtacat       300
ctacgtatta gtcatcgcta ttaccatggt gatgcggttt tg                          342

<210> SEQ ID NO 21
<211> LENGTH: 219
<212> TYPE: DNA
<213> ORGANISM: Artificial Sequence
<220> FEATURE:
<223> OTHER INFORMATION: CMV promoter

<400> SEQUENCE: 21
gtgatgcggt tttggcagta catcaatggg cgtggatagc ggtttgactc acggggattt         60
ccaagtctcc accccattga cgtcaatggg agtttgtttt ggcaccaaaa tcaacgggac       120
tttccaaaat gtcgtaacaa ctccgcccca ttgacgcaaa tgggcggtag gcgtgtacgg       180
tgggaggtct atataagcag agctcgttta gtgaaccgt                              219

<210> SEQ ID NO 22
<211> LENGTH: 276
<212> TYPE: DNA
<213> ORGANISM: Artificial Sequence
<220> FEATURE:
<223> OTHER INFORMATION: CBA promoter

<400> SEQUENCE: 22
tcgaggtgag ccccacgttc tgcttcactc tccccatctc ccccccctcc ccacccccaa         60
ttttgtattt atttattttt taattatttt gtgcagcgat ggggggcgggg ggggggggg       120 cgcgcgccag gcggggcggg gcggggcgag ggcggggcg gggcgaggcg gagaggtgcg        180
gcggcagcca atcagagcgg cgcgctccga aagtttcctt ttatggcgag gcggcggcg        240 cggcggccct ataaaaagcg aagcgcgcgg cgggcg                                276
```

<210> SEQ ID NO 23
<211> LENGTH: 1013
<212> TYPE: DNA
<213> ORGANISM: Artificial Sequence
<220> FEATURE:
<223> OTHER INFORMATION: Chimeric intron

<400> SEQUENCE: 23

| | |
|---|---|
| ggagtcgctg cgttgccttc gccccgtgcc ccgctccgcg ccgcctcgcg ccgcccgccc | 60 |
| cggctctgac tgaccgcgtt actcccacag gtgagcgggc gggacggccc ttctcctccg | 120 |
| ggctgtaatt agcgcttggt ttaatgacgg ctcgtttctt ttctgtggct gcgtgaaagc | 180 |
| cttaaagggc tccgggaggg ccctttgtgc gggggggagc ggctcggggg gtgcgtgcgt | 240 |
| gtgtgtgtgc gtggggagcg ccgcgtgcgg ccgcgctgc ccggcggctg tgagcgctgc | 300 |
| gggcgcggcg cggggctttg tgcgctccgc gtgtgcgcga ggggagcgcg gccggggggcg | 360 |
| gtgccccgcg gtgcggggg gctgcgaggg gaacaaaggc tgcgtgcggg gtgtgtgcgt | 420 |
| ggggggggtga gcaggggtg tgggcgcggc ggtcggctg taaccccccc ctgcacccc | 480 |
| ctccccgagt tgctgagcac ggcccggctt cgggtgcggg gctccgtgcg gggcgtggcg | 540 |
| cggggctcgc cgtgccgggc gggggtggc ggcaggtggg ggtgccgggc ggggcggggc | 600 |
| cgcctcgggc cggggagggc tcgggggagg gcgcggcgg ccccggagc gccggcggct | 660 |
| gtcgaggcgc ggcgagccgc agccattgcc ttttatggta atcgtgcgag agggcgcagg | 720 |
| gacttccttt gtcccaaatc tgtgcggagc cgaaatctgg gaggcgccgc cgcacccct | 780 |
| ctagcgggcg cggggcgaag cggtgcggcg ccggcaggaa ggaaatgggc ggggagggcc | 840 |
| ttcgtgcgtc gccgcgccgc cgtcccttc tccctctcca gcctcgggc tgtccgcggg | 900 |
| gggacggctg ccttcggggg ggacggggca gggcggggtt cggcttctgg cgtgtgaccg | 960 |
| gcggctctag agcctctgct aaccatgttc atgccttctt cttttttccta cag | 1013 |

<210> SEQ ID NO 24
<211> LENGTH: 73
<212> TYPE: DNA
<213> ORGANISM: Artificial Sequence
<220> FEATURE:
<223> OTHER INFORMATION: 5' UTR

<400> SEQUENCE: 24

| | |
|---|---|
| gccctgccct cacctggcta tcccacacag gtgagaataa ccagaactca cctccggtac | 60 |
| cagtgttcac ttg | 73 |

<210> SEQ ID NO 25
<211> LENGTH: 2196
<212> TYPE: DNA
<213> ORGANISM: Artificial Sequence
<220> FEATURE:
<223> OTHER INFORMATION: 5' STRC

<400> SEQUENCE: 25

| | |
|---|---|
| atggctctca gcctctggcc cctgctgctg ctgctgctgc tgctgctgct gctgtcctt | 60 |
| gcagtgactc tggcccctac tgggcctcat tccctgacc ctggtctctc cttcctgaag | 120 |
| tcattgctct ccactctgga ccaggctccc cagggctccc tgagccgctc acggttcttt | 180 |
| acattcctgg ccaacatttc ttcttccttt gagcctggga gaatggggga aggaccagta | 240 |
| ggagagcccc cacctctcca gccgcctgct ctgcggctcc atgattttct agtgacactg | 300 |

```
agaggtagcc ccgactggga gccaatgcta gggctgctag gggatatgct ggcactgctg    360
ggacaggagc agactcccg agatttcctg gtgcaccagg cagggggtgct gggtggactt    420 gtggaggtgc tgctgggagc cttagttcct gggggccccc ctaccccaac tcggccccca    480
tgcacccgtg atgggccgtc tgactgtgtc ctggctgctg actggttgcc ttctctgctg    540
ctgttgttag agggcacacg ctggcaagct ctggtgcagg tgcagcccag tgtggacccc    600
accaatgcca caggcctcga tgggagggag gcagctcctc acttttttgca gggtctgttg    660 ggtttgctta ccccaacagg ggagctaggc tccaaggagg ctctttgggg cggtctgcta    720
cgcacagtgg gggccccccct ctatgctgcc tttcaggagg ggctgctccg tgtcactcac    780
tccttgcagg atgaggtctt ctccattttg gggcagccag agcctgatac caatgggcag    840
tgccagggag gtaaccttca acagctgctc ttatggggcg tccggcacaa cctttcctgg    900
gatgtccagg cgctgggctt tctgtctgga tcaccacccc cacccccctgc cctccttcac    960 tgcctgagca cgggcgtgcc tctgcccaga gcttctcagc cgtcagccca catcagccca    1020
cgccaacggc gagccatcac tgtggaggcc ctctgtgaga accacttagg cccagcacca    1080
ccctacagca tttccaactt ctccatccac ttgctctgcc agcacaccaa gcctgccact    1140
ccacagcccc atcccagcac cactgccatc tgccagacag ctgtgtggta tgcagtgtcc    1200
tgggcaccag gtgcccaagg ctggctacag gcctgccacg accagtttcc tgatgagttt    1260
ttggatgcga tctgcagtaa cctctccttt tcagccctgt ctggctccaa ccgccgcctg    1320
gtgaagcggc tctgtgctgg cctgctccca cccctacca gctgccctga aggcctgccc    1380
cctgttcccc tcaccccaga catcttttgg ggctgcttct tggagaatga gactctgtgg    1440
gctgagcgac tgtgtgggga ggcaagtcta caggctgtgc cccccagcaa ccaggcttgg    1500
gtccagcatg tgtgccaggg ccccaccccca gatgtcactg cctccccacc atgccacatt    1560
ggaccctgtg gggaacgctg cccggatggg ggcagcttcc tggtgatggt ctgtgccaat    1620
gacaccatgt atgaggtcct ggtgcccttc tggccttggc tagcaggcca atgcaggata    1680
agtcgtgggg gcaatgacac ttgcttccta gaagggctgc tgggccccct tctgccctct    1740
ctgccaccac tgggaccatc cccactctgt ctgacccctg gccccttcct ccttggcatg    1800
ctatcccagt tgccacgctg tcagtcctct gtcccagctc ttgctcaccc cacacgccta    1860
cactatctcc tccgcctgct gaccttcctc ttgggtccag gggctggggg cgctgaggcc    1920
caggggatgc tgggtcgggc cctactgctc tccagtctcc cagacaactg ctccttctgg    1980
gatgcctttc gcccagaggg ccggcgcagt gtgctacgga cgattgggga atacctggaa    2040
caagatgagg agcagccaac cccatcaggc tttgaaccca ctgtcaaccc cagctctggt    2100
ataagcaaga tggagctgct ggcctgcttt agtcctgtgc tgtgggatct gctccagagg    2160
gaaaagagtg tttgggccct gcagattcta gtgcag                              2196
```

<210> SEQ ID NO 26
<211> LENGTH: 77
<212> TYPE: DNA
<213> ORGANISM: Artificial Sequence
<220> FEATURE:
<223> OTHER INFORMATION: AK sequence

<400> SEQUENCE: 26

```
gggattttgc cgatttcggc ctattggtta aaaatgagc tgatttaaca aaaatttaac     60
gcgaatttta acaaaat                                                    77
```

<210> SEQ ID NO 27
<211> LENGTH: 872
<212> TYPE: DNA
<213> ORGANISM: Artificial Sequence
<220> FEATURE:
<223> OTHER INFORMATION: AP sequence

<400> SEQUENCE: 27

```
ctaggtggag gccgaaagta catgtttcgc atgggaaccc cagaccctga gtacccagat      60
gactacagcc aaggtgggac caggctggac gggaagaatc tggtgcagga atggctggcg     120
aagcgccagg gtgcccggta tgtgtggaac cgcactgagc tcatgcaggc ttccctggac     180
ccgtctgtga cccatctcat gggtctcttt gagcctggag acatgaaata cgagatccac     240
cgagactcca cactggaccc ctccctgatg gagatgacag aggctgccct gcgcctgctg     300
agcaggaacc cccgcggctt cttcctcttc gtggagggtg gtcgcatcga ccatggtcat     360
catgaaagca gggcttaccg ggcactgact gagacgatca tgttcgacga cgccattgag     420
agggcgggcc agctcaccag cgaggaggac acgctgagcc tcgtcactgc cgaccactcc     480
cacgtcttct ccttcggagg ctaccccctg cgagggagct ccatcttcgg gctggcccct     540
ggcaaggccc gggacaggaa ggcctacacg gtcctcctat acggaaacgg tccaggctat     600
gtgctcaagg acggcgcccg gccggatgtt accgagagcg agagcgggag ccccgagtat     660
cggcagcagt cagcagtgcc cctggacgaa gagacccacg caggcgagga cgtggcggtg     720
ttcgcgcgcg gcccgcaggc gcacctggtt cacggcgtgc aggagcagac cttcatagcg     780
cacgtcatgg ccttcgccgc ctgcctggag ccctacaccg cctgcgacct ggcgcccccc     840
gccggcacca ccgacgccgc gcacccgggg cg                                    872
```

<210> SEQ ID NO 28
<211> LENGTH: 3129
<212> TYPE: DNA
<213> ORGANISM: Artificial Sequence
<220> FEATURE:
<223> OTHER INFORMATION: 3' STRC

<400> SEQUENCE: 28

```
gcgtacctgc atatgccccc agaaaacctc cagcagctgg tgctttcagc agagagggag      60
gctgcacagg gcttcctgac actcatgctg caggggaagc tgcagggaa gctgcaggta     120 ccaccatccg aggagcaggc cctgggtcgc ctgacagccc tgctgctcca gcggtaccca     180
cgcctcacct cccagctctt cattgacctg tcaccactca tccctttctt ggctgtctct     240
gacctgatgc gcttcccacc atccctgtta gccaacgaca gtgtcctggc tgccatccgg     300
gattacagcc aggaatgag gcctgaacag aaggaggctc tggcaaagcg actgctggcc     360
cctgaactgt ttggggaagt gcctgcctgg ccccaggagc tgctgtgggc agtgctgccc     420
ctgctccccc acctccctct ggagaacttt ttgcagctca gccctcacca gatccaggcc     480
ctggaggata gctggccagc agcaggtctg ggccagggc atgcccgcca tgtgctgcgc     540
agcctggtaa accagagtgt ccaggatggt gaggagcagg tacgcaggct tgggcccctc     600
gcctgtttcc tgagccctga ggagctgcag agcctagtgc ccctgagtga tccaacgggg     660
ccagtagaac gggggctgct ggaatgtgca gccaatggga ccctcagccc agaaggacgg     720
gtggcatatg aacttctggg tgtgttgcgc tcatctggag agcggtgct gagccccgg     780 gagctgcggg tctgggcccc tctcttctct cagctgggcc tccgcttcct tcaggagctg     840
tcagagcccc agcttagagc catgcttcct gtcctccagg gaactagtgt tacacctgct     900
```

```
caggctgtcc tgctgcttgg acggctcctt cctaggcacg atctatccct ggaggaactc    960
tgctccttgc accttctgct accaggcctc agcccccaga cactccaggc catccctagg   1020
cgagtcctgg tcggggcttg ttcctgcctg cccctgaac tgtcacgcct ctcagcctgc    1080
cagaccgcag cactgctgca gacctttcgg gttaaagatg gtgttaaaaa tatgggtaca   1140
acaggtgctg gtccagctgt gtgtatccct ggtcagccta ttcccaccac ctggccagac   1200
tgcctgcttc ccctgctccc attaaagctg ctacaactgg attccttggc tcttctggca   1260
aatcgaagac gctactggga gctgccctgg tctgagcagc aggcacagtt tctctggaag   1320
aagatgcaag tacccaccaa ccttaccctc aggaatctgc aggctctggg caccctggca   1380
ggaggcatgt cctgtgagtt tctgcagcag atcaactcca tggtagactt ccttgaagtg   1440
gtgcacatga tctatcagct gcccactaga gttcgaggga gcctgagggc ctgtatctgg   1500
gcagagctac agcggaggat ggcaatgcca gaaccagaat ggacaactgt agggccagaa   1560
ctgaacgggc tggatagcaa gctactcctg gacttaccga tccagttgat ggacagacta   1620
tccaatgaat ccattatgtt ggtggtggag ctggtgcaaa gagctccaga gcagctgctg   1680
gcactgaccc ccctccacca ggcagccctg gcagagaggg cactacaaaa cctggctcca   1740
aaggagactc cagtctcagg ggaagtgctg gagaccttag gccctttggt tggattcctg   1800
gggacagaga gcacacgaca gatccccta cagatcctgc tgtcccatct cagtcagctg    1860
caaggcttct gcctaggaga gacatttgcc acagagctgg gatggctgct attgcaggag   1920
tctgttcttg ggaaaccaga gttgtggagc caggatgaag tagagcaagc tggacgccta   1980
gtattcactc tgtctactga ggcaatttcc ttgatcccca gggaggcctt gggtccagag   2040
accctggagc ggcttctaga aaagcagcag agctgggagc agagcagagt tggacagctg   2100
tgtagggagc cacagcttgc tgccaagaaa gcagccctgg tagcaggggt ggtgcgacca   2160
gctgctgagg atcttccaga acctgtgcca aattgtgcag atgtacgagg acattccca   2220
gcagcctggt ctgcaaccca gattgcagag atggagctct cagactttga ggactgcctg   2280
acattatttg caggagaccc aggacttggg cctgaggaac tgcgggcagc catgggcaaa   2340
gcaaaacagt tgtggggtcc cccccgggga tttcgtcctg agcagatcct gcagcttggt   2400
aggctcttaa taggtctagg agatcgggaa ctacaggagc tgatcctagt ggactgggga   2460
gtgctgagca ccctggggca gatagatggc tggagcacca ctcagctccg cattgtggtc   2520
tccagtttcc tacggcagag tggtcggcat gtgagccacc tggacttcgt tcatctgaca   2580
gcgctgggtt atactctctg tggactgcgg ccagaggagc tccagcacat cagcagttgg   2640
gagttcagcc aagcagctct cttcctcggc accctgcatc tccagtgctc tgaggaacaa   2700
ctggaggttc tggcccacct acttgtactg cctggtgggt ttggcccaat cagtaactgg   2760
gggcctgaga tcttcactga aattggcacc atagcagctg ggatcccaga cctggctctt   2820
tcagcactgc tgcggggaca gatccagggc gttactcctc ttgccatttc tgtcatccct   2880
cctcctaaat ttgctgtggt gtttagtccc atccaactat ctagtctcac cagtgctcag   2940
gctgtggctg tcactcctga gcaaatggcc tttctgagtc ctgagcagcg acgagcagtt   3000
gcatgggccc aacatgaggg aaaggagagc ccagaacagc aaggtcgaag tacagcctgg   3060
ggcctccagg actggtcacg accttcctgg tccctggtat tgactatcag cttccttggc   3120
cacctgcta                                                           3129
```

<210> SEQ ID NO 29
<211> LENGTH: 54

```
<212> TYPE: DNA
<213> ORGANISM: Artificial Sequence
<220> FEATURE:
<223> OTHER INFORMATION: T2A sequence

<400> SEQUENCE: 29
gagggcagag gaagtctgct aacatgcggt gacgtcgagg agaatcctgg ccca        54

<210> SEQ ID NO 30
<211> LENGTH: 21
<212> TYPE: PRT
<213> ORGANISM: Artificial Sequence
<220> FEATURE:
<223> OTHER INFORMATION: T2A sequence

<400> SEQUENCE: 30

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 31
<211> LENGTH: 696
<212> TYPE: DNA
<213> ORGANISM: Artificial Sequence
<220> FEATURE:
<223> OTHER INFORMATION: tGFP

<400> SEQUENCE: 31
atggagagcg acgagagcgg cctgcccgcc atggagatcg agtgccgcat caccggcacc       60
ctgaacggcg tggagttcga gctggtgggc ggcggagagg gcaccccga gcagggccgc      120 atgaccaaca agatgaagag caccaaaggc gccctgacct tcagccccta cctgctgagc      180
cacgtgatgg gctacggctt ctaccacttc ggcacctacc ccagcggcta cgagaacccc      240
ttcctgcacg ccatcaacaa cggcggctac accaacaccc gcatcgagaa gtacgaggac      300
ggcggcgtgc tgcacgtgag cttcagctac cgctacgagg ccggccgcgt gatcggcgac      360
ttcaaggtga tgggcaccgg cttccccgag gacagcgtga tcttcaccga caagatcatc      420
cgcagcaacg ccaccgtgga gcacctgcac cccatgggcg ataacgatct ggatggcagc      480
ttcacccgca ccttcagcct gcgcgacggc ggctactaca gctccgtggt ggacagccac      540
atgcacttca gagcgccat ccaccccagc atcctgcaga acgggggccc catgttcgcc       600
ttccgccgcg tggaggagga tcacagcaac accgagctgg gcatcgtgga gtaccagcac      660
gccttcaaga ccccggatgc agatgccggt gaagaa                                696

<210> SEQ ID NO 32
<211> LENGTH: 232
<212> TYPE: PRT
<213> ORGANISM: Artificial Sequence
<220> FEATURE:
<223> OTHER INFORMATION: tGFP

<400> SEQUENCE: 32

Met Glu Ser Asp Glu Ser Gly Leu Pro Ala Met Glu Ile Glu Cys Arg
1               5                   10                  15

Ile Thr Gly Thr Leu Asn Gly Val Glu Phe Glu Leu Val Gly Gly Gly
            20                  25                  30

Glu Gly Thr Pro Glu Gln Gly Arg Met Thr Asn Lys Met Lys Ser Thr
        35                  40                  45

Lys Gly Ala Leu Thr Phe Ser Pro Tyr Leu Leu Ser His Val Met Gly
```

```
                     50                  55                  60
Tyr Gly Phe Tyr His Phe Gly Thr Tyr Pro Ser Gly Tyr Glu Asn Pro
 65                  70                  75                  80

Phe Leu His Ala Ile Asn Asn Gly Gly Tyr Thr Asn Thr Arg Ile Glu
                 85                  90                  95

Lys Tyr Glu Asp Gly Gly Val Leu His Val Ser Phe Ser Tyr Arg Tyr
            100                 105                 110

Glu Ala Gly Arg Val Ile Gly Asp Phe Lys Val Met Gly Thr Gly Phe
        115                 120                 125

Pro Glu Asp Ser Val Ile Phe Thr Asp Lys Ile Ile Arg Ser Asn Ala
    130                 135                 140

Thr Val Glu His Leu His Pro Met Gly Asp Asn Asp Leu Asp Gly Ser
145                 150                 155                 160

Phe Thr Arg Thr Phe Ser Leu Arg Asp Gly Tyr Tyr Ser Ser Val
                165                 170                 175

Val Asp Ser His Met His Phe Lys Ser Ala Ile His Pro Ser Ile Leu
            180                 185                 190

Gln Asn Gly Gly Pro Met Phe Ala Phe Arg Arg Val Glu Glu Asp His
        195                 200                 205

Ser Asn Thr Glu Leu Gly Ile Val Glu Tyr Gln His Ala Phe Lys Thr
    210                 215                 220

Pro Asp Ala Asp Ala Gly Glu Glu
225                 230

<210> SEQ ID NO 33
<211> LENGTH: 109
<212> TYPE: DNA
<213> ORGANISM: Artificial Sequence
<220> FEATURE:
<223> OTHER INFORMATION: 3' UTR

<400> SEQUENCE: 33
gcctgtctct acagtagaag gagattgtgg ggagagaaat cttaagtcat aatgaataaa     60
gtgcaaacag aagtgcatcc tgattatttt cagaagctga tgaggaata              109

<210> SEQ ID NO 34
<211> LENGTH: 240
<212> TYPE: DNA
<213> ORGANISM: Artificial Sequence
<220> FEATURE:
<223> OTHER INFORMATION: bGHpA

<400> SEQUENCE: 34
gctgatcagc ctcgactgtg ccttctagtt gccagccatc tgttgtttgc ccctcccccg     60
tgccttcctt gaccctggaa ggtgccactc ccactgtcct ttcctaataa atgaggaaa    120 ttgcatcgca ttgtctgagt aggtgtcatt ctattctggg gggtggggtg gggcaggaca   180
gcaaggggga ggattgggaa gacaatagca ggcatgctgg gatgcggtg ggctctatgg    240

<210> SEQ ID NO 35
<211> LENGTH: 500
<212> TYPE: DNA
<213> ORGANISM: Artificial Sequence
<220> FEATURE:
<223> OTHER INFORMATION: 3' FVIII stuffer

<400> SEQUENCE: 35
caattcagac tcccactaga agaaacagaa cttgaaaaaa ggataattgt ggtgaacacc     60
```

```
tcaacccagt ggtccaaaaa ctgaaaaact ttgaccccga gcaccctcac acagatagac    120
tactgaaaga aggagaaagg ggcacttact cagtctccct tatcagattg ccttacgagg    180
agtactagac tccctcaagc aaatagatct cacttaccac ttgcaaaggt atactacttt    240
cactctatta gacctatata tctgaccagg gtcctattcc aagacaactc ttctactctt    300
ccagcagact cttatagaaa gaaagattct ggggtccaag aaagcagtac tttcttacaa    360
ggagccaaaa aaaataacct ttctttagca cttctaacct tggagtgaac tggtgatcaa    420
agagaggttg gctccctggg gacaagtgcc acaaattcag tcaactacaa gaaagttgag    480
aacactgttc tcccgaaacc                                                500
```

<210> SEQ ID NO 36
<211> LENGTH: 141
<212> TYPE: DNA
<213> ORGANISM: Artificial Sequence
<220> FEATURE:
<223> OTHER INFORMATION: 3' ITR

<400> SEQUENCE: 36

```
aggaacccct agtgatggag ttggccactc cctctctgcg cgctcgctcg ctcactgagg     60
ccgggcgacc aaaggtcgcc cgacgcccgg gctttgcccg ggcggcctca gtgagcgagc    120
gagcgcgcag ctgcctgcag g                                              141
```

<210> SEQ ID NO 37
<211> LENGTH: 500
<212> TYPE: DNA
<213> ORGANISM: Artificial Sequence
<220> FEATURE:
<223> OTHER INFORMATION: 5' FVIII stuffer_500

<400> SEQUENCE: 37

```
agacttgccc aaaaactctg gcaaagttga attgcttcca aaagttcaac tttatcagaa     60
ggacctattc cctacggaaa ctagctgaag gtctcctggc actctggatc tcgtggaagg    120
gagccttctt cagggaacag agggagcgat taagtggtga aaagcaaaca gacctggaaa    180
agttcccttt ctgagagtag caacagaaag ctctgcaaag actccctcca agctattgga    240
tcctcttgct tgggataacc acttgagtac tcagatacca aaagaagagt ggaaatccca    300
agagaagtca ccagaaaaaa cagcttttaa gaaaaaggat acacttttgt ccctgaacgc    360
ttgtgaaagc aatctgacaa tagcagcaat tgaaaaggga caaaataagc ccgaaataga    420
agtcacctgg gcaaagcaag gtaggactga aaggctgtgc tctcaaaacc caccagtctt    480
gaaacgcact caacgggtga                                                500
```

<210> SEQ ID NO 38
<211> LENGTH: 17
<212> TYPE: DNA
<213> ORGANISM: Pan troglodytes

<400> SEQUENCE: 38

```
aaataaaata cgaaatg                                                    17
```

METHODS OF TREATING NON-SYNDROMIC SENSORINEURAL HEARING LOSS

CROSS-REFERENCE TO RELATED APPLICATIONS

This application claims priority to U.S. Provisional Patent Application Ser. No. 62/697,652, filed Jul. 13, 2018; the entire contents of which are herein incorporated by reference.

TECHNICAL FIELD

The present disclosure relates generally to the use of nucleic acids to treat hearing loss in a human subject.

BACKGROUND OF THE INVENTION

Non-syndromic deafness, in contrast to syndromic deafness, is hearing loss that is not associated with other signs and symptoms. Seventy to eighty percent of cases of genetic deafness are non-syndromic. While the causes of non-syndromic deafness are complex, researchers have identified more than 30 genes that, when altered, are associated with non-syndromic deafness (e.g., stereocilin (STRC)). Current treatments consist mainly of hearing amplification for mild to severe hearing loss and cochlear implants for severe to profound hearing loss; however, a long-felt need remains for agents and methods for preventing or reversing non-syndromic deafness.

Hearing loss can be conductive (arising from the ear canal or middle ear), sensorineural (arising from the inner ear or auditory nerve), or mixed. Most forms of non-syndromic deafness are associated with permanent hearing loss caused by damage to structures in the inner ear (sensorineural deafness), although some forms may involve changes in the middle ear (conductive hearing loss). The great majority of human sensorineural hearing loss is caused by abnormalities in the hair cells of the organ of *Corti* in the cochlea (poor hair cell function). The hair cells may be abnormal at birth, or may be damaged during the lifetime of an individual (e.g., as a result of noise trauma or infection).

SUMMARY

The present invention is based on the discovery that a composition including at least two different nucleic acid vectors, where each of the at least two different vectors includes a coding sequence that encodes a different portion of a stereocilin protein, can be used to generate a sequence encoding an active stereocilin protein (e.g., a full-length stereocilin protein) in a mammalian cell, and thereby treat non-syndromic sensorineural hearing loss in a subject in need thereof.

Provided herein are compositions that include at least two different nucleic acid vectors, where: each of the at least two different vectors includes a coding sequence that encodes a different portion of a stereocilin protein, each of the encoded portions being at least 30 amino acid residues in length, wherein the amino acid sequence of each of the encoded portions may optionally partially overlap with the amino acid sequence of a different one of the encoded portions; no single vector of the at least two different vectors encodes a full-length stereocilin protein; at least one of the coding sequences includes a nucleotide sequence spanning two neighboring exons of stereocilin genomic DNA, and lacks an intronic sequence between the two neighboring exons; and when introduced into a mammalian cell the at least two different vectors undergo homologous recombination with each other, thereby forming a recombined nucleic acid that encodes a full-length stereocilin protein. In some embodiments of any of the compositions described herein, each of the at least two different vectors is a plasmid, a transposon, a cosmid, an artificial chromosome, or a viral vector. In some embodiments of any of the compositions described herein, each of the at least two different vectors is a human artificial chromosome (HAC), yeast artificial chromosome (YAC), bacterial artificial chromosome (BAC), or a P1-derived artificial chromosome (PAC). In some embodiments of any of the compositions described herein, each of the at least two different vectors is a viral vector selected from an adeno-associated virus (AAV) vector, an adenovirus vector, a lentivirus vector, or a retrovirus vector. In some embodiments of any of the compositions described herein, the viral vector is an AAV vector.

In some embodiments of any of the compositions described herein, the amino acid sequence of none of the encoded portions overlaps with the amino acid sequence of a different one of the encoded portions. In some embodiments of any of the compositions described herein, the amino acid sequence of each of the encoded portions partially overlaps with the amino acid sequence of a different one of the encoded portions. In some embodiments of any of the compositions described herein, the overlapping amino acid sequence is between about 30 amino acid residues to about 1000 amino acid residues in length.

In some embodiments of any of the compositions described herein, the vectors include two different vectors, each of which includes a different segment of an intron, wherein the intron includes the nucleotide sequence of an intron that is present in stereocilin genomic DNA, and wherein the two different segments overlap in sequence by at least 100 nucleotides. In some embodiments of any of the compositions described herein, the two different segments overlap in sequence by about 100 nucleotides to about 800 nucleotides. In some embodiments of any of the compositions described herein, the nucleotide sequence of each of the at least two different vectors is between about 500 nucleotides to about 10,000 nucleotides in length (e.g., between about 500 nucleotides to about 5,000 nucleotides in length).

In some embodiments of any of the compositions described herein, the number of different vectors in the composition is two. In some embodiments, one of the two vectors includes SEQ ID NO: 13 and the second of the two vectors includes SEQ ID NO: 17.

In some embodiments of any of the compositions described herein, one of the at least two different vectors includes a sequence encoding a stereocilin protein. In some embodiments, the sequence encoding a stereocilin protein is at least 90% (e.g., at least 92%, at least 94%, at least 95%, at least 96%, at least 97%, at least 98%, at least 99%, or 100%) identical to SEQ ID NO: 11.

In some embodiments of any of the compositions described herein, a first of the two different vectors includes a coding sequence that encodes an N-terminal portion of the stereocilin protein. In some embodiments of any of the compositions described herein, the N-terminal portion of the stereocilin protein is between 30 amino acids to 1600 amino acids in length (e.g., between about 200 amino acids to about 1500 amino acids in length). In some embodiments of any of the compositions described herein, the first vector further includes one or both of a promoter and a Kozak sequence.

In some embodiments of any of the compositions described herein, the first vector includes a promoter that is an inducible promoter, a constitutive promoter, or a tissue-specific promoter.

In some embodiments of any of the compositions described herein, the second of the two different vectors includes a coding sequence that encodes a C-terminal portion of the stereocilin protein. In some embodiments of any of the compositions described herein, the C-terminal portion of the stereocilin protein is between 30 amino acids to 1600 amino acids in length (e.g., between 200 amino acids to 1500 amino acids in length). In some embodiments of any of the compositions described herein, the second vector further includes a poly(dA) sequence. Some embodiments of any of the compositions described herein further include a pharmaceutically acceptable excipient.

Also provided herein are kits that include any of the compositions described herein. Some embodiments of any of the kits described herein further include a pre-loaded syringe containing the composition.

Also provided herein are methods that include introducing into a cochlea of a mammal a therapeutically effective amount of any of the compositions described herein. In some embodiments of any of the methods described herein, the mammal is a human. In some embodiments of any of the methods described herein, the mammal has been previously identified as having a defective stereocilin gene.

Also provided herein are methods of increasing expression of a full-length stereocilin protein in a mammalian cell that include introducing any of the compositions described herein into the mammalian cell. In some embodiments of any of the methods described herein, the mammalian cell is a cochlear outer hair cell. In some embodiments of any of the methods described herein, the mammalian cell is a human cell. In some embodiments of any of the methods described herein, the mammalian cell has previously been determined to have a defective stereocilin gene.

Also provided herein are methods of increasing expression of a full-length stereocilin protein in an outer hair cell in a cochlea of a mammal that include introducing into the cochlea of the mammal a therapeutically effective amount of any of the compositions described herein. In some embodiments of any of the methods described herein, the mammal has been previously identified as having a defective stereocilin gene. In some embodiments of any of the methods described herein, the mammal is a human.

Also provided herein are methods of treating non-symptomatic sensorineural hearing loss in a subject identified as having a defective stereocilin gene that include administering a therapeutically effective amount of any of the compositions described herein into the cochlea of the subject. In some embodiments of any of the methods described herein, the subject is a human. Some embodiments of any of the methods described herein further include, prior to the administering step, determining that the subject has a defective stereocilin gene.

Also provided herein are compositions that include two different nucleic acid vectors, where: a first nucleic acid vector of the two different nucleic acid vectors includes a promoter, a first coding sequence that encodes an N-terminal portion of a stereocilin protein positioned 3' of the promoter, and a splicing donor signal sequence positioned at the 3' end of the first coding sequence; and a second nucleic acid vector of the two different nucleic acid vectors including a splicing acceptor signal sequence, a second coding sequence that encodes a C-terminal portion of a stereocilin protein positioned at the 3' end of the splicing acceptor signal sequence, and a polyadenylation sequence at the 3' end of the second coding sequence; where each of the encoded portions is at least 30 amino acid residues in length, where the amino acid sequence of each of the encoded portions do not overlap; where no single vector of the two different vectors encodes a full-length stereocilin protein; and when introduced into a mammalian cell, splicing occurs between the splicing donor signal sequence and the splicing acceptor signal sequence, thereby forming a recombined nucleic acid that encodes a full-length stereocilin protein. In some embodiments of any of the compositions described herein, at least one of the coding sequences includes a nucleotide sequence spanning two neighboring exons of stereocilin genomic DNA, and lacks an intronic sequence between the two neighboring exons.

Also provided are compositions that include two different nucleic acid vectors, where: a first nucleic acid vector of the two different nucleic acid vectors includes a promoter, a first coding sequence that encodes an N-terminal portion of a stereocilin protein positioned 3' of the promoter, a splicing donor signal sequence positioned at the 3' end of the first coding sequence, and a first detectable marker gene positioned 3' of the splicing donor signal sequence; and a second nucleic acid vector of the two different nucleic acid vectors includes a second detectable marker gene, a splicing acceptor signal sequence positioned 3' of the second detectable marker gene, a second coding sequence that encodes a C-terminal portion of a stereocilin protein positioned at the 3' end of the splicing acceptor signal sequence, and a polyadenylation sequence positioned at the 3' end of the second coding sequence; where each of the encoded portions is at least 30 amino acid residues in length, where the amino acid sequence of each of the encoded portions do not overlap; where no single vector of the two different vectors encodes a full-length stereocilin protein; and when introduced into a mammalian cell, splicing occurs between the splicing donor signal and the splicing acceptor signal, thereby forming a recombined nucleic acid that encodes a full-length stereocilin protein. In some embodiments of any of the compositions described herein, at least one of the coding sequences includes a nucleotide sequence spanning two neighboring exons of stereocilin genomic DNA, and lacks an intronic sequence between the two neighboring exons. In some embodiments of any of the compositions described herein, the first or second detectable marker gene is alkaline phosphatase. In some embodiments of any of the compositions described herein, the first and second detectable marker genes are the same.

Also provided herein are compositions that include two different nucleic acid vectors, where: a first nucleic acid vector of the two different nucleic acid vectors includes a promoter, a first coding sequence that encodes an N-terminal portion of a stereocilin protein positioned 3' to the promoter, a splicing donor signal sequence positioned at the 3' end of the first coding sequence, and a F1 phage recombinogenic region positioned 3' to the splicing donor signal sequence; and a second nucleic acid vector of the two different nucleic acid vectors includes a F1 phage recombinogenic region, a splicing acceptor signal sequence positioned 3' of the F1 phage recombinogenic region, a second coding sequence that encodes a C-terminal portion of a stereocilin protein positioned at the 3' end of the splicing acceptor signal sequence, and a polyadenylation sequence positioned at the 3' end of the second coding sequence; where each of the encoded portions is at least 30 amino acid residues in length, where the amino acid sequence of each of the encoded portions do not overlap; where no single vector of the two different vectors encodes a full-length stereocilin protein; and when introduced into a mammalian cell, splicing occurs between the splicing donor signal and the splicing acceptor signal, thereby forming a recombined nucleic acid that encodes a full-length stereocilin protein. In some embodiments of any of the compositions described herein, at least one of the coding sequences includes a nucleotide sequence spanning two neighboring exons of stereocilin genomic DNA, and lacks an intronic sequence between the two neighboring exons.

Also provided herein are compositions that include: a Cas9 nuclease; a guide RNA that includes at the 5' end of the guide RNA a complementary region consisting of 20 nucleotides that are complementary to 20 consecutive nucleotides within positions 13955-14151 of SEQ ID NO:5, that can be used in CRISPR/Cas9 RNA-guided genome editing to remove a nonsense mutation at a predetermined site in the endogenous stereocilin pseudogene sequence of SEQ ID NO: 5; and when introduced into a mammalian cell, a nucleic acid encoding a full-length stereocilin protein is reconstituted at the locus of the stereocilin pseudogene.

Also provided are compositions that include at least one nucleic acid vector, wherein the at least one nucleic acid vector includes an adeno-associated virus (AAV) vector that includes an antisense oligonucleotide that is at least 80% complementary to a contiguous nucleotide sequence of SEQ ID NO: 5 at positions 13955-14151, where the antisense oligonucleotide is between 15-30 nucleotides in length; and when introduced into a mammalian cell, a nucleic acid encoding a full-length stereocilin protein is generated at the locus of the stereocilin pseudogene.

Also provided herein are kits that include any of the compositions described herein. Some embodiments of any of the kits described herein further include a pre-loaded syringe containing the composition.

Also provided are methods that include introducing into a cochlea of a mammal a therapeutically effective amount of any of the compositions described herein. In some embodiments of any of the methods described herein, the mammal is a human. In some embodiments of any of the methods described herein, the mammal has been previously identified as having a defective stereocilin gene.

Also provided herein are methods of increasing expression of a full-length stereocilin protein in a mammalian cell that include introducing any of the compositions described herein into the mammalian cell. In some embodiments of any of the methods described herein, the mammalian cell is a cochlear outer hair cell. In some embodiments of any of the methods described herein, the mammalian cell is a human cell. In some embodiments of any of the methods described herein, the mammalian cell has previously been determined to have a defective stereocilin gene.

Also provided herein are methods of increasing expression of a full-length stereocilin protein in an outer hair cell in a cochlea of a mammal that include introducing into the cochlea of the mammal a therapeutically effective amount of any of the compositions described herein. In some embodiments of any of the methods described herein, the mammal has been previously identified as having a defective stereocilin gene. In some embodiments of any of the methods described herein, the mammal is a human.

Also provided herein are methods of treating non-symptomatic sensorineural hearing loss in a subject identified as having a defective stereocilin gene that include administering a therapeutically effective amount of any of the compositions described herein into the cochlea of the subject. In some embodiments of any of the methods described herein, the subject is a human. Some embodiments of any of the methods described herein further include, prior to the administering step, determining that the subject has a defective stereocilin gene.

The term "a" and "an" refers to one or to more than one (i.e., at least one) of the grammatical object of the article. By way of example, "an element" encompasses one element and more than one element.

The term "mutation in a stereocilin gene" refers to a modification in a wildtype stereocilin gene that results in the production of a stereocilin protein having one or more of: a deletion in one or more amino acids, one or more amino acid substitutions, and one or more amino acid insertions as compared to the wildtype stereocilin protein, and/or results in a decrease in the expressed level of the encoded stereocilin protein in a mammalian cell as compared to the expressed level of the encoded stereocilin protein in a mammalian cell not having a mutation. In some embodiments, a mutation can result in the production of a stereocilin protein having a deletion in one or more amino acids (e.g., 2, 3, 4, 5, 6, 7, 8, 9, 10, 11, 12, 13, 14, 15 16, 17, 18, 19, or 20 amino acids). In some embodiments, the mutation can result in a frameshift in the stereocilin gene. The term "frameshift" is known in the art to encompass any mutation in a coding sequence that results in a shift in the reading frame of the coding sequence. In some embodiments, a frameshift can result in a nonfunctional protein. In some embodiments, a point mutation can be a nonsense mutation (i.e., result in a premature stop codon in an exon of the gene). A nonsense mutation can result in the production of a truncated protein (as compared to a corresponding wildtype protein) that may or may not be functional. In some embodiments, the mutation can result in the loss (or a decrease in the level) of expression of stereocilin mRNA or stereocilin protein or both the mRNA and protein. In some embodiments, the mutation can result in the production of an altered stereocilin protein having a loss or decrease in one or more biological activities (functions) as compared to a wildtype stereocilin protein.

In some embodiments, the mutation is an insertion of one or more nucleotides into a stereocilin gene. In some embodiments, the mutation is in a regulatory sequence of the stereocilin gene, i.e., a portion of the gene that is not coding sequence. In some embodiments, a mutation in a regulatory sequence may be in a promoter or enhancer region and prevent or reduce the proper transcription of the stereocilin gene. The term "conservative mutation" refers to a mutation that does not change the amino acid encoded at the site of the mutation (due to codon degeneracy).

Modifications can be introduced into a nucleotide sequence by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, and histidine), acidic side chains (e.g., aspartic acid and glutamic acid), uncharged polar side chains (e.g., glycine, asparagine, glutamine, serine, threonine, tyrosine, cysteine, and tryptophan), nonpolar side chains (e.g., alanine, valine, leucine, isoleucine, proline, phenylalanine, and methionine), beta-branched side chains (e.g., threonine, valine, and isoleucine), and aromatic side chains (e.g., tyrosine, phenylalanine, tryptophan, and histidine).

Unless otherwise specified, a "nucleotide sequence encoding an amino acid sequence" includes all nucleotide sequences that are degenerate versions of each other and thus encode the same amino acid sequence.

The term "endogenous" refers to any material originating from within an organism, cell, or tissue.

The term "exogenous" refers to any material introduced from or originating from outside an organism, cell, or tissue that is not produced or does not originate from the same organism, cell, or tissue in which it is being introduced.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "transfected," "transformed," or "transduced" refers to a process by which exogenous nucleic acid is transferred or introduced into a cell. A "transfected," "transformed," or "transduced" mammalian cell is one that has been transfected, transformed or transduced with exogenous nucleic acid.

The term "expression" refers to the transcription and/or translation of a particular nucleotide sequence encoding a protein.

The term "transient expression" refers to the expression of a non-integrated coding sequence for a short period of time (e.g., hours or days). The coding sequence that is transiently expressed in a cell (e.g., a mammalian cell) is lost upon multiple rounds of cell division.

The term "subject" is intended to include any mammal. In some embodiments, the subject is a rodent (e.g., a rat or mouse), a rabbit, a non-human primate, or a human. In some embodiments, the subject has or is at risk of developing non-syndromic deafness. In some embodiments, the subject has been previously identified as having a mutation in a stereocilin gene. In some embodiments, the subject has been identified as having a mutation in a stereocilin gene and has been diagnosed with non-symptomatic sensorineural hearing loss. In some embodiments, the subject has been identified as having non-symptomatic sensorineural hearing loss.

A treatment is "therapeutically effective" when it results in a reduction in one or more of the number, severity, and frequency of one or more symptoms of a disease state (e.g., non-symptomatic sensorineural hearing loss) in a subject (e.g., a human). In some embodiments, a therapeutically effective amount of a composition can result in an increase in the expression level of an active stereocilin protein (e.g., a wildtype, full-length stereocilin protein or of a variant of a stereocilin protein that has the desired activity) (e.g., as compared to the expression level prior to treatment with the composition). In some embodiments, a therapeutically effective amount of a composition can result in an increase in the expression level of an active stereocilin protein (e.g., a wildtype, full-length stereocilin protein or active variant) in a target cell (e.g., a cochlear outer hair cell). In some embodiments, a therapeutically effective amount of a composition can result in an increase in the expression level of an active stereocilin protein (e.g., a wildtype, full-length stereocilin protein or active variant), and/or an increase in one or more activities of a stereocilin protein in a target cell (e.g., as compared to a reference level, such as the level(s) in a subject prior to treatment, the level(s) in a subject having a mutation in a stereocilin gene, or the level(s) in a subject or a population of subjects having non-symptomatic sensorineural hearing loss).

The term "nucleic acid" or "polynucleotide" refers to deoxyribonucleic acid (DNA) or ribonucleic acid (RNA), or a combination thereof, in either single- or double-stranded form. Unless specifically limited, the term encompasses nucleic acids containing known analogues of natural nucleotides that have similar binding properties as the reference nucleotides. Unless otherwise indicated, a particular nucleic acid sequence also implicitly encompasses complementary sequences as well as the sequence explicitly indicated. In some embodiments of any of the nucleic acids described herein, the nucleic acid is DNA. In some embodiments of any of the nucleic acids described herein, the nucleic acid is RNA.

The term "active stereocilin protein" means a protein encoded by DNA that, if substituted for both wildtype alleles encoding full-length stereocilin protein in auditory hair cells of what is otherwise a wildtype mammal, and if expressed in the auditory hair cells of that mammal, results in that mammal's having a level of hearing approximating the normal level of hearing of a similar mammal that is entirely wildtype. Non-limiting examples of active stereocilin proteins are full-length stereocilin proteins (e.g., any of the full-length stereocilin proteins described herein).

For example, an active stereocilin protein can include a sequence of a wildtype, full-length stereocilin protein (e.g., a wildtype, human, full-length stereocilin protein) including 1 amino acid substitution to about 160 amino acid substitutions, 1 amino acid substitution to about 155 amino acid substitutions, 1 amino acid substitution to about 150 amino acid substitutions, 1 amino acid substitution to about 145 amino acid substitutions, 1 amino acid substitution to about 140 amino acid substitutions, 1 amino acid substitution to about 135 amino acid substitutions, 1 amino acid substitution to about 130 amino acid substitutions, 1 amino acid substitution to about 125 amino acid substitutions, 1 amino acid substitution to about 120 amino acid substitutions, 1 amino acid substitution to about 115 amino acid substitutions, 1 amino acid substitution to about 110 amino acid substitutions, 1 amino acid substitution to about 105 amino acid substitutions, 1 amino acid substitution to about 100 amino acid substitutions, 1 amino acid substitution to about 95 amino acid substitutions, 1 amino acid substitution to about 90 amino acid substitutions, 1 amino acid substitution to about 85 amino acid substitutions, 1 amino acid substitution to about 80 amino acid substitutions, 1 amino acid substitution to about 75 amino acid substitutions, 1 amino acid substitution to about 70 amino acid substitutions, 1 amino acid substitution to about 65 amino acid substitutions, 1 amino acid substitution to about 60 amino acid substitutions, 1 amino acid substitution to about 55 amino acid substitutions, 1 amino acid substitution to about 50 amino acid substitutions, 1 amino acid substitution to about 45 amino acid substitutions, 1 amino acid substitution to about 40 amino acid substitutions, 1 amino acid substitution to about 35 amino acid substitutions, 1 amino acid substitution to about 30 amino acid substitutions, 1 amino acid substitution to about 25 amino acid substitutions, 1 amino acid substitution to about 20 amino acid substitutions, 1 amino acid substitution to about 15 amino acid substitutions, 1 amino acid substitution to about 10 amino acid substitutions, 1 amino acid substitution to about 9 amino acid substitutions, 1 amino acid substitution to about 8 amino acid substitutions, 1 amino acid substitution to about 7 amino acid substitutions, 1 amino acid substitution to about 6 amino acid substitutions, 1 amino acid substitution to about 5 amino acid substitutions, 1 amino acid substitution to about 4 amino acid substitutions, 1 amino acid substitution to about 3 amino acid substitutions, between about 2 amino acid substitutions to about 160 amino acid substitutions, about 2 amino acid substitutions to about 155 amino acid substitutions, about 2 amino acid substitutions to about 150 amino acid substitutions, about 2 amino acid substitutions to about 145 amino acid substitutions, about 2 amino acid substitutions to about 140 amino acid substitutions, about 2 amino acid substitutions to about 135 amino acid substitutions, about 2 amino acid substitutions to about 130 amino acid substitutions, about 2 amino acid substitutions to about 125 amino acid substitutions, about 2 amino acid substitutions to about 120 amino acid substitutions, about 2 amino acid substitutions to about 115 amino acid substitutions, about 2 amino acid substitutions to about 110 amino acid substitutions, about 2 amino acid substitutions to about 105 amino acid substitutions, about 2 amino acid substitutions to about 100 amino acid substitutions, about 2 amino acid substitutions to about 95 amino acid substitutions, about 2 amino acid substitutions to about 90 amino acid substitutions, about 2 amino acid substitutions to about 85 amino acid substitutions, about 2 amino acid substitutions to about 80 amino acid substitutions, about 2 amino acid substitutions to about 75 amino acid substitutions, about 2 amino acid substitutions to about 70 amino acid substitutions, about 2 amino acid substitutions to about 65 amino acid substitutions, about 2 amino acid substitutions to about 60 amino acid substitutions, about 2 amino acid substitutions to about 55 amino acid substitutions, about 2 amino acid substitutions to about 50 amino acid substitutions, about 2 amino acid substitutions to about 45 amino acid substitutions, about 2 amino acid substitutions to about 40 amino acid substitutions, about 2 amino acid substitutions to about 35 amino acid substitutions, about 2 amino acid substitutions to about 30 amino acid substitutions, about 2 amino acid substitutions to about 25 amino acid substitutions, about 2 amino acid substitutions to about 20 amino acid substitutions, about 2 amino acid substitutions to about 15 amino acid substitutions, about 2 amino acid substitutions to about 10 amino acid substitutions, about 2 amino acid substitutions to about 9 amino acid substitutions, about 2 amino acid substitutions to about 8 amino acid substitutions, about 2 amino acid substitutions to about 7 amino acid substitutions, about 2 amino acid substitutions to about 6 amino acid substitutions, about 2 amino acid substitutions to about 5 amino acid substitutions, about 2 amino acid substitutions to about 4 amino acid substitutions, between about 3 amino acid substitutions to about 160 amino acid substitutions, about 3 amino acid substitutions to about 155 amino acid substitutions, about 3 amino acid substitutions to about 150 amino acid substitutions, about 3 amino acid substitutions to about 145 amino acid substitutions, about 3 amino acid substitutions to about 140 amino acid substitutions, about 3 amino acid substitutions to about 135 amino acid substitutions, about 3 amino acid substitutions to about 130 amino acid substitutions, about 3 amino acid substitutions to about 125 amino acid substitutions, about 3 amino acid substitutions to about 120 amino acid substitutions, about 3 amino acid substitutions to about 115 amino acid substitutions, about 3 amino acid substitutions to about 110 amino acid substitutions, about 3 amino acid substitutions to about 105 amino acid substitutions, about 3 amino acid substitutions to about 100 amino acid substitutions, about 3 amino acid substitutions to about 95 amino acid substitutions, about 3 amino acid substitutions to about 90 amino acid substitutions, about 3 amino acid substitutions to about 85 amino acid substitutions, about 3 amino acid substitutions to about 80 amino acid substitutions, about 3 amino acid substitutions to about 75 amino acid substitutions, about 3 amino acid substitutions to about 70 amino acid substitutions, about 3 amino acid substitutions to about 65 amino acid substitutions, about 3 amino acid substitutions to about 60 amino acid substitutions, about 3 amino acid substitutions to about 55 amino acid substitutions, about 3 amino acid substitutions to about 50 amino acid substitutions, about 3 amino acid substitutions to about 45 amino acid substitutions, about 3 amino acid substitutions to about 40 amino acid substitutions, about 3 amino acid substitutions to about 35 amino acid substitutions, about 3 amino acid substitutions to about 30 amino acid substitutions, about 3 amino acid substitutions to about 25 amino acid substitutions, about 3 amino acid substitutions to about 20 amino acid substitutions, about 3 amino acid substitutions to about 15 amino acid substitutions, about 3 amino acid substitutions to about 10 amino acid substitutions, about 3 amino acid substitutions to about 9 amino acid substitutions, about 3 amino acid substitutions to about 8 amino acid substitutions, about 3 amino acid substitutions to about 7 amino acid substitutions, about 3 amino acid substitutions to about 6 amino acid substitutions, about 3 amino acid substitutions to about 5 amino acid substitutions, between about 4 amino acid substitutions to about 160 amino acid substitutions, about 4 amino acid substitutions to about 155 amino acid substitutions, about 4 amino acid substitutions to about 150 amino acid substitutions, about 4 amino acid substitutions to about 145 amino acid substitutions, about 4 amino acid substitutions to about 140 amino acid substitutions, about 4 amino acid substitutions to about 135 amino acid substitutions, about 4 amino acid substitutions to about 130 amino acid substitutions, about 4 amino acid substitutions to about 125 amino acid substitutions, about 4 amino acid substitutions to about 120 amino acid substitutions, about 4 amino acid substitutions to about 115 amino acid substitutions, about 4 amino acid substitutions to about 110 amino acid substitutions, about 4 amino acid substitutions to about 105 amino acid substitutions, about 4 amino acid substitutions to about 100 amino acid substitutions, about 4 amino acid substitutions to about 95 amino acid substitutions, about 4 amino acid substitutions to about 90 amino acid substitutions, about 4 amino acid substitutions to about 85 amino acid substitutions, about 4 amino acid substitutions to about 80 amino acid substitutions, about 4 amino acid substitutions to about 75 amino acid substitutions, about 4 amino acid substitutions to about 70 amino acid substitutions, about 4 amino acid substitutions to about 65 amino acid substitutions, about 4 amino acid substitutions to about 60 amino acid substitutions, about 4 amino acid substitutions to about 55 amino acid substitutions, about 4 amino acid substitutions to about 50 amino acid substitutions, about 4 amino acid substitutions to about 45 amino acid substitutions, about 4 amino acid substitutions to about 40 amino acid substitutions, about 4 amino acid substitutions to about 35 amino acid substitutions, about 4 amino acid substitutions to about 30 amino acid substitutions, about 4 amino acid substitutions to about 25 amino acid substitutions, about 4 amino acid substitutions to about 20 amino acid substitutions, about 4 amino acid substitutions to about 15 amino acid substitutions, about 4 amino acid substitutions to about 10 amino acid substitutions, about 4 amino acid substitutions to about 9 amino acid substitutions, about 4 amino acid substitutions to about 8 amino acid substitutions, about 4 amino acid substitutions to about 7 amino acid substitutions, about 4 amino acid substitutions to about 6 amino acid substitutions, between about 5 amino acid substitutions to about 160 amino acid substitutions, about 5 amino acid substitutions to about 155 amino acid substitutions, about 5 amino acid substitutions to about 150 amino acid substitutions, about 5 amino acid substitutions to about 145 amino acid substitutions, about 5 amino acid substitutions to about 140 amino acid substitutions, about 5 amino acid substitutions to about 135 amino acid substitutions, about 5 amino acid substitutions to about 130 amino acid substitutions, about 5 amino acid substitutions to about 125 amino acid substitutions, about 5 amino acid substitutions to about 120 amino acid substitutions, about 5 amino acid substitutions to about 115 amino acid substitutions, about 5 amino acid substitutions to about 110 amino acid substitutions, about 5 amino acid substitutions to about 105 amino acid substitutions, about 5 amino acid substitutions to about 100 amino acid substitutions, about 5 amino acid substitutions to about 95 amino acid substitutions, about 5 amino acid substitutions to about 90 amino acid substitutions, about 5 amino acid substitutions to about 85 amino acid substitutions, about 5 amino acid substitutions to about 80 amino acid substitutions, about 5 amino acid substitutions to about 75 amino acid substitutions, about 5 amino acid substitutions to about 70 amino acid substitutions, about 5 amino acid substitutions to about 65 amino acid substitutions, about 5 amino acid substitutions to about 60 amino acid substitutions, about 5 amino acid substitutions to about 55 amino acid substitutions, about 5 amino acid substitutions to about 50 amino acid substitutions, about 5 amino acid substitutions to about 45 amino acid substitutions, about 5 amino acid substitutions to about 40 amino acid substitutions, about 5 amino acid substitutions to about 35 amino acid substitutions, about 5 amino acid substitutions to about 30 amino acid substitutions, about 5 amino acid substitutions to about 25 amino acid substitutions, about 5 amino acid substitutions to about 20 amino acid substitutions, about 5 amino acid substitutions to about 15 amino acid substitutions, about 5 amino acid substitutions to about 10 amino acid substitutions, about 5 amino acid substitutions to about 9 amino acid substitutions, about 5 amino acid substitutions to about 8 amino acid substitutions, about 5 amino acid substitutions to about 7 amino acid substitutions, between about 6 amino acid substitutions to about 160 amino acid substitutions, about 6 amino acid substitutions to about 155 amino acid substitutions, about 6 amino acid substitutions to about 150 amino acid substitutions, about 6 amino acid substitutions to about 145 amino acid substitutions, about 6 amino acid substitutions to about 140 amino acid substitutions, about 6 amino acid substitutions to about 135 amino acid substitutions, about 6 amino acid substitutions to about 130 amino acid substitutions, about 6 amino acid substitutions to about 125 amino acid substitutions, about 6 amino acid substitutions to about 120 amino acid substitutions, about 6 amino acid substitutions to about 115 amino acid substitutions, about 6 amino acid substitutions to about 110 amino acid substitutions, about 6 amino acid substitutions to about 105 amino acid substitutions, about 6 amino acid substitutions to about 100 amino acid substitutions, about 6 amino acid substitutions to about 95 amino acid substitutions, about 6 amino acid substitutions to about 90 amino acid substitutions, about 6 amino acid substitutions to about 85 amino acid substitutions, about 6 amino acid substitutions to about 80 amino acid substitutions, about 6 amino acid substitutions to about 75 amino acid substitutions, about 6 amino acid substitutions to about 70 amino acid substitutions, about 6 amino acid substitutions to about 65 amino acid substitutions, about 6 amino acid substitutions to about 60 amino acid substitutions, about 6 amino acid substitutions to about 55 amino acid substitutions, about 6 amino acid substitutions to about 50 amino acid substitutions, about 6 amino acid substitutions to about 45 amino acid substitutions, about 6 amino acid substitutions to about 40 amino acid substitutions, about 6 amino acid substitutions to about 35 amino acid substitutions, about 6 amino acid substitutions to about 30 amino acid substitutions, about 6 amino acid substitutions to about 25 amino acid substitutions, about 6 amino acid substitutions to about 20 amino acid substitutions, about 6 amino acid substitutions to about 15 amino acid substitutions, about 6 amino acid substitutions to about 10 amino acid substitutions, about 6 amino acid substitutions to about 9 amino acid substitutions, about 6 amino acid substitutions to about 8 amino acid substitutions, between about 7 amino acid substitutions to about 160 amino acid substitutions, about 7 amino acid substitutions to about 155 amino acid substitutions, about 7 amino acid substitutions to about 150 amino acid substitutions, about 7 amino acid substitutions to about 145 amino acid substitutions, about 7 amino acid substitutions to about 140 amino acid substitutions, about 7 amino acid substitutions to about 135 amino acid substitutions, about 7 amino acid substitutions to about 130 amino acid substitutions, about 7 amino acid substitutions to about 125 amino acid substitutions, about 7 amino acid substitutions to about 120 amino acid substitutions, about 7 amino acid substitutions to about 115 amino acid substitutions, about 7 amino acid substitutions to about 110 amino acid substitutions, about 7 amino acid substitutions to about 105 amino acid substitutions, about 7 amino acid substitutions to about 100 amino acid substitutions, about 7 amino acid substitutions to about 95 amino acid substitutions, about 7 amino acid substitutions to about 90 amino acid substitutions, about 7 amino acid substitutions to about 85 amino acid substitutions, about 7 amino acid substitutions to about 80 amino acid substitutions, about 7 amino acid substitutions to about 75 amino acid substitutions, about 7 amino acid substitutions to about 70 amino acid substitutions, about 7 amino acid substitutions to about 65 amino acid substitutions, about 7 amino acid substitutions to about 60 amino acid substitutions, about 7 amino acid substitutions to about 55 amino acid substitutions, about 7 amino acid substitutions to about 50 amino acid substitutions, about 7 amino acid substitutions to about 45 amino acid substitutions, about 7 amino acid substitutions to about 40 amino acid substitutions, about 7 amino acid substitutions to about 35 amino acid substitutions, about 7 amino acid substitutions to about 30 amino acid substitutions, about 7 amino acid substitutions to about 25 amino acid substitutions, about 7 amino acid substitutions to about 20 amino acid substitutions, about 7 amino acid substitutions to about 15 amino acid substitutions, about 7 amino acid substitutions to about 10 amino acid substitutions, about 7 amino acid substitutions to about 9 amino acid substitutions, between about 8 amino acid substitutions to about 160 amino acid substitutions, about 8 amino acid substitutions to about 155 amino acid substitutions, about 8 amino acid substitutions to about 150 amino acid substitutions, about 8 amino acid substitutions to about 145 amino acid substitutions, about 8 amino acid substitutions to about 140 amino acid substitutions, about 8 amino acid substitutions to about 135 amino acid substitutions, about 8 amino acid substitutions to about 130 amino acid substitutions, about 8 amino acid substitutions to about 125 amino acid substitutions, about 8 amino acid substitutions to about 120 amino acid substitutions, about 8 amino acid substitutions to about 115 amino acid substitutions, about 8 amino acid substitutions to about 110 amino acid substitutions, about 8 amino acid substitutions to about 105 amino acid substitutions, about 8 amino acid substitutions to about 100 amino acid substitutions, about 8 amino acid substitutions to about 95 amino acid substitutions, about 8 amino acid substitutions to about 90 amino acid substitutions, about 8 amino acid substitutions to about 85 amino acid substitutions, about 8 amino acid substitutions to about 80 amino acid substitutions, about 8 amino acid substitutions to about 75 amino acid substitutions, about 8 amino acid substitutions to about 70 amino acid substitutions, about 8 amino acid substitutions to about 65 amino acid substitutions, about 8 amino acid substitutions to about 60 amino acid substitutions, about 8 amino acid substitutions to about 55 amino acid substitutions, about 8 amino acid substitutions to about 50 amino acid substitutions, about 8 amino acid substitutions to about 45 amino acid substitutions, about 8 amino acid substitutions to about 40 amino acid substitutions, about 8 amino acid substitutions to about 35 amino acid substitutions, about 8 amino acid substitutions to about 30 amino acid substitutions, about 8 amino acid substitutions to about 25 amino acid substitutions, about 8 amino acid substitutions to about 20 amino acid substitutions, about 8 amino acid substitutions to about 15 amino acid substitutions, about 8 amino acid substitutions to about 10 amino acid substitutions, between about 10 amino acid substitutions to about 160 amino acid substitutions, about 10 amino acid substitutions to about 155 amino acid substitutions, about 10 amino acid substitutions to about 150 amino acid substitutions, about 10 amino acid substitutions to about 145 amino acid substitutions, about 10 amino acid substitutions to about 140 amino acid substitutions, about 10 amino acid substitutions to about 135 amino acid substitutions, about 10 amino acid substitutions to about 130 amino acid substitutions, about 10 amino acid substitutions to about 125 amino acid substitutions, about 10 amino acid substitutions to about 120 amino acid substitutions, about 10 amino acid substitutions to about 115 amino acid substitutions, about 10 amino acid substitutions to about 110 amino acid substitutions, about 10 amino acid substitutions to about 105 amino acid substitutions, about 10 amino acid substitutions to about 100 amino acid substitutions, about 10 amino acid substitutions to about 95 amino acid substitutions, about 10 amino acid substitutions to about 90 amino acid substitutions, about 10 amino acid substitutions to about 85 amino acid substitutions, about 10 amino acid substitutions to about 80 amino acid substitutions, about 10 amino acid substitutions to about 75 amino acid substitutions, about 10 amino acid substitutions to about 70 amino acid substitutions, about 10 amino acid substitutions to about 65 amino acid substitutions, about 10 amino acid substitutions to about 60 amino acid substitutions, about 10 amino acid substitutions to about 55 amino acid substitutions, about 10 amino acid substitutions to about 50 amino acid substitutions, about 10 amino acid substitutions to about 45 amino acid substitutions, about 10 amino acid substitutions to about 40 amino acid substitutions, about 10 amino acid substitutions to about 35 amino acid substitutions, about 10 amino acid substitutions to about 30 amino acid substitutions, about 10 amino acid substitutions to about 25 amino acid substitutions, about 10 amino acid substitutions to about 20 amino acid substitutions, about 10 amino acid substitutions to about 15 amino acid substitutions, between about 15 amino acid substitutions to about 160 amino acid substitutions, about 15 amino acid substitutions to about 155 amino acid substitutions, about 15 amino acid substitutions to about 150 amino acid substitutions, about 15 amino acid substitutions to about 145 amino acid substitutions, about 15 amino acid substitutions to about 140 amino acid substitutions, about 15 amino acid substitutions to about 135 amino acid substitutions, about 15 amino acid substitutions to about 130 amino acid substitutions, about 15 amino acid substitutions to about 125 amino acid substitutions, about 15 amino acid substitutions to about 120 amino acid substitutions, about 15 amino acid substitutions to about 115 amino acid substitutions, about 15 amino acid substitutions to about 110 amino acid substitutions, about 15 amino acid substitutions to about 105 amino acid substitutions, about 15 amino acid substitutions to about 100 amino acid substitutions, about 15 amino acid substitutions to about 95 amino acid substitutions, about 15 amino acid substitutions to about 90 amino acid substitutions, about 15 amino acid substitutions to about 85 amino acid substitutions, about 15 amino acid substitutions to about 80 amino acid substitutions, about 15 amino acid substitutions to about 75 amino acid substitutions, about 15 amino acid substitutions to about 70 amino acid substitutions, about 15 amino acid substitutions to about 65 amino acid substitutions, about 15 amino acid substitutions to about 60 amino acid substitutions, about 15 amino acid substitutions to about 55 amino acid substitutions, about 15 amino acid substitutions to about 50 amino acid substitutions, about 15 amino acid substitutions to about 45 amino acid substitutions, about 15 amino acid substitutions to about 40 amino acid substitutions, about 15 amino acid substitutions to about 35 amino acid substitutions, about 15 amino acid substitutions to about 30 amino acid substitutions, about 15 amino acid substitutions to about 25 amino acid substitutions, about 15 amino acid substitutions to about 20 amino acid substitutions, between about 20 amino acid substitutions to about 160 amino acid substitutions, about 20 amino acid substitutions to about 155 amino acid substitutions, about 20 amino acid substitutions to about 150 amino acid substitutions, about 20 amino acid substitutions to about 145 amino acid substitutions, about 20 amino acid substitutions to about 140 amino acid substitutions, about 20 amino acid substitutions to about 135 amino acid substitutions, about 20 amino acid substitutions to about 130 amino acid substitutions, about 20 amino acid substitutions to about 125 amino acid substitutions, about 20 amino acid substitutions to about 120 amino acid substitutions, about 20 amino acid substitutions to about 115 amino acid substitutions, about 20 amino acid substitutions to about 110 amino acid substitutions, about 20 amino acid substitutions to about 105 amino acid substitutions, about 20 amino acid substitutions to about 100 amino acid substitutions, about 20 amino acid substitutions to about 95 amino acid substitutions, about 20 amino acid substitutions to about 90 amino acid substitutions, about 20 amino acid substitutions to about 85 amino acid substitutions, about 20 amino acid substitutions to about 80 amino acid substitutions, about 20 amino acid substitutions to about 75 amino acid substitutions, about 20 amino acid substitutions to about 70 amino acid substitutions, about 20 amino acid substitutions to about 65 amino acid substitutions, about 20 amino acid substitutions to about 60 amino acid substitutions, about 20 amino acid substitutions to about 55 amino acid substitutions, about 20 amino acid substitutions to about 50 amino acid substitutions, about 20 amino acid substitutions to about 45 amino acid substitutions, about 20 amino acid substitutions to about 40 amino acid substitutions, about 20 amino acid substitutions to about 35 amino acid substitutions, about 20 amino acid substitutions to about 30 amino acid substitutions, about 20 amino acid substitutions to about 25 amino acid substitutions, between about 25 amino acid substitutions to about 160 amino acid substitutions, about 25 amino acid substitutions to about 155 amino acid substitutions, about 25 amino acid substitutions to about 150 amino acid substitutions, about 25 amino acid substitutions to about 145 amino acid substitutions, about 25 amino acid substitutions to about 140 amino acid substitutions, about 25 amino acid substitutions to about 135 amino acid substitutions, about 25 amino acid substitutions to about 130 amino acid substitutions, about 25 amino acid substitutions to about 125 amino acid substitutions, about 25 amino acid substitutions to about 120 amino acid substitutions, about 25 amino acid substitutions to about 115 amino acid substitutions, about 25 amino acid substitutions to about 110 amino acid substitutions, about 25 amino acid substitutions to about 105 amino acid substitutions, about 25 amino acid substitutions to about 100 amino acid substitutions, about 25 amino acid substitutions to about 95 amino acid substitutions, about 25 amino acid substitutions to about 90 amino acid substitutions, about 25 amino acid substitutions to about 85 amino acid substitutions, about 25 amino acid substitutions to about 80 amino acid substitutions, about 25 amino acid substitutions to about 75 amino acid substitutions, about 25 amino acid substitutions to about 70 amino acid substitutions, about 25 amino acid substitutions to about 65 amino acid substitutions, about 25 amino acid substitutions to about 60 amino acid substitutions, about 25 amino acid substitutions to about 55 amino acid substitutions, about 25 amino acid substitutions to about 50 amino acid substitutions, about 25 amino acid substitutions to about 45 amino acid substitutions, about 25 amino acid substitutions to about 40 amino acid substitutions, about 25 amino acid substitutions to about 35 amino acid substitutions, about 25 amino acid substitutions to about 30 amino acid substitutions, between about 30 amino acid substitutions to about 160 amino acid substitutions, about 30 amino acid substitutions to about 155 amino acid substitutions, about 30 amino acid substitutions to about 150 amino acid substitutions, about 30 amino acid substitutions to about 145 amino acid substitutions, about 30 amino acid substitutions to about 140 amino acid substitutions, about 30 amino acid substitutions to about 135 amino acid substitutions, about 30 amino acid substitutions to about 130 amino acid substitutions, about 30 amino acid substitutions to about 125 amino acid substitutions, about 30 amino acid substitutions to about 120 amino acid substitutions, about 30 amino acid substitutions to about 115 amino acid substitutions, about 30 amino acid substitutions to about 110 amino acid substitutions, about 30 amino acid substitutions to about 105 amino acid substitutions, about 30 amino acid substitutions to about 100 amino acid substitutions, about 30 amino acid substitutions to about 95 amino acid substitutions, about 30 amino acid substitutions to about 90 amino acid substitutions, about 30 amino acid substitutions to about 85 amino acid substitutions, about 30 amino acid substitutions to about 80 amino acid substitutions, about 30 amino acid substitutions to about 75 amino acid substitutions, about 30 amino acid substitutions to about 70 amino acid substitutions, about 30 amino acid substitutions to about 65 amino acid substitutions, about 30 amino acid substitutions to about 60 amino acid substitutions, about 30 amino acid substitutions to about 55 amino acid substitutions, about 30 amino acid substitutions to about 50 amino acid substitutions, about 30 amino acid substitutions to about 45 amino acid substitutions, about 30 amino acid substitutions to about 40 amino acid substitutions to about 35 amino acid substitutions, between about 35 amino acid substitutions to about 160 amino acid substitutions, about 35 amino acid substitutions to about 155 amino acid substitutions, about 35 amino acid substitutions to about 150 amino acid substitutions, about 35 amino acid substitutions to about 145 amino acid substitutions, about 35 amino acid substitutions to about 140 amino acid substitutions, about 35 amino acid substitutions to about 135 amino acid substitutions, about 35 amino acid substitutions to about 130 amino acid substitutions, about 35 amino acid substitutions to about 125 amino acid substitutions, about 35 amino acid substitutions to about 120 amino acid substitutions, about 35 amino acid substitutions to about 115 amino acid substitutions, about 35 amino acid substitutions to about 110 amino acid substitutions, about 35 amino acid substitutions to about 105 amino acid substitutions, about 35 amino acid substitutions to about 100 amino acid substitutions, about 35 amino acid substitutions to about 95 amino acid substitutions, about 35 amino acid substitutions to about 90 amino acid substitutions, about 35 amino acid substitutions to about 85 amino acid substitutions, about 35 amino acid substitutions to about 80 amino acid substitutions, about 35 amino acid substitutions to about 75 amino acid substitutions, about 35 amino acid substitutions to about 70 amino acid substitutions, about 35 amino acid substitutions to about 65 amino acid substitutions, about 35 amino acid substitutions to about 60 amino acid substitutions, about 35 amino acid substitutions to about 55 amino acid substitutions, about 35 amino acid substitutions to about 50 amino acid substitutions, about 35 amino acid substitutions to about 45 amino acid substitutions, about 35 amino acid substitutions to about 40 amino acid substitutions, between about 40 amino acid substitutions to about 160 amino acid substitutions, about 40 amino acid substitutions to about 155 amino acid substitutions, about 40 amino acid substitutions to about 150 amino acid substitutions, about 40 amino acid substitutions to about 145 amino acid substitutions, about 40 amino acid substitutions to about 140 amino acid substitutions, about 40 amino acid substitutions to about 135 amino acid substitutions, about 40 amino acid substitutions to about 130 amino acid substitutions, about 40 amino acid substitutions to about 125 amino acid substitutions, about 40 amino acid substitutions to about 120 amino acid substitutions, about 40 amino acid substitutions to about 115 amino acid substitutions, about 40 amino acid substitutions to about 110 amino acid substitutions, about 40 amino acid substitutions to about 105 amino acid substitutions, about 40 amino acid substitutions to about 100 amino acid substitutions, about 40 amino acid substitutions to about 95 amino acid substitutions, about 40 amino acid substitutions to about 90 amino acid substitutions, about 40 amino acid substitutions to about 85 amino acid substitutions, about 40 amino acid substitutions to about 80 amino acid substitutions, about 40 amino acid substitutions to about 75 amino acid substitutions, about 40 amino acid substitutions to about 70 amino acid substitutions, about 40 amino acid substitutions to about 65 amino acid substitutions, about 40 amino acid substitutions to about 60 amino acid substitutions, about 40 amino acid substitutions to about 55 amino acid substitutions, about 40 amino acid substitutions to about 50 amino acid substitutions, about 40 amino acid substitutions to about 45 amino acid substitutions, between about 45 amino acid substitutions to about 160 amino acid substitutions, about 45 amino acid substitutions to about 155 amino acid substitutions, about 45 amino acid substitutions to about 150 amino acid substitutions, about 45 amino acid substitutions to about 145 amino acid substitutions, about 45 amino acid substitutions to about 140 amino acid substitutions, about 45 amino acid substitutions to about 135 amino acid substitutions, about 45 amino acid substitutions to about 130 amino acid substitutions, about 45 amino acid substitutions to about 125 amino acid substitutions, about 45 amino acid substitutions to about 120 amino acid substitutions, about 45 amino acid substitutions to about 115 amino acid substitutions, about 45 amino acid substitutions to about 110 amino acid substitutions, about 45 amino acid substitutions to about 105 amino acid substitutions, about 45 amino acid substitutions to about 100 amino acid substitutions, about 45 amino acid substitutions to about 95 amino acid substitutions, about 45 amino acid substitutions to about 90 amino acid substitutions, about 45 amino acid substitutions to about 85 amino acid substitutions, about 45 amino acid substitutions to about 80 amino acid substitutions, about 45 amino acid substitutions to about 75 amino acid substitutions, about 45 amino acid substitutions to about 70 amino acid substitutions, about 45 amino acid substitutions to about 65 amino acid substitutions, about 45 amino acid substitutions to about 60 amino acid substitutions, about 45 amino acid substitutions to about 55 amino acid substitutions, about 45 amino acid substitutions to about 50 amino acid substitutions, between about 50 amino acid substitutions to about 160 amino acid substitutions, about 50 amino acid substitutions to about 155 amino acid substitutions, about 50 amino acid substitutions to about 150 amino acid substitutions, about 50 amino acid substitutions to about 145 amino acid substitutions, about 50 amino acid substitutions to about 140 amino acid substitutions, about 50 amino acid substitutions to about 135 amino acid substitutions, about 50 amino acid substitutions to about 130 amino acid substitutions, about 50 amino acid substitutions to about 125 amino acid substitutions, about 50 amino acid substitutions to about 120 amino acid substitutions, about 50 amino acid substitutions to about 115 amino acid substitutions, about 50 amino acid substitutions to about 110 amino acid substitutions, about 50 amino acid substitutions to about 105 amino acid substitutions, about 50 amino acid substitutions to about 100 amino acid substitutions, about 50 amino acid substitutions to about 95 amino acid substitutions, about 50 amino acid substitutions to about 90 amino acid substitutions, about 50 amino acid substitutions to about 85 amino acid substitutions, about 50 amino acid substitutions to about 80 amino acid substitutions, about 50 amino acid substitutions to about 75 amino acid substitutions, about 50 amino acid substitutions to about 70 amino acid substitutions, about 50 amino acid substitutions to about 65 amino acid substitutions, about 50 amino acid substitutions to about 60 amino acid substitutions, about 50 amino acid substitutions to about 55 amino acid substitutions, between about 60 amino acid substitutions to about 160 amino acid substitutions, about 60 amino acid substitutions to about 155 amino acid substitutions, about 60 amino acid substitutions to about 150 amino acid substitutions, about 60 amino acid substitutions to about 145 amino acid substitutions, about 60 amino acid substitutions to about 140 amino acid substitutions, about 60 amino acid substitutions to about 135 amino acid substitutions, about 60 amino acid substitutions to about 130 amino acid substitutions, about 60 amino acid substitutions to about 125 amino acid substitutions, about 60 amino acid substitutions to about 120 amino acid substitutions, about 60 amino acid substitutions to about 115 amino acid substitutions, about 60 amino acid substitutions to about 110 amino acid substitutions, about 60 amino acid substitutions to about 105 amino acid substitutions, about 60 amino acid substitutions to about 100 amino acid substitutions, about 60 amino acid substitutions to about 95 amino acid substitutions, about 60 amino acid substitutions to about 90 amino acid substitutions, about 60 amino acid substitutions to about 85 amino acid substitutions, about 60 amino acid substitutions to about 80 amino acid substitutions, about 60 amino acid substitutions to about 75 amino acid substitutions, about 60 amino acid substitutions to about 70 amino acid substitutions, about 60 amino acid substitutions to about 65 amino acid substitutions, between about 70 amino acid substitutions to about 160 amino acid substitutions, about 70 amino acid substitutions to about 155 amino acid substitutions, about 70 amino acid substitutions to about 150 amino acid substitutions, about 70 amino acid substitutions to about 145 amino acid substitutions, about 70 amino acid substitutions to about 140 amino acid substitutions, about 70 amino acid substitutions to about 135 amino acid substitutions, about 70 amino acid substitutions to about 130 amino acid substitutions, about 70 amino acid substitutions to about 125 amino acid substitutions, about 70 amino acid substitutions to about 120 amino acid substitutions, about 70 amino acid substitutions to about 115 amino acid substitutions, about 70 amino acid substitutions to about 110 amino acid substitutions, about 70 amino acid substitutions to about 105 amino acid substitutions, about 70 amino acid substitutions to about 100 amino acid substitutions, about 70 amino acid substitutions to about 95 amino acid substitutions, about 70 amino acid substitutions to about 90 amino acid substitutions, about 70 amino acid substitutions to about 85 amino acid substitutions, about 70 amino acid substitutions to about 80 amino acid substitutions, about 70 amino acid substitutions to about 75 amino acid substitutions, between about 80 amino acid substitutions to about 160 amino acid substitutions, about 80 amino acid substitutions to about 155 amino acid substitutions, about 80 amino acid substitutions to about 150 amino acid substitutions, about 80 amino acid substitutions to about 145 amino acid substitutions, about 80 amino acid substitutions to about 140 amino acid substitutions, about 80 amino acid substitutions to about 135 amino acid substitutions, about 80 amino acid substitutions to about 130 amino acid substitutions, about 80 amino acid substitutions to about 125 amino acid substitutions, about 80 amino acid substitutions to about 120 amino acid substitutions, about 80 amino acid substitutions to about 115 amino acid substitutions, about 80 amino acid substitutions to about 110 amino acid substitutions, about 80 amino acid substitutions to about 105 amino acid substitutions, about 80 amino acid substitutions to about 100 amino acid substitutions, about 80 amino acid substitutions to about 95 amino acid substitutions, about 80 amino acid substitutions to about 90 amino acid substitutions, about 80 amino acid substitutions to about 85 amino acid substitutions, between about 90 amino acid substitutions to about 160 amino acid substitutions, about 90 amino acid substitutions to about 155 amino acid substitutions, about 90 amino acid substitutions to about 150 amino acid substitutions, about 90 amino acid substitutions to about 145 amino acid substitutions, about 90 amino acid substitutions to about 140 amino acid substitutions, about 90 amino acid substitutions to about 135 amino acid substitutions, about 90 amino acid substitutions to about 130 amino acid substitutions, about 90 amino acid substitutions to about 125 amino acid substitutions, about 90 amino acid substitutions to about 120 amino acid substitutions, about 90 amino acid substitutions to about 115 amino acid substitutions, about 90 amino acid substitutions to about 110 amino acid substitutions, about 90 amino acid substitutions to about 105 amino acid substitutions, about 90 amino acid substitutions to about 100 amino acid substitutions, about 90 amino acid substitutions to about 95 amino acid substitutions, between about 100 amino acid substitutions to about 160 amino acid substitutions, about 100 amino acid substitutions to about 155 amino acid substitutions, about 100 amino acid substitutions to about 150 amino acid substitutions, about 100 amino acid substitutions to about 145 amino acid substitutions, about 100 amino acid substitutions to about 140 amino acid substitutions, about 100 amino acid substitutions to about 135 amino acid substitutions, about 100 amino acid substitutions to about 130 amino acid substitutions, about 100 amino acid substitutions to about 125 amino acid substitutions, about 100 amino acid substitutions to about 120 amino acid substitutions, about 100 amino acid substitutions to about 115 amino acid substitutions, about 100 amino acid substitutions to about 110 amino acid substitutions, about 100 amino acid substitutions to about 105 amino acid substitutions, between about 110 amino acid substitutions to about 160 amino acid substitutions, about 110 amino acid substitutions to about 155 amino acid substitutions, about 110 amino acid substitutions to about 150 amino acid substitutions, about 110 amino acid substitutions to about 145 amino acid substitutions, about 110 amino acid substitutions to about 140 amino acid substitutions, about 110 amino acid substitutions to about 135 amino acid substitutions, about 110 amino acid substitutions to about 130 amino acid substitutions, about 110 amino acid substitutions to about 125 amino acid substitutions, about 110 amino acid substitutions to about 120 amino acid substitutions, about 110 amino acid substitutions to about 115 amino acid substitutions, between about 120 amino acid substitutions to about 160 amino acid substitutions, about 120 amino acid substitutions to about 155 amino acid substitutions, about 120 amino acid substitutions to about 150 amino acid substitutions, about 120 amino acid substitutions to about 145 amino acid substitutions, about 120 amino acid substitutions to about 140 amino acid substitutions, about 120 amino acid substitutions to about 135 amino acid substitutions, about 120 amino acid substitutions to about 130 amino acid substitutions, about 120 amino acid substitutions to about 125 amino acid substitutions, between about 130 amino acid substitutions to about 160 amino acid substitutions, about 130 amino acid substitutions to about 155 amino acid substitutions, about 130 amino acid substitutions to about 150 amino acid substitutions, about 130 amino acid substitutions to about 145 amino acid substitutions, about 130 amino acid substitutions to about 140 amino acid substitutions, about 130 amino acid substitutions to about 135 amino acid substitutions, between about 140 amino acid substitutions to about 160 amino acid substitutions, about 140 amino acid substitutions to about 155 amino acid substitutions, about 140 amino acid substitutions to about 150 amino acid substitutions, about 140 amino acid substitutions to about 145 amino acid substitutions, between about 150 amino acid substitutions to about 160 amino acid substitutions, or about 150 amino acid substitutions to about 155 amino acid substitutions. One skilled in the art would appreciate that amino acids that are conserved between wildtype stereocilin proteins from different species can be mutated without losing activity, while those amino acids that are not conserved between wildtype stereocilin proteins from different species should not be mutated as they are more likely (than amino acids that are not conserved between different species) to be involved in activity.

An active stereocilin protein can include, e.g., a sequence of a wildtype, full-length stereocilin protein (e.g., a wildtype, human, full-length stereocilin protein) that has 1 amino acid to about 50 amino acids, 1 amino acid to about 45 amino acids, 1 amino acid to about 40 amino acids, 1 amino acid to about 35 amino acids, 1 amino acid to about 30 amino acids, 1 amino acid to about 25 amino acids, 1 amino acid to about 20 amino acids, 1 amino acid to about 15 amino acids, 1 amino acid to about 10 amino acids, 1 amino acid to about 9 amino acids, 1 amino acid to about 8 amino acids, 1 amino acid to about 7 amino acids, 1 amino acid to about 6 amino acids, 1 amino acid to about 5 amino acids, 1 amino acid to about 4 amino acids, 1 amino acid to about 3 amino acids, about 2 amino acids to about 50 amino acids, about 2 amino acids to about 45 amino acids, about 2 amino acids to about 40 amino acids, about 2 amino acids to about 35 amino acids, about 2 amino acids to about 30 amino acids, about 2 amino acids to about 25 amino acids, about 2 amino acids to about 20 amino acids, about 2 amino acids to about 15 amino acids, about 2 amino acids to about 10 amino acids, about 2 amino acids to about 9 amino acids, about 2 amino acids to about 8 amino acids, about 2 amino acids to about 7 amino acids, about 2 amino acids to about 6 amino acids, about 2 amino acids to about 5 amino acids, about 2 amino acids to about 4 amino acids, about 3 amino acids to about 50 amino acids, about 3 amino acids to about 45 amino acids, about 3 amino acids to about 40 amino acids, about 3 amino acids to about 35 amino acids, about 3 amino acids to about 30 amino acids, about 3 amino acids to about 25 amino acids, about 3 amino acids to about 20 amino acids, about 3 amino acids to about 15 amino acids, about 3 amino acids to about 10 amino acids, about 3 amino acids to about 9 amino acids, about 3 amino acids to about 8 amino acids, about 3 amino acids to about 7 amino acids, about 3 amino acids to about 6 amino acids, about 3 amino acids to about 5 amino acids, about 4 amino acids to about 50 amino acids, about 4 amino acids to about 45 amino acids, about 4 amino acids to about 40 amino acids, about 4 amino acids to about 35 amino acids, about 4 amino acids to about 30 amino acids, about 4 amino acids to about 25 amino acids, about 4 amino acids to about 20 amino acids, about 4 amino acids to about 15 amino acids, about 4 amino acids to about 10 amino acids, about 4 amino acids to about 9 amino acids, about 4 amino acids to about 8 amino acids, about 4 amino acids to about 7 amino acids, about 4 amino acids to about 6 amino acids, about 5 amino acids to about 50 amino acids, about 5 amino acids to about 45 amino acids, about 5 amino acids to about 40 amino acids, about 5 amino acids to about 35 amino acids, about 5 amino acids to about 30 amino acids, about 5 amino acids to about 25 amino acids, about 5 amino acids to about 20 amino acids, about 5 amino acids to about 15 amino acids, about 5 amino acids to about 10 amino acids, about 5 amino acids to about 9 amino acids, about 5 amino acids to about 8 amino acids, about 5 amino acids to about 7 amino acids, about 6 amino acids to about 50 amino acids, about 6 amino acids to about 45 amino acids, about 6 amino acids to about 40 amino acids, about 6 amino acids to about 35 amino acids, about 6 amino acids to about 30 amino acids, about 6 amino acids to about 25 amino acids, about 6 amino acids to about 20 amino acids, about 6 amino acids to about 15 amino acids, about 6 amino acids to about 10 amino acids, about 6 amino acids to about 9 amino acids, about 6 amino acids to about 8 amino acids, about 7 amino acids to about 50 amino acids, about 7 amino acids to about 45 amino acids, about 7 amino acids to about 40 amino acids, about 7 amino acids to about 35 amino acids, about 7 amino acids to about 30 amino acids, about 7 amino acids to about 25 amino acids, about 7 amino acids to about 20 amino acids, about 7 amino acids to about 15 amino acids, about 7 amino acids to about 10 amino acids, about 7 amino acids to about 9 amino acids, about 8 amino acids to about 50 amino acids, about 8 amino acids to about 45 amino acids, about 8 amino acids to about 40 amino acids, about 8 amino acids to about 35 amino acids, about 8 amino acids to about 30 amino acids, about 8 amino acids to about 25 amino acids, about 8 amino acids to about 20 amino acids, about 8 amino acids to about 15 amino acids, about 8 amino acids to about 10 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 20 amino acids, about 10 amino acids to about 15 amino acids, about 15 amino acids to about 50 amino acids, about 15 amino acids to about 45 amino acids, about 15 amino acids to about 40 amino acids, about 15 amino acids to about 35 amino acids, about 15 amino acids to about 30 amino acids, about 15 amino acids to about 25 amino acids, about 15 amino acids to about 20 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 50 amino acids, about 30 amino acids to about 45 amino acids, about 30 amino acids to about 40 amino acids, about 30 amino acids to about 35 amino acids, about 35 amino acids to about 50 amino acids, about 35 amino acids to about 45 amino acids, about 35 amino acids to about 40 amino acids, about 40 amino acids to about 50 amino acids, about 40 amino acids to about 45 amino acids, about 45 amino acids to about 50 amino acids, deleted. In some embodiments where two or more amino acids are deleted from the sequence of a wildtype, full-length stereocilin protein, the two or more deleted amino acids can be contiguous in the sequence of the wildtype, full-length protein. In other examples where two or more amino acids are deleted from the sequence of a wildtype, full-length stereocilin protein, the two or more deleted amino acids are not contiguous in the sequence of the wildtype, full-length protein. One skilled in the art would appreciate that amino acids that are not conserved between wildtype, full-length stereocilin proteins from different species can be deleted without losing activity, while those amino acids that are conserved between wildtype, full-length stereocilin proteins from different species should not be deleted as they are more likely (than amino acids that are not conserved between different species) to be involved in activity.

In some examples, an active stereocilin protein can, e.g., include a sequence of a wildtype, full-length stereocilin protein that has between 1 amino acid to about 100 amino acids, 1 amino acid to about 95 amino acids, 1 amino acid to about 90 amino acids, 1 amino acid to about 85 amino acids, 1 amino acid to about 80 amino acids, 1 amino acid to about 75 amino acids, 1 amino acid to about 70 amino acids, 1 amino acid to about 65 amino acids, 1 amino acid to about 60 amino acids, 1 amino acid to about 55 amino acids, 1 amino acid to about 50 amino acids, 1 amino acid to about 45 amino acids, 1 amino acid to about 40 amino acids, 1 amino acid to about 35 amino acids, 1 amino acid to about 30 amino acids, 1 amino acid to about 25 amino acids, 1 amino acid to about 20 amino acids, 1 amino acid to about 15 amino acids, 1 amino acid to about 10 amino acids, 1 amino acid to about 9 amino acids, 1 amino acid to about 8 amino acids, 1 amino acid to about 7 amino acids, 1 amino acid to about 6 amino acids, 1 amino acid to about 5 amino acids, 1 amino acid to about 4 amino acids, 1 amino acid to about 3 amino acids, about 2 amino acids to about 100 amino acids, about 2 amino acid to about 95 amino acids, about 2 amino acids to about 90 amino acids, about 2 amino acids to about 85 amino acids, about 2 amino acids to about 80 amino acids, about 2 amino acids to about 75 amino acids, about 2 amino acids to about 70 amino acids, about 2 amino acids to about 65 amino acids, about 2 amino acids to about 60 amino acids, about 2 amino acids to about 55 amino acids, about 2 amino acids to about 50 amino acids, about 2 amino acids to about 45 amino acids, about 2 amino acids to about 40 amino acids, about 2 amino acids to about 35 amino acids, about 2 amino acids to about 30 amino acids, about 2 amino acids to about 25 amino acids, about 2 amino acids to about 20 amino acids, about 2 amino acids to about 15 amino acids, about 2 amino acids to about 10 amino acids, about 2 amino acids to about 9 amino acids, about 2 amino acids to about 8 amino acids, about 2 amino acids to about 7 amino acids, about 2 amino acids to about 6 amino acids, about 2 amino acids to about 5 amino acids, about 2 amino acids to about 4 amino acids, about 3 amino acids to about 100 amino acids, about 3 amino acid to about 95 amino acids, about 3 amino acids to about 90 amino acids, about 3 amino acids to about 85 amino acids, about 3 amino acids to about 80 amino acids, about 3 amino acids to about 75 amino acids, about 3 amino acids to about 70 amino acids, about 3 amino acids to about 65 amino acids, about 3 amino acids to about 60 amino acids, about 3 amino acids to about 55 amino acids, about 3 amino acids to about 50 amino acids, about 3 amino acids to about 45 amino acids, about 3 amino acids to about 40 amino acids, about 3 amino acids to about 35 amino acids, about 3 amino acids to about 30 amino acids, about 3 amino acids to about 25 amino acids, about 3 amino acids to about 20 amino acids, about 3 amino acids to about 15 amino acids, about 3 amino acids to about 10 amino acids, about 3 amino acids to about 9 amino acids, about 3 amino acids to about 8 amino acids, about 3 amino acids to about 7 amino acids, about 3 amino acids to about 6 amino acids, about 3 amino acids to about 5 amino acids, about 4 amino acids to about 100 amino acids, about 4 amino acid to about 95 amino acids, about 4 amino acids to about 90 amino acids, about 4 amino acids to about 85 amino acids, about 4 amino acids to about 80 amino acids, about 4 amino acids to about 75 amino acids, about 4 amino acids to about 70 amino acids, about 4 amino acids to about 65 amino acids, about 4 amino acids to about 60 amino acids, about 4 amino acids to about 55 amino acids, about 4 amino acids to about 50 amino acids, about 4 amino acids to about 45 amino acids, about 4 amino acids to about 40 amino acids, about 4 amino acids to about 35 amino acids, about 4 amino acids to about 30 amino acids, about 4 amino acids to about 25 amino acids, about 4 amino acids to about 20 amino acids, about 4 amino acids to about 15 amino acids, about 4 amino acids to about 10 amino acids, about 4 amino acids to about 9 amino acids, about 4 amino acids to about 8 amino acids, about 4 amino acids to about 7 amino acids, about 4 amino acids to about 6 amino acids, about 5 amino acids to about 100 amino acids, about 5 amino acid to about 95 amino acids, about 5 amino acids to about 90 amino acids, about 5 amino acids to about 85 amino acids, about 5 amino acids to about 80 amino acids, about 5 amino acids to about 75 amino acids, about 5 amino acids to about 70 amino acids, about 5 amino acids to about 65 amino acids, about 5 amino acids to about 60 amino acids, about 5 amino acids to about 55 amino acids, about 5 amino acids to about 50 amino acids, about 5 amino acids to about 45 amino acids, about 5 amino acids to about 40 amino acids, about 5 amino acids to about 35 amino acids, about 5 amino acids to about 30 amino acids, about 5 amino acids to about 25 amino acids, about 5 amino acids to about 20 amino acids, about 5 amino acids to about 15 amino acids, about 5 amino acids to about 10 amino acids, about 5 amino acids to about 9 amino acids, about 5 amino acids to about 8 amino acids, about 5 amino acids to about 7 amino acids, about 6 amino acids to about 100 amino acids, about 6 amino acid to about 95 amino acids, about 6 amino acids to about 90 amino acids, about 6 amino acids to about 85 amino acids, about 6 amino acids to about 80 amino acids, about 6 amino acids to about 75 amino acids, about 6 amino acids to about 70 amino acids, about 6 amino acids to about 65 amino acids, about 6 amino acids to about 60 amino acids, about 6 amino acids to about 55 amino acids, about 6 amino acids to about 50 amino acids, about 6 amino acids to about 45 amino acids, about 6 amino acids to about 40 amino acids, about 6 amino acids to about 35 amino acids, about 6 amino acids to about 30 amino acids, about 6 amino acids to about 25 amino acids, about 6 amino acids to about 20 amino acids, about 6 amino acids to about 15 amino acids, about 6 amino acids to about 10 amino acids, about 6 amino acids to about 9 amino acids, about 6 amino acids to about 8 amino acids, about 7 amino acids to about 100 amino acids, about 7 amino acid to about 95 amino acids, about 7 amino acids to about 90 amino acids, about 7 amino acids to about 85 amino acids, about 7 amino acids to about 80 amino acids, about 7 amino acids to about 75 amino acids, about 7 amino acids to about 70 amino acids, about 7 amino acids to about 65 amino acids, about 7 amino acids to about 60 amino acids, about 7 amino acids to about 55 amino acids, about 7 amino acids to about 50 amino acids, about 7 amino acids to about 45 amino acids, about 7 amino acids to about 40 amino acids, about 7 amino acids to about 35 amino acids, about 7 amino acids to about 30 amino acids, about 7 amino acids to about 25 amino acids, about 7 amino acids to about 20 amino acids, about 7 amino acids to about 15 amino acids, about 7 amino acids to about 10 amino acids, about 7 amino acids to about 9 amino acids, about 8 amino acids to about 100 amino acids, about 8 amino acid to about 95 amino acids, about 8 amino acids to about 90 amino acids, about 8 amino acids to about 85 amino acids, about 8 amino acids to about 80 amino acids, about 8 amino acids to about 75 amino acids, about 8 amino acids to about 70 amino acids, about 8 amino acids to about 65 amino acids, about 8 amino acids to about 60 amino acids, about 8 amino acids to about 55 amino acids, about 8 amino acids to about 50 amino acids, about 8 amino acids to about 45 amino acids, about 8 amino acids to about 40 amino acids, about 8 amino acids to about 35 amino acids, about 8 amino acids to about 30 amino acids, about 8 amino acids to about 25 amino acids, about 8 amino acids to about 20 amino acids, about 8 amino acids to about 15 amino acids, about 8 amino acids to about 10 amino acids, about 10 amino acids to about 100 amino acids, about 10 amino acid to about 95 amino acids, about 10 amino acids to about 90 amino acids, about 10 amino acids to about 85 amino acids, about 10 amino acids to about 80 amino acids, about 10 amino acids to about 75 amino acids, about 10 amino acids to about 70 amino acids, about 10 amino acids to about 65 amino acids, about 10 amino acids to about 60 amino acids, about 10 amino acids to about 55 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 20 amino acids, about 10 amino acids to about 15 amino acids, about 20 amino acids to about 100 amino acids, about 20 amino acid to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 65 amino acids, about 20 amino acids to about 60 amino acids, about 20 amino acids to about 55 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 30 amino acids to about 100 amino acids, about 30 amino acid to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 65 amino acids, about 30 amino acids to about 60 amino acids, about 30 amino acids to about 55 amino acids, about 30 amino acids to about 50 amino acids, about 30 amino acids to about 45 amino acids, about 30 amino acids to about 40 amino acids, about 30 amino acids to about 35 amino acids, about 40 amino acids to about 100 amino acids, about 40 amino acid to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 65 amino acids, about 40 amino acids to about 60 amino acids, about 40 amino acids to about 55 amino acids, about 40 amino acids to about 50 amino acids, about 40 amino acids to about 45 amino acids, about 50 amino acids to about 100 amino acids, about 50 amino acid to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 65 amino acids, about 50 amino acids to about 60 amino acids, about 50 amino acids to about 55 amino acids, about 60 amino acids to about 100 amino acids, about 60 amino acid to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 60 amino acids to about 65 amino acids, about 70 amino acids to about 100 amino acids, about 70 amino acid to about 95 amino acids, about 70 amino acids to about 90 amino acids, about 70 amino acids to about 85 amino acids, about 70 amino acids to about 80 amino acids, about 70 amino acids to about 75 amino acids, about 80 amino acids to about 100 amino acids, about 80 amino acid to about 95 amino acids, about 80 amino acids to about 90 amino acids, about 80 amino acids to about 85 amino acids, about 90 amino acids to about 100 amino acids, about 90 amino acids to about 95 amino acids, or about 95 amino acids to about 100 amino acids, removed from its N-terminus and/or 1 amino acid to 100 amino acids (or any of the subranges of this range described herein) removed from its C-terminus.

In some embodiments, an active stereocilin protein can, e.g., include the sequence of a wildtype, full-length stereocilin protein where 1 amino acid to 50 amino acids, 1 amino acid to 45 amino acids, 1 amino acid to 40 amino acids, 1 amino acid to 35 amino acids, 1 amino acid to 30 amino acids, 1 amino acid to 25 amino acids, 1 amino acid to 20 amino acids, 1 amino acid to 15 amino acids, 1 amino acid to 10 amino acids, 1 amino acid to 9 amino acids, 1 amino acid to 8 amino acids, 1 amino acid to 7 amino acids, 1 amino acid to 6 amino acids, 1 amino acid to 5 amino acids, 1 amino acid to 4 amino acids, 1 amino acid to 3 amino acids, about 2 amino acids to 50 amino acids, about 2 amino acids to 45 amino acids, about 2 amino acids to 40 amino acids, about 2 amino acids to 35 amino acids, about 2 amino acids to 30 amino acids, about 2 amino acids to 25 amino acids, about 2 amino acids to 20 amino acids, about 2 amino acids to 15 amino acids, about 2 amino acids to 10 amino acids, about 2 amino acids to 9 amino acids, about 2 amino acids to 8 amino acids, about 2 amino acids to 7 amino acids, about 2 amino acids to 6 amino acids, about 2 amino acids to 5 amino acids, about 2 amino acids to 4 amino acids, about 3 amino acids to 50 amino acids, about 3 amino acids to 45 amino acids, about 3 amino acids to 40 amino acids, about 3 amino acids to 35 amino acids, about 3 amino acids to 30 amino acids, about 3 amino acids to 25 amino acids, about 3 amino acids to 20 amino acids, about 3 amino acids to 15 amino acids, about 3 amino acids to 10 amino acids, about 3 amino acids to 9 amino acids, about 3 amino acids to 8 amino acids, about 3 amino acids to 7 amino acids, about 3 amino acids to 6 amino acids, about 3 amino acids to 5 amino acids, about 4 amino acids to 50 amino acids, about 4 amino acids to 45 amino acids, about 4 amino acids to 40 amino acids, about 4 amino acids to 35 amino acids, about 4 amino acids to 30 amino acids, about 4 amino acids to 25 amino acids, about 4 amino acids to 20 amino acids, about 4 amino acids to 15 amino acids, about 4 amino acids to 10 amino acids, about 4 amino acids to 9 amino acids, about 4 amino acids to 8 amino acids, about 4 amino acids to 7 amino acids, about 4 amino acids to 6 amino acids, about 5 amino acids to 50 amino acids, about 5 amino acids to 45 amino acids, about 5 amino acids to 40 amino acids, about 5 amino acids to 35 amino acids, about 5 amino acids to 30 amino acids, about 5 amino acids to 25 amino acids, about 5 amino acids to 20 amino acids, about 5 amino acids to 15 amino acids, about 5 amino acids to 10 amino acids, about 5 amino acids to 9 amino acids, about 5 amino acids to 8 amino acids, about 5 amino acids to 7 amino acids, about 6 amino acids to 50 amino acids, about 6 amino acids to 45 amino acids, about 6 amino acids to 40 amino acids, about 6 amino acids to 35 amino acids, about 6 amino acids to 30 amino acids, about 6 amino acids to 25 amino acids, about 6 amino acids to 20 amino acids, about 6 amino acids to 15 amino acids, about 6 amino acids to 10 amino acids, about 6 amino acids to 9 amino acids, about 6 amino acids to 8 amino acids, about 7 amino acids to 50 amino acids, about 7 amino acids to 45 amino acids, about 7 amino acids to 40 amino acids, about 7 amino acids to 35 amino acids, about 7 amino acids to 30 amino acids, about 7 amino acids to 25 amino acids, about 7 amino acids to 20 amino acids, about 7 amino acids to 15 amino acids, about 7 amino acids to 10 amino acids, about 7 amino acids to 9 amino acids, about 8 amino acids to 50 amino acids, about 8 amino acids to 45 amino acids, about 8 amino acids to 40 amino acids, about 8 amino acids to 35 amino acids, about 8 amino acids to 30 amino acids, about 8 amino acids to 25 amino acids, about 8 amino acids to 20 amino acids, about 8 amino acids to 15 amino acids, about 8 amino acids to 10 amino acids, about 10 amino acids to 50 amino acids, about 10 amino acids to 45 amino acids, about 10 amino acids to 40 amino acids, about 10 amino acids to 35 amino acids, about 10 amino acids to 30 amino acids, about 10 amino acids to 25 amino acids, about 10 amino acids to 20 amino acids, about 10 amino acids to 15 amino acids, about 15 amino acids to 50 amino acids, about 15 amino acids to 45 amino acids, about 15 amino acids to 40 amino acids, about 15 amino acids to 35 amino acids, about 15 amino acids to 30 amino acids, about 15 amino acids to 25 amino acids, about 15 amino acids to 20 amino acids, about 20 amino acids to 50 amino acids, about 20 amino acids to 45 amino acids, about 20 amino acids to 40 amino acids, about 20 amino acids to 35 amino acids, about 20 amino acids to 30 amino acids, about 20 amino acids to 25 amino acids, about 25 amino acids to 50 amino acids, about 25 amino acids to 45 amino acids, about 25 amino acids to 40 amino acids, about 25 amino acids to 35 amino acids, about 25 amino acids to 30 amino acids, about 30 amino acids to 50 amino acids, about 30 amino acids to 45 amino acids, about 30 amino acids to 40 amino acids, about 30 amino acids to 35 amino acids, about 35 amino acids to 50 amino acids, about 35 amino acids to 45 amino acids, about 35 amino acids to 40 amino acids, about 40 amino acids to 50 amino acids, about 40 amino acids to 45 amino acids, or about 45 amino acids to about 50 amino acids, are inserted. In some examples, the 1 amino acid to 50 amino acids (or any subrange thereof) can be inserted as a contiguous sequence into the sequence of a wildtype, full-length protein. In some examples, the 1 amino acid to 50 amino acids (or any subrange thereof) are not inserted as a contiguous sequence into the sequence of a wildtype, full-length protein. As can be appreciated in the art, the 1 amino acid to 50 amino acids can be inserted into a portion of the sequence of a wildtype, full-length protein that is not well-conserved between species.

Unless otherwise defined, all technical and scientific terms used herein have the same meaning as commonly understood by one of ordinary skill in the art to which this invention belongs. Methods and materials are described herein for use in the present invention; other suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DETAILED DESCRIPTION

Figure 1:
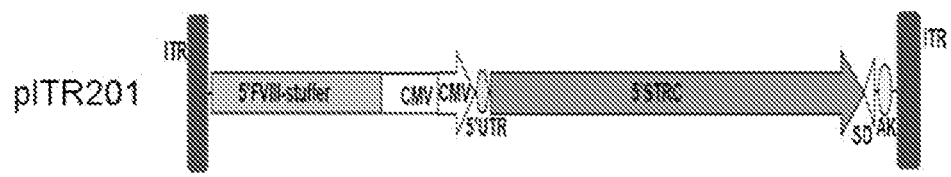
FIG. 1 is an exemplary schematic representation of a genetic map of a STRC vector (pITR-201; SEQ ID NO: 12; 4324 basepairs (bp)) that can be used in any of the present methods described herein. The vector includes an inverted terminal repeat (ITR) sequence (SEQ ID NO: 18), a 5' FVIII stuffer sequence (SEQ ID NO: 19), a CMV enhancer (SEQ ID NO: 20), a CMV promoter (SEQ ID NO: 21), a 5' untranslated region (UTR) sequence (SEQ ID NO: 24), a 5' STRC coding sequence (SEQ ID NO: 25), a splicing donor signal sequence (SD) (SEQ ID NO: 6), a highly recombinogenic sequence from F1 phage (AK; SEQ ID NO: 26), and an ITR sequence (SEQ ID NO: 36).

Provided herein are compositions that include at least two different nucleic acid vectors, where: each of the at least two different vectors includes a coding sequence that encodes a different portion of a stereocilin protein, each of the encoded portions being at least 30 amino acid residues in length, where the amino acid sequence of each of the encoded portions may optionally partially overlap with the amino acid sequence of a different one of the encoded portions; no single vector of the at least two different vectors encodes an active stereocilin protein (e.g., a full-length stereocilin protein); at least one of the coding sequences comprises a nucleotide sequence spanning two neighboring exons of stereocilin genomic DNA, and lacks an intronic sequence between the two neighboring exons; and, when introduced into a mammalian cell comprising chromosomal DNA, the at least two different vectors undergo homologous recombination with each other and with the chromosomal DNA of the cell, thereby forming a recombined nucleic acid inserted into the chromosomal DNA, where the recombined nucleic acid encodes an active stereocilin protein (e.g., a full-length stereocilin protein). Also provided are kits that include any of the compositions described herein. Also provided herein are methods that include introducing into a cochlea of a mammal a therapeutically effective amount of any of the compositions described herein.

Also provided herein are methods of increasing expression of an active stereocilin protein (e.g., a full-length stereocilin protein) in a mammalian cell that include introducing any of the compositions described herein into the mammalian cell. Also provided herein are methods of increasing expression of an active stereocilin protein (e.g., a full-length stereocilin protein) in an outer hair cell in a cochlea of a mammal that include introducing into the cochlea of the mammal a therapeutically effective amount of any of the compositions described herein. Also provided herein are methods of treating non-symptomatic sensorineural hearing loss in a subject identified as having a defective stereocilin gene that include: administering a therapeutically effective amount of any of the compositions described herein into the cochlea of the subject.

Additional non-limiting aspects of the compositions, kits, and methods are described herein and can be used in any combination without limitation.

Stereocilin

The STRC gene encodes stereocilin, a protein that is normally expressed in the inner ear and is associated with the stereocilia of specialized hair cells in the inner ear (see, e.g., Verpy et al., *Nature* 456:255-258, 2008; and Zhang et al., *J. Med. Genet.* 44:233-240, 2007). Stereocilia, which are about 10-50 µm in length, are important for hearing and balance. Stereocilia play a mechanosensing role in hearing. By bending in response to sound, they form a structure for mechanoreception of sound stimulation.

The human STRC gene is located on chromosome 15q15. It contains 29 exons encompassing ~19 kilobases (kb) (Verpy et al., *Nature Genetics* 29 (3): 345-349, 2001; NCBI Accession No. NG011636.1). The gene is tandemly duplicated on chromosome 15q15 in a telomere-to-centromere orientation, with the tandem copies located less than 100 kb apart on the chromosome. The coding sequence of the second copy is interrupted by a stop codon in exon 20, meaning that it is a "pseudogene" that encodes a nonfunctional truncated protein. (Hereinafter, references to "the STRC gene" mean the gene that does not have that stop codon in exon 20, while references to the "pseudogene" or the "STRC pseudogene" denote the gene that does have that stop codon in exon 20.) In some examples, the full-length STRC protein is a full-length wildtype STRC protein. The full-length wildtype STRC protein expressed from the human STRC gene is 1775 residues in length, and contains a signal peptide and several hydrophobic segments. When the signal peptide is cleaved off during processing of the wildtype protein, the resulting mature wildtype stereocilin protein is 1719 residues in length. In some embodiments, a full-length STRC protein can include a heterologous signal peptide positioned N-terminal to an amino acid sequence of a mature wildtype stereocilin protein.

Various mutations in the STRC gene have been associated with hearing loss (e.g., non-symptomatic sensorineural hearing loss). For example, a homozygous 1-bp insertion was identified in exon 13 in a consanguineous Pakistani family with autosomal recessive non-syndromic sensorineural deafness-16 (DFNB16) (Verpy et al. (2001). Another example found in a family with DFNB16 includes both a 4-bp deletion in exon 5 and a larger deletion encompassing exons 17-29. The two deletions were inherited from the father and mother, respectively. The 4-bp deletion was predicted to result in the translation of 5 out-of-frame amino acids and a premature stop codon in exon 5.

Additional exemplary mutations in a stereocilin gene detected in subjects having non-symptomatic sensorineural hearing loss and methods of sequencing a nucleic acid encoding stereocilin are described in, e.g., Verpy et al., *Nature* 456:255-259, 2008; Verpy et al., *Res. Systems Neurosci.* 519:194-210, 2011; Hofrichter et al., *Clinical Genetics* 87:49-55, 2015; and Mandelker et al., *J. Mol. Diagnostics* 16:639-647, 2014. Methods of detecting mutations in a gene are well-known in the art. Non-limiting examples of such techniques include: real-time polymerase chain reaction (RT-PCR), PCR, sequencing, Southern blotting, and Northern blotting.

An exemplary human wildtype stereocilin protein is or includes the sequence of SEQ ID NO: 1. Non-limiting examples of nucleic acid encoding a wildtype stereocilin protein are or include SEQ ID NO: 2 and SEQ ID NO: 3. As can be appreciated in the art, at least some or all of the codons in SEQ ID NO: 2 can be codon-optimized to allow for optimal expression in a non-human mammal or in a human.

In some embodiments of any of the compositions described herein, the stereocilin protein comprises a sequence that is at least 75% (e.g., at least 80%, at least 85%, at least 90%, at least 91%, at least 92%, at least 93%, at least 94%, at least 95%, at least 96%, at least 97%, at least 98%, at least 99%, or 100%) identical to SEQ ID NO: 1 or SEQ ID NO: 11. In some embodiments, a stereocilin protein can include a sequence that is identical to SEQ ID NO: 1, except that it includes 1, 2, 3, 4, 5, 6, 7, 8, 9, 10, 11, 12, 13, 14, 15, 16, 17, 18, 19, or 20 amino acid substitutions and/or deletions.

```
Human Full-length Wildtype Stereocilin Protein (Signal
sequence shown in bold)
                                                     (SEQ ID NO: 1)
MALSLWPLLLLLLLLLLLSFAVTLAPTGPHSLDPGLSFLKSLLSTLDQAPQGSLSRSRFFTFLANISSS

FEPGRMGEGPVGEPPPLQPPALRLHDFLVTLRGSPDWEPMLGLLGDMLALLGQEQTPRDFLVHQAGVLG

GLVEVLLGALVPGGPPTPTRPPCTRDGPSDCVLAADWLPSLLLLLEGTRWQALVQVQPSVDPTNATGLD

GREAAPHFLQGLLGLLTPTGELGSKEALWGGLLRTVGAPLYAAFQEGLLRVTHSLQDEVFSILGQPEPD

TNGQCQGVFFLTLSLLGNLQQLLLWGVRHNLSWDVQALGFLSGSPPPPPALLHCLSTGVPLPRASQPSA

HISPRQRRAITVEALCENHLGPAPPYSISNFSIHLLCQHTKPATPQPHPSTTAICQTAVWYAVSWAPGA

QGWLQACHDQFPDEFLDAICSNLSFSALSGSNRRLVKRLCAGLLPPPTSCPEGLPPVPLTPDIFWGCFL

ENETLWAERLCGEASLQAVPPSNQAWVQHVCQGPTPDVTASPPCHIGPCGERCPDGGSFLVMVCANDTM

YEVLVPFWPWLAGQCRISRGGNDTCFLEGLLGPLLPSLPPLGPSPLCLTPGPFLLGMLSQLPRCQSSVP

ALAHPTRLHYLLRLLTFLLGPGAGGAEAQGMLGRALLLSSLPDNCSFWDAFRPEGRRSVLRTIGEYLEQ

DEEQPTPSGFEPTVNPSSGISKMELLACFSPVLWDLLQREKSVWALQILVQAYLHMPPENLQQLVLSAE

REAAQGFLTLMLQGKLQGKLQVPPSEEQALGRLTALLLQRYPRLTSQLFIDLSPLIPFLAVSDLMRFPP
```

-continued

SLLANDSVQQGYRGSEENSLEEDKGLRPMTPRSLAAIRDYSPGMRPEQKEALAKRLLAPELFGEVPAWP

QELLWAVLPLLPHLPLENFLQLSPHQIQALEDSWPAAGLGPGHARHVLRSLVNQSVQDGEEQVRRLGPL

ACFLSPEELQSLVPLSDPTGPVERGLLECAANGTLSPEGRVAYELLGVLRSSGGAVLSPRELRVWAPLF

SQLGLRFLQELSEPQLRAMLPVLQGTSVTPAQAVLLLGRLLPRHDLSLEELCSLHLLLPGLSPQTLQAT

PRRVLVGACSCLAPELSRLSACQTAALLQTERVKDGVKNMGTTGAGPAVCIPGQQPIPTTWPDCLLPLL

PLKLLQLDSLALLANRRRYWELPWSEQQAQFLWKKMQVPTNLTLRNLQALGTLAGGMSCEFLQQINSMV

DFLEVVHMIYQLPTRVRGSLRACIWAELQRRMAMPEPEWTTVGPELNGLDSKLLLDLPIQLMDRLSNES

IMLVVELVQRAPEQLLALTPLHQAALAERALQNLAPKETPVSGEVLETLGPLVGFLGTESTRQIPLQIL

LSHLSQLQGFCLGETFATELGWLLLQESVLGKPELWSQDEVEQAGRLVFTLSTEAISLIPREALGPETL

ERLLEKQQSWEQSRVGQLCREPQLAAKKAALVAGVVRPAAEDLPEPVPNCADVRGTFPAAWSATQTAEM

ELSDFEDCLTLFAGDPGLGPEELRAAMGKAKQLWGPPRGFRPEQILQLGRLLIGLGDRELQELILVDWG

VLSTLGQIDGWSTTQLRIVVSSFLRQSGRHVSHLDFVHLTALGYTLCGLRPEELQHISSWEFSQAALFL

GTLHLQCSEEQLEVLAHLLVLPGGFGPISNWGPEIFTEIGTIAAGIPDLALSALLRGQIQGVTPLAISV

IPPPKFAVVESPIQLSSLTSAQAVAVTPEQMAFLSPEQRRAVAWAQHEGKESPEQQGRSTAWGLQDWSR

PSWSLVLTISFLGHLL

Human Stereocilin Signal Sequence
(SEQ ID NO: 10)
MALSLWPLLLLLLLLLLLSFAV

Human Full-length Wildtype Stereocilin Protein (Signal Sequence in Bold)
(SEQ ID NO: 11)
MALSLWPLLLLLLLLLLLSFAVTLAPTGPHSLDPGLSFLKSLLSTLDQAPQGSLSRSRFFTFLANISSS

FEPGRMGEGPVGEPPPLQPPALRLHDFLVTLRGSPDWEPMLGLLGDMLALLGQEQTPRDFLVHQAGVLG

GLVEVLLGALVPGGPPTPTRPPCTRDGPSDCVLAADWLPSLLLLLEGTRWQALVQVQPSVDPTNATGLD

GREAAPHFLQGLLGLLTPTGELGSKEALWGGLLRTVGAPLYAAFQEGLLRVTHSLQDEVFSILGQPEPD

TNGQCQGGNLQQLLLWGVRHNLSWDVQALGFLSGSPPPPPALLHCLSTGVPLPRASQPSAHISPRQRRA

ITVEALCENHLGPAPPYSISNFSIHLLCQHTKPATPQPHPSTTAICQTAVWYAVSWAPGAQGWLQACHD

QFPDEFLDAICSNLSFSALSGSNRRLVKRLCAGLLPPPTSCPEGLPPVPLTPDIFWGCFLENETLWAER

LCGEASLQAVPPSNQAWVQHVCQGPTPDVTASPPCHIGPCGERCPDGGSFLVMVCANDTMYEVLVPFWP

WLAGQCRISRGGNDTCFLEGLLGPLLPSLPPLGPSPLCLTPGPFLLGMLSQLPRCQSSVPALAHPTRLH

YLLRLLTFLLGPGAGGAEAQGMLGRALLLSSLPDNCSFWDAFRPEGRRSVLRTIGEYLEQDEEQPTPSG

FEPTVNPSSGISKMELLACFSPVLWDLLQREKSVWALQILVQAYLHMPPENLQQLVLSAEREAAQGFLT

LMLQGKLQGKLQVPPSEEQALGRLTALLLQRYPRLTSQLFIDLSPLIPFLAVSDLMRFPPSLLANDSVL

AAIRDYSPGMRPEQKEALAKRLLAPELFGEVPAWPQELLWAVLPLLPHLPLENFLQLSPHQIQALEDSW

PAAGLGPGHARHVLRSLVNQSVQDGEEQVRRLGPLACFLSPEELQSLVPLSDPTGPVERGLLECAANGT

LSPEGRVAYELLGVLRSSGGAVLSPRELRVWAPLFSQLGLRFLQELSEPQLRAMLPVLQGTSVTPAQAV

LLLGRLLPRHDLSLEELCSLHLLLPGLSPQTLQAIPRRVLVGACSCLAPELSRLSACQTAALLQTFRVK

DGVKNMGTTGAGPAVCIPGQPIPTTWPDCLLPLLPLKLLQLDSLALLANRRRYWELPWSEQQAQFLWKK

MQVPTNLTLRNLQALGTLAGGMSCEFLQQINSMVDFLEVVHMIYQLPTRVRGSLRACIWAELQRRMAMP

EPEWTTVGPELNGLDSKLLLDLPIQLMDRLSNESIMLVVELVQRAPEQLLALTPLHQAALAERALQNLA

PKETPVSGEVLETLGPLVGFLGTESTRQIPLQILLSHLSQLQGFCLGETFATELGWLLLQESVLGKPEL

WSQDEVEQAGRLVFTLSTEATSLIPREALGPETLERLLEKQQSWEQSRVGQLCREPQLAAKKAALVAGV

VRPAAEDLPEPVPNCADVRGTFPAAWSATQIAEMELSDFEDCLTLFAGDPGLGPEELRAAMGKAKQLWG

-continued

PPRGFRPEQILQLGRLLIGLGDRELQELILVDWGVLSTLGQIDGWSTTQLRIVVSSFLRQSGRHVSHLD

FVHLTALGYTLCGLRPEELQHISSWEFSQAALFLGTLHLQCSEEQLEVLAHLLVLPGGFGPISNWGPEI

FTEIGTIAAGIPDLALSALLRGQIQGVTPLAISVIPPPKFAVVFSPIQLSSLTSAQAVAVTPEQMAFLS

PEQRRAVAWAQHEGKESPEQQGRSTAWGLQDWSRPSWSLVLTISFLGHLL

Human Wildtype Stereocilin cDNA (SEQ ID NO: 2)
ATGGCTCTCAGCCTCTGGCCCCTGCTGCTGCTGCTGCTGCTGCTGCTGCTGTCCTTTGCAGTGACT

CTGGCCCCTACTGGGCCTCATTCCCTGGACCCTGGTCTCTCCTTCCTGAAGTCATTGCTCTCCACTCTG

GACCAGGCTCCCCAGGGCTCCCTGAGCCGCTCACGGTTCTTTACATTCCTGGCCAACATTTCTTCTTCC

TTTGAGCCTGGGAGAATGGGGGAAGGACCAGTAGGAGAGCCCCCACCTCTCCAGCCGCCTGCTCTGCGG

CTCCATGATTTTCTAGTGACACTGAGAGGTAGCCCCGACTGGGAGCCAATGCTAGGGCTGCTAGGGGAT

ATGCTGGCACTGCTGGGACAGGAGCAGACTCCCCGAGATTTCCTGGTGCACCAGGCAGGGGTGCTGGGT

GGACTTGTGGAGGTGCTGCTGGGAGCCTTAGTTCCTGGGGGCCCCCCTACCCCAACTCGGCCCCCATGC

ACCCGTGATGGGCCGTCTGACTGTGTCCTGGCTGCTGACTGGTTGCCTTCTCTGCTGCTGTTGTTAGAG

GGCACACGCTGGCAAGCTCTGGTGCAGGTGCAGCCCAGTGTGGACCCCACCAATGCCACAGGCCTCGAT

GGGAGGGAGGCAGCTCCTCACTTTTTGCAGGGTCTGTTGGGTTTGCTTACCCCAACAGGGGAGCTAGGC

TCCAAGGAGGCTCTTTGGGCGGTCTGCTACGCACAGTGGGGCCCCCCTCTATGCTGCCTTTCAGGAG

GGGCTGCTCCGTGTCACTCACTCCCTGCAGGATGAGGTCTTCTCCATTTTGGGGCAGCCAGAGCCTGAT

ACCAATGGGCAGTGCCAGGGAGTTTTCTTCCTTACTCTTTCCCTCCTAGGTAACCTTCAACAGCTGCTC

TTATGGGCGTCCGGCACAACCTTTCCTGGGATGTCCAGGCGCTGGGCTTTCTGTCTGGATCACCACCC

CCACCCCCTGCCCTCCTTCACTGCCTGAGCACGGGCGTGCCTCTGCCCAGAGCTTCTCAGCCGTCAGCC

CACATCAGCCCACGCCAACGGCGAGCCATCACTGTGGAGGCCCTCTGTGAGAACCACTTAGGCCCAGCA

CCACCCTACAGCATTTCCAACTTCTCCATCCACTTGCTCTGCCAGCACACCAAGCCTGCCACTCCACAG

CCCCATCCCAGCACCACTGCCATCTGCCAGACAGCTGTGTGGTATGCAGTGTCCTGGGCACCAGGTGCC

CAAGGCTGGCTACAGGCCTGCCACGACCAGTTTCCTGATGAGTTTTTGGATGCGATCTGCAGTAACCTC

TCCTTTTCAGCCCTGTCTGGCTCCAACCGCCGCCTGGTGAAGCGGCTCTGTGCTGGCCTGCTCCCACCC

CCTACCAGCTGCCCTGAAGGCCTGCCCCCTGTTCCCCTCACCCCAGACATCTTTTGGGGCTGCTTCTTG

GAGAATGAGACTCTGTGGGCTGAGCGACTGTGTGGGGAGGCAAGTCTACAGGCTGTGCCCCCCAGCAAC

CAGGCTTGGGTCCAGCATGTGTGCCAGGGCCCCACCCCAGATGTCACTGCCTCCCCACCATGCCACATT

GGACCCTGTGGGGAACGCTGCCCGGATGGGGGCAGCTTCCTGGTGATGGTCTGTGCCAATGACACCATG

TATGAGGTCCTGGTGCCCTTCTGGCCTTGGCTAGCAGGCCAATGCAGGATAAGTCGTGGGGGCAATGAC

ACTTGCTTCCTAGAAGGGCTGCTGGGCCCCTTCTGCCCTCTCTGCCACCACTGGGACCATCCCCACTC

TGTCTGACCCCTGGCCCCTTCCTCCTTGGCATGCTATCCCAGTTGCCACGCTGTCAGTCCTCTGTCCCA

GCTCTTGCTCACCCCACACGCCTACACTATCTCCTCCGCCTGCTGACCTTCCTCTTGGGTCCAGGGGCT

GGGGGCGCTGAGGCCCAGGGGATGCTGGGTCGGGCCCTACTGCTCTCCAGTCTCCCAGACAACTGCTCC

TTCTGGGATGCCTTTCGCCCAGAGGGCCGGCGCAGTGTGCTACGACGATTGGGGAATACCTGGAACAA

GATGAGGAGCAGCCAACCCCATCAGGCTTTGAACCCACTGTCAACCCCAGCTCTGGTATAAGCAAGATG

GAGCTGCTGGCCTGCTTTAGTCCTGTGCTGTGGGATCTGCTCCAGAGGGAAAAGAGTGTTTGGGCCCTG

CAGATTCTAGTGCAGGCGTACCTGCATATGCCCCCAGAAAACCTCCAGCAGCTGGTGCTTTCAGCAGAG

AGGGAGGCTGCACAGGGCTTCCTGACACTCATGCTGCAGGGGAAGCTGCAGGGGAAGCTGCAGGTACCA

CCATCCGAGGAGCAGGCCCTGGGTCGCCTGACAGCCCTGCTGCTCCAGCGGTACCCACGCCTCACCTCC

CAGCTCTTCATTGACCTGTCACCACTCATCCCTTTCTTGGCTGTCTCTGACCTGATGCGCTTCCCACCA

-continued

```
TCCCTGTTAGCCAACGACAGTGTACAGCAGGGCTACAGAGGGTCAGAGGAAAACAGTTTGGAGGAAGAC

AAAGGGTTAAGACCCATGACTCCTCGCAGCCTGGCTGCCATCCGGGATTACAGCCCAGGAATGAGGCCT

GAACAGAAGGAGGCTCTGGCAAAGCGACTGCTGGCCCCTGAACTGTTTGGGGAAGTGCCTGCCTGGCCC

CAGGGAGCTGCTGTGGGCAGTGCTGCCCCTGCTCCCCACCTCCCTCTGGAGAACTTTTTGCAGCTCAGC

CCTCACCAGATCCAGGCCCTGGAGGATAGCTGGCCAGCAGCAGGTCTGGGGCCAGGGCATGCCCGCCAT

GTGCTGCGCAGCCTGGTAAACCAGAGTGTCCAGGATGGTGAGGAGCAGGTACGCAGGCTTGGGCCCCTC

GCCTGTTTCCTGAGCCCTGAGGAGCTGCAGAGCCTAGTGCCCCTGAGTGATCCAACGGGGCCAGTAGAA

CGGGGGCTGCTGGAATGTGCAGCCAATGGGACCCTCAGCCCAGAAGGACGGGTGGCATATGAACTTCTG

GGTGTGTTGCGCTCATCTGGAGGAGCGGTGCTGAGCCCCCGGGAGCTGCGGGTCTGGGCCCCTCTCTTC

TCTCAGCTGGGCCTCCGCTTCCTTCAGGAGCTGTCAGAGCCCCAGCTTAGAGCCATGCTTCCTGTCCTG

CAGGGAACTAGTGTTACACCTGCTCAGGCTGTCCTGCTGCTTGGACGGCTCCTTCCTAGGCACGATCTA

TCCCTGGAGGAACTCTGCTCCTTGCACCTTCTGCTACCAGGCCTCAGCCCCCAGACACTCCAGGCCATC

CCTAGGCGAGTCCTGGTCGGGGCTTGTTCCTGCCTGGCCCCTGAACTGTCACGCCTCTCAGCCTGCCAG

ACCGCAGCACTGCTGCAGACCTTTCGGGTTAAAGATGGTGTTAAAAATATGGGTACAACAGGTGCTGGT

CCAGCTGTGTGTATCCCTGGTCAGCAGCCTATTCCCACCACCTGGCCAGACTGCCTGCTTCCCCTGCTC

CCATTAAAGCTGCTACAACTGGATTCCTTGGCTCTTCTGGCAAATCGAAGACGCTACTGGGAGCTGCCC

TGGTCTGAGCAGCAGGCACAGTTTCTCTGGAAGAAGATGCAAGTACCCACCAACCTTACCCTCAGGAAT

CTGCAGGCTCTGGGCACCCTGGCAGGAGGCATGTCCTGTGAGTTTCTGCAGCAGATCAACTCCATGGTA

GACTTCCTTGAAGTGGTGCACATGATCTATCAGCTGCCCACTAGAGTTCGAGGGAGCCTGAGGGCCTGT

ATCTGGGCAGAGCTACAGCGGAGGATGGCAATGCCAGAACCAGAATGGACAACTGTAGGGCCAGAACTG

AACGGGCTGGATAGCAAGCTACTCCTGGACTTACCGATCCAGTTGATGGACAGACTATCCAATGAATCC

ATTATGTTGGTGGTGGAGCTGGTGCAAAGAGCTCCAGAGCAGCTGCTGGCACTGACCCCCCTCCACCAG

GCAGCCCTGGCAGAGAGGGCACTACAAAACCTGGCTCCAAAGGAGACTCCAGTCTCAGGGGAAGTGCTG

GAGACCTTAGGCCCTTTGGTTGGATTCCTGGGGACAGAGAGCACACGACAGATCCCCCTACAGATCCTG

CTGTCCCATCTCAGTCAGCTGCAAGGCTTCTGCCTAGGAGAGACATTTGCCACAGAGCTGGGATGGCTG

CTATTGCAGGAGTCTGTTCTTGGGAAACCAGAGTTGTGGAGCCAGGATGAAGTAGAGCAAGCTGGACGC

CTAGTATTCACTCTGTCTACTGAGGCAATTTCCTTGATCCCCAGGGAGGCCTTGGGTCCAGAGACCCTG

GAGCGGCTTCTAGAAAAGCAGCAGAGCTGGGAGCAGAGCAGAGTTGGACAGCTGTGTAGGGAGCCACAG

CTTGCTGCCAAGAAAGCAGCCCTGGTAGCAGGGGTGGTGCGACCAGCTGCTGAGGATCTTCCAGAACCT

GTGCCAAATTGTGCAGATGTACGAGGGACATTCCCAGCAGCCTGGTCTGCAACCCAGATTGCAGAGATG

GAGCTCTCAGACTTTGAGGACTGCCTGACATTATTTGCAGGAGACCCAGGACTTGGGCCTGAGGAACTG

CGGGCAGCCATGGGCAAAGCAAAACAGTTGTGGGTCCCCCCCGGGGATTTCGTCCTGAGCAGATCCTG

CAGCTTGGTAGGCTCTTAATAGGTCTAGGAGATCGGGAACTACAGGAGCTGATCCTAGTGGACTGGGGA

GTGCTGAGCACCCTGGGGCAGATAGATGGCTGGAGCACCACTCAGCTCCGCATTGTGGTCTCCAGTTTC

CTACGGCAGAGTGGTCGGCATGTGAGCCACCTGGACTTCGTTCATCTGACAGCGCTGGGTTATACTCTC

TGTGGACTGCGGCCAGAGGAGCTCCAGCACATCAGCAGTTGGGAGTTCAGCCAAGCAGCTCTCTTCCTC

GGCACCCTGCATCTCCAGTGCTCTGAGGAACAACTGGAGGTTCTGGCCCACCTACTTGTACTGCCTGGT

GGGTTTGGCCCAATCAGTAACTGGGGGCCTGAGATCTTCACTGAAATTGGCACCATAGCAGCTGGGATC

CCAGACCTGGCTCTTTCAGCACTGCTGCGGGACAGATCCAGGGCGTTACTCCTCTTGCCATTTCTGTC

ATCCCTCCTCCTAAATTTGCTGTGGTGTTTAGTCCCATCCAACTATCTAGTCTCACCAGTGCTCAGGCT
```

-continued

GTGGCTGTCACTCCTGAGCAAATGGCCTTTCTGAGTCCTGAGCAGCGACGAGCAGTTGCATGGGCCCAA

CATGAGGGAAAGGAGAGCCCAGAACAGCAAGGTCGAAGTACAGCCTGGGGCCTCCAGGACTGGTCACGA

CCTTCCTGGTCCCTGGTATTGACTATCAGCTTCCTTGGCCACCTGCTATGA

Human Wildtype Stereocilin cDNA - Codon Optimized (SEQ ID NO: 3)

ATGGCTCTGTCTCTGTGGCCTCTGCTGCTGCTCCTGTTGCTGCTTCTGCTGCTCAGCTTCGCCGTGACA

CTGGCTCCAACAGGACCCCACTCTCTGGATCCTGGCCTGAGCTTTCTGAAGTCCCTGCTGAGCACCCTG

GATCAGGCTCCTCAGGGCAGCCTGAGCAGATCCAGATTCTTCACCTTCCTGGCCAACATCAGCAGCAGC

TTCGAGCCTGGCAGAATGGGAGAAGGACCTGTGGGAGAACCTCCTCCACTGCAACCTCCAGCTCTGCGG

CTGCACGATTTTCTGGTCACACTGAGAGGCAGCCCCGACTGGGAACCTATGCTGGGACTGCTGGGAGAT

ATGCTGGCCCTGCTCGGACAAGAGCAGACCCCTAGAGATTTCCTGGTGCATCAGGCTGGCGTGCTCGGA

GGACTGGTTGAAGTTCTGCTTGGAGCACTGGTGCCTGGCGGACCTCCTACACCTACAAGACCTCCATGC

ACCAGAGATGGCCCCAGCGATTGTGTGCTGGCTGCTGATTGGCTGCCTAGCCTGCTCCTGCTTCTGGAA

GGCACAAGATGGCAGGCCCTGGTGCAGGTTCAGCCTTCTGTGGATCCTACCAATGCCACCGGCCTGGAT

GGAAGAGAAGCCGCTCCACACTTTCTGCAGGGACTGCTTGGACTGCTCACACCTACTGGCGAGCTGGGC

TCTAAAGAAGCCCTTTGGGGAGGCCTGCTGAGAACAGTTGGAGCCCCTCTGTACGCCGCCTTTCAAGAG

GGACTCCTGAGAGTGACACACAGCCTGCAGGACGAGGTGTTCAGCATCCTGGGACAGCCAGAGCCTGAC

ACCAATGGACAGTGTCAGGGCGTGTTCTTTCTGACCCTGAGCCTGCTGGGCAACCTGCAGCAACTGCTT

CTGTGGGGCGTCAGACACAACCTGAGCTGGGATGTGCAGGCACTGGGCTTTCTGTCTGGAAGCCCTCCA

CCTCCACCAGCACTGCTGCATTGTCTGTCTACTGGCGTGCCACTGCCTAGAGCCTCTCAGCCTAGCGCT

CACATCAGCCCCAGACAGAGAAGGGCCATCACCGTGGAAGCTCTGTGCGAGAATCACCTGGGACCTGCT

CCTCCATACAGCATCAGCAACTTCTCCATCCATCTGCTGTGTCAGCACACCAAGCCTGCCACACCTCAG

CCTCATCCTAGCACCACAGCCATCTGTCAGACCGCCGTTTGGTACGCCGTTTCTTGGGCTCCTGGTGCT

CAAGGATGGCTGCAGGCCTGTCACGATCAGTTCCCCGACGAGTTCCTGGACGCCATCTGCAGCAATCTG

AGCTTCTCTGCCCTGTCCGGCAGCAATCGGAGACTGGTCAAAAGACTGTGCGCCGGACTGCTGCCTCCT

CCAACATCTTGTCCTGAGGGACTGCCTCCTGTGCCTCTGACTCCCGATATCTTTTGGGGCTGCTTCCTG

GAAAACGAGACACTGTGGGCCGAGAGACTGTGTGGCGAAGCCTCTCTGCAAGCCGTGCCTCCATCTAAT

CAGGCCTGGGTGCAGCACGTTTGTCAGGGCCCTACACCTGACGTGACAGCCTCTCCTCCTTGTCACATC

GGACCTTGCGGCGAGAGATGTCCTGATGGCGGCAGCTTTCTCGTGATGGTCTGCGCCAACGACACTATG

TACGAGGTGCTGGTGCCCTTCTGGCCTTGGCTGGCTGGCCAGTGTAGAATCTCCAGAGGCGGCAACGAT

ACCTGTTTCCTGGAAGGACTCCTGGGACCACTGCTTCCATCTCTGCCTCCGCTTGGACCCTCTCCTCTG

TGTCTTACCCCTGGACCTTTCCTGCTGGGGATGCTGTCTCAGCTGCCTAGATGCCAGTCTAGCGTGCCA

GCTCTGGCCCATCCAACCAGACTGCACTATCTGTTGCGGCTGCTGACCTTCCTCCTTGGACCTGGCGCT

GGCGGAGCTGAAGCTCAAGGCATGCTTGGCAGAGCCCTGCTGCTGTCATCCCTGCCTGACAACTGCAGC

TTCTGGGACGCCTTCAGACCTGAAGGACGCAGAAGCGTGCTGAGGACCATCGGCGAGTACCTGGAACAG

GATGAGGAACAGCCTACACCAAGCGGCTTCGAACCCACCGTGAATCCTAGCAGCGGCATCTCCAAGATG

GAACTGCTGGCCTGCTTCAGCCCCGTGCTGTGGGATCTGCTGCAGAGGGAAAAAGCGTGTGGGCCCTG

CAGATCCTGGTCCAGGCCTATCTGCACATGCCTCCAGAGAACCTGCAACAGCTGGTGCTGTCTGCCGAG

AGAGAAGCTGCCCAGGGATTCCTGACTCTGATGCTGCAGGGAAAGCTGCAGGGCAAACTCCAGGTGCCA

CCTAGCGAAGAACAGGCCCTTGGCAGACTGACAGCACTCCTGCTCCAGAGATACCCCAGACTGACCTCT

CAGCTGTTTATCGATCTGAGCCCTCTGATCCCATTCCTGGCCGTGTCCGACCTGATGAGATTCCCTCCT

AGTCTGCTGGCCAACGACTCCGTGCAGCAGGGATACAGAGGCAGCGAGGAAAACAGCCTGGAAGAGGAC

-continued

```
AAAGGCCTGCGGCCTATGACACCTAGATCTCTGGCCGCCATCCGGGATTACAGCCCTGGAATGAGGCCC

GAGCAGAAAGAGGCCCTGGCTAAGAGACTGCTGGCTCCCGAGCTGTTTGGCGAAGTTCCAGCCTGGCCT

CAAGAACTGCTGTGGGCTGTTCTGCCCCTGCTGCCACATCTGCCTCTGGAAAACTTCCTGCAGCTGAGC

CCACACCAGATTCAGGCCCTCGAGGATTCTTGGCCTGCCGCTGGACTCGGACCTGGACATGCTAGACAC

GTGCTGAGAAGCCTGGTCAACCAGAGCGTTCAGGACGGCGAGGAACAAGTGCGGAGACTTGGACCCCTG

GCCTGTTTTCTGAGCCCCGAGGAACTGCAGAGTCTGGTGCCTCTGTCTGACCCTACAGGCCCTGTTGAA

AGGGGCCTGCTGGAATGTGCCGCCAATGGAACACTGAGCCCTGAGGGCAGAGTGGCCTATGAACTTCTG

GGAGTGCTGAGATCTAGCGGCGGAGCCGTTCTGTCCCCTAGGGAACTTAGAGTGTGGGCACCCCTGTTT

AGCCAGCTGGGCCTGAGATTCCTGCAAGAGCTGTCTGAGCCACAGCTGAGGGCTATGCTGCCTGTGCTC

CAGGGCACATCTGTGACACCAGCTCAAGCCGTCCTGCTGTTGGGCAGACTGCTCCCTAGACACGATCTG

TCCCTGGAAGAACTGTGCAGCCTGCACTTGCTGCTGCCTGGACTGTCTCCTCAGACACTGCAGGCCATT

CCTCGGAGAGTGCTTGTGGGAGCCTGTAGCTGTCTGGCCCCTGAGCTGTCTAGACTGAGCGCCTGTCAA

ACAGCCGCTCTCCTGCAGACCTTCAGAGTGAAGGATGGCGTGAAGAACATGGGCACCACAGGCGCTGGA

CCTGCCGTGTGTATTCCTGGACAGCAGCCCATTCCTACCACCTGGCCAGATTGTCTGCTCCCACTGCTG

CCCCTGAAACTGCTGCAGCTGGATTCTCTGGCTCTGCTGGCTAACCGGCGGAGATATTGGGAACTGCCT

TGGAGCGAACAGCAGGCACAGTTCCTGTGGAAGAAGATGCAGGTCCCCACCAATCTGACACTGCGGAAT

CTGCAGGCTCTCGGCACACTTGCTGGCGGAATGAGCTGCGAGTTCCTCCAGCAGATCAACAGCATGGTG

GACTTTCTGGAAGTGGTGCACATGATCTACCAGCTGCCAACCAGAGTGCGGGGAAGCCTGAGAGCTTGT

ATTTGGGCTGAACTGCAGCGGCGGATGGCCATGCCTGAACCTGAATGGACAACAGTGGGCCCCGAGCTG

AACGGCCTGGACTCTAAACTTCTGCTGGATCTCCCCATCCAGCTGATGGACAGACTGAGCAACGAGAGC

ATCATGCTGGTGGTGGAACTGGTGCAGAGAGCCCCAGAACAGCTGCTGGCACTGACACCTCTGCATCAA

GCTGCTCTGGCCGAACGGGCCCTTCAGAATCTGGCTCCCAAAGAAACCCCTGTGTCCGGGGAAGTGCTG

GAAACACTGGGACCTCTTGTGGGCTTCCTGGGCACCGAGTCTACCAGACAGATTCCTCTCCAGATCCTG

CTGTCCCACCTGAGCCAGCTCCAGGGATTTTGTCTGGGCGAGACATTCGCCACCGAACTCGGATGGTTG

CTGCTCCAAGAGAGCGTGCTGGGAAAGCCCGAACTGTGGTCACAGGACGAAGTGGAACAGGCCGGCAGA

CTGGTGTTTACCCTGTCTACCGAGGCCATCAGTCTGATCCCCAGAGAAGCACTGGGCCCTGAAACACTC

GAGAGGCTGCTGGAAAAGCAGCAGTCTTGGGAACAGAGCAGAGTGGGCCAGCTGTGTAGAGAACCTCAG

CTGGCCGCTAAAAAGGCCGCACTGGTTGCTGGCGTTGTCAGACCTGCTGCCGAGGATCTGCCAGAGCCA

GTGCCTAATTGTGCCGATGTGCGGGGCACATTTCCTGCCGCTTGGAGCGCTACACAGATCGCCGAAATG

GAACTGAGCGACTTCGAGGACTGTCTGACTCTGTTTGCCGGCGATCCTGGACTGGGACCAGAAGAACTG

AGAGCCGCCATGGGCAAAGCCAAGCAACTTTGGGGACCTCCAAGAGGCTTCAGACCCGAACAGATTCTG

CAGCTCGGCCGCCTGCTTATCGGACTGGGCGATAGAGAGCTGCAAGAACTGATCCTGGTGGACTGGGGC

GTGCTGTCTACTCTGGGACAAATCGACGGCTGGTCCACCACACAGCTGCGGATTGTGGTGTCCAGCTTC

CTGAGGCAGTCTGGCAGACATGTGTCTCACCTGGACTTCGTGCACCTGACTGCCCTGGGCTACACACTG

TGTGGACTGCGGCCTGAGGAACTTCAGCACATCAGCTCTTGGGAGTTCAGCCAGGCAGCCCTGTTTCTG

GGAACCCTGCATCTGCAGTGCTCCGAAGAACAACTGGAAGTGCTCGCCCATCTGCTCGTGCTGCCAGGC

GGATTTGGCCCCATCTCTAATTGGGGACCCGAGATCTTCACCGAGATCGGCACCATTGCCGCTGGCATC

CCTGATCTGGCCCTGTCTGCACTGCTGAGAGGACAGATCCAGGGCGTGACACCACTGGCCATTAGCGTG

ATCCCTCCACCAAAGTTCGCCGTGGTGTTTAGCCCCATTCAGCTGTCCAGCCTGACATCTGCCCAAGCC

GTGGCTGTGACCCCTGAACAGATGGCATTTCTGTCTCCCGAGCAGCGGAGAGCTGTTGCTTGGGCTCAA
```

```
-continued
CACGAGGGCAAAGAGAGTCCTGAGCAACAGGGAAGAAGCACCGCTTGGGGACTGCAGGATTGGTCCAGA

CCTTCTTGGTCACTGGTGCTGACCATCAGCTTTCTGGGCCACCTCCTGTGA
```

A non-limiting example of a human wildtype stereocilin genomic DNA sequence is SEQ ID NO: 4. The exons in SEQ ID NO: 4 are: nucleotide positions 1-142 (exon 1), nucleotide positions 445-1230 (exon 2), nucleotide positions 1319-1343 (exon 3), nucleotide positions 2111-3368 (exon 4), nucleotide positions 4325-4387 (exon 5), nucleotide positions 4489-4605 (exon 6), nucleotide positions 4748-4914 (exon 7), nucleotide positions 5570-5756 (exon 8), nucleotide positions 5895-6010 (exon 9), nucleotide positions 6292-6424 (exon 10), nucleotide positions 6777-6959 (exon 11), nucleotide positions 7264-7302 (exon 12), nucleotide positions 7486-7653 (exon 13), nucleotide positions 7817-7882 (exon 14), nucleotide positions 8364-8489 (exon 15), nucleotide positions 9467-9525 (exon 16), nucleotide positions 10598-10721 (exon 17), nucleotide positions 10826-10938 (exon 18), nucleotide positions 13402-13537 (exon 19), nucleotide positions 13955-14151 (exon 20), nucleotide positions 14350-14440 (exon 21), nucleotide positions 14649-14805 (exon 22), nucleotide positions 15390-15559 (exon 23), nucleotide positions 17250-17405 (exon 24), nucleotide positions 17787-17929 (exon 25), nucleotide positions 18119-18267 (exon 26), nucleotide positions 18509-18605 (exon 27), nucleotide positions 18694-18841 (exon 28), and nucleotide positions 19041-19238 (exon 29). The introns are located between each of these exons in SEQ ID NO: 4, i.e., at nucleotide positions 143-444 (intron 1), nucleotide positions 1231 to 1318 (intron 2), nucleotide positions 1344-2110 (intron 3), nucleotide positions 3369-4324 (intron 4), nucleotide positions 4388-4488 (intron 5), nucleotide positions 4606-4747 (intron 6), nucleotide positions 4915-5569 (intron 7), nucleotide positions 5757-5894 (intron 8), nucleotide positions 6011-6291 (intron 9), nucleotide positions 6425-6776 (intron 10), nucleotide position 6960-7263 (intron 11), nucleotide positions 7303-7485 (intron 12), nucleotide positions 7654-7816 (intron 13), nucleotide positions 7883-8363 (intron 14), nucleotide positions 8490-9466 (intron 15), nucleotide positions 9526-10597 (intron 16), nucleotide positions 10722-10825 (intron 17), nucleotide positions 10939-13401 (intron 18), nucleotide positions 13538-13954 (intron 19), nucleotide positions 14152-14349 (intron 20), nucleotide positions 14441-14648 (intron 21), nucleotide positions 14806-15389 (intron 22), nucleotide positions 15560-17249 (intron 23), nucleotide positions 17406-17786 (intron 24), nucleotide positions 17930-18118 (intron 25), nucleotide positions 18268-18508 (intron 26), nucleotide positions 18606-18693 (intron 27), and nucleotide positions 18842-19040 (intron 28).

```
Human Wildtype Stereocilin Gene
                                                                  (SEQ ID NO: 4)
    gccctgccct cacctggcta tcccacacag gtgagaataa ccagaactca cctccggtac cagtgttcac ttggaaacat ggctctcagc ctctggcccc tgctgctgct gctgctgctg ctgctgctgc tgtcctttgc aggtaagaag aacagtgagc agaactgggg atgaggagga gggtggctgg aaaaagactt taagaatatg gaggtgaacc tgttagatag aaggacaaag gagagaggca gagacttgtg caaaagggaa aaatgagggt taagaaaagc aggccaagac ttactgtagg ccagtgaaag gggttcagct caccatcccc tcacctcatc tttagatcca ggtagggaac tgtgctcagg ggcagggttg agtttgggct ctgtgttcct ctccttcagt gacctctggt ttctctcctt acagtgactc tggcccctac tgggcctcat tccctggacc ctggtctctc cttcctgaag tcattgctct ccactctgga ccaggctccc cagggctccc tgagccgctc acggttcttt acattcctgg ccaacatttc ttcttccttt gagcctggga gaatggggga aggaccagta ggagagcccc cacctctcca gccgcctgct ctgcggctcc atgattttct agtgacactg agaggtagcc ccgactggga gccaatgcta gggctgctag gggatatgct ggcactgctg ggacaggagc agactccccg agatttcctg gtgcaccagg cagggtgct gggtggactt gtggaggtgc tgctgggagc cttagttcct gggggccccc ctaccccaac tcggccccca tgcaccgtg atgggccgtc tgactgtgtc ctggctgctg actggttgcc ttctctgctg ctgttgttag agggcacacg ctggcaagct ctggtgcagg tgcagcccag tgtggacccc accaatgcca caggcctcga tgggagggag gcagctcctc acttttgca gggtctgttg ggtttgctta ccccaacagg ggagctaggc tccaaggagg ctctttgggg cggtctgcta cgcacagtgg gggcccccct ctatgctgcc tttcaggagg ggctgctccg tgtcactcac tccctgcagg atgaggtctt ctccattttg gggcagccag agcctgatac caatgggcag tgccagggag gtgagtgtgg ccagggctgg gactgggatg
```

```
tggcagggca aggaaagtga aattgggtta gttttcttcc ttactctttc cctcctaggt aaccttcaac agctgctctt atggtaagta acaggagacc agttctgagg gattgggcct ggaaaatctg gaggtgaaga gctgaagacc tcagcctcta gagaggaaaa ctgatgggag gagtgtagtt tagtggtttt ggggtgtgac tgtctgggtt ggtgtcccag ctccacctct tcctagccat atgaccttga gcaggttaca tagtctttct atacctcagt ttccccattt ataaaatgag aatgataata ttagttacca cagagttgtt gcacccggtt aaatgagttg atactgtgta tgcaaacgac ttaaaaccgt gctggcacat agcgcttaat aatgttagct agtaaagatg ggatttggaa aataaggaca cagctggatt cctctacccc cttactactt cagtacaaca atgccagaca gtagttagac atattgagtt gctgagcaga tttcctaaca tgaggcccgc tgagggttgt gtttaagcta tctaaaagca tacgaagaaa ggagacagaa gggggccagg tggacagaaa gaattccaac tggggcttct cctaggtgat tttggacctt ggcagggcag cttttctctt tttgccccgt tgcagcattt caaccagtaa cgcctaaact ctcagggacc tcgcttgtag aaaagcctat gcttgccatg cccttgagg gctctgagtc agggtcagaa tcttcagctg gaggaaatgt gaactgacca gatcctgcct gctcctccct ctgcacccag gggcgtccgg cacaaccttt cctgggatgt ccaggcgctg ggctttctgt ctggatcacc accccaccc cctgccctcc ttcactgcct gagcacgggc gtgcctctgc ccagagcttc tcagccgtca gcccacatca gcccacgcca acggcgagcc atcactgtgg aggccctctg tgagaaccac ttaggcccag caccacccta cagcatttcc aacttctcca tccacttgct ctgccagcac accaagcctg ccactccaca gccccatccc agcaccactg ccatctgcca gacagctgtg tggtatgcag tgtcctgggc accaggtgcc caaggctggc tacaggcctg ccacgaccag tttcctgatg agttttggaa tgcgatctgc agtaacctct ccttttcagc cctgtctggc tccaaccgcc gcctggtgaa gcggctctgt gctggcctgc tcccacccc taccagctgc cctgaaggcc tgcccctgt tccctcacc ccagacatct tttggggctg cttcttggag aatgagactc tgtgggctga gcgactgtgt ggggaggcaa gtctacaggc tgtgcccccc agcaaccagg cttgggtcca gcatgtgtgc cagggcccca ccccagatgt cactgcctcc ccaccatgcc acattggacc ctgtggggaa cgctgcccgg atgggggcag cttcctggtg atggtctgtg ccaatgacac catgtatgag gtcctggtgc ccttctggcc ttggctagca ggccaatgca ggataagtcg tgggggcaat gacacttgct tcctagaagg gctgctgggc ccccttctgc cctctctgcc accactggga ccatccccac tctgtctgac ccctggcccc ttcctccttg gcatgctatc ccagttgcca cgctgtcagt cctctgtccc agctcttgct caccccacac gcctacacta tctcctccgc ctgctgacct tcctcttggg tccaggggct gggggcgctg aggcccaggg gatgctgggt cgggccctac tgctctccag tctcccagac aactgctcct tctgggatgc ctttcgccca gagggccggc gcagtgtgct acggacgatt ggggaatacc tggaacaaga tgaggagcag ccaacccat caggctttga acccactgtc aaccccagct ctggtataag caagatggag ctgctggcct gctttagtgt gagtgctctg ccagagggaa agctcctaga acagtgagaa ggccctccag gggaattcct cgaatactca gaggcagtag tgtggggtag tagttgaagc acacagctct agagtcagac aggcttggat tcatatcttg gttctgtgac cagccttgaa tgagttattt aacttctctg agcaatattt ttctcgtctc atttataaac tagggatgat aatggtatat gagataaatac atgctgtggg cttagcacag tgcatgatac acaaacatgc aataaatatt accttgttat tcttttgggc tctttgactc tctcactttc tgcaccagaa agaaaaagga
```

-continued

```
tcaagttaga ggactctaaa tttttcccct agagagtgag aattggaggc tggcagaata
caggaagata aggtaggaat gagaaagatt cagggacact accaatcaga agactttggt
tctaggttca actgtgccac aaattagtgt gatcttaggc aagcaatttc atttagtttt
tctgggcttc agttttttagt ctgtagaatg gaggggtgag aatatgttaa acaccataat
taattcactg agtgcctatt atatgcaagg cactttgcta ggttctgtag gatatataaa
gatttcttac tccatgttgg ggccacctttt ttcaaaccct gggcccagta aaatggaatt
agatagtctc atagtatttg gttcaggtct acaagtatta attgagccaa ctatggacct
ggcatgggag agggtacaag agaaattaga gatatgatcc cggacctaaa agagcttaat
atctgaagaa tcacacttga gatgatggac aagcatccca gcaagtggag ctggaatgcc
tgggggagct gcaggagaga cagagaagac agctctgttg gcatattgtc tttcttccca
ccagcctgtg ctgtgggatc tgctccagag ggaaaagagt gtttgggccc tgcagattct
agtgcaggta acaggtggag ggcacatggg tgggctgggt gacagccatg gctggaggtc
cctgccccgt gaggtgaggc catacccacc atgacctcct attcgcaggc gtacctgcat
atgcccccag aaaacctcca gcagctggtg cttttcagcag agagggaggc tgcacagggc
ttcctgacac tcatgctgca ggggaagctg caggggaagc tgcaggtgag cactgagaaa
ggggagcaag ggcacctgga gcctagtgtt cagagggctt gctttagtgg gaggaggaac
tccagagagg aaatggcagg gatactgagc atctccagag gcagaatcca ttcctgtgcc
cctacaggta ccaccatccg aggagcaggc cctgggtcgc ctgacagccc tgctgctcca
gcggtaccca cgcctcacct cccagctctt cattgacctg tcaccactca tcctttcttt
ggctgtctct gacctgatgc gcttcccacc atccctgtta gccaacgaca gtgtgtaagg
ttcttgcact actcctcctg ctcctgtcac ggtcaggcca accgcatcca cctggagcag
ccccttccgg agctcctctc tgttttttttc tttcatgcca gataggcaat gtgccaacat
cgtagcaagg tttgagagag gcacatctca cgcctgagtg tgaaacccca atcattatgc
taatgaacta caaaggatc agagagctcc tctctattaa aaccagggag aggatgggcg
tggtggctca tgcctgtaat cccagcacgt gggagcccg aggcaggtgg atcactaggt
ccgcctagtg agttcgagac cagcctggcc aatatggtga aaccccgtct ctattaaact
acaaaaatta gccaggcatg gtggtgggcg cttgtagtcc cagttactct ggaggctgag
gcaggaggat agcttgaacc tgggaggcag aggttgcagt gaaccaagat cgtgccactg
cactccagcc tgggtgacag agcgagactc cgtcttaaaa aaaacaaaaa acaaaacaaa
acaaaaaaac agggagagtc tccttcctat ctagacagca gggctacaga gggtcagagg
aaaacagttt ggaggaagac aaagggttaa gacccatgac tcctcgcagc ctggctgcca
tccgggatta cagcccagga atgaggcctg aacagaagga ggctctggca aagcgactgc
tggcccctga actgtttggg gaagtgcctg cctggcccca ggagctgctg tgggcagtgc
tgcccctgct cccccacctc cctctggaga acttttttgca gctcagccct caccaggtat
gagaatcatc ttctttactt gactggccca tcttctgcta gtggggacaa agagtcaatg
gcatgtctct cagtggcccc tccctgcaag aaccctatag tgacccccagt gcgagctaac
cttccccatc tcagatccag gccctggagg atagctggcc agcagcaggt ctggggccag
ggcatgcccg ccatgtgctg cgcagcctgg taaaccagag tgtccaggat ggtgaggagc
aggtacgcag gtgagttgtt gtgggatcag taaccaaggc aagagtggaa gaggtagaga
gaggaaggca cagctgtcac gctgggtcgg tgttctagga agaaagggggc aagagagtag
```

-continued

```
gcagtggcct caggcagcat agagttccag gagagaggtc tatagatggt gccctgtgt agtggtgtag tgtcagagtg cccagtgtat gtaccatac catctgctgc caggcctgcc ttagtgctag tcttggggac cacacaaagg tcagcttcat gccctcctca ggcttgggcc cctcgcctgt ttcctgagcc ctgaggagct gcagagccta gtgccctga gtgatccaac ggggccagta aacgggggc tgctggaatg tgcagccaat gggaccctca gcccagaagg acgggtgagc ccctcagcac aagcctacaa gactttaggc ttcccctggg tctgtgtgga tggcttccc attgtgtcaa cttgagcaca gtggtgccag ccccatccc acttttgcaa cctccattcc ttactccatg gccattctta cctgttacca cctcttcctg gcccttctct atctggtctg tagcaccca aacatacct ttgccatttt gaacctaatc tactccagtc caatccctag ttccaaaccc tagcccaggc cctgggaaat tcagatgtgg gattagagag gaagttcaag gttcatctgt cttttctctc cagtcctaaa ccttctttgg ttacaggtgg catatgaact tctgggtgtg ttgcgctcat ctggaggagc ggtgctgagc cccgggagc tgcgggtctg ggccctctc ttctctcagc tgggcctccg cttccttcag gagctgtcag agccccagct tagagccatg cttcctgtcc tgcaggaac tagtgttaca cctgctcagg tttgcctgtc tcactccctg gcatgtaccc tccatccccg cttgagcccc agtcaagaga atcccattca gggataaaag cagcccctcc tttccctggg tgaacagtag aggtaaactc tgtctgcagg aggacgcctt cattccctt cctcagatca agaagggacc tgagtcactg aggatggtta ctagggatgg ttaagaggca gcgggaagtt ttggaggtt tgccttagga acccacttag gacctggctg ctgggtcctg agagctgttg ttttcggtcc catcccaaca caggctgtcc tgctgcttgg acggctcctt cctaggcacg atgtgagtag cagcaacttc tcagcctccc gccagaggtc tctatcctct tttaacctgg ctcctgcatc tgcccctcct ctctctccgc tccctcata cttactgcct tgctgcattg tgattgttgt cttccccaac acccttccct tcttcttcag gcctcttgtc tctcttgctc tttagctatc cctggaggaa ctctgctcct tgcaccttct gctaccaggc ctcagccccc agacactcca ggccatccct aggcgagtcc tggtcggggc ttgttcctgc ctggcccctg aactgtcacg cctctcagcc tgccagaccg cagcactgct gcagaccttt cgggtatgag agtggcaagg aggatgagat aatcagggat accggctctt tctggttggg aggaaggcat cttccctgag gccagggaag gcctttcata cctccccact tacacacaca cacacacaca cacacacaca cacacacaca accaattctc atgcaggtta aagatggtgt taaaaatatg ggtacaacag gtgctggtcc agctgtgtgt atccctggtc aggtaagtgt gagatctccc aactgagctc ctctccccat tctggggcag tttcatatgg ctggtgctac ctcccacact accctgcagt ggccctgaga gttctggtta gctctgtgcc cattagcagc cctccccagt gccagatgca ggacagcatg atccactcac attgtcctag actaatgtca aagctggaag ggcctgagaa atcttccagg ccacccaccc tgctttcaga tgaaaagacc aaggctggga gaagctaagg gactttgttt gcctggtgcc taactagcag caacacttga ccacagcagc ctgcagtgtg aggctcttag gcgtttattg ctacagtggc aaatgccatt ccacttctgt cctagctttg gtcccttcc acccccatgg ttccttttct ctgagtgcta agtacagact ctctcaccta tcactacact gctatacca tcaccgccag cagcctattc ccaccacctg gccagactgc ctgcttcccc tgctcccatt aaagctgcta caactggatt ccttggctct tctggcaaat cgaagacgct actgggagct gccctggtct gagcagcagg taattctccc cacttaattt cagaacttcc tccctcaatg tagtctacct tctttaccta tcccttagcc ctatttggcc agcttatccc
```

-continued

```
tactatcctt tatttgattg tttgagatac agtctcactc tgttgcccag gctgcagtgc agtggcatga tcagagttcg ctgtaacctc aaactcctga gctcaggcaa tctttctgcc tcagcctcct gaatagctag gacgacaggt ggttaccacc atgcctggct aattttaaa ttttttttt gttttttgag atgaagtctt gctctgtcac ccaggcttga gtacagtggc acaagcttgg ctcactgcaa cctctgtctc ccgggttcaa gcgattctcc tgcctcagcc tcccgagtag ctgggactac aggcactccc acaatgcct ggctaatttt ttttttgttt tagtagagac agggtttcac catattggcc aggctggtct cgaactgctg accttgtgat ctgcctgcct ctgcctctca aagtgctggg attacaggtg tgagccacca tgcccggcca attttaaat ttttgtaga gacagacaat acaaaaatgt ggacactatg tggagacact atgttgaggt actatgctgt ccagattggt cttgaactcc tggcctcaag caatcctcct gccttggcct cccaaagtgc tgggattaca gacctgagcc actgcaccca gcccctagt atctcttata atgtgacttg cttttctttt tctttctcct tccctttct ttcatttctt tctcactctc gagagaagag tgggcatctg ggagagtggg aggctggtgg gtcccacaga gtgaggaggc aggactgggt ccaaggcagt cctgcctctc cactctaggg ggtatccttg gacagtgtct cttctgggaa ggggctcgtc tttctttctc ttgtaggcac agtttctctg gaagaagatg caagtaccca ccaaccttac cctcaggaat ctgcagtgag taacttgtgt tgagcagtgc gctgaattcg accaacattt ttttgagtgc ttactatgtg ccaggcacca tgtgatatgg aatgggggat atagggatga atgatgcata gtccctgcct cgtggacgtt ctcctagcac ctccctttgc cctcctttcc ttccacagtg ccatgcctat cctgactaga gccaaaggac tcagaaaacc tggattcagg ttccagtcct gtcacctact tgtcctcttg ggcaagtcat ttaacgtccc tgtgtcagtt ttcccttctt taaatgagaa ttacaatggc accagcctca taggtagtta ctgtgaagat taaatgaggt aggtcatgta agatatttaa cacagtgttt ggtccattgt aaagtcccag tagtcatttg ctactgttag tttacttcag gatgacttca gaggcactgg ccaagcaaga ataaatagga ataagaaggt atcactttac ttacacccac attagaagaa caatgggctt cagaatcttt tttttttt tttttcgag acagtcttgc tctgttgccc aggctggagt gcagtggcgc gatttcggct cactgcaacc tctgcctccc aggttcaagc gattctcctg tctcagcctc tggagtagct gggattacag gaatgtgcca ccatacccag ctaatttttg tatttttagt agagatgggg tttcaccatt ttggccaggc tggtctcaaa ctcctgacct caggtgatcc acccgcctca gcctcccaag ggcttcagaa tctaagacat ggctctagtt tcagtttacc acatttctag cagaatgatg ttgggaatgt cacctgactt ccataaatcc ttattttctc ctctgataaa cagcagtgat gttatgggga gctgatgaga tatctatgta aaaacatttc tcaaaccata aattacggtg gatgaacatc tgtacttgtg ttgagagtac tgatatcaag gagcaaacag gctgttgtat gtgttgaatg agcctctccc cactcacaca cccacagggc tctgggcacc ctggcaggag gcatgtcctg tgagtttctg cagcagatca actccatggt agacttcctt gaagtggtgc acatgatcta tcagctgccc actagagttc gagggagcct ggtgagaggg ggtgcctgga ctttagtggg agcagggagg ctgggaccct aggtatagaa cccagctcct atgttctgct ctggcctcac actgcttccc tacagagggc ctgtatctgg gcagagctac agcggaggat ggcaatgcca gaaccagaat ggacaactgt agggccagaa ctgaacgggc tggatagcaa gctactcctg gacttaccgt aagtactgca gctagagata ttggcccctc agaaagctca
```

-continued

```
atctggggtg aagatctgcc cttagggaat gccctggagg aggtagtttt tctgtctggt
agttccctga cataatttat agcccaaagc agaggatttt attcaaagtt gctctatgta
ttgactggtt cccagaatat gctccagcac agggcagctg agggtggcaa cactgtattg
aagcctgcca agtaatctta caataaccta gtccacatta attgagattg agacagagca
tctgaagtga gggaggcaat gctccaaatc tgccccagag gattgtagtt tgctcagggc
actgtgttct tagtgcattc agaggagtag atcgagagaa aaatatatga aaaatgtgat
aaataccttc aaatacctga ggggctatca agtagaaatt agattgtcat atttatgagt
ggccccattg ggcaagacta agagtagtta acggagatca gatttttaca tagtataaga
aaaactaagg tagtgagttc ctggtccttg gagctgttcg agcctaagcc agatggcccc
atggcaggaa tgttgtagag cacgttcata tacaggttgt gggaagaaaa ggctatagga
acccaaggct cctccctacc catggagaaa tttattagta tgttactcat atgctgcttt
tctcatttta ccctaccac caccccgttg ccatccgcac tgtaagtcag gataggaaaa
tgctggtgtt acagtcttcc tggggaatat ggagctgaag tggagtaaaa gcagttgact
tcattcctac ttttttcttt ttttcttt ttttttttt tgagacagag ttttgctgtg
tcaccaaggc tggagtgcag tgacgtgatc tcggctcact gcaacctcca tcttccaggt
tcaagcaatt ctcctgcctc agtctcccga gtagctggga ctgtaggtgt gcaccaccat
gccaggctaa ttttgtatt tgttgtaggg acgagctttc accatgttgg ccaggctggt
cttgaactcc tggcttcaag tgatctgccc acctcggctt cccaacattc ttatattttt
ataggccttt ccacagattt cagctcttgt atgacttagc ccagttccag aactggtaat
cctaggtagg gtacaggtta tcacctctga tttcgggtaa aagggattta tttatttatt
tgtttattta tttatatttt tgagacagag tctcgctctg tcacccaggc tggagtgcaa
tggtgccatc tcggctcact gcaacctctc cctctggggt tcaagcaatt ctcctgcctc
agcctgctga gtagctggga ttacaggcgc gtgccaccac acccggctaa tttttgcatt
tttagtagag acggggtttc accatgttgc tcagggtggt ctcgaatttc tgaccctgtg
atctgcctgc ctcggcctcc caaagtgctg ggattacagg catgagccac tgcgtccggc
ctgttttac ttttttttaa tgccattcag atctgtttaa atatgtgggt tctgtgagat
aatttagaat cccaaggtta cagatgaggt gaaagatcct agaccatgca tcaaaaaact
tgagtttctc atttgtgaaa gaaggataag agaaacacct attttgtctg ggtgcagtgg
ctcatgccta taatcccagc atttggggag gccaaggtgg gtggatcacg gaggtcaggt
gttcaagacc agactggcca acatggcaaa acaccatctc tactaaaaat acaaaagtta
gctgggcgtg gtggcacgtg cgtgtaattc cagctattcg ggaggctgag gcacgagaat
tgcttgaacc tgggaggtgc gggttgcagt gaactgagat cgcagcacca ctgtgctcca
gcctgagtga tggagtgagg ccaggtcttg ttgtaggatc aaatgagata cacctgaaa
gaactttgta aattgtatag cacgtacaaa caagaaggga cctcttcaca agcagaggaa
gggtggtcct gtggaaaaaa acgggaattg ggagtgagag acctcaacat ttgatctctg
tgaacctcag tttttaatc tataaaatgg ggaaatgtta atggtactta atatttggag
cttttgagtc cattagatca ggtaggattg ttcgttattt ttttttttta ggaagactag
aaatatgttg ctcccttttt ctcccccact caagcttgat ggtgggaatt ggccctggag
ctgtttacta tcagttcctg tccagcttca ctaaatttgg tctggggtca catcttagct
gcggactgtg gggttttgtg gtcccttctc gacttggccc agctccacct gaatcctgtt
gttgtcaaat tgctgtaata ggatccagtt gatggacaga ctatccaatg aatccattat
```

-continued

```
gttggtggtg gagctggtgc aaagagctcc agagcagctg ctggcactga ccccctcca ccaggcagcc ctggcagaga gggcactaca aaacctggta agagtccacc ctaccagact cagatttgct gccctgggca attcttgctc ctcagacaat gctctctgac tgtcccccaa ccctctactt cttgctttct tgctgccaaa cagattcctg tctacaaggc ctggcccctg ttttgcctct gggttctgtt ccttgataat atgcttcacg ttacttgtcc atacctcttg gagtccgaga atctcttgg agtccacctc tcagtctttc tgcctgctcc tatctgggct cattgcttaa ggaagtgaac aaaggtagtg agcatcatag ggtgctgagc tgggagcagg agggagggaa ggttaggggg cttggtgtct tgatcaaggt gtctggtatt ctgagtcaga agtgcattgt ccaagttctg atgctcttct ccaggctcca aaggagactc cagtctcagg ggaagtgctg gagaccttag gcccttggt tggattcctg gggacagaga gcacacgaca gatcccccta cagatcctgc tgtcccatct cagtcagctg caaggcttct gcctaggaga gacatttgcc acagagctgg gatggctgct attgcaggag tctgttcttg ggtatggacc ttcgagaact tcagattcta actcattcta tacccagtcc ctcagccacc atcatcagtg gcagcctgtt ccatattctt aaggtcccct ggagccctgt gtccgaaatc ctagcatgtc ctctttttccc cttccttttc ctcacagttc cctcagctcc ccagccccg attttcttcc tgtccccagg aaaccagagt tgtggagcca ggatgaagta gagcaagctg gacgcctagt attcactctg tctactgagg caatttcctt gatccccagg gtgagatgaa ggaagaaggg aagggagtaa atgcatagag gggactggtg agctggttat ggggacccgt ggccaaagag ggcaaaggat atgaagccta gatctggggg gagactgcaa aacagagaca ggactttgga cttagagcta tagcagcagg tcctgatctg tccagatctc cccactctcc ttctaccttc tcatgcagga ggccttgggt ccagagaccc tggagcggct tctagaaaag cagcagagct gggagcagag cagagttgga cagctgtgta gggagccaca gcttgctgcc aagaaagcag ccctggtagc aggggtggtg cgaccagctg ctgaggatct tccaggtgaa actacccaaa tacttatatg tccagcagga tgtacaggga gtatcaaacg gtctgggttc tacatgtgct cttccctggg actgggtttt ctaatttata aagcaaagag tttagaggga tgatcttcaa gcctcttgta gttctagaat tctgtagttc tgggagtttg taaactatta agttttcttt tagcccagaa cttccatttt cctgctctct cgtgtctgct ctagactcag ctctagctcg gctaagtgtg gagctctctg ctggggagat ccctagaagc tttgaaggag acattgtgag gctggagaac tgggttcaaa ttcagtgcta ccattaaatc tctgaataac atcctcagtc ttccatctat aaaagtcttg gcatctccaa tcacttcttg ttctattatc tcctaagccc tatacatatt actctgtaat actcctttga tccctatttc tcacagtgct ctatcctcca aaggttggaa gactcactct atctacagat atctctctgg gcatattta ttactgcgct gacctcctgg ccctgccttc ccccttcaga acctgtgcca aattgtgcag atgtacgagg gacattccca gcagcctggt ctgcaaccca gattgcagag atggagctct cagactttga ggactgcctg acattatttg caggagaccc aggacttggg cctgaggaac tgcgggcagc catgggcaaa gcaaaacagg ttagggatgg agagccaact ggggttggcc atgaggaagc tatttgggtg tgatgtagga cacaaagaga atggagagtt ggatgagagg tgggggaagc aagagataga agagttagaa gatttgggtc acaagtagga ggtgaaggga gataaatatt gaggaaagag agctagtata atgaatagag ggacgaaagc agtggttacc aaatttttaat gcatatcacg atcatcaagg gaacagattt ttttctttat tttttttttct ttcttaaaaa
```

-continued

```
aataatggca tgcttcggct gggtgcagcg gctcacgcct ataatctcag aactttggga
ggccaaggcg ggcagatcac gaggtcagga gatcaagacc atcctgtcta acacggcgaa
acacggtctc tactaaaaat acaaaaaagt tagccgggca tggtggtgca cacttgttgt
cccagctact tgggaggctg aggcaggaga atggcgtgaa cctgggaggg ggagcttgca
gtgagccgaa gtcaagccaa tgcactccat cctgggtgac agagcaagac tccatctcaa
aaaaaaaaaa aaaaaaaaaa ggcatgcttc atgaatttgc gtgttatcct tgcacaggcg
ccatgcaaat ctctgtatca ttccaatttt ttggggtatg tgctgctgaa ctgagcatgg
gaacagtgcc agtgccagat taccatgctt cactgactta ataaaaacct tggggaggc
tgggcgcagt gactcatgcc tgtaatcaca gcactttggg aggcggaggc aggtggattg
cttgagccca ggagttagag accagactgg gcaacatggt gaaaccctgt ctctactaaa
aatagaaaaa acattagctg ggtgtggcgg cacatgcctg taatcccagc tactcaggag
gctgggggtag gagaatccca tgagtgcagg aggtggaggg tgcaatgtgc caagatcgca
ccactgccct ccagcctggg tgtcagagca agacccgtc tcataaatta aaaaataagc
ctctgggga aagagtctag acatctgcat ctccttttt ttttttttt tttttttttg
agacagagtc tcactctgtc acccagcatc caggctggag tgcagtggtg tgatcttggc
tcactgtaac ctctacatcc tgggttcaaa cgatcctcct gcctcagcct ctcaagtagc
tgggactaca ggtgcaccac acctggctaa ttttgtatc tttggtagag atggggtttc
actatgttgc ccaggatggt ctcgaacttc tgggctcaag caatcctccc acctcagcct
cccaaagtgc tgggattaca gctgttagcc actgtgctgg gccctaggca tctgttttaa
taagcgtctc tgtgtctgat gcacataaaa gtgtggaact catggactag agttagtttg
ctcttctttt ccactgattg taatgtcttt caaaacacct tagaggaact gtaaggcaac
ggtctcattt tatagtggag gaaactaaag aaaaggcaaa tgatttacct agagttatac
agctaagggc agaggcaaga cttaaaaccc agcagtatga ctcccaatcc actgcttttc
cactcacatt gttcctgtct ttctcctagt tgtggggtcc cccccgggga tttcgtcctg
agcagatcct gcagcttggt aggctcttaa taggtctagg agatcgggaa ctacaggagc
tgatcctagt ggactgggga gtgctgagca ccctggggca gatagatggc tggagcacca
ctcaggtaac acttttcctc ctccctacgg cttcccaaac acccatccca cagacccagc
cctatagatc atctaaagcc caaggaattt ttttcctgtg accctacctg gtccttcttt
ctatcttttg ttgataccccc atactagtga ccttcaggac tctgatttat tcactctgag
gccctggaca cataatactg tctcctacct cttttcctgg aggcttcctc tttttctttc
cttttctttt ctgagtcctc agccttcccc atgactcctt aggtcttaat agtaacagaa
tataacccag taacacctat cacttccctg tccattaatt ctccataact ttcctccttc
ccctcttctc ccacccccca ccccagctcc gcattgtggt ctccagtttc ctacggcaga
gtggtcggca tgtgagccac ctggacttcg ttcatctgac agcgctgggt tatactctct
gtggactgcg gccagaggag ctccagcaca tcagcagttg ggagttcagg tcatttgtga
aggggctgag ggtggtggtg ctgaggtaaa ggtggactta ctggggaaag aaggatcatg
aaggtctggt cccatggagg aagggaactc atttgaagcc atctcttcct ttgtctcatg
accacagccc ctttcactga agccgaattc ttcttccttc cttcctactg ttctacagcc
aagcagctct cttcctcggc accctgcatc tccagtgctc tgaggaacaa ctggaggttc
tggcccacct acttgtactg cctggtgggt ttggcccaat cagtaactgg gggcctgaga
tcttcactga aattggcacc atagcaggtg gggagctggg ccactgctgg tgcaagttgg
```

```
tttggtttct ataccatggg tggactggat ggaagactgc cctgcaattc ttaaggtggg ggcctgaggg tgtttaaata aggggctaga gacatattgg ggaaggtcta tgatagggca ctttgggagt agttagagaa ggtctatagg tttgaagaga gggaaggtca gtctaagaca atgtttggat gccacttgct tcaacagctg ggatcccaga cctggctctt tcagcactgc tgcggggaca gatccagggc gttactcctc ttgccatttc tgtcatccct cctcctaaat ttgctgtaag tattaatgga ctggggtgac cacaggagag ccagggccca atggggacta catgcatgca ctgattccta ccctgccct caggtggtgt ttagtcccat ccaactatct agtctcacca gtgctcaggc tgtggctgtc actcctgagc aaatggcctt tctgagtcct gagcagcgac gagcagttgc atgggcccaa catgagggaa aggagagccc agaacagcaa ggtgagttcc cagctgcaca gcttgatcct ccatctcctg acccagaatc aaaccctaa tttggtgctg tctggctctt agagtgcacc cagggagatc cctggagtga aggagtctac aggcagagcg ctaatttcca agtatcaatg ctcctggaga gctgagttgt gatattactc ccattccctg tctattatag gtcgaagtac agcctggggc ctccaggact ggtcacgacc ttcctggtcc ctggtattga ctatcagctt ccttggccac ctgctatgag cctgtctcta cagtagaagg agattgtggg gagagaaatc ttaagtcata atgaataaag tgcaaacaga agtgcatcct gattattttc agaagctgat gaggaata
```

The nucleotide sequence of the human STRC pseudogene is shown in SEQ ID NO: 5.
Human Stereocilin Pseudogene 1 (STRCP1)

(SEQ ID NO: 5)

```
gccctgccct cacctggcta tcccacacag gtgagaataa ccagaactca cctccggtac cagtgttcac ttggaaacat ggctctcagc ctctggcccc tgctgctgct gctgctgctg ctgctgctgc tgtcctttgc aggtaagaag aacagtgagc agaactgggg atgaggagga gggtggctgg aaaaagactt taagaatatg gaggtgaacc tgttagatag aaggacaaag gagagaggca gagacttgtg caaaagggaa aaatgagggt taagaaaagc aggccaagac ttactgtagg ccagtgaaag gggttcagct caccatcccc tcacctcatc tttagatcca ggtagggaac tgtgctcagg ggcagggttg agtttgggct ctgtgttcct ctccttcagt gacctctggt ttctctcctt acagtgactc tggcccctac tgggcctcat tccctggacc ctggtctctc cttcctgaag tcattgctct ccactctgga ccaggctccc cagggctccc tgagccgctc acggttcttt acattcctgg ccaacatttc ttcttccttt gagcctggga gaatggggga aggaccagta ggagagcccc cacctctcca gccgcctgct ctgcggctcc atgattttct agtgacactg agaggtagcc ccgactggga gccaatgcta gggctgctag gggatatgct ggcactgctg ggacaggagc agactcccg agatttcctg gtgcaccagg caggggtgct gggtggactt gtggaggtgc tgctgggagc cttagttcct gggggccccc ctacccaac tcagcccca tgcacccgtg atgggccgtc tgactgtgtc ctggctgctg actggttgcc ttctctgctg ctgttgttag agggcacacg ctggcaagct ctggtgcagg tgcagcccag tgtggacccc accaatgcca caggcctcga tgggagggag gcagctcctc acttttgca gggtctgttg ggtttgctta ccccaacagg ggagctaggc tccaaggagg ctctttgggg cggtctgcta cgcacagtgg gggcccccct ctatgctgcc tttcaggagg ggctgctccg tgtcactcac tccctgcagg atgaggtctt ctccattttg gggcagccag agcctgatac caatgggcag tgccaggag gtgagtgtgg ccagggctgg gactgggatg tggcagggca aggaaagtga aattggggta gttttcttcc ttactctttc cctcctaggt aaccttcaac agctgctctt atggtaagta acaggagacc agttctgagg gattgggcct
```

-continued

```
ggaaaatctg gaggtgaaga gctgaagacc tcagcctcta gagaggaaaa ctgatgggag gagtgtagtt tagtggtttt ggggtgtgac tgtctgggtt ggtgtcccag ctccacctct tcctagccat atgaccttga gcaggttaca tagtctttct atacctcagt ttccccattt ataaaatgag aatgataata ttagttacca cagagttgtt gcacccggtt aaatgagttg atactgtgta tgcaaacgac ttaaaaccgt gctggcacat agcgcttaat aatgttagct agtaaagatg ggatttggaa aataaggaca cagctggatt cctctacccc cttactactt cagtacaaca atgccagaca gtagttagac atattgagtt gctgagcaga tttcctaaca tgaggcccgc tgagggttgt gtttaagcta tctaaaagca tatgaagaaa ggagacagaa gggggccagg tggacagaaa gaattccaac tggggcttct cctaggtgat tttggacctt ggcagggcag ctttctcttt tttgccccgt tgcagcattt caaccagtaa cgcctaaact ctcagggacc tcgcttgtag aaaagcctat gcttgccatg cccttgagg gctctgagtc agggtcagaa tcttcagctg gagaaatgt gaactgacca gatcctgcct gctcctccct ctgcacccag gggcgtccgg cacaaccttt cctgggatgt ccaggcgctg ggctttctgt ctggatcacc acccccaccc cctgccctcc ttcactgcct gagcacgggc gtgcctctgc ccagagcttc tcagccgtca gcccacatca gcccacgcca acggcgagcc atcactgtgg aggccctctg tgagaaccac ttaggcccag caccaccca cagcatttcc aacttctcca tccacttgct ctgccagcac accaagcctg ccactccaca gccccatccc agcaccactg ccatctgcca gacagctgtg tggtatgcag tgtcctgggc accaggtgcc caaggctggc tacaggcctg ccacgaccag tttcctgatg agttttgga tgcgatctgc agtaacctct cctttccagc cctgtctggc tccaaccgcc gcctggtgaa gcggctctgt gctggcctgc tcccaccccc taccagctgc cctgaaggcc tgcccctgt tccctcacc ccagacatct tttgggctg cttcttggag aatgagactc tgtgggctga gcgactgtgt ggggaggcaa gtctacaggc tgtgcccccc agcaaccagg cttgggtcca gcatgtgtgc cagggcccca ccccagatgt cactgcctcc ccaccatgcc acattggacc ctgtggggaa cgctgcccgg atgggggcag cttcctggtg atggtctgtg ccaatgacac catgtatgag gtcctggtgc ccttctggcc ttggctagca ggccaatgca ggataagtcg tgggggcaat gacacttgct tcctagaagg gctgctgggc ccccttctgc cctctctgcc accactggga ccatccccac tctgtctgac ccctggcccc ttcctccttg gcatgctatc ccagttgcca cgctgtcagt cctctgtccc agctcttgct caccccacac gcctacacta tctcctccgc ctgctgacct tcctcttggg tccaggggct gggggcgctg aggcccaggg gatgctgggt cgggccctac tgctctccag tctcccagac aactgctcct tctgggatgc cttcgccca gagggccggc gcagtgtgct acggacgatt ggggaatacc tggaacaaga tgaggagcag ccaacccat caggctttga acccactgtc aaccccagct ctggtataag caagatggag ctgctggcct gctttagtgt gagtgctctg ccagagggaa agctcctaga acagtgagaa ggccctccag gggaattcct cgaatactca gaggcagtag tgtggggtag tagttgaagc acacagctct agagtcagac aggcttggat tcatatcttg gttctgtgac cagccttgaa tgagttattt aacttctctg agcaatattt ttctcgtctc atttataaac tagggatgat aatggtatat gagataatac atgctgtggg cttagcacag tgcatgatac acaaacatgc aataaatatt accttgttat tcttttgggc tctttgactc tctcactttc tgcaccagaa agaaaaagga tcaagttaga ggactctaaa ttttcccct agagagtgag aattggaggc tggcagaata
```

-continued

```
caggaagata aggtaggaat gagaaagatt cagggacact accaatcaga agactttggt tctaggttca actgtgccac aaattagtgt gatcttaggc aagcaatttc atttagtttt tctgggcttc agttttagt ctgtagaatg gaggggtgag aatatgttaa acaccataat taattcactg agtgcctatt atatgcaagg cactttgcta ggttctgtag gatatataaa gatttcttac tccatgttgg ggccaccttt ttcaaaccct gggcccagta aaatggaatt agatagtctc atagtatttg gttcaggtct acaagtatta attgagccaa ctatggacct ggcatgggag agggtacaag agaaattaga gatatgatcc cggacctaaa agagcttaat atctgaagaa tcacacttga gatgatggac aagcatccca gcaagtggag ttggaatgcc tgggggagct gcaggagaga cagagaagac agctctgttg gcatattgtc tttcttccca ccagcctgtg ctgtgggatc tgctccagag ggaaaagagt gtttgggccc tgcagattct agtgcaggta acaggtggag ggcacatggg tgggctgggt gacagccatg gctggaggtc cctgccccgt gaggtgaggc catacccacc atgacctcct attcgcaggc gtacctgcat atgcccccag aaaacctcca gcagctggtg ctttcagcag agagggaggc tgcacagggc ttcctgacac tcatgctgca ggggaagctg caggggaagc tgcaggtgag cactgagaaa ggggagcaag ggcacctgga gcctagtgtt cagagggctt gctttagtgg gaggaggaac tccagagagg aaatggcagg gatactgagc atctccagag gcagaatcca ttcctgtgcc cctacaggta ccaccatccg aggagcaggc cctgggtcgc ctgacagccc tgctgctcca gcggtaccca cgcctcacct cccagctctt cattgacctg tcaccactca tcccttcttt ggctgtctct gacctgatgc gcttcccacc atccctgtta gccaacgaca gtgtgtaagg ttcttgcact actcctcctg ctcctgtcac ggtcaggcca accgcatcca cctggagcag ccccttccgg agctcctctc tgttttttc tttcatgcca gataggcaat gtgccaacat cgtagcaagg tttgagagag gcacatctca cgcctgagtg tgaaaaccca atcattatgc taatgaacta caaaggatc agagagctcc tctctattaa aaccagggag aggatgggcg tggtggctca tgcctgtaat cccagcacgt tgggagcccg aggcaggtgg atcactaggt ccgcctagtg agttcgagac cagcctggcc aatatggtga aaccctgtct ctattaaact acaaaaatta gccaggcatg gtggtgggcg cttgtagtcc cagttactct ggaggctgag gcaggaggat agcttgaacc tgggaggcag aggttgcagt gagccaagat cgtgccactg cactccagcc tgggtgacag agcgagactc cgtcttaaaa aaaacaaaaa acaaaacaaa acaaaaaaac agggagagtc tccttcctat ctagacagca gggctacaga gggtcagagg aaaacagttt ggaggaagac aaagggttaa gacccatgac tcctcgcagc ctggctgcca tccgggatta cagcccagga atgaggcctg aacagaagga ggctctggca aagcgactgc tggcccctga actgtttggg gaagtgcctg cctggcccca ggagctgctg tgggcagtgc tgcccctgct cccccacctc cctctggaga acttttttgca gctcagccct caccaggtat gagaatcatc ttctttactt gactggccca tcttctgcta gtggggacaa agagtcaatg gcatgtctct cagtggcccc tccctgcaag aaccctatag tgaccccagt gcgagctaac cttccccatc tcagatccag gccctggagg atagctggcc agcagcaggt ctggggccag ggcatgcccg ccatgtgctg cgcagcctgg taaaccagag tgtccaggat ggtgaggagc aggtacgcag gtgagttgtt gtgggatcag taaccaaggc aagagtggaa gaggtagaga gaggaaggca cagctgtcac gctgggtcgg tgttctagga agaaaggggc aagagagtag gcagtggcct caggcagcat agagttccag gagagaggtc tatagatggt gcccctgtgt agtggtgtag tgtcagagtg cccagtgtat gtacccatac catctgctgc caggcctgcc
```

-continued

```
ttagtgctag tcttggggac cacacaaagg tcagcttcat gccctcctca ggcttgggcc
cctcgcctgt ttcctgagcc ctgaggagct gcagagccta gtgccctga gtgatccaac
ggggccagta aacggggc tgctggaatg tgcagccaat gggaccctca gcccagaagg
acgggtgagc ccctcagcac aagcctacaa gactttaggc ttcccctggg tctgtgtgga
tggctttccc attgtgtcaa cttgagcaca gtggtgccag ccccatccc acttttgcaa
cctccattcc ttactccatg gccattctta cctgttacca cctcttcctg cccttctct
atctggtctg tagcaccca aacatacct ttgccatttt gaacctaatc tactccagtc
caatccctag ttccaaaccc tagcccaggc cctgggaaat tcagatgtgg gattagagag
gaagttcaag gttcatctgt cttttctctc cagtcctaaa ccttctttgg ttacaggtgg
catatgaact tctgggtgtg ttgcgctcat ctggaggagc ggtgctgagc ccccgggagc
tgcgggtctg ggcccctctc ttctctcagc tgggcctccg cttccttcag gagctgtcag
agccccagct tagagccatg cttcctgtcc tgcagggaac tagtgttaca cctgctcagg
tttgcctgtc tcactccctg gcatgtaccc tccatcccg cttgagcccc agtcaagaga
atcccattca gggataaaag cagcccctcc tttccctggg tgaacagtag aggtaaactc
tgtctgcagg aggacgcctt cattcccttt cctcagatca agaagggacc tgagtcactg
aggatggtta ctggggatgg ttaagaggca gcgggaagtt ttggagggtt tgccttagga
acccacttag gacctggctg ctgggtcctg agagctgttg ttttcggtcc catcccaaca
caggctgtcc tgctgcttgg acggctcctt cctaggcacg atgtgagtag cagcaacttc
tcagcctccc gccagaggtc tctatcctct tttaacctgg ctcctgcatc tgcccctcct
ctctctccgc tcccctcata cttactgcct tgctgcattg tgattgttgt cttcccaac
acccttccct tcttcttcag gcctcttgtc tctcttgctc tttagctatc cctggaggaa
ctctgctcct tgcaccttct gctaccaggc ctcagcccc agacactcca ggccatccct
aggcgagtcc tggtcggggc ttgttcctgc ctggcccctg aactgtcacg cctctcagcc
tgccagaccg cagcactgct gcagacctt cgggtatgag agtggcaagg aggatgagat
aatcagggat accggctctt tctggttggg aggaaggcat cttccctgag gccagggaag
gcctttcata cctccccact tacacacaca cacacacaca cacacacaca accaattctc
atgcaggtta aagatggtgt taaaaatatg ggtacaacag gtgctggtcc agctgtgtgc
atccctggtc aggtaagtgt gagatctccc aactgagctc ctctccccat tctggggcag
tttcatatgg ctggtgctac ctcccacact accctgcagt ggccctgaga gttctggtta
gctctgtgcc cattagcagc cctccccagt gccagatgca ggacagcatg atccactcac
attgtcctag actaatgtca aagctggaag ggcctgagaa atcttccagg ccacccaccc
tgctttcaga tgaaaagacc aaggctggga gaagctaagg gactttgttt gcctggtgcc
taactagcag caacacttga ccacagcagc ctgcagtgtg aggctcttag gcgtttattg
ctacagtggc aaatgccatt ccacttctgt cctagctttg gtccctttcc accccatgg
ttccttttct ctgagtgcta agtacagact ctctcaccta tcactacact gctataccca
tcaccgccag cagcctattc ccaccacctg gccagactgc ctgcttcccc tgctcccatt
aaagctgcta caactggatt ccttggctct tctggcaaat cgaagacgct actgggagct
gccctggtct gagcagcagg taattctccc cacttaattt cagaacttcc tccctcaatg
tagtctacct tctttaccta tcccttagcc ctatttggcc agcttatccc tactatcctt
tatttgattg tttgagatac agtctcactc tgttgcccag gctgcagtgc agtggcatga
```

-continued

```
tcagagttcg ctgtaacctc aaactcatga gctcaggcaa tctttctgcc tcagcctcct gaatagctag gatgacaggt ggttaccacc atgcctggct aattttttaaa tttttttttt gttttttgag atgaagtctt gctctgtcac ccaggcttga gtacagtggc acaagcttgg ctcactgcaa cctctgtctc ccgggttcaa gcgattctcc tgcctcagcc tcccgagtag ctgggactac aggcactccc cacaatgccc ggctaatttt tttttgttt tagtagagac agggtttcac catattggcc aggctggtct cgaactgctg accttgtgat ctgcctgcct ctgcctctca aagtgctggg attacaggtg tgagccacca tgcccggcca attttaaat tttttgtaga gacagacaat acaaaaatgt ggacactatg tggagacact atgttgaggt actatgctgt ccagattggt cttgaactcc tggcctcaag caatcctcct gccttggcct cccaaagtgc tgggattaca gacctgagcc actgcaccca gcccctagt atcccttata atgtgacttg cttttctttt tctttctcct tccctttct ttcatttctt tctcactctc gagagaagag tgggcatctg ggagagtggg aggctggtgg gtcccacaga gtgaggaggc aggactgggt ccaaggcagt cctgcctctc cactctaggg ggtatccttg acagtgtct cttctgggaa ggggctcgtc tttctttctc ttgtaggcac agtttctctg gaagaagatg caagtaccca ccaacctgac cctcaggaat ctacagtgag taacttgtgt tgagcagtgc gctgaattcg accaacattt ttttgagtgc ttactatgtg ccaggcacca tatgatatgg aatgggggat ataggatga atgatgcata gtccctgcct cgtggacgtt ctcctagcac ctccctttgc cctcctttcc ttccacagtg ccatgcctat cctgactaga gccaaggac tcagaaaacc tggattcagg ttccagtcct gtcacctact tgtcctcttg ggcaagtcat ttaacgtccc tgtgtcagtt ttcccttctt taaatgagaa ttacaatggc accagcctca taggtagtta ctgtgaagat taaatgaggt aggtcatgta agatatttaa cacagtgttt ggtccattgt aaagttccag tagtcatttg ctactgttag tttacttcag gatgacttca gaggcactgg ccaagcaaga ataaatagga ataagaaggt atcactttac ttatacccac attagaagaa caatgggctt cagaatcttt tttttttttt ttttcgagac agtcttgctc tgttgcccag gctggagtgc agtggcgcga tttcggctca ctgcaacctc tgcctcccag gttcaagcga ttctcctgtc tcagcctctg gagtagctgg gattacagga atgtgccacc atacccagct aattttgta tttttagtag agatgggggtt tcaccatttt ggccaggctg gtctcaaact cctgacctca ggtgatccac ccgcctcagc ctcccaaggg cttcagaatc taagacatgt ctctagtttc agtttaccac atttctagca gaatgatgtt gggaatgtca cctgacttcc ataaatcctt attttctcct ctgataaaca gcagtgatgt tatggggagc tgatgagata tctatgtaaa aacatttctc aaaccataaa ttacggtgga tgaacatctg tacttgtgtt gagagtactg atatcaagga gcaaacaggc tgttgtatgt gttgaatgag cctctcccca ctcacacacc cacagggctc tgggcaccct ggcaggaggc atgtcctgtg agtttctgca gcagatcaac tccatggtag acttccttga agtggtgcac atgatctatc agctgcccac tagagttcga gggagcctgg tgagagggga tgcctggact ttagtgggag caggaggct gggaccctag gtatagaacc cagctcctat gttctgctct ggcctcactc tgcttcccta cagagggcct gtatctgggc agagctacag cggaggatgg caatgccaga accagaatgg acaactgtag ggccagaact gaacgggctg gatagcaagc tactcctgga cttaccgtaa gtactgcagc tagagatatt ggcccctcag aaagctcaat ctggggtgaa gatctgccct tagggaatgc cctggaggag gtagtttttc tgtctggtag ttccctgaca taatttatag cccaaagcag aggattttat tcaaagttgc tctatgtatt gactggttcc
```

-continued

```
cagaatatgc tccagcacag ggcagctgag ggtggcaaca ctgtattgaa gcctgccaag taatcttaca ataacctagt ccacattaat tgagattgag acagagcatc tgaagtgagg gaggcaatgc tccaaatctg ccccagagga ttgtagtttg ctcagggcac tgtgttctta gtgcattcag aggagtggat cgagagaaaa atatatgaaa aatgtgataa ataccttcaa atacctgagg ggctatcaag tagaaattag attgtcatat ttatgagtgg ccccattggg caagactaag agtagttaac ggagatcaga tttttacata gtataagaaa aactaaggta gtgagttcct ggtccttgga gctgttcgag cctaagccag atggcnccat ggcaggaatg
```

```
gtgagttcct ggtccttgga gctgttcgag cctaagccag atggcnccat ggcaggaatg ttgtagagca cgttcatata caggttgtgg gaagaaaagg ctataggaac ccaaggctcc tccctaccca tggagaaatt tattagtatg ttactcatat gctgcttttc tcattttacc cctaccacca ccccgttgcc atccgcactg taagtcagga taggaaaatg ctggtgttac agtcttcctg gggaatatgg agctgaagtg gagtaaaagc agttgacttc attcttactt ttttcttttt ctttttttt ttttttttga dacagagttt tgctgtgtca ccaaggctgg agtgcagtga cgtgatctcg gctcactgca acctccatct tccaggttca agcaattctc ctgcctcagt ctcccgagta gctgggactg taggtgtgca ccaccatgcc aggctaattt ttgtatttgt tgtagggacg agctttcacc atgttggcca ggctggtctt gaactcctgg cttcaagtga tctgcccacc tcggcttccc aacattctta tattttata ggcctttcca cagatttcag ctcttgtatg acttagccca gttccagaac tggtaatcct aggtaggta caggttatca cctctgattt cgggtaaaag ggatttattt atttatttgt ttatttattt atattttga dacagagtct cgctctgtca cccaggctgg agtgcaatgg tgccatctcg gctcactgca acctctccct ctgggttca agcacttctg cctcagcctc ctgagtagct gggattacag gcgcgtgcca ccacacccgg ctaattttttg cattttttagt agagacggg tttcaccatg ttgctcaggg tggtctcgaa tttctgaccc tgtgatctgc ctgcctcggc ctcccaaagt gctgggatta caggcatgag ccactgcgtc cggcctgttt ttactttttt ttaatgccat tcagatctgt ttaaatatgt gggttctgtg agataattta gaatcccaag gttacagatg aggtgaaaga tcctagacca tgcatcaaaa aacttgagtt tctcatttgt gaaagaagga taagagaaac acctattttg tctgggtgca gtggctcatg cctataatcc cagcatttgg ggaggccaag gtgggtggat cacggaggtc aggtgttcaa gaccagactg gccaacatgg caaaacacca tctctactaa aaatacaaaa gttagctggg cgtggtggca cgtgcgtgta attccagcta tcgggaggc tgaggcacga gaattgcttg aacctgggag gtgcgggttg cagtgaactg agatcgcagc accactgtgc tccagcctga gtgatggagt gaggccaggt cttgttgtag gatcaaatga gataacacct gaaagaactt tgtaaattgt atagcacgta caaacaagaa gggacctctt cacaagcaga ggaagggtgg tcctgtggaa aaaaacggga attgggagtg agagacctca acatttgatc tctgtgaacc tcagttttt aatctataaa atggggaaat gttaatggta cttaatattt ggagcttttg agtccattag atcaggtagg attgttcgtt attttttttt tttaggaaga ctagaaatat gttgctccct ttttctcccc cactcaagct tgatggtggg aattggccct ggagctgttt actgtcagtt cctgtccagc ttcactaaat ttggtctggg gtcacatctt agctggggac tgtggggttc tgtggtccct tctcgacttg gcccagctcc acttgaatga tattgttgtc aaattgctat aatagaatcc agttgatgga cagactatcc aatgaatcca ttatgttggt ggtggagctg gtgcaaagag ctccagagca gctgctggca ctgaccccc tccaccaggc agccctggca
```

```
gagagggcac tacaaaacct ggtaagagtc caccctacca gactcagatt tgctgccctg
ggcaattctt gctcctcaga caatgctctc tgactgtcct ccaaccctct acttcttgct
ttcttgctgc caaacaggtt cctgtctaca aggcctggcc cgttttgcct ctgggttctg
ttccttgata atatgcttca cgttacttgt ccatacctct tggagtccga gaaatctctt
ggagtccacc tctcagtctt tctgcctgct cctatctggt ctcattgctt aagaaagtga
acaaaggtag tgagcatcat agggtgctga gttgggagca ggagggaggg aaggtcaggg
ggcttggtgt cttgatcaag gtgtctggta ttctgagtca gaagtgcatt gtccaagttc
tgatgctctt ctccaggctc caaaggagac tccagtctca ggggaagtgc tggagacctt
aggccctttg gttggattcc tggggacaga gagcacacga cagatccccc tacagatcct
gctgtcccat ctcagtcagc tgtaaggctt ctgcctagga gagacatttg ccacagagct
gggatggctg ctattgcagg agtctgttct tgggtatgga tcttcgagaa cttcagattc
taactcattc tatcccagt ccctcagcca ccatcatcag tggcagcctg ttccatattc
ctaagggccc ttggagccct gtgtccgaaa tcctagcatg tcctcttttc cccttccttt
tcctcacagt tccctcagct ccccagcccc cgattttctt cctgtcccca ggaaaccaga
gttgtggagc caggatgaag tagagcaagc tggacgccta gtattcactc tgtctactga
ggcaatttcc ttgatcccca gggtgagatg aaggaagaag ggaagggagt aaatgcatag
agggactgg tgagctggtt atggggaccc gtggccaacg agggcaaagg atatgaagcc
tagatctggg gggatactgc gaaacagaga caggactttg gacttatagc tatagcagca
ggtcctgatc tgtccagatc tccccactct ccttctacct tctcatgcag gaggccttgg
gtccagagac cctggagcgg cttctagaaa agcagcagag ctgggagcag agcagagttg
gacagctgtg taggggggcca cagcttgctg ccaagaaagc agccctggta gcaggggtgg
tgcgaccagc tgctgaggat cttccaggtg aaactaccca aatacttata tgtccagcag
gatgtacagg gagtatcaaa cggtctgggt tctacatgtg ctttctctg ggactgggtt
ttctaatttta taaagcaaag agtttagagg gatgatcttc aagtctcgtc tagttctaaa
attctatagc tctgggagtg tgtaaactat taagtttcc tttagcccag aacttccatt
ttcctgctgt cttgtctctt taaacagctg actcagctct agctcggcta agtgtggagc
tctctgctgg ggagatccct cgaaggagac attgtgaggc tagagaactg gtttcaaatt
cagctctgcc atgaaatccc tgaccaacat cctcagtctt ccatctataa aatgagggac
ttggcatctc caatcacttc ttgttcaatt cacttctaag ccctatacat cttaacctgt
aatactccct cgatccctac ttcccacagt gctccatcct ccaaaggttg gaagagtcat
tccatctaca gatacctcct ggccctgcct tcccccttca gaacctgtgc caaattgtgc
agatgtacga gggacattcc cagcagcctg ctctgcaacc cagattgctg agatggagct
ctcagacttt aaggactgcc tgacactatt tgcaggagac ccaggacttg ggcctgagga
accacgggca gccatgggca aagcaaaatg ggtcagggac ggagagccaa ctgaggttgg
ccatgaggaa gctgtgtggg tgtgatgtag gacacgaaga gaatagagag ttggatgaga
ggtgggggaa gcagaagata aaagagttag aagatttggg tcacaagtag aaggtgagga
gagataaaata ttgaggaaag agagctacta taatgaatag agggactaaa gcagtgatta
ccaaatttta atgcatatca caatcatcaa gggaacagat ttttttcttt ttctttttt
tttctttctt aaaaaataat ggcatacttc atgaatttgt gtgttatcct tgcgcaggcg
ccatgctaat ctctgtatca ttccaatttt tttttgtata tgtgctgctg aaccgagcac
gggaacagtg ccaatgctgg attaccatgc tagactgact taataaaaac ctttgcggag
```

-continued

```
gctggacgga gtggctcgtg cctgtaatca cagcactttg ggaggctgag gcaggtggat tgcttgagcc caggagtttg agaccagact gggcaacatg gtgaagccct gtctctacta aaaatagaaa aaaaattagc tgggtgtggc ggcacatgcc tgtaatccca gctactcagg aggctggggt aggagaatcc cctgagcgca ggaggtggag ggtgcaatga gccaagatca caccactgca ctccagcctg ggtgtcagag caagaccctg tctcataaat aaaaaataa gcctctggga gaaagtctag acatctgcat ctgcttttt tttttttt ttttttgaga cacagtctca ctctgtcacc cagcatccag gctggagtgc ggtggtgtga tcttggctca ctgtaacctc tacatcctgg gctcaaacga tcctcctgcc tcagcctctc gagaagctgg gactacaggt gcacaccact acacctggct aattttgta ttttggtag agatgaggtt tcgctgtgtt gcccaggatg gtcttgaact cctgggctca agcattcctc ccacctcagc ctcccaaagt gctgggatta cagctgtgag ccactgtgct gggcccagg catctgcatt ttaataagcg tctctgtgtc tgatgcacat aaaagtgtgg aactcatgga ctagagttag tttgctcttc ttttccactg attgtaatgt ctttcaaaac accttagagg aactgtaagg caacggtctc attttatagt ggaggaaacc aaagaaaagg caagtgactt gcctagagtt atacagctaa ggtcagaggc aagacttaaa acccagcatt ctgactccca atctactggt tttccactca cattgttcct ctctttctcc tagttgtggg gtcccccccg gggatttggt cctgagcaga tcctgcagct cggtagactc ttaataggtc tgggagatca ggaactacag gagctgatcc tagtggactg gggagtgctg agcaccctgg ggcagataga tggctggagc tccactcagg taacactttt actcctccct accgcttccc aaacacccat cccacagacc cagcctata gatcatctaa agcccaagga attttttcct gtgaccctac ctggtcattc tttctgtctt ttgttaatat cccatactag tgaccttcag gactcttgat ttattcactc tgaggccctg gacacataat actgtctcct acctctttc ctggaggctt cctcttttc ttccttttc ttttctgagt cctcagcctt ccccatgact ccttaggtct taatagtaac agaatataac ccagtaacac ctatcacttc cctgtccatt aattctccat aactttcctc cttccctct tctcccaccc cccacccag ctccgcattg tggtctccag tttcctacgg cagagtggtc ggcatgtgag ccacctggac ttcgttcatc tgacagcgct gggttatact ctctgtggac tgcggccaga ggagctccag cacatcagca gttgggagtt taggtcattt gtgaagggc tgagggtggt cgtgttcagg taaaggtgga cttgctgggg aaaggaggat catgaagtta tagtcccatg gaggaaggga actcatttga agccatctct tcctttgtct catgaccaca gtcccttca ctgaagccga attcttcttc cttccttccc actgttctac agccaagcag ctctcttcct gggcaccctg catctgcagt gctctgagga caactggag tttctggccc acctctttgt actgcctggt gggtttggcc caatcagtaa ctgggggcct gagatcttca ctgaaattgg caccatagca ggtggggagc tgggccactg ctggtgcaag ttggtttggt ttctatacca tgggtggact ggatggaaga ctgccctgca attcttcagg tgtgggcctg agagggtgtt taaataaggg gctagagaca tattggggaa ggtctatgat agggcacttt gggagtagtt agagaaggtc tataggtttg aagagaggga aggtcagtct aagacaatgt ttggatgcca cttgcttcaa cagctgggat cccagacctg gctctttcag cactgctgcg gggacagatc cagggcgtta ctcctcttgc catttctgtc atccctcctc ctaaatttgc tgtaagtatt aatggactgg ggtgaccaca ggagagccag ggcccaatgg ggactacatg catgcactga ttcctacccc tgccctcagg tggtgtttag tcccatccaa
```

-continued

```
ctatctagtc tcgccagtgc tcaggctgtg gctgtcactc ctgagcaaat ggcctttctg agtcctgagc agcgacgagc agttgcatgg gcccaacatg agggaaagga gagcccagaa cagcaaggtg agttcccagc tgcacagctt gatcctccat ctcctgaccc agaatcaaac ccctaatttg gtgctgtctg gctcttagag tgcacccagg gagatccctg gagtgaagga gtctacaggc agagcgctaa tttccaagta tcaatgctcc tggagagctg agttgtgata ttactcccat tccctgtcta ttataggtcg aagtacagcc tggggcctcc aggactggtc acgaccttcc tggtccctgg tattgactat cagcttcctt ggccacctgc tatgagcctg tctctacagt agaaggagat tgtggggaga gaaatcttaa gtcataatga ataaagtgca aacagaagtg catcctgatt attttcagaa gctgatgagg aata
```

In some embodiments, a stereocilin can be encoded by a sequence that is at least 70%, at least 72%, at least 74%, at least 75%, at least 76%, at least 78%, at least 80%, at least 82%, at least 84%, at least 85%, at least 86%, at least 88%, at least 90%, at least 92%, at least 94%, at least 95%, at least 96%, at least 98%, at least 99%, or 100% identical to SEQ ID NO: 8 or SEQ ID NO: 9.

One skilled in the art would appreciate that mutation of amino acids that are not conserved between the same protein from different species is less likely to have an effect on the function of a protein and therefore, these amino acids should be selected for mutation. Amino acids that are conserved between the same protein from different species should not be mutated, as these mutations are more likely to result in a change in the function of the protein. Non-limiting examples of stereocilin from other mammalian species are shown below.

```
Mouse Stereocilin Protein
                                                    (SEQ ID NO: 8)
malslqpqll lllsllpqev tsaptgpqsl daglsllksf vatldqapqr slsqsrfsaf lanisssfql grmgegpvge ppplqppalr lhdflvtlrg spdwepmlgl lgdvlallgq eqtprdflvh qagvlgglve allgalvpgg ppaptrppct rdgpsdcvla adwlpslmll legtrwqalv qlqpsvdptn atgldgrepa phflqgllgl ltpagelgse ealwggllrt vgaplyaafq egllrvthsl qdevfsimgq pepdasgqcq ggnlqqlllw gmrnnlswda ralgflsgsp ppppallhcl srgvplpras qpaahisprq rraisvealc enhsgpeppy sisnfsiyll cqhikpatpr pppttprppp ttpqpppttt qpipdttqpp pvtprppptt pqpppstavi cqtavwyays wapgargwlq achdqfpdqf ldmicgnlsf salsgpnrrl vkqlcagllp pptscppgli pvpltpeifw gcflenetlw aerlcvedsl qavpprnqaw vqhvcrgptl datdfppcrv gpcgercpdg gsfllmvcan dtlyealvpf wawlagqcri srggndtcfl egmlgpllps llplgpsplc lapgpfllgm lsqlprcqss vpalahptrl hyllrlltfl lgpgtggaet qgmlgqalll sslpdncsfw dafrpegrrs vlrtvgeylq reeptppgld sslslgsgms kmellscfsp vlwdllqrek svwalrtivk aylrmppedl qqlvlsaeme aaqgfltlml rswaklkvqp seeqamgrlt alllqryprl tsqlfidmsp lipflavpdl mrfppsllan dsvlaairdh ssgmkpeqke alakrllape lfgevpdwpq ellwaalpll phlplesflq lsphqiqale dswpvaglgp gharhvlrsl vnqsmedgee qvlrlgslac flspeelqsl vplsdpmgpv eqgllecaan gtlspegrva yellgvlrss ggtvlsprel rvwaplfpql glrflqelse tqlramlpal qgasvtpaqa vllfgrllpk hdlsleelcs lhpllpglsp qtlqaipkrv lvgacsclgp elsrlsacqi aallqtfrvk dgvknmgaag agsavcipgq pttwpdcllp llplkllqld aaallanrrl yrqlpwseqq aqflwkkmqv ptnlslrnlq algnlaggmt ceflqqissm vdfldvvhml yqlptgvres lraciwtelq rrmtmpepel ttlgpelsel dtklllldlpi qlmdrlsnds imlvvemvqg apeqllaltp lhqtalaera lknlapketp iskevletlg plvgflgies trriplpill shlsqlqgfc lgetfatelg willqepvlg kpelwsqdei eqagrlvftl saeaissipr
```

-continued

```
ealgpetler llgkhqsweq srvghlcges qlahkkaalv agivhpaaeg lqepvpncad irgtfpaaws atqisemels dfedclslfa gdpglgpeel raamgkakql wgpprgfrpe qilqlgrlli glgerelqel tivdwgvlss lgqidgwssm qlravvssfl rqsgrhvshl dfiyltalgy tlcglrpeel qhisswefsq aalflgslhl pcseeqlevl ayllvlpggf gpvsnwgpei fteigtiaag ipdlalsall rgqiqgltpl aisvipapkf avvfnpiqls sltrgqavav tpeqlaylsp eqrravawaq hegkeipeql grnsawglyd wfqaswalal pvsifghll
```

Dog Stereocilin Protein (SEQ ID NO: 9)

```
malslwpvll lltcaatlvs sgiqsldpdl sllksllstm dqapqgslsr sqfsaflani sssfesgrmg egpvgepppl qspalrlhdf lvtlrgspdw epmlgllgdv lallgqeqtp rdflghqagv lgglaevllg alvpigpptp trppcirdgp sdcvlvadwl pslllllegt rwqalvqvqp svdptnatgl dgrepaphfl qgllglltpv gelgseealw ggllrtvgap lyaafqegll rvtdslrnev fsilgqpepd angqcqggnl rqlllwgirh nlswdvqalg flsgsppppp allhclstgv plprasqpsa hinprqrrai svealcenhs gpappysisn fsihllcqha qpatpqppps taavcqtamw yayswapgaq gwlqachdqf pdqfleaics nlsfsalsgp nrrlvkqlca gllpppptncp eglppapltp evfwgcflen etlwaerlcg eaglqavpps nqawvqhvcq gptpdvtafp pchvgpcger cpdggsflmm vcandtmyea lvpfwpwlag qcrisrggnd tcflegllgp llpslpplgp splclapapf llgmlsqlpr cqssvpalah strlhyllrl ltfllgpgag gteaqgmlgq almlsslpdn csfwdafrpe grrsvlrtvg eylereeqlt ppgfeptasp ssgitkmell acfspvlwdl qreksvwal qilvqaylhm ppenlqqlvl saereaaqgf ltlmhrswaq lqvppseeqa lgrltalllq ryprltsqlf idlsplipfl aysdlmrfpp sllandsvla airdyspgmr peqkealakr llapelfgev pawsqellwa vlpllphlpl enflqlsphq iqaledswpa aglgpgharh virslvnqsv qdgeeqvrrl gplacflspe elqslvplsd pmgpvergll ecaangtlsp qgrvayellg vlrssggavl splelrvwap lfpqlglrfl qelsepqlra mlpalqgtsv tpaqavlllg rllprhdlsl eelcslhpll pglssqtlqa iprrvligac sclapelsrl sacqtaallq tfrvkdgvkn igttgasaav cipgqqpipt twpdcllpll plkllqldsa allanrrryr dlpwseqqaq flwkkmqvpt nitlrnlqal gtlaggmsce flqqinlmad flevvhmiyq lptgvrgslr aciwaelqrk mtmpepelat lgselsgldt kllldspiyl mdrlsnesim lmvelvrrap eqllaltplh rvalaeralq nlapkettvs revletlgpl vgflgiestr riplpillah lnqlqgfclg epfatelgwl lsqepilgkp elwsegeveq agrlvltlst eaisliprea lgpetlerll ekqqsweqsr vgqlcgtpql apkkaalvag vvrptaedls epvpncadvr gtfpaawsat qiaemelsdf edclalfagd pglgpeelra amgkakqlwg pprgfrpeqi lqlsrlligl gerelqelil vdwgvlstlg qidgwssiql rvvvssflrq sgrhvshldf lhltalgytl cglrpeelqh isswefsqaa lflgnlhlqc seeqlevlaq llvlpggfgp vsnwgpeift eigtiaagip dlalsallqe qiqgltplai svipapkfav vfsptqlssl tsvqamavtp eqmaflspeq rravvwaqhe gkespeqqgr stawglqdws qpswamalti cflgnli
```

Vectors

The compositions provided herein include at least two (e.g., two, three, four, five, or six) nucleic acid vectors, where: each of the at least two different vectors includes a coding sequence that encodes a different portion of a stereocilin protein, each of the encoded portions being at least 30 amino acids (e.g., between about 30 amino acids to about 1600 amino acids, about 30 amino acids to about 1550 amino acids, about 30 amino acids to about 1500 amino acids, about 30 amino acids to about 1450 amino acids, about 30 amino acids to about 1400 amino acids, about 30 amino acids to about 1350 amino acids, about 30 amino acids to about 1300 amino acids, about 30 amino acids to about 1250 amino acids, about 30 amino acids to about 1200 amino acids, about 30 amino acids to about 1150 amino acids, about 30 amino acids to about 1100 amino acids, about 30 amino acids to about 1050 amino acids, about 30 amino acids to about 1000 amino acids, about 30 amino acids to about 950 amino acids, about 30 amino acids to about 900 amino acids, about 30 amino acids to about 850 amino acids, about 30 amino acids to about 800 amino acids, about 30 amino acids to about 750 amino acids, about 30 amino acids to about 700 amino acids, about 30 amino acids to about 650 amino acids, about 30 amino acids to about 600 amino acids, about 30 amino acids to about 550 amino acids, about 30 amino acids to about 500 amino acids, about 30 amino acids to about 450 amino acids, about 30 amino acids to about 400 amino acids, about 30 amino acids to about 350 amino acids, about 30 amino acids to about 300 amino acids, about 30 amino acids to about 250 amino acids, about 30 amino acids to about 200 amino acids, about 30 amino acids to about 150 amino acids, about 30 amino acids to about 100 amino acids, about 30 amino acids to about 50 amino acids, about 50 amino acids to about 1600 amino acids, about 50 amino acids to about 1550 amino acids, about 50 amino acids to about 1500 amino acids, about 50 amino acids to about 1450 amino acids, about 50 amino acids to about 1400 amino acids, about 50 amino acids to about 1350 amino acids, about 50 amino acids to about 1300 amino acids, about 50 amino acids to about 1250 amino acids, about 50 amino acids to about 1200 amino acids, about 50 amino acids to about 1150 amino acids, about 50 amino acids to about 1100 amino acids, about 50 amino acids to about 1050 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 450 amino acids, about 50 amino acids to about 400 amino acids, about 50 amino acids to about 350 amino acids, about 50 amino acids to about 300 amino acids, about 50 amino acids to about 250 amino acids, about 50 amino acids to about 200 amino acids, about 50 amino acids to about 150 amino acids, about 50 amino acids to about 100 amino acids, about 100 amino acids to about 1600 amino acids, about 100 amino acids to about 1550 amino acids, about 100 amino acids to about 1500 amino acids, about 100 amino acids to about 1450 amino acids, about 100 amino acids to about 1400 amino acids, about 100 amino acids to about 1350 amino acids, about 100 amino acids to about 1300 amino acids, about 100 amino acids to about 1250 amino acids, about 100 amino acids to about 1200 amino acids, about 100 amino acids to about 1150 amino acids, about 100 amino acids to about 1100 amino acids, about 100 amino acids to about 1050 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 450 amino acids, about 100 amino acids to about 400 amino acids, about 100 amino acids to about 350 amino acids, about 100 amino acids to about 300 amino acids, about 100 amino acids to about 250 amino acids, about 100 amino acids to about 200 amino acids, about 100 amino acids to about 150 amino acids, about 150 amino acids to about 1600 amino acids, about 150 amino acids to about 1550 amino acids, about 150 amino acids to about 1500 amino acids, about 150 amino acids to about 1450 amino acids, about 150 amino acids to about 1400 amino acids, about 150 amino acids to about 1350 amino acids, about 150 amino acids to about 1300 amino acids, about 150 amino acids to about 1250 amino acids, about 150 amino acids to about 1200 amino acids, about 150 amino acids to about 1150 amino acids, about 150 amino acids to about 1100 amino acids, about 150 amino acids to about 1050 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 450 amino acids, about 150 amino acids to about 400 amino acids, about 150 amino acids to about 350 amino acids, about 150 amino acids to about 300 amino acids, about 150 amino acids to about 250 amino acids, about 150 amino acids to about 200 amino acids, about 200 amino acids to about 1600 amino acids, about 200 amino acids to about 1550 amino acids, about 200 amino acids to about 1500 amino acids, about 200 amino acids to about 1450 amino acids, about 200 amino acids to about 1400 amino acids, about 200 amino acids to about 1350 amino acids, about 200 amino acids to about 1300 amino acids, about 200 amino acids to about 1250 amino acids, about 200 amino acids to about 1200 amino acids, about 200 amino acids to about 1150 amino acids, about 200 amino acids to about 1100 amino acids, about 200 amino acids to about 1050 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 450 amino acids, about 200 amino acids to about 400 amino acids, about 200 amino acids to about 350 amino acids, about 200 amino acids to about 300 amino acids, about 200 amino acids to about 250 amino acids, about 250 amino acids to about 1600 amino acids, about 250 amino acids to about 1550 amino acids, about 250 amino acids to about 1500 amino acids, about 250 amino acids to about 1450 amino acids, about 250 amino acids to about 1400 amino acids, about 250 amino acids to about 1350 amino acids, about 250 amino acids to about 1300 amino acids, about 250 amino acids to about 1250 amino acids, about 250 amino acids to about 1200 amino acids, about 250 amino acids to about 1150 amino acids, about 250 amino acids to about 1100 amino acids, about 250 amino acids to about 1050 amino acids, about 250 amino acids to about 1000 amino acids, about 250 amino acids to about 950 amino acids, about 250 amino acids to about 900 amino acids, about 250 amino acids to about 850 amino acids, about 250 amino acids to about 800 amino acids, about 250 amino acids to about 750 amino acids, about 250 amino acids to about 700 amino acids, about 250 amino acids to about 650 amino acids, about 250 amino acids to about 600 amino acids, about 250 amino acids to about 550 amino acids, about 250 amino acids to about 500 amino acids, about 250 amino acids to about 450 amino acids, about 250 amino acids to about 400 amino acids, about 250 amino acids to about 350 amino acids, about 250 amino acids to about 300 amino acids, about 300 amino acids to about 1600 amino acids, about 300 amino acids to about 1550 amino acids, about 300 amino acids to about 1500 amino acids, about 300 amino acids to about 1450 amino acids, about 300 amino acids to about 1400 amino acids, about 300 amino acids to about 1350 amino acids, about 300 amino acids to about 1300 amino acids, about 300 amino acids to about 1250 amino acids, about 300 amino acids to about 1200 amino acids, about 300 amino acids to about 1150 amino acids, about 300 amino acids to about 1100 amino acids, about 300 amino acids to about 1050 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 450 amino acids, about 300 amino acids to about 400 amino acids, about 300 amino acids to about 350 amino acids, about 350 amino acids to about 1600 amino acids, about 350 amino acids to about 1550 amino acids, about 350 amino acids to about 1500 amino acids, about 350 amino acids to about 1450 amino acids, about 350 amino acids to about 1400 amino acids, about 350 amino acids to about 1350 amino acids, about 350 amino acids to about 1300 amino acids, about 350 amino acids to about 1250 amino acids, about 350 amino acids to about 1200 amino acids, about 350 amino acids to about 1150 amino acids, about 350 amino acids to about 1100 amino acids, about 350 amino acids to about 1050 amino acids, about 350 amino acids to about 1000 amino acids, about 350 amino acids to about 950 amino acids, about 350 amino acids to about 900 amino acids, about 350 amino acids to about 850 amino acids, about 350 amino acids to about 800 amino acids, about 350 amino acids to about 750 amino acids, about 350 amino acids to about 700 amino acids, about 350 amino acids to about 650 amino acids, about 350 amino acids to about 600 amino acids, about 350 amino acids to about 550 amino acids, about 350 amino acids to about 500 amino acids, about 350 amino acids to about 450 amino acids, about 350 amino acids to about 400 amino acids, about 400 amino acids to about 1600 amino acids, about 400 amino acids to about 1550 amino acids, about 400 amino acids to about 1500 amino acids, about 400 amino acids to about 1450 amino acids, about 400 amino acids to about 1400 amino acids, about 400 amino acids to about 1350 amino acids, about 400 amino acids to about 1300 amino acids, about 400 amino acids to about 1250 amino acids, about 400 amino acids to about 1200 amino acids, about 400 amino acids to about 1150 amino acids, about 400 amino acids to about 1100 amino acids, about 400 amino acids to about 1050 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 450 amino acids, about 450 amino acids to about 1600 amino acids, about 450 amino acids to about 1550 amino acids, about 450 amino acids to about 1500 amino acids, about 450 amino acids to about 1450 amino acids, about 450 amino acids to about 1400 amino acids, about 450 amino acids to about 1350 amino acids, about 450 amino acids to about 1300 amino acids, about 450 amino acids to about 1250 amino acids, about 450 amino acids to about 1200 amino acids, about 450 amino acids to about 1150 amino acids, about 450 amino acids to about 1100 amino acids, about 450 amino acids to about 1050 amino acids, about 450 amino acids to about 1000 amino acids, about 450 amino acids to about 950 amino acids, about 450 amino acids to about 900 amino acids, about 450 amino acids to about 850 amino acids, about 450 amino acids to about 800 amino acids, about 450 amino acids to about 750 amino acids, about 450 amino acids to about 700 amino acids, about 450 amino acids to about 650 amino acids, about 450 amino acids to about 600 amino acids, about 450 amino acids to about 550 amino acids, about 450 amino acids to about 500 amino acids, about 500 amino acids to about 1600 amino acids, about 500 amino acids to about 1550 amino acids, about 500 amino acids to about 1500 amino acids, about 500 amino acids to about 1450 amino acids, about 500 amino acids to about 1400 amino acids, about 500 amino acids to about 1350 amino acids, about 500 amino acids to about 1300 amino acids, about 500 amino acids to about 1250 amino acids, about 500 amino acids to about 1200 amino acids, about 500 amino acids to about 1150 amino acids, about 500 amino acids to about 1100 amino acids, about 500 amino acids to about 1050 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 1600 amino acids, about 550 amino acids to about 1550 amino acids, about 550 amino acids to about 1500 amino acids, about 550 amino acids to about 1450 amino acids, about 550 amino acids to about 1400 amino acids, about 550 amino acids to about 1350 amino acids, about 550 amino acids to about 1300 amino acids, about 550 amino acids to about 1250 amino acids, about 550 amino acids to about 1200 amino acids, about 550 amino acids to about 1150 amino acids, about 550 amino acids to about 1100 amino acids, about 550 amino acids to about 1050 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 1600 amino acids, about 600 amino acids to about 1550 amino acids, about 600 amino acids to about 1500 amino acids, about 600 amino acids to about 1450 amino acids, about 600 amino acids to about 1400 amino acids, about 600 amino acids to about 1350 amino acids, about 600 amino acids to about 1300 amino acids, about 600 amino acids to about 1250 amino acids, about 600 amino acids to about 1200 amino acids, about 600 amino acids to about 1150 amino acids, about 600 amino acids to about 1100 amino acids, about 600 amino acids to about 1050 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 1600 amino acids, about 650 amino acids to about 1550 amino acids, about 650 amino acids to about 1500 amino acids, about 650 amino acids to about 1450 amino acids, about 650 amino acids to about 1400 amino acids, about 650 amino acids to about 1350 amino acids, about 650 amino acids to about 1300 amino acids, about 650 amino acids to about 1250 amino acids, about 650 amino acids to about 1200 amino acids, about 650 amino acids to about 1150 amino acids, about 650 amino acids to about 1100 amino acids, about 650 amino acids to about 1050 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 1600 amino acids, about 700 amino acids to about 1550 amino acids, about 700 amino acids to about 1500 amino acids, about 700 amino acids to about 1450 amino acids, about 700 amino acids to about 1400 amino acids, about 700 amino acids to about 1350 amino acids, about 700 amino acids to about 1300 amino acids, about 700 amino acids to about 1250 amino acids, about 700 amino acids to about 1200 amino acids, about 700 amino acids to about 1150 amino acids, about 700 amino acids to about 1100 amino acids, about 700 amino acids to about 1050 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 1600 amino acids, about 750 amino acids to about 1550 amino acids, about 750 amino acids to about 1500 amino acids, about 750 amino acids to about 1450 amino acids, about 750 amino acids to about 1400 amino acids, about 750 amino acids to about 1350 amino acids, about 750 amino acids to about 1250 amino acids, about 750 amino acids to about 1200 amino acids, about 750 amino acids to about 1150 amino acids, about 750 amino acids to about 1100 amino acids, about 750 amino acids to about 1050 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 1600 amino acids, about 800 amino acids to about 1550 amino acids, about 800 amino acids to about 1500 amino acids, about 800 amino acids to about 1450 amino acids, about 800 amino acids to about 1400 amino acids, about 800 amino acids to about 1350 amino acids, about 800 amino acids to about 1300 amino acids, about 800 amino acids to about 1250 amino acids, about 800 amino acids to about 1200 amino acids, about 800 amino acids to about 1150 amino acids, about 800 amino acids to about 1100 amino acids, about 800 amino acids to about 1050 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 1600 amino acids, about 850 amino acids to about 1550 amino acids, about 850 amino acids to about 1500 amino acids, about 850 amino acids to about 1450 amino acids, about 850 amino acids to about 1400 amino acids, about 850 amino acids to about 1350 amino acids, about 850 amino acids to about 1300 amino acids, about 850 amino acids to about 1250 amino acids, about 850 amino acids to about 1200 amino acids, about 850 amino acids to about 1150 amino acids, about 850 amino acids to about 1100 amino acids, about 850 amino acids to about 1050 amino acids, about 850 amino acids to about 1000 amino acids, about 850 amino acids to about 950 amino acids, about 850 amino acids to about 900 amino acids, about 900 amino acids to about 1600 amino acids, about 900 amino acids to about 1550 amino acids, about 900 amino acids to about 1500 amino acids, about 900 amino acids to about 1450 amino acids, about 900 amino acids to about 1400 amino acids, about 900 amino acids to about 1350 amino acids, about 900 amino acids to about 1300 amino acids, about 900 amino acids to about 1250 amino acids, about 900 amino acids to about 1200 amino acids, about 900 amino acids to about 1150 amino acids, about 900 amino acids to about 1100 amino acids, about 900 amino acids to about 1050 amino acids, about 900 amino acids to about 1000 amino acids, about 900 amino acids to about 950 amino acids, about 950 amino acids to about 1600 amino acids, about 950 amino acids to about 1550 amino acids, about 950 amino acids to about 1500 amino acids, about 950 amino acids to about 1450 amino acids, about 950 amino acids to about 1400 amino acids, about 950 amino acids to about 1350 amino acids, about 950 amino acids to about 1300 amino acids, about 950 amino acids to about 1250 amino acids, about 950 amino acids to about 1200 amino acids, about 950 amino acids to about 1150 amino acids, about 950 amino acids to about 1100 amino acids, about 950 amino acids to about 1050 amino acids, about 950 amino acids to about 1000 amino acids, about 1000 amino acids to about 1600 amino acids, about 1000 amino acids to about 1550 amino acids, about 1000 amino acids to about 1500 amino acids, about 1000 amino acids to about 1450 amino acids, about 1000 amino acids to about 1400 amino acids, about 1000 amino acids to about 1350 amino acids, about 1000 amino acids to about 1300 amino acids, about 1000 amino acids to about 1250 amino acids, about 1000 amino acids to about 1200 amino acids, about 1000 amino acids to about 1150 amino acids, about 1000 amino acids to about 1100 amino acids, about 1000 amino acids to about 1050 amino acids, about 1050 amino acids to about 1600 amino acids, about 1050 amino acids to about 1550 amino acids, about 1050 amino acids to about 1500 amino acids, about 1050 amino acids to about 1450 amino acids, about 1050 amino acids to about 1400 amino acids, about 1050 amino acids to about 1350 amino acids, about 1050 amino acids to about 1300 amino acids, about 1050 amino acids to about 1250 amino acids, about 1050 amino acids to about 1200 amino acids, about 1050 amino acids to about 1150 amino acids, about 1050 amino acids to about 1100 amino acids, about 1100 amino acids to about 1600 amino acids, about 1100 amino acids to about 1550 amino acids, about 1100 amino acids to about 1500 amino acids, about 1100 amino acids to about 1450 amino acids, about 1100 amino acids to about 1400 amino acids, about 1100 amino acids to about 1350 amino acids, about 1100 amino acids to about 1300 amino acids, about 1100 amino acids to about 1250 amino acids, about 1100 amino acids to about 1200 amino acids, about 1100 amino acids to about 1150 amino acids, about 1150 amino acids to about 1600 amino acids, about 1150 amino acids to about 1550 amino acids, about 1150 amino acids to about 1500 amino acids, about 1150 amino acids to about 1450 amino acids, about 1150 amino acids to about 1400 amino acids, about 1150 amino acids to about 1350 amino acids, about 1150 amino acids to about 1300 amino acids, about 1150 amino acids to about 1250 amino acids, about 1150 amino acids to about 1200 amino acids, about 1200 amino acids to about 1600 amino acids, about 1200 amino acids to about 1550 amino acids, about 1200 amino acids to about 1500 amino acids, about 1200 amino acids to about 1450 amino acids, about 1200 amino acids to about 1400 amino acids, about 1200 amino acids to about 1350 amino acids, about 1200 amino acids to about 1300 amino acids, about 1200 amino acids to about 1250 amino acids, about 1250 amino acids to about 1600 amino acids, about 1250 amino acids to about 1550 amino acids, about 1250 amino acids to about 1500 amino acids, about 1250 amino acids to about 1450 amino acids, about 1250 amino acids to about 1400 amino acids, about 1250 amino acids to about 1350 amino acids, about 1250 amino acids to about 1300 amino acids, about 1300 amino acids to about 1600 amino acids, about 1300 amino acids to about 1550 amino acids, about 1300 amino acids to about 1500 amino acids, about 1300 amino acids to about 1450 amino acids, about 1300 amino acids to about 1400 amino acids, about 1300 amino acids to about 1350 amino acids, about 1350 amino acids to about 1600 amino acids, about 1350 amino acids to about 1550 amino acids, about 1350 amino acids to about 1500 amino acids, about 1350 amino acids to about 1450 amino acids, about 1350 amino acids to about 1400 amino acids, about 1400 amino acids to about 1600 amino acids, about 1400 amino acids to about 1550 amino acids, about 1400 amino acids to about 1500 amino acids, about 1400 amino acids to about 1450 amino acids, about 1450 amino acids to about 1600 amino acids, about 1450 amino acids to about 1550 amino acids, about 1450 amino acids to about 1500 amino acids, about 1500 amino acids to about 1600 amino acids, about 1500 amino acids to about 1550 amino acids, or about 1550 amino acids to about 1600 amino acids), wherein the amino acid sequence of each of the encoded portions may optionally partially overlap with the amino acid sequence of a different one of the encoded portions; no single vector of the at least two different vectors encodes an active stereocilin protein (e.g., a full-length stereocilin protein (e.g., a full-length wildtype stereocilin protein)); and, when introduced into a mammalian cell that contains chromosomal DNA, the at least two different vectors undergo homologous recombination with each other and with the chromosomal DNA of the cell, thereby forming a recombined nucleic acid inserted into the chromosomal DNA, where the recombined nucleic acid encodes an active stereocilin protein (e.g., a full-length stereocilin protein). In some embodiments, one of the nucleic acid vectors can include a coding sequence that encodes a portion of a stereocilin protein, where the encoded portion is, e.g., about 900 amino acids to about 1600 amino acids, about 900 amino acids to about 1550 amino acids, about 900 amino acids to about 1500 amino acids, about 900 amino acids to about 1450 amino acids, about 900 amino acids to about 1400 amino acids, about 900 amino acids to about 1350 amino acids, about 900 amino acids to about 1300 amino acids, about 900 amino acids to about 1250 amino acids, about 900 amino acids to about 1200 amino acids, about 900 amino acids to about 1150 amino acids, about 900 amino acids to about 1100 amino acids, about 900 amino acids to about 1050 amino acids, about 900 amino acids to about 1000 amino acids, about 900 amino acids to about 950 amino acids, about 950 amino acids to about 1600 amino acids, about 950 amino acids to about 1550 amino acids, about 950 amino acids to about 1500 amino acids, about 950 amino acids to about 1450 amino acids, about 950 amino acids to about 1400 amino acids, about 950 amino acids to about 1350 amino acids, about 950 amino acids to about 1300 amino acids, about 950 amino acids to about 1250 amino acids, about 950 amino acids to about 1200 amino acids, about 950 amino acids to about 1150 amino acids, about 950 amino acids to about 1100 amino acids, about 950 amino acids to about 1050 amino acids, about 950 amino acids to about 1000 amino acids, about 1000 amino acids to about 1600 amino acids, about 1000 amino acids to about 1550 amino acids, about 1000 amino acids to about 1500 amino acids, about 1000 amino acids to about 1450 amino acids, about 1000 amino acids to about 1400 amino acids, about 1000 amino acids to about 1350 amino acids, about 1000 amino acids to about 1300 amino acids, about 1000 amino acids to about 1250 amino acids, about 1000 amino acids to about 1200 amino acids, about 1000 amino acids to about 1150 amino acids, about 1000 amino acids to about 1100 amino acids, about 1000 amino acids to about 1050 amino acids, about 1050 amino acids to about 1600 amino acids, about 1050 amino acids to about 1550 amino acids, about 1050 amino acids to about 1500 amino acids, about 1050 amino acids to about 1450 amino acids, about 1050 amino acids to about 1400 amino acids, about 1050 amino acids to about 1350 amino acids, about 1050 amino acids to about 1300 amino acids, about 1050 amino acids to about 1250 amino acids, about 1050 amino acids to about 1200 amino acids, about 1050 amino acids to about 1150 amino acids, about 1050 amino acids to about 1100 amino acids, about 1100 amino acids to about 1600 amino acids, about 1100 amino acids to about 1550 amino acids, about 1100 amino acids to about 1500 amino acids, about 1100 amino acids to about 1450 amino acids, about 1100 amino acids to about 1400 amino acids, about 1100 amino acids to about 1350 amino acids, about 1100 amino acids to about 1300 amino acids, about 1100 amino acids to about 1250 amino acids, about 1100 amino acids to about 1200 amino acids, about 1100 amino acids to about 1150 amino acids, about 1150 amino acids to about 1600 amino acids, about 1150 amino acids to about 1550 amino acids, about 1150 amino acids to about 1500 amino acids, about 1150 amino acids to about 1450 amino acids, about 1150 amino acids to about 1400 amino acids, about 1150 amino acids to about 1350 amino acids, about 1150 amino acids to about 1300 amino acids, about 1150 amino acids to about 1250 amino acids, about 1150 amino acids to about 1200 amino acids, about 1200 amino acids to about 1600 amino acids, about 1200 amino acids to about 1550 amino acids, about 1200 amino acids to about 1500 amino acids, about 1200 amino acids to about 1450 amino acids, about 1200 amino acids to about 1400 amino acids, about 1200 amino acids to about 1350 amino acids, about 1200 amino acids to about 1300 amino acids, about 1200 amino acids to about 1250 amino acids, about 1250 amino acids to about 1600 amino acids, about 1250 amino acids to about 1550 amino acids, about 1250 amino acids to about 1500 amino acids, about 1250 amino acids to about 1450 amino acids, about 1250 amino acids to about 1400 amino acids, about 1250 amino acids to about 1350 amino acids, about 1250 amino acids to about 1300 amino acids, about 1300 amino acids to about 1600 amino acids, about 1300 amino acids to about 1550 amino acids, about 1300 amino acids to about 1500 amino acids, about 1300 amino acids to about 1450 amino acids, about 1300 amino acids to about 1400 amino acids, about 1300 amino acids to about 1350 amino acids, about 1350 amino acids to about 1600 amino acids, about 1350 amino acids to about 1550 amino acids, about 1350 amino acids to about 1500 amino acids, about 1350 amino acids to about 1450 amino acids, about 1350 amino acids to about 1400 amino acids, about 1400 amino acids to about 1600 amino acids, about 1400 amino acids to about 1550 amino acids, about 1400 amino acids to about 1500 amino acids, about 1400 amino acids to about 1450 amino acids, about 1450 amino acids to about 1600 amino acids, about 1450 amino acids to about 1550 amino acids, about 1450 amino acids to about 1500 amino acids, about 1500 amino acids to about 1600 amino acids, about 1500 amino acids to about 1550 amino acids, or about 1550 amino acids to about 1600 amino acids in length.

In some embodiments of these compositions, at least one of the coding sequences includes a nucleotide sequence spanning two neighboring exons of stereocilin genomic DNA, and lacks the intronic sequence that naturally occurs between the two neighboring exons.

In some embodiments, the amino acid sequence of none of the encoded portions overlaps even in part with the amino acid sequence of a different one of the encoded portions. In some embodiments, the amino acid sequence of one or more of the encoded portions partially overlaps with the amino acid sequence of a different one of the encoded portions. In some embodiments, the amino acid sequence of each of the encoded portions partially overlaps with the amino acid sequence of a different one of the encoded portions.

In some embodiments, the overlapping amino acid sequence is between about 30 amino acid residues to about 1000 amino acids (e.g., or any of the subranges of this range described herein) in length.

In some examples, the vectors include two different vectors, each of which comprises a different segment of an intron, wherein the intron includes the nucleotide sequence of an intron that is present in a stereocilin genomic DNA (e.g., any of the exemplary introns in SEQ ID NO: 4 described herein), and wherein the two different segments overlap in sequence by at least 100 nucleotides (e.g., about 100 nucleotides to about 5,000 nucleotides, about 100 nucleotides to about 4,500 nucleotides, about 100 nucleotides to about 4,000 nucleotides, about 100 nucleotides to about 3,500 nucleotides, about 100 nucleotides to about 3,000 nucleotides, about 100 nucleotides to about 2,500 nucleotides, about 100 nucleotides to about 2,000 nucleotides, about 100 nucleotides to about 1,500 nucleotides, about 100 nucleotides to about 1,000 nucleotides, about 100 nucleotides to about 800 nucleotides, about 100 nucleotides to about 600 nucleotides, about 100 nucleotides to about 400 nucleotides, about 100 nucleotides to about 200 nucleotides, about 200 nucleotides to about 5,000 nucleotides, about 200 nucleotides to about 4,500 nucleotides, about 200 nucleotides to about 4,000 nucleotides, about 200 nucleotides to about 3,500 nucleotides, about 200 nucleotides to about 3,000 nucleotides, about 200 nucleotides to about 2,500 nucleotides, about 200 nucleotides to about 2,000 nucleotides, about 200 nucleotides to about 1,500 nucleotides, about 200 nucleotides to about 1,000 nucleotides, about 200 nucleotides to about 800 nucleotides, about 200 nucleotides to about 600 nucleotides, about 200 nucleotides to about 400 nucleotides, about 400 nucleotides to about 5,000 nucleotides, about 400 nucleotides to about 4,500 nucleotides, about 400 nucleotides to about 4,000 nucleotides, about 400 nucleotides to about 3,500 nucleotides, about 400 nucleotides to about 3,000 nucleotides, about 400 nucleotides to about 2,500 nucleotides, about 400 nucleotides to about 2,000 nucleotides, about 400 nucleotides to about 1,500 nucleotides, about 400 nucleotides to about 1,000 nucleotides, about 400 nucleotides to about 800 nucleotides, about 400 nucleotides to about 600 nucleotides, about 600 nucleotides to about 5,000 nucleotides, about 600 nucleotides to about 4,500 nucleotides, about 600 nucleotides to about 4,000 nucleotides, about 600 nucleotides to about 3,500 nucleotides, about 600 nucleotides to about 3,000 nucleotides, about 600 nucleotides to about 2,500 nucleotides, about 600 nucleotides to about 2,000 nucleotides, about 600 nucleotides to about 1,500 nucleotides, about 600 nucleotides to about 1,000 nucleotides, about 600 nucleotides to about 800 nucleotides, about 800 nucleotides to about 5,000 nucleotides, about 800 nucleotides to about 4,500 nucleotides, about 800 nucleotides to about 4,000 nucleotides, about 800 nucleotides to about 3,500 nucleotides, about 800 nucleotides to about 3,000 nucleotides, about 800 nucleotides to about 2,500 nucleotides, about 800 nucleotides to about 2,000 nucleotides, about 800 nucleotides to about 1,500 nucleotides, about 800 nucleotides to about 1,000 nucleotides, about 1,000 nucleotides to about 5,000 nucleotides, about 1,000 nucleotides to about 4,500 nucleotides, about 1,000 nucleotides to about 4,000 nucleotides, about 1,000 nucleotides to about 3,500 nucleotides, about 1,000 nucleotides to about 3,000 nucleotides, about 1,000 nucleotides to about 2,500 nucleotides, about 1,000 nucleotides to about 2,000 nucleotides, about 1,000 nucleotides to about 1,500 nucleotides, about 1,500 nucleotides to about 5,000 nucleotides, about 1,500 nucleotides to about 4,500 nucleotides, about 1,500 nucleotides to about 4,000 nucleotides, about 1,500 nucleotides to about 3,500 nucleotides, about 1,500 nucleotides to about 3,000 nucleotides, about 1,500 nucleotides to about 2,500 nucleotides, about 1,500 nucleotides to about 2,000 nucleotides, about 2,000 nucleotides to about 5,000 nucleotides, about 2,000 nucleotides to about 4,500 nucleotides, about 2,000 nucleotides to about 4,000 nucleotides, about 2,000 nucleotides to about 3,500 nucleotides, about 2,000 nucleotides to about 3,000 nucleotides, about 2,000 nucleotides to about 2,500 nucleotides, about 2,500 nucleotides to about 5,000 nucleotides, about 2,500 nucleotides to about 4,500 nucleotides, about 2,500 nucleotides to about 4,000 nucleotides, about 2,500 nucleotides to about 3,500 nucleotides, about 2,500 nucleotides to about 3,000 nucleotides, about 3,000 nucleotides to about 5,000 nucleotides, about 3,000 nucleotides to about 4,500 nucleotides, about 3,000 nucleotides to about 4,000 nucleotides, about 3,000 nucleotides to about 3,500 nucleotides, about 3,500 nucleotides to about 5,000 nucleotides, about 3,500 nucleotides to about 4,500 nucleotides, about 3,500 nucleotides to about 4,000 nucleotides, about 4,000 nucleotides to about 5,000 nucleotides, about 4,000 nucleotides to about 4,500 nucleotides, about 4,500 nucleotides to about 5,000 nucleotides), in length.

The overlapping nucleotide sequence in any two of the different vectors can include part or all of one or more exons of a stereocilin gene (e.g., any one or more of the exemplary exons in SEQ ID NO: 4 described herein).

In some embodiments, the number of different vectors in the composition is two, three, four, or five. In compositions where the number of different vectors in the composition is two, the first of the two different vectors can include a coding sequence that encodes an N-terminal portion of the stereocilin protein. In some examples, the N-terminal portion of the stereocilin gene is between about 30 amino acids to about 1780 amino acids (or any of the subranges of this range described above) in length. In some examples, the first vector further includes one or both of a promoter (e.g., any of the promoters described herein or known in the art) and a Kozak sequence (e.g., any of the exemplary Kozak sequences described herein or known in the art). In some examples, the first vector includes a promoter that is an inducible promoter, a constitutive promoter, or a tissue-specific promoter. In some examples, the second of the two different vectors includes a coding sequence that encodes a C-terminal portion of the stereocilin protein. In some examples, the C-terminal portion of the stereocilin protein is between 30 amino acids to about 1780 amino acids (or any of the subranges of this range described above) in length. In some examples, the second vector further includes a poly(A) sequence.

In some examples where the number of different vectors in the composition is two, the N-terminal portion encoded by one of the two vectors can include a portion comprising amino acid position 1 to about amino acid position 1,500, about amino acid position 1,490, about amino acid position 1,480, about amino acid position 1,470, about amino acid position 1,460, about amino acid position 1,450, about amino acid position 1,440, about amino acid position 1,430, about amino acid position 1,420, about amino acid position 1,410, about amino acid position 1,400, about amino acid position 1,390, about amino acid position 1,380, about amino acid position 1,370, about amino acid position 1,360, about amino acid position 1,350, about amino acid position 1,340, about amino acid position 1,330, about amino acid position 1,320, about amino acid position 1,310, about amino acid position 1,300, about amino acid position 1,290, about amino acid position 1,280, about amino acid position 1,270, about amino acid position 1,260, about amino acid position 1,250, about amino acid position 1,240, about amino acid position 1,230, about amino acid position 1,220, about amino acid position 1,210, about amino acid position 1,200, about amino acid position 1,190, about amino acid position 1,180, about amino acid position 1,170, about amino acid position 1,160, about amino acid position 1,150, about amino acid position 1,140, about amino acid position 1,130, about amino acid position 1,120, about amino acid position 1,110, about amino acid position 1,100, about amino acid position 1,090, about amino acid position 1,080, about amino acid position 1,070, about amino acid position 1,060, about amino acid position 1,050, about amino acid position 1,040, about amino acid position 1,030, about amino acid position 1,020, about amino acid position 1,010, about amino acid position 1,000, about amino acid position 990, about amino acid position 980, about amino acid position 970, about amino acid position 960, about amino acid position 950, about amino acid position 940, about amino acid position 930, about amino acid position 920, about amino acid position 910, about amino acid position 900, about amino acid position 890, about amino acid position 880, about amino acid position 870, about amino acid position 860, about amino acid position 850, about amino acid position 840, about amino acid position 830, about amino acid position 820, about amino acid position 810, about amino acid position 800, about amino acid position 790, about amino acid position 780, about amino acid position 770, about amino acid position 760, about amino acid position 750, about amino acid position 740, about amino acid position 730, about amino acid position 720, about amino acid position 710, about amino acid position 700, about amino acid position 690, about amino acid position 680, about amino acid position 670, about amino acid position 660, about amino acid position 650, about amino acid position 640, about amino acid position 630, about amino acid position 620, about amino acid position 610, about amino acid position 600, about amino acid position 590, about amino acid position 580, about amino acid position 570, about amino acid position 560, about amino acid position 550, about amino acid position 540, about amino acid position 530, about amino acid position 520, about amino acid position 510, about amino acid position 500, about amino acid position 490, about amino acid position 480, about amino acid position 470, about amino acid position 460, about amino acid position 450, about amino acid position 440, about amino acid position 430, about amino acid position 420, about amino acid position 410, about amino acid position 400, about amino acid position 390, about amino acid position 380, about amino acid position 370, about amino acid position 360, about amino acid position 350, about amino acid position 340, about amino acid position 330, about amino acid position 320, about amino acid position 310, about amino acid position 300, about amino acid position 290, about amino acid position 280, about amino acid position 270, about amino acid position 260, about amino acid position 250, about amino acid position 240, about amino acid position 230, about amino acid position 220, about amino acid position 210, about amino acid position 200, about amino acid position 190, about amino acid position 180, about amino acid position 170, about amino acid position 160, about amino acid position 150, about amino acid position 140, about amino acid position 130, about amino acid position 120, about amino acid position 110, about amino acid position 100, about amino acid position 90, about amino acid position 80, about amino acid position 70, about amino acid position 60, about amino acid position 50, or about amino acid position 40 of a wildtype stereocilin protein (e.g., SEQ ID NO: 1).

In some examples where the number of different vectors in the composition is two, the N-terminal portion of the precursor stereocilin protein can include a portion comprising amino acid position 1 to amino acid position 310, amino acid position 1 to about amino acid position 320, amino acid position 1 to about amino acid position 330, amino acid position 1 to about amino acid position 340, amino acid position 1 to about amino acid position 350, amino acid position 1 to about amino acid position 360, amino acid position 1 to about amino acid position 370, amino acid position 1 to about amino acid position 380, amino acid position 1 to about amino acid position 390, amino acid position 1 to about amino acid position 400, amino acid position 1 to about amino acid position 410, amino acid position 1 to about amino acid position 420, amino acid position 1 to about amino acid position 430, amino acid position 1 to about amino acid position 440, amino acid position 1 to about amino acid position 450, amino acid position 1 to about amino acid position 460, amino acid position 1 to about amino acid position 470, amino acid position 1 to about amino acid position 480, amino acid position 1 to about amino acid position 490, amino acid position 1 to about amino acid position 500, amino acid position 1 to about amino acid position 510, amino acid position 1 to about amino acid position 520, amino acid position 1 to about amino acid position 530, amino acid position 1 to about amino acid position 540, amino acid position 1 to about amino acid position 550, amino acid position 1 to about amino acid position 560, amino acid position 1 to about amino acid position 570, amino acid position 1 to about amino acid position 580, amino acid position 1 to about amino acid position 590, amino acid position 1 to about amino acid position 600, amino acid position 1 to about amino acid position 610, amino acid position 1 to about amino acid position 620, amino acid position 1 to about amino acid position 630, amino acid position 1 to about amino acid position 640, amino acid position 1 to about amino acid position 650, amino acid position 1 to about amino acid position 660, amino acid position 1 to about amino acid position 670, amino acid position 1 to about amino acid position 680, amino acid position 1 to about amino acid position 690, amino acid position 1 to about amino acid position 700, amino acid position 1 to about amino acid position 710, amino acid position 1 to about amino acid position 720, amino acid position 1 to about amino acid position 730, amino acid position 1 to about amino acid position 740, amino acid position 1 to about amino acid position 750, amino acid position 1 to about amino acid position 760, amino acid position 1 to about amino acid position 770, amino acid position 1 to about amino acid position 780, amino acid position 1 to about amino acid position 790, amino acid position 1 to about amino acid position 800, amino acid position 1 to about amino acid position 810, amino acid position 1 to about amino acid position 820, amino acid position 1 to about amino acid position 830, amino acid position 1 to about amino acid position 840, amino acid position 1 to about amino acid position 850, amino acid position 1 to about amino acid position 860, amino acid position 1 to about amino acid position 870, amino acid position 1 to about amino acid position 880, amino acid position 1 to about amino acid position 890, amino acid position 1 to about amino acid position 900, amino acid position 1 to about amino acid position 910, amino acid position 1 to about amino acid position 920, amino acid position 1 to about amino acid position 930, amino acid position 1 to about amino acid position 940, amino acid position 1 to about amino acid position 950, amino acid position 1 to about amino acid position 960, amino acid position 1 to about amino acid position 970, amino acid position 1 to about amino acid position 980, amino acid position 1 to about amino acid position 990, amino acid position 1 to about amino acid position 1,000, amino acid position 1 to about amino acid position 1,010, amino acid position 1 to about amino acid position 1,020, amino acid position 1 to about amino acid position 1,030, amino acid position 1 to about amino acid position 1,040, amino acid position 1 to about amino acid position 1,050, amino acid position 1 to about amino acid position 1,060, amino acid position 1 to about amino acid position 1,070, amino acid position 1 to about amino acid position 1,080, amino acid position 1 to about amino acid position 1,090, amino acid position 1 to about amino acid position 1,100, amino acid position 1 to about amino acid position 1,110, amino acid position 1 to about amino acid position 1,120, amino acid position 1 to about amino acid position 1,130, amino acid position 1 to about amino acid position 1,140, amino acid position 1 to about amino acid position 1,150, amino acid position 1 to about amino acid position 1,160, amino acid position 1 to about amino acid position 1,170, amino acid position 1 to about amino acid position 1,180, amino acid position 1 to about amino acid position 1,190, amino acid position 1 to about amino acid position 1,200, amino acid position 1 to about amino acid position 1,210, amino acid position 1 to about amino acid position 1,220, amino acid position 1 to about amino acid position 1,230, amino acid position 1 to about amino acid position 1,240, amino acid position 1 to about amino acid position 1,250, amino acid position 1 to about amino acid position 1,260, amino acid position 1 to about amino acid position 1,270, amino acid position 1 to about amino acid position 1,280, amino acid position 1 to about amino acid position 1,290, amino acid position 1 to about amino acid position 1,300, amino acid position 1 to about amino acid position 1,310, amino acid position 1 to about amino acid position 1,320, amino acid position 1 to about amino acid position 1,330, amino acid position 1 to about amino acid position 1,340, amino acid position 1 to about amino acid position 1,350, amino acid position 1 to about amino acid position 1,360, amino acid position 1 to about amino acid position 1,370, amino acid position 1 to about amino acid position 1,380, amino acid position 1 to about amino acid position 1,390, amino acid position 1 to about amino acid position 1,400, amino acid position 1 to about amino acid position 1,410, amino acid position 1 to about amino acid position 1,420, amino acid position 1 to about amino acid position 1,430, amino acid position 1 to about amino acid position 1,440, amino acid position 1 to about amino acid position 1,450, amino acid position 1 to about amino acid position 1,460, amino acid position 1 to about amino acid position 1,470, amino acid position 1 to about amino acid position 1,480, amino acid position 1 to about amino acid position 1,490, amino acid position 1 to about amino acid position 1,500, amino acid position 1 to about amino acid position 1,510, amino acid position 1 to about amino acid position 1,520, amino acid position 1 to about amino acid position 1,530, amino acid position 1 to about amino acid position 1,540, amino acid position 1 to about amino acid position 1,550, amino acid position 1 to about amino acid position 1,560, amino acid position 1 to about amino acid position 1,570, amino acid position 1 to about amino acid position 1,580, amino acid position 1 to about amino acid position 1,590, or amino acid position 1 to about amino acid position 1,600 of a wildtype stereocilin protein (e.g., SEQ ID NO: 1).

As used herein, the term "vector" means a composition including a polynucleotide capable of carrying at least one exogenous nucleic acid fragment, e.g., a plasmid vector, a transposon, a cosmid, an artificial chromosome (e.g., a human artificial chromosome (HAC), a yeast artificial chromosome (YAC), a bacterial artificial chromosome (BAC), or a P1-derived artificial chromosome (PAC)) or a viral vector (e.g., any adenoviral vectors (e.g., pSV or pCMV vectors), any retroviral vectors as described herein) and any Gateway® vectors. A vector can, e.g., include sufficient cis-acting elements for expression; other elements for expression can be supplied by the host mammalian cell or in an in vitro expression system. The term "vector" includes any genetic element (e.g., a plasmid, a transposon, a cosmid, an artificial chromosome, or a viral vector, etc.) that is capable of replicating when associated with the proper control elements. Thus, the term includes cloning and expression vectors, as well as viral vectors (e.g., an adeno-associated virus (AAV) vector, an adenovirus vector, a lentivirus vector, or a retrovirus vector).

Vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide. Skilled practitioners will be capable of selecting suitable vectors and mammalian cells for making any of the nucleic acids described herein. In some embodiments, the vector is a plasmid (i.e. a circular DNA molecule that can autonomously replicate inside a cell). In some embodiments, the vector can be a cosmid (e.g., pWE and sCos series (Wahl et al. (1987), Evans et al. (1989)).

In some embodiments, the vector(s) is an artificial chromosome. An artificial chromosome is a genetically engineered chromosome that can be used as a vector to carry large DNA inserts. In some embodiments, the artificial chromosome is human artificial chromosome (HAC) (see, e.g., Kouprina et al., *Expert Opin. Drug Deliv* 11 (4): 517-535, 2014; Basu et al., *Pediatr. Clin. North Am.* 53:843-853, 2006; Ren et al., *Stem. Cell Rev.* 2 (1): 43-50, 2006; Kazuki et al., *Mol. Ther.* 19 (9): 1591-1601, 2011; Kazuki et al., *Gen. Ther.* 18:384-393, 2011; and Katoh et al., *Biochem. Biophys. Res. Commun.* 321:280-290, 2004).

In some embodiments, the vector(s) is a yeast artificial chromosome (YAC) (see, e.g., Murray et al., *Nature* 305: 189-193, 1983; Ikeno et al. (1998) *Nat. Biotech.* 16:431-439, 1998). In some embodiments, the vector(s) is a bacterial artificial chromosome (BAC) (e.g., pBeloBAC11, pECBAC1, and pBAC108L). In some embodiments, the vector(s) is a P1-derived artificial chromosome (PAC). Examples of artificial chromosome are known in the art.

In some embodiments, the vector(s) is a viral vector (e.g., adeno-associated virus, adenovirus, lentivirus, and retrovirus). Non-limiting examples of viral vectors are described herein. In some embodiments, the vector(s) is an adeno-associated viral vector (AAV) (see, e.g., Asokan et al., *Mol. Ther.* 20:699-7080, 2012). "Recombinant AAV vectors" or "rAAVs" are typically composed of, at a minimum, a transgene or a portion thereof and a regulatory sequence, and optionally 5' and 3' AAV inverted terminal repeats (ITRs). Such a recombinant AAV vector is packaged into a capsid and delivered to a selected target cell (e.g., an outer hair cell).

The AAV sequences of the vector typically comprise the cis-acting 5' and 3' ITR sequences (See, e.g., B. J. Carter, in "Handbook of Parvoviruses", ed., P. Tijsser, CRC Press, pp. 155 168, 1990). Typical AAV ITR sequences are about 145 nucleotides in length. In some embodiments, at least 75% of a typical ITR sequence (e.g., at least 80%, at least 85%, at least 90%, or at least 95%) is incorporated into the AAV vector. The ability to modify these ITR sequences is within the skill of the art. (Sec, e.g., texts such as Sambrook et al., "Molecular Cloning. A Laboratory Manual", 2d ed., Cold Spring Harbor Laboratory, New York, 1989; and K. Fisher et al., *J Virol.* 70:520 532, 1996). In some embodiments, any of the coding sequences described herein are flanked by 5' and 3' AAV ITR sequences in the AAV vectors. The AAV ITR sequences may be obtained from any known AAV, including presently identified AAV types.

A non-limiting example of a 5' AAV ITR sequence is SEQ ID NO: 18. A non-limiting example of a 3' AAV ITR sequence is SEQ ID NO: 36.

AAV vectors as described herein may include any of the regulatory elements described herein (e.g., one or more of a promoter, a polyA sequence, and an IRES). In some embodiments, the AAV vector is selected from the group consisting of: an AAV1 vector, an AAV2 vector, an AAV3 vector, an AAV4 vector, an AAV5 vector, an AAV6 vector, an AAV7 vector, an AAV8 vector, an AAV9 vector, an AAV2.7m8 vector, an AAV8BP2 vector, and an AAV293 vector. Additional exemplary AAV vectors that can be used herein are known in the art. See, e.g., Kanaan et al., *Mol. Ther. Nucleic Acids* 8:184-197, 2017; Li et al., *Mol. Ther.* 16 (7): 1252-1260; Adachi et al., *Nat. Commun.* 5:3075, 2014; Isgrig et al., *Nat. Commun.* 10 (1): 427, 2019; and Gao et al., *J. Virol.* 78 (12): 6381-6388.

In some embodiments, an AAV vector provided herein includes or consists of a sequence that is at least 80% identical (e.g., at least 82%, at least 84%, at least 85%, at least 86%, at least 88%, at least 90%, at least 92%, at least 94%, at least 95%, at least 96%, at least 98%, at least 99%, or 100% identical) to SEQ ID NOs: 12-17.

```
pITR-201
                                                          (SEQ ID NO: 12)
cctgcaggcagctgcgcgctcgctcgctcactgaggccgcccgggcgtcgggcgacctttggtcgcccg gcctcagtgagcgagcgagcgcgcagagagggagtggccaactccatcactaggggttcctgcggccgc acgcgtagacttgcccaaaaactctggcaaagttgaattgcttccaaaagttcaactttatcagaagga cctattccctacggaaactagctgaaggtctcctggcactctggatctcgtggaagggagccttcttca gggaacagagggagcgattaagtggtgaaaagcaaacagacctggaaaagttcccttctgagagtagc aacagaaagctctgcaaagactccctccaagctattggatcctcttgcttgggataaccacttgagtac tcagataccaaaagaagagtggaaatcccaagagaagtcaccagaaaaaacagcttttaagaaaaagga tacacttttgtccctgaacgcttgtgaaagcaatctgacaatagcagcaattgaaaagggacaaaataa gcccgaaatagaagtcacctgggcaaagcaaggtaggactgaaaggctgtgctctcaaaacccaccagt cttgaaacgcactcaacgggtgaaagtagtaggaaagggtgaatttacaaaggacgtaggactcaaaga gtgagtttttccaagcagcagaaacctatttcttactaacttggataatttactgaaaaataatacaca caatcaagaaaaaaaattcaggaagaaatagaaaagaaggaaaacttaatccaagagtgaatagtttt
```

-continued

```
gcctcagataactacagtgactggcactaagaatttctgaaagaaccttttcttactgagcactaggct gaaaatagaaggttacttgaacggggacttgactccagtacttcaagattttaggtactttgaaaattc aacaaatagaacaaagaaacacacagctactttctcaaaaaaggggaggaagaaaacttggaaggctt gggaaatcaaaccaagcaaattgtagagaaattgactgacaccacaaggatatctcctaatacaagcca gcagaattttgtcacgcaacgtagtaagagagctttgaaactagatcccatatatggagttccgcgtta cataacttacggtaaatggcccgcctggctgaccgcccaacgaccccgcccattgacgtcaataatga cgtatgttcccatagtaacgccaatagggactttccattgacgtcaatgggtggagtatttacggtaaa ctgcccacttggcagtacatcaagtgtatcatatgccaagtacgccccctattgacgtcaatgacggta aatggcccgcctggcattatgcccagtacatgaccttatgggactttcctacttggcagtacatctacg tattagtcatcgctattaccatggtgatgcggttttggtgatgcggttttggcagtacatcaatgggcg tggatagcggtttgactcacggggatttccaagtctccaccccattgacgtcaatgggagtttgttttg gcaccaaaatcaacgggactttccaaaatgtcgtaacaactccgccccattgacgcaaatgggcggtag gcgtgtacggtgggaggtctatataagcagagctcgtttagtgaaccgtcaccggtggtgcccctgcct cacctggctatcccacacaggtgagaataaccagaactcacctccggtaccagtgttcacttggccacc atggctctcagcctctggcccctgctgctgctgctgctgctgctgctgtcctttgcagtgact ctggcccctactgggcctcattccctggaccctggtctctccttcctgaagtcattgctctccactctg gaccaggctccccagggctccctgagccgctcacggttctttacattcctggccaacatttcttcttcc tttgagcctgggagaatgggggaaggaccagtaggagagcccccacctctccagccgcctgctctgcgg ctccatgatttttctagtgacactgagaggtagccccgactgggagccaatgctagggctgctaggggat atgctggcactgctgggacaggagcagactccccgagatttcctggtgcaccaggcagggggtgctgggt ggacttgtggaggtgctgctgggagccttagttcctgggggccccctaccccaactcggcccccatgc acccgtgatgggccgtctgactgtgtcctggctgctgactggttgccttctctgctgctgttgttagag ggcacacgctggcaagctctggtgcaggtgcagcccagtgtggacccaccaatgccacaggcctcgat gggagggaggcagctcctcacttttttgcagggtctgttgggtttgcttaccccaacaggggagctaggc tccaaggaggctctttggggcggtctgctacgcacagtggggccccctctatgctgcctttcaggag gggctgctccgtgtcactcactccttgcaggatgaggtcttctccattttggggcagccagagcctgat accaatgggcagtgccaggaggtaaccttcaacagctgctcttatggggcgtccggcacaacctttcc tgggatgtccaggcgctgggctttctgtctggatcaccaccccacccctgccctccttcactgcctg agcacgggcgtgcctctgcccagagcttctcagccgtcagcccacatcagcccacgccaacggcgagcc atcactgtggaggccctctgtgagaaccacttaggcccagcaccaccctacagcatttccaacttctcc atccacttgctctgccagcacaccaagcctgccactccacagccccatcccagcaccactgccatctgc cagacagctgtgtggtatgcagtgtcctgggcaccaggtgcccaaggctggctacaggcctgccacgac cagtttcctgatgagttttggatgcgatctgcagtaacctctccttttcagccctgtctggctccaac cgccgcctggtgaagcggctctgtgctggcctgctcccaccccctaccagctgccctgaaggcctgccc cctgttcccctcaccccagacatcttttggggctgcttcttggagaatgagactctgtgggctgagcga ctgtgtggggaggcaagtctacaggctgtgccccccagcaaccaggcttgggtccagcatgtgtgccag ggccccaccccagatgtcactgcctcccaccatgccacattggaccctgtggggaacgctgcccggat gggggcagcttcctggtgatggtctgtgccaatgacaccatgtatgaggtcctggtgcccttctggcct tggctagcaggccaatgcaggataagtcgtggggggcaatgacacttgcttcctagaagggctgctgggc cccttctgccctctctgccaccactgggaccatccccactctgtctgacccctggccccttcctccatt
```

-continued ggcatgctatcccagttgccacgctgtcagtcctctgtcccagctcttgctcaccccacacgcctacac tatctcctccgcctgctgaccttcctcttgggtccaggggctgggggcgctgaggcccaggggatgctg ggtcgggccctactgctctccagtctcccagacaactgctccttctgggatgcctttcgcccagagggc cggcgcagtgtgctacggacgattggggaatacctggaacaagatgaggagcagccaacccccatcaggc tttgaacccactgtcaaccccagctctggtataagcaagatggagctgctggcctgctttagtcctgtg ctgtgggatctgctccagagggaaaagagtgtttgggccctgcagattctagtgcaggtaagtatcaag gttacaagacaggtttaaggagaccaatagaaactgggcttgtcgagacagagaagactcttgcgtttc tgggattttgccgatttcggcctattggttaaaaaatgagctgatttaacaaaaatttaacgcgaattt taacaaaataagcttgaattcagctgacgtgcctcggaccgctaggaaccccctagtgatggagttggcc actccctctctgcgcgctcgctcgctcactgaggccgggcgaccaaaggtcgcccgacgcccgggcttt gcccgggcggcctcagtgagcgagcgagcgcgcagctgcctgcagg pITR-202

(SEQ ID NO: 13)

cctgcaggcagctgcgcgctcgctcgctcactgaggccgcccgggcgtcgggcgacctttggtcgcccg gcctcagtgagcgagcgagcgcgcagagagggagtggccaactccatcactaggggttcctgcggccgc acgcgtgggattttgccgatttcggcctattggttaaaaaatgagctgatttaacaaaaatttaacgcg aattttaacaaaatgataggcacctattggtcttactgacatccactttgcctttctctccacaggcgt acctgcatatgcccccagaaaacctccagcagctggtgctttcagcagagggaggctgcacagggct tcctgacactcatgctgcaggggaagctgcaggggaagctgcaggtaccaccatccgaggagcaggccc tgggtcgcctgacagccctgctgctccagcggtacccacgcctcacctcccagctcttcattgacctgt caccactcatccctttcttggctgtctctgacctgatgcgcttccaccatccctgttagccaacgaca gtgtcctggctgccatccgggattacagcccaggaatgaggcctgaacagaaggaggctctggcaaagc gactgctggcccctgaactgtttggggaagtgcctgcctggccccaggagctgctgtgggcagtgctgc ccctgctccccacctccctctggagaacttttttgcagctcagccctcaccagatccaggccctggagg atagctggccagcagcaggtctggggccagggcatgcccgccatgtgctgcgcagcctggtaaaccaga gtgtccaggatggtgaggagcaggtacgcaggcttgggcccctcgcctgtttcctgagcccgaggagc tgcagagcctagtgcccctgagtgatccaacggggccagtagaacgggggctgctggaatgtgcagcca atgggaccctcagcccagaaggacgggtggcatatgaacttctgggtgtgttgcgctcatctggaggag cggtgctgagccccgggagctgcgggtctgggcccctctcttctctcagctgggcctccgcttccttc aggagctgtcagagcccccagcttagagccatgcttcctgtcctccagggaactagtgttacacctgctc aggctgtcctgctgcttggacggctccttcctaggcacgatctatccctggaggaactctgctccttgc accttctgctaccaggcctcagcccccagacactccaggccatccctaggcgagtcctggtcggggctt gttcctgcctggcccctgaactgtcacgcctctcagcctgccagaccgcagcactgctgcagacctttc gggttaaagatggtgttaaaaatatgggtacaacaggtgctggtccagctgtgtgtatccctggtcagc ctattcccaccacctggccagactgcctgcttcccctgctcccattaaagctgctacaactggattcct tggctcttctggcaaatcgaagacgctactgggagctgcctggtctgagcagcaggcacagtttctct ggaagaagatgcaagtacccaccaaccttaccctcaggaatctgcaggctctgggcaccctggcaggag gcatgtcctgtgagtttctgcagcagatcaactccatggtagacttccttgaagtggtgcacatgatct atcagctgcccactagagttcgagggagcctgagggcctgtatctgggcagagctacagcggaggatgg caatgccagaaccagaatggacaactgtagggccagaactgaacgggctggatagcaagctactcctgg acttaccgatccagttgatggacagactatccaatgaatccattatgttggtggtggagctggtgcaaa gagctccagagcagctgctggcactgaccccccctccaccaggcagccctggcagagagggcactacaaa -continued

```
acctggctccaaaggagactccagtctcaggggaagtgctggagaccttaggccctttggttggattcc tggggacagagagcacacgacagatcccctacagatcctgctgtcccatctcagtcagctgcaaggct tctgcctaggagagacatttgccacagagctgggatggctgctattgcaggagtctgttcttgggaaac cagagttgtggagccaggatgaagtagagcaagctggacgcctagtattcactctgtctactgaggcaa tttccttgatccccagggaggccttgggtccagagaccctggagcggcttctagaaaagcagcagagct gggagcagagcagagttggacagctgtgtagggagccacagcttgctgccaagaaagcagccctggtag caggggtggtgcgaccagctgctgaggatcttccagaacctgtgccaaattgtgcagatgtacgaggga cattcccagcagcctggtctgcaacccagattgcagagatggagctctcagactttgaggactgcctga cattatttgcaggagacccaggacttgggcctgaggaactgcgggcagccatgggcaaagcaaaacagt tgtgggtccccccgggatttcgtcctgagcagatcctgcagcttggtaggctcttaataggtctag gagatcgggaactacaggagctgatcctagtggactggggagtgctgagcaccctggggcagatagatg gctggagcaccactcagctccgcattgtggtctccagtttcctacggcagagtggtcggcatgtgagcc acctggacttcgttcatctgacagcgctgggttatactctctgtggactgcggccagaggagctccagc acatcagcagttgggagttcagccaagcagctctcttcctcggcaccctgcatctccagtgctctgagg aacaactggaggttctggcccacctacttgtactgcctggtgggtttggcccaatcagtaactgggggc ctgagatcttcactgaaattggcaccatagcagctgggatcccagacctggctcttcagcactgctgc ggggacagatccagggcgttactcctcttgccatttctgtcatccctcctcctaaatttgctgtggtgt ttagtcccatccaactatctagtctcaccagtgctcaggctgtggctgtcactcctgagcaaatggcct ttctgagtcctgagcagcgacgagcagttgcatgggcccaacatgagggaaaggagagcccagaacagc aaggtcgaagtacagcctggggcctccaggactggtcacgaccttcctggtccctggtattgactatca gcttccttggccacctgctatgagcctgtctctacagtagaaggagattgtggggagagaaatcttaag tcataatgaataaagtgcaaacagaagtgcatcctgattattttcagaagctgatgaggaataactagt gctgatcagcctcgactgtgccttctagttgccagccatctgttgtttgcccctccccgtgccttcct tgaccctggaaggtgccactcccactgtcctttcctaataaaatgaggaaattgcatcgcattgtctga gtaggtgtcattctattctggggggtggggtggggcaggacagcaaggggaggattgggaagacaata gcaggcatgctggggatgcggtgggctctatggcaattcagactcccactagaagaaacagaacttgaa aaaggataattgtggtgaacacctcaacccagtggtccaaaaactgaaaaactttgaccccgagcacc ctcacacagatagactactgaaagaaggagaaaggggcacttactcagtctcccttatcagattgcctt acgaggagtactagactccctcaagcaaatagatctcattaccacttgcaaaggtatactactttcac tctattagacctatatatctgaccagggtcctattccaagacaactcttctactcttccagcagactct tatagaaagaaagattctggggtccaagaaagcagtactttcttacaaggagccaaaaaaaataaccttt tctttagcacttctaaccttggagtgaactggtgatcaaagagaggttggctccctggggacaagtgcc acaaattcagtcaactacaagaaagttgagaacactgttctcccgaaaccaagcttgaattcagctgac gtgcctcggaccgctaggaaccctagtgatggagttggccactccctctctgcgcgctcgctcgctca ctgaggccgggcgaccaaaggtcgcccgacgcccgggctttgcccgggcggcctcagtgagcgagcgag cgcgcagctgcctgcagg
``` pITR-202GFP (SEQ ID NO: 14)
```
cctgcaggcagctgcgcgctcgctcgctcactgaggccgcccgggcgtcgggcgacctttggtcgcccg gcctcagtgagcgagcgagcgcgcagagagggagtggccaactccatcactaggggttcctgcggccgc acgcgtgggattttgccgatttcggcctattggttaaaaaatgagctgatttaacaaaaatttaacgcg
```

-continued

```
aattttaacaaaatgataggcacctattggtcttactgacatccactttgcctttctctccacaggcgt
acctgcatatgcccccagaaaacctccagcagctggtgctttcagcagagagggaggctgcacagggct
tcctgacactcatgctgcaggggaagctgcaggggaagctgcaggtaccaccatccgaggagcaggccc
tgggtcgcctgacagccctgctgctccagcggtacccacgcctcacctcccagctcttcattgacctgt
caccactcatccctttcttggctgtctctgacctgatgcgcttccaccatccctgttagccaacgaca
gtgtcctggctgccatccgggattacagcccaggaatgaggcctgaacagaaggaggctctggcaaagc
gactgctggcccctgaactgtttggggaagtgcctgcctggccccaggagctgctgtgggcagtgctgc
ccctgctcccccacctccctctggagaactttttgcagctcagccctcaccagatccaggccctggagg
atagctggccagcagcaggtctggggccagggcatgcccgccatgtgctgcgcagcctggtaaaccaga
gtgtccaggatggtgaggagcaggtacgcaggcttgggcccctcgcctgtttcctgagccctgaggagc
tgcagagcctagtgcccctgagtgatccaacggggccagtagaacggggctgctggaatgtgcagcca
atggaccctcagcccagaaggacgggtggcatatgaacttctgggtgtgttgcgctcatctggaggag
cggtgctgagccccgggagctgcgggtctgggcccctctcttctctcagctgggcctccgcttccttc
aggagctgtcagagcccagcttagagccatgcttcctgtcctcagggaactagtgttacacctgctc
aggctgtcctgctgcttggacggctccttcctaggcacgatctatccctggaggaactctgctccttgc
accttctgctaccaggcctcagcccccagacactccaggccatccctaggcgagtcctggtcgggctt
gttcctgcctggcccctgaactgtcacgcctctcagcctgccagaccgcagcactgctgcagacctttc
gggttaaagatggtgttaaaaatatgggtacaacaggtgctggtccagctgtgtgtatccctggtcagc
ctattcccaccacctggccagactgcctgcttcccctgctcccattaaagctgctacaactggattcct
tggctcttctggcaaatcgaagacgctactgggagctgccctggtctgagcagcaggcacagtttctct
ggaagaagatgcaagtacccaccaaccttaccctcaggaatctgcaggctctgggcaccctggcaggag
gcatgtcctgtgagtttctgcagcagatcaactccatggtagacttccttgaagtggtgcacatgatct
atcagctgcccactagagttcgagggagcctgagggcctgtatctgggcagagctacagcggaggatgg
caatgccagaaccagaatggacaactgtagggccagaactgaacgggctggatagcaagctactcctgg
acttaccgatccagttgatggacagactatccaatgaatccattatgttggtggtggagctggtgcaaa
gagctccagagcagctgctggcactgaccccccctccaccaggcagccctggcagagagggcactacaaa
acctggctccaaaggagactccagtctcaggggaagtgctggagaccttaggccctttggttggattcc
tggggacagagagcacacgacagatccccctacagatcctgctgtcccatctcagtcagctgcaaggct
tctgcctaggagagacatttgccacagagctgggatggctgctattgcaggagtctgttcttgggaaac
cagagttgtggagccaggatgaagtagagcaagctggacgcctagtattcactctgtctactgaggcaa
tttccttgatccccagggaggccttgggtccagagacccctggagcggcttctagaaaagcagcagagct
gggagcagagcagagttggacagctgtgtagggagccacagcttgctgccaagaaagcagccctggtag
cagggggtggtgcgaccagctgctgaggatcttccagaacctgtgccaaattgtgcagatgtacgaggga
cattcccagcagcctggtctgcaacccagattgcagagatggagctctcagactttgaggactgcctga
cattatttgcaggagacccaggacttgggcctgaggaactgcgggcagccatgggcaaagcaaaacagt
tgtgggtcccccccggggatttcgtcctgagcagatcctgcagcttggtaggctcttaataggtctag
gagatcgggaactacaggagctgatcctagtggactggggagtgctgagcaccctggggcagatagatg
gctggagcaccactcagctccgcattgtggtctccagtttcctacggcagagtggtcggcatgtgagcc
acctggacttcgttcatctgacagcgctgggttatactctctgtggactgcggccagaggagctccagc
acatcagcagttgggagttcagccaagcagctctcttcctcggcaccctgcatctccagtgctctgagg
aacaactggaggttctggcccacctacttgtactgcctggtgggtttggcccaatcagtaactgggggc
```

-continued ctgagatcttcactgaaattggcaccatagcagctgggatcccagacctggctctttcagcactgctgc ggggacagatccagggcgttactcctcttgccatttctgtcatccctcctcctaaatttgctgtggtgt ttagtcccatccaactatctagtctcaccagtgctcaggctgtggctgtcactcctgagcaaatggcct ttctgagtcctgagcagcgacgagcagttgcatgggcccaacatgagggaaaggagagcccagaacagc aaggtcgaagtacagcctggggcctccaggactggtcacgaccttcctggtccctggtattgactatca gcttccttggccacctgctaggctccggagagggcagaggaagtctgctaacatgcggtgacgtcgagg agaatcctggcccaatggagagcgacgagagcggcctgcccgccatggagatcgagtgccgcatcaccg gcaccctgaacggcgtggagttcgagctggtgggcggcggagagggcaccccgagcagggccgcatga ccaacaagatgaagagcaccaaaggcgccctgaccttcagcccctacctgctgagccacgtgatgggct acggcttctaccacttcggcacctaccccagcggctacgagaacccccttcctgcacgccatcaacaacg gcggctacaccaacacccgcatcgagaagtacgaggacggcggcgtgctgcacgtgagcttcagctacc gctacgaggccggccgcgtgatcggcgacttcaaggtgatgggcaccggcttccccgaggacagcgtga tcttcaccgacaagatcatccgcagcaacgccaccgtggagcacctgcacccatgggcgataacgatc tggatggcagcttcacccgcaccttcagcctgcgcgacggcggctactacagctccgtggtggacagcc acatgcacttcaagagcgccatccaccccagcatcctgcagaacggggggccccatgttcgccttccgcc gcgtggaggaggatcacagcaacaccgagctgggcatcgtggagtaccagcacgccttcaagaccccgg atgcagatgccggtgaagaataagcctgtctctacagtagaaggagattgtgggggagagaaatcttaag tcataatgaataaagtgcaaacagaagtgcatcctgattattttcagaagctgatgaggaataactagt gctgatcagcctcgactgtgccttctagttgccagccatctgttgtttgcccctccccgtgccttcct tgaccctggaaggtgccactcccactgtccttcctaataaaatgaggaaattgcatcgcattgtctga gtaggtgtcattctattctggggggtggggtggggcaggacagcaagggggaggattgggaagacaata gcaggcatgctggggatgcggtgggctctatggaagcttgaattcagctgacgtgcctcggaccgctag gaaccctagtgatggagttggccactccctctctgcgcgctcgctcgctcactgaggccgggcgacca aaggtcgcccgacgcccgggctttgcccgggcggcctcagtgagcgagcgagcgcgcagctgcctgcag g pITR-203

(SEQ ID NO: 15)
cctgcaggcagctgcgcgctcgctcgctcactgaggccgcccgggcgtcgggcgacctttggtcgcccg gcctcagtgagcgagcgagcgcgcagagagggagtggccaactccatcactagggggttcctgcggccgc acgcgtagacttgcccaaaaactctggcaaagttgaattgcttccaaaagttcaactttatcagaagga cctattccctacggaaactagctgaaggtctcctggcactctggatctcgtggaagggagccttcttca gggaacagagggagcgattaagtggtgaaaagcaaacagacctgaaaagttcccttttctgagagtagc aacagaaagctctgcaaagactccctccaagctattggatcctcttgcttgggataaccacttgagtac tcagataccaaaagaagagtggaaatcccaagagaagtcaccagaaaaaacagcttttaagaaaaagga tacacttttgtccctgaacgcttgtgaaagcaatctgacaatagcagcaattgaaaagggacaaaataa gcccgaaatagaagtcacctgggcaaagcaaggtaggactgaaaggctgtgctctcaaaacccaccagt cttgaaacgcactcaacgggtgactagatcccatatatggagttccgcgttacataacttacggtaaat ggcccgcctggctgaccgcccaacgaccccgcccattgacgtcaataatgacgtatgttcccatagta acgccaatagggactttccattgacgtcaatgggtggagtatttacggtaaactgcccacttggcagta catcaagtgtatcatatgccaagtacgccccctattgacgtcaatgacggtaaatggcccgcctggcat tatgcccagtacatgaccttatgggactttcctacttggcagtacatctacgtattagtcatcgctatt -continued

```
accatggtgatgcggttttggtgatgcggttttggcagtacatcaatgggcgtggatagcggtttgact cacggggatttccaagtctccaccccattgacgtcaatgggagtttgttttggcaccaaaatcaacggg actttccaaaatgtcgtaacaactccgcccattgacgcaaatgggcggtaggcgtgtacggtgggagg tctatataagcagagctcgtttagtgaaccgtcaccggtggtgccctgccctcacctggctatcccaca caggtgagaataaccagaactcacctccggtaccagtgttcacttggccaccatggctctcagcctctg gcccctgctgctgctgctgctgctgctgctgctgtccttttgcagtgactctggcccctactgggcc tcattccctggaccctggtctctccttcctgaagtcattgctctccactctggaccaggctccccaggg ctccctgagccgctcacggttctttacattcctggccaacatttcttcttccttttgagcctgggagaat ggggaaggaccagtaggagagcccccacctctccagccgcctgctctgcggctccatgattttctagt gacactgagaggtagccccgactgggagccaatgctaggggctgctaggggatatgctggcactgctggg acaggagcagactccccgagatttcctggtgcaccaggcaggggctggtggacttgtggaggtgct gctgggagccttagttcctgggggccccctaccccaactcggccccatgcacccgtgatgggccgtc tgactgtgtcctggctgctgactggttgccttctctgctgctgttgttagagggcacacgctggcaagc tctggtgcaggtgcagcccagtgtggaccccaccaatgccacaggcctcgatgggagggaggcagctcc tcacttttgcagggtctgtttgggttgcttaccccaacaggggagctaggctccaaggaggctctttg gggcggtctgctacgcacagtgggggccccctctatgctgcctttcaggagggctgctccgtgtcac tcactccttgcaggatgaggtcttctccatttttggggcagcagagcctgataccaatgggcagtgcca gggaggtaaccttcaacagctgctcttatggggcgtccggcacaaccttcctgggatgtccaggcgct gggctttctgtctggatcaccaccccccacccctgccctccttcactgcctgagcacgggcgtgcctct gcccagagcttctcagccgtcagcccacatcagcccacgccaacggcgagccatcactgtggaggccct ctgtgagaaccacttaggcccagcaccaccctacagcatttccaacttctccatccacttgctctgcca gcacaccaagcctgccactccacagccccatcccagcaccactgccatctgccagacagctgtgtggta tgcagtgtcctgggcaccaggtgcccaaggctggctacaggcctgccacgaccagtttcctgatgagtt tttggatgcgatctgcagtaacctctccttttcagccctgtctggctccaaccgccgcctggtgaagcg gctctgtgctggcctgctccaccccctaccagctgccctgaaggcctgcccctgttcccctcacccc agacatcttttggggctgcttcttggagaatgagactctgtgggctgagcgactgtgtggggaggcaag tctacaggctgtgcccccagcaaccaggcttgggtccagcatgtgtgccagggccccaccccagatgt cactgcctcccaccatgccacattggaccctgtggggaacgctgcccggatgggggcagcttcctggt gatggtctgtgccaatgacaccatgtatgaggtcctggtgcccttctggccttggctagcaggccaatg caggataagtcgtgggggcaatgacacttgcttcctagaagggctgctgggcccccttctgccctctct gccaccactgggaccatccccactctgtctgaccctggccccttcctccttggcatgctatcccagtt gccacgctgtcagtcctctgtcccagctcttgctcaccccacacgcctacactatctcctccgcctgct gaccttcctcttgggtccaggggctggggcgctgaggcccaggggatgctggctcgggccctactgct ctccagtctcccagacaactgctccttctgggatgcctttcgcccagagggccggcgcagtgtgctacg gacgattggggaatacctggaacaagatgaggagcagccaacccccatcaggctttgaacccactgtcaa ccccagctctggtataagcaagatggagctgctggcctgctttagtcctgtgctgtgggatctgctcca gagggaaaagagtgtttgggccctgcagattctagtgcaggtaagtatcaaggttacaagacaggttta aggagaccaatagaaactgggcttgtcgagacagagaagactcttgcgtttctctaggtggaggccgaa agtacatgtttcgcatgggaaccccagaccctgagtacccagatgactacagccaaggtgggaccaggc tggacgggaagaatctggtgcaggaatggctggcgaagcgccagggtgcccggtatgtgtggaaccgca ctgagctcatgcaggcttccctggacccgtctgtgacccatctcatgggtctctttgagcctggagaca
```

-continued tgaaatacgagatccaccgagactccacactggacccctccctgatggagatgacagaggctgccctgc gcctgctgagcaggaaccccgcggcttcttcctcttcgtggagggtggtcgcatcgaccatggtcatc atgaaagcagggcttaccgggcactgactgagacgatcatgttcgacgacgccattgagagggcgggcc agctcaccagcgaggaggacacgctgagcctcgtcactgccgaccactcccacgtcttctccttcggag gctaccccctgcgagggagctccatcttcgggctggcccctggcaaggcccgggacaggaaggcctaca cggtcctcctatacggaaacggtccaggctatgtgctcaaggacggcgcccggccggatgttaccgaga gcgagagcgggagccccgagtatcggcagcagtcagcagtgcccctggacgaagagacccacgcaggcg aggacgtggcggtgttcgcgcgcgggcccgcaggcgcacctggttcacggcgtgcaggagcagaccttca tagcgcacgtcatggccttcgccgcctgcctggagccctacaccgcctgcgacctggcgcccccgccg gcaccaccgacgccgcgcacccggggcgaagcttgaattcagctgacgtgcctcggaccgctaggaacc cctagtgatggagttggccactccctctctgcgcgctcgctcgctcactgaggccgggcgaccaaaggt cgcccgacgcccgggctttgcccgggcggcctcagtgagcgagcgagcgcgcagctgcctgcagg pITR-204                                                              (SEQ ID NO: 16)
cctgcaggcagctgcgcgctcgctcgctcactgaggccgcccgggcgtcgggcgacctttggtcgcccg gcctcagtgagcgagcgagcgcgcagagagggagtggccaactccatcactagggggttcctgcggccgc acgcgtctaggtggaggccgaaagtacatgtttcgcatgggaaccccagaccctgagtacccagatgac tacagccaaggtgggaccaggctggacgggaagaatctggtgcaggaatggctggcgaagcgccagggt gcccggtatgtgtggaaccgcactgagctcatgcaggcttccctggacccgtctgtgacccatctcatg ggtctctttgagcctggagacatgaaatacgagatccaccgagactccacactggaccccctccctgatg gagatgacagaggctgccctgcgcctgctgagcaggaaccccgcggcttcttcctcttcgtggagggt ggtcgcatcgaccatggtcatcatgaaagcagggcttaccgggcactgactgagacgatcatgttcgac gacgccattgagagggcgggccagctcaccagcgaggaggacacgctgagcctcgtcactgccgaccac tcccacgtcttctccttcggaggctaccccctgcgagggagctccatcttcgggctggcccctggcaag gcccgggacaggaaggcctacacggtcctcctatacggaaacggtccaggctatgtgctcaaggacggc gcccggccggatgttaccgagagcgagagcgggagccccgagtatcggcagcagtcagcagtgcccctg gacgaagagacccacgcaggcgaggacgtggcggtgttcgcgcgcgggcccgcaggcgcacctggttcac ggcgtgcaggagcagaccttcatagcgcacgtcatggccttcgccgcctgcctggagccctacaccgcc tgcgacctggcgcccccgccggcaccaccgacgccgcgcacccggggcggataggcacctattggtct tactgacatccactttgcctttctctccacaggcgtacctgcatatgccccagaaaacctccagcagc tggtgctttcagcagagagggaggctgcacagggcttcctgacactcatgctgcaggggaagctgcagg ggaagctgcaggtaccaccatccgaggagcaggccctgggtcgcctgacagccctgctgctccagcggt acccacgcctcacctcccagctcttcattgacctgtcaccactcatccctttcttggctgtctctgacc tgatgcgcttcccaccatccctgttagccaacgacagtgtcctggctgccatccgggattacagcccag gaatgaggcctgaacagaaggaggctctggcaaagcgactgctggcccctgaactgtttggggaagtgc ctgcctggccccaggagctgctgtgggcagtgctgcccctgctccccacctccctctggagaacttt tgcagctcagccctcaccagatccaggccctggaggatagctggccagcagcaggtctggggccaggc atgcccgccatgtgctgcgcagcctggtaaaccagagtgtccaggatggtgaggagcaggtacgcaggc ttgggcccctcgcctgtttcctgagccctgaggagctgcagagcctagtgcccctgagtgatccaacgg ggccagtagaacggggcgctgctggaatgtgcagccaatgggaccctcagcccagaaggacgggtggcat atgaacttctgggtgtgttgcgctcatctggaggagcggtgctgagccccgggagctgcgggtctggg -continued

```
cccctctcttctctcagctgggcctccgcttccttcaggagctgtcagagcccagcttagagccatgc ttcctgtcctccagggaactagtgttacacctgctcaggctgtcctgctgcttggacggctccttccta ggcacgatctatccctggaggaactctgctccttgcaccttctgctaccaggcctcagccccagacac tccaggccatccctaggcgagtcctggtcggggcttgttcctgcctggcccctgaactgtcacgcctct cagcctgccagaccgcagcactgctgcagacctttcgggttaaagatggtgttaaaaatatgggtacaa caggtgctggtccagctgtgtgtatccctggtcagcctattccaccacctggccagactgcctgcttc ccctgctcccattaaagctgctacaactggattccttggctcttctggcaaatcgaagacgctactggg agctgccctggtctgagcagcaggcacagtttctctggaagaagatgcaagtacccaccaaccttaccc tcaggaatctgcaggctctgggcaccctggcaggaggcatgtcctgtgagtttctgcagcagatcaact ccatggtagacttccttgaagtggtgcacatgatctatcagctgcccactagagttcgagggagcctga gggcctgtatctgggcagagctacagcggaggatggcaatgccagaaccagaatggcaactgtagggc cagaactgaacgggctggatagcaagctactcctggacttaccgatccagttgatggacagactatcca atgaatccattatgttggtggtggagctggtgcaaagagctccagagcagctgctggcactgaccccccc tccaccaggcagccctggcagagagggcactacaaaacctggctccaaaggagactccagtctcagggg aagtgctggagaccttaggccctttggttggattcctggggacagagagcacacgacagatcccctac agatcctgctgtcccatctcagtcagctgcaaggcttctgcctaggagagacatttgccacagagctgg gatggctgctattgcaggagtctgttcttgggaaaccagagttgtggagccaggatgaagtagagcaag ctggacgcctagtattcactctgtctactgaggcaatttccttgatcccagggaggccttgggtccag agaccctggagcggcttctagaaaagcagcagagctgggagcagagcagagttggacagctgtgtaggg agccacagcttgctgccaagaaagcagccctggtagcaggggtggtgcgaccagctgctgaggatcttc cagaacctgtgccaaattgtgcagatgtacgagggacattcccagcagcctggtctgcaacccagattg cagagatggagctctcagactttgaggactgcctgacattatttgcaggagacccaggacttgggcctg aggaactgcgggcagccatgggcaaagcaaaacagttgtggggtcccccccggggatttcgtcctgagc agatcctgcagcttggtaggctcttaataggtctaggagatcgggaactacaggagctgatcctagtgg actggggagtgctgagcaccctggggcagatagatggctggagcaccactcagctccgcattgtggtct ccagtttcctacggcagagtggtcggcatgtgagccacctggacttcgttcatctgacagcgctgggtt atactctctgtggactgcggccagaggagctccagcacatcagcagttgggagttcagccaagcagctc tcttcctcggcaccctgcatctccagtgctctgaggaacaactggaggttctggcccacctacttgtac tgcctggtgggtttggcccaatcagtaactgggggcctgagatcttcactgaaattggcaccatagcag ctgggatcccagacctggctctttcagcactgctgcggggacagatccagggcgttactcctcttgcca tttctgtcatccctcctcctaaatttgctgtggtgtttagtcccatccaactatctagtctcaccagtg ctcaggctgtggctgtcactcctgagcaaatggcctttctgagtcctgagcagcgacgagcagttgcat gggcccaacatgagggaaaggagagcccagaacagcaaggtcgaagtacagcctggggcctccaggact ggtcacgaccttcctggtccctggtattgactatcagcttccttggccacctgctatgagcctgtctct acagtagaaggagattgtggggagagaaatcttaagtcataatgaataaagtgcaaacagaagtgcatc ctgattattttcagaagctgatgaggaataactagtgctgatcagcctcgactgtgccttctagttgcc agccatctgttgtttgcccctcccccgtgccttccttgaccctggaaggtgccactcccactgtcctttt cctaataaaatgaggaaattgcatcgcattgtctgagtaggtgtcattctattctggggggtggggtgg ggcaggacagcaaggggaggattgggaagacaatagcaggcatgctggggatgcggtgggctctatgg
```

-continued aagcttgaattcagctgacgtgcctcggaccgctaggaaccccta gtgatggagttggccactccctct ctgcgcgctcgctcgctcactgaggccgggcgaccaaaggtcgcccgacgcccgggctttgcccgggcg gcctcagtgagcgagcgagcgcgcagctgcctgcagg pITR-205

(SEQ ID NO: 17)

cctgcaggcagctgcgcgctcgctcgctcactgaggccgccgggcgtcgggcgacctttggtcgcccg gcctcagtgagcgagcgagcgcgcagagagggagtggccaactccatcactaggggttcctgcggccgc acgcgtgacattgattattgactagttattaatagtaatcaattacggggtcattagttcatagcccat atatggagttccgcgttacataacttacggtaaatggcccgcctggctgaccgcccaacgacccccgcc cattgacgtcaataatgacgtatgttcccatagtaacgccaatagggactttccattgacgtcaatggg tggactatttacggtaaactgcccacttggcagtacatcaagtgtatcatatgccaagtacgccccctat tgacgtcaatgacggtaaatggcccgcctggcattatgcccagtacatgaccttatgggactttccta cttggcagtacatctacgtattagtcatcgctattaccatgg tcgaggtgagccccacgttctgcttc actctccccatctcccccccctccccaccccaattttgtatttatttattttttaattattttgtgca gcgatggggcggggggggggggcgcgcgccaggcggggcggggcggggcgaggggcggggcgggggc gaggcggagaggtgcggcggcagccaatcagagcggcgcgctccgaaagtttccttttatggcgaggcg gcggcggcggcggccctataaaaagcgaagcgcgcggcgggcgggagtcgctgcgttgccttcgccccg tgccccgctccgcgccgcctcgcgccgcccgccccggctctgactgaccgcgttactcccacaggtgag cgggcgggacggcccttctcctccgggctgtaattagcgcttggtttaatgacggctcgtttcttttct gtggctgcgtgaaagccttaaagggctccgggagggccctttgtgcggggggagcggctcgggggtg cgtgcgtgtgtgtgcgtggggagcgccgcgtgcggcccgcgctgcccggcggctgtgagcgctgcgg gcgcggcgcggggctttgtgcgctccgcgtgtgcgcgaggggagcgcggccggggcggtgccccgcgg tgcgggggggctgcgaggggaacaaaggctgcgtgcggggtgtgtgcgtggggggtgagcaggggtg tgggcgcggcggtcgggctgtaacccccccctgcaccccctccccgagttgctgagcacggcccggct tcgggtgcggggctccgtgcggggcgtggcgcggggctcgccgtgccgggcgggggtggcggcaggtg ggggtgccgggcggggcggggccgcctcgggccgggagggctcggggagggcgcggcggccccgg agcgccggcggctgtcgaggcgcggcgagccgcagccattgccttttatggtaatcgtgcgagagggcg cagggacttcctttgtcccaaatctgtgcggagccgaaatctgggaggcgccgccgcaccccctctagc gggcgcggggcgaagcggtgcggcgccggcaggaaggaaatgggcggggagggccttcgtgcgtcgccg cgccgccgtcccctctccctctccagcctcggggctgtccgcgggggacggctgccttcgggggga cggggcagggcggggttcggcttctggcgtgtgaccggcggctctagagcctctgctaaccatgttcat gccttcttcttttcctacagctcctgggcaacgtgctggttattgtgaccggtggtgccctgccctca cctggctatcccacacaggtgagaataaccagaactcacctccggtaccagtgttcacttggccaccat ggctctcagcctctggcccctgctgctgctgctgctgctgctgctgtccttt gcagtgactct ggcccctactgggcctcattccctggaccctggtctctccttcctgaagtcattgctctccactctgga ccaggctccccaggctccctgagccgctcacggttctttacattcctggccaacatttcttcttcctt tgagcctgggagaatgggggaaggaccagtaggagagcccccacctctccagccgcctgctctgcggct ccatgattttctagtgacactgagaggtagccccgactgggagccaatgctagggctgctaggggatat gctggcactgctgggacaggagcagactccccgagatttcctggtgcaccaggcaggggctgggtgg acttgtggaggtgctgctgggagccttagttcctgggggccccctaccccaactcggcccccatgcac ccgtgatgggccgtctgactgtgtcctggctgctgactggttgccttctctgctgctgttgttagaggg cacacgctggcaagctctggtgcaggtgcagcccagtgtggaccccaccaatgccacaggcctcgatgg -continued

```
gagggaggcagctcctcacttttttgcagggtctgttgggtttgcttaccccaacaggggagctaggctc caaggaggctctttggggcggtctgctacgcacagtgggggccccctctatgctgcctttcaggaggg gctgctccgtgtcactcactccttgcaggatgaggtcttctccattttggggcagccagagcctgatac caatgggcagtgccagggaggtaaccttcaacagctgctcttatgggcgtccggcacaaccttttcctg ggatgtccaggcgctgggctttctgtctggatcaccaccccacccctgccctccttcactgcctgag cacgggcgtgcctctgcccagagcttctcagccgtcagcccacatcagcccacgccaacggcgagccat cactgtggaggccctctgtgagaaccacttaggcccagcaccaccctacagcatttccaacttctccat ccacttgctctgccagcacaccaagcctgccactccacagcccatcccagcaccactgccatctgcca gacagctgtgtggtatgcagtgtcctgggcaccaggtgcccaaggctggctacaggcctgccacgacca gtttcctgatgagtttttggatgcgatctgcagtaacctctccttttcagccctgtctggctccaaccg ccgcctggtgaagcggctctgtgctggcctgctccaccccctaccagctgccctgaaggcctgccccc tgttcccctcaccccagacatcttttggggctgcttcttggagaatgagactctgtgggctgagcgact gtgtggggaggcaagtctacaggctgtgcccccagcaaccaggcttgggtccagcatgtgtgccaggg ccccacccagatgtcactgcctcccaccatgccacattggaccctgtggggaacgctgcccggatgg gggcagcttcctggtgatggtctgtgccaatgacaccatgtatgaggtcctggtgcccttctggccttg gctagcaggccaatgcaggataagtcgtgggggcaatgacacttgcttcctagaagggctgctgggccc ccttctgccctctctgccaccactgggaccatccccactctgtctgaccctggcccttcctccttgg catgctatcccagttgccacgctgtcagtcctctgtcccagctcttgctcacccacacgcctacacta tctcctccgcctgctgaccttcctcttgggtccagggctggggcgctgaggcccaggggatgctggg tcgggccctactgctctccagtctcccagacaactgctccttctgggatgcctttcgcccagagggccg gcgcagtgtgctacggacgattggggaatacctggaacaagatgaggagcagccaacccatcaggctt tgaacccactgtcaacccagctctggtataagcaagatggagctgctggcctgctttagtcctgtgct gtgggatctgctccagagggaaaagagtgtttgggccctgcagattctagtgcaggtaagtatcaaggt tacaagacaggtttaaggagaccaatagaaactgggcttgtcgagacagagaagactcttgcgtttctg ggattttgccgatttcggcctattggttaaaaaatgagctgatttaacaaaaatttaacgcgaatttta acaaaataagcttgaattcagctgacgtgcctcggaccgctaggaaccccctagtgatggagttggccac tccctctctgcgcgctcgctcgctcactgaggccgggcgaccaaaggtcgcccgacgcccgggctttgc ccgggcggcctcagtgagcgagcgagcgcgcagctgcctgcagg
```

In some embodiments, the vector(s) is an adenovirus (see, e.g., Dmitriev et al. (1998) *J. Virol.* 72:9706-9713; and Poulin et al., *J. Virol* 8:10074-10086, 2010). In some embodiments, the vector(s) is a retrovirus (see, e.g., Maier et al. (2010) *Future Microbiol* 5:1507-23).

In some embodiments, the vector(s) is a lentivirus (see, e.g., Matrai et al. (2010) *Mol Ther.* 18:477-490; Banasik et al. (2010) *Gene Ther.* 17:150-7; and Wanisch et al. (2009) *Mol. Ther.* 17:1316-32). A lentiviral vector refers to a vector derived from at least a portion of a lentivirus genome, including especially a self-inactivating lentiviral vector as provided in Milone et al., *Mol. Ther.* 17 (8): 1453-1464 (2009). Non-limiting lentivirus vectors that may be used in the clinic include the LENTIVECTOR® gene delivery technology from Oxford BioMedica, the LENTIMAX™ vector system from Lentigen, and the like. Other types of lentiviral vectors are also available and would be known to one skilled in the art.

The vectors provided herein can be of different sizes. The choice of vector that is used in any of the compositions, kits, and methods described herein may depend on the size of the vector.

In some embodiments, the vector(s) is a plasmid and can include a total length of up to about 1 kb, up to about 2 kb, up to about 3 kb, up to about 4 kb, up to about 5 kb, up to about 6 kb, up to about 7 kb, up to about 8 kb, up to about 9 kb, up to about 10 kb, up to about 11 kb, up to about 12 kb, up to about 13 kb, up to about 14 kb, or up to about 15 kb. In some embodiments, the vector(s) is a plasmid and can have a total length in a range of about 1 kb to about 2 kb, about 1 kb to about 3 kb, about 1 kb to about 4 kb, about 1 kb to about 5 kb, about 1 kb to about 6 kb, about 1 kb to about 7 kb, about 1 kb to about 8 kb, about 1 kb to about 9 kb, about 1 kb to about 10 kb, about 1 kb to about 11 kb, about 1 kb to about 12 kb, about 1 kb to about 13 kb, about 1 kb to about 14 kb, or about 1 kb to about 15 kb.

In some embodiments, the vector(s) is a transposon (e.g., PiggyBac transposon) and can include greater than 200 kb.

In some examples, the vector(s) is a transposon having a total length in the range of about 1 kb to about 10 kb, about 1 kb to about 20 kb, about 1 kb to about 30 kb, about 1 kb to about 40 kb, about 1 kb to about 50 kb, about 1 kb to about 60 kb, about 1 kb to about 70 kb, about 1 kb to about 80 kb, about 1 kb to about 90 kb, about 10 kb to about 20 kb, about 10 kb to about 30 kb, about 10 kb to about 40 kb, about 10 kb to about 50 kb, about 10 kb to about 60 kb, about 10 kb to about 70 kb, about 10 kb to about 90 kb, about 10 kb to about 100 kb, about 20 kb to about 30 kb, about 20 kb to about 40 kb, about 20 kb to about 50 kb, about 20 kb to about 60 kb, about 20 kb to about 70 kb, about 20 kb to about 80 kb, about 20 kb to about 90 kb, about 20 kb to about 100 kb, about 30 kb to about 40 kb, about 30 kb to about 50 kb, about 30 kb to about 60 kb, about 30 kb to about 70 kb, about 30 kb to about 80 kb, about 30 kb to about 90 kb, about 30 kb to about 100 kb, about 40 kb to about 50 kb, about 40 kb to about 60 kb, about 40 kb to about 70 kb, about 40 kb to about 80 kb, about 40 kb to about 90 kb, about 40 kb to about 100 kb, about 50 kb to about 60 kb, about 50 kb to about 70 kb, about 50 kb to about 80 kb, about 50 kb to about 90 kb, about 50 kb to about 100 kb, about 60 kb to about 70 kb, about 60 kb to about 80 kb, about 60 kb to about 90 kb, about 60 kb to about 100 kb, about 70 kb to about 80 kb, about 70 kb to about 90 kb, about 70 kb to about 100 kb, about 80 kb to about 90 kb, about 80 kb to about 100 kb, about 90 kb to about 100 kb, about 1 kb to about 100 kb, about 100 kb to about 200 kb, about 100 kb to about 300 kb, about 100 kb to about 400 kb, or about 100 kb to about 500 kb.

In some embodiments, the vector is a cosmid and can have a total length of up to 55 kb. In some examples, the vector is a cosmid and has a total number of nucleotides of about 1 kb to about 10 kb, about 1 kb to about 20 kb, about 1 kb to about 30 kb, about 1 kb to about 40 kb, about 1 kb to about 50 kb, about 1 kb to about 55 kb, about 10 kb to about 20 kb, about 10 kb to about 30 kb, about 10 kb to about 40 kb, about 10 kb to about 50 kb, about 10 kb to about 55 kb, about 15 kb to about 55 kb, about 15 kb to about 50 kb, about 15 kb to about 40 kb, about 15 kb to about 30 kb, about 15 kb to about 20 kb, about 20 kb to about 55 kb, about 20 kb to about 50 kb, about 20 kb to about 40 kb, about 20 kb to about 30 kb, about 25 kb to about 55 kb, about 25 kb to about 50 kb, about 25 kb to about 40 kb, about 25 kb to about 30 kb, about 30 kb to about 55 kb, about 30 kb to about 50 kb, about 30 kb to about 40 kb, about 35 kb to about 55 kb, about 40 kb to about 55 kb, about 40 kb to about 50 kb, or about 45 kb to about 55 kb.

In some embodiments, the vector(s) is an artificial chromosome and can have a total number of nucleotides of about 100 kb to about 2000 kb. In some embodiments, the artificial chromosome(s) is a human artificial chromosome (HAC) and can have a total number of nucleotides in the range of about 1 kb to about 10 kb, 1 kb to about 20 kb, about 1 kb to about 30 kb, about 1 kb to about 40 kb, about 1 kb to about 50 kb, about 1 kb to about 60 kb, about 10 kb to about 20 kb, about 10 kb to about 30 kb, about 10 kb to about 40 kb, about 10 kb to about 50 kb, about 10 kb to about 60 kb, about 20 kb to about 30 kb, about 20 kb to about 40 kb, about 20 kb to about 50 kb, about 20 kb to about 60 kb, about 30 kb to about 40 kb, about 30 kb to about 50 kb, about 30 kb to about 60 kb, about 40 kb to about 50 kb, about 40 kb to about 60 kb, or about 50 kb to about 60 kb.

In some embodiments, the artificial chromosome(s) is a yeast artificial chromosome (YAC) and can have a total number of nucleotides up to 1000 kb. In some embodiments, the artificial chromosome(s) is a YAC having a total number of nucleotides in the range of about 100 kb to about 1,000 kb, about 100 kb to about 900 kb, about 100 kb to about 800 kb, about 100 kb to about 700 kb, about 100 kb to about 600 kb, about 100 kb to about 500 kb, about 100 kb to about 400 kb, about 100 kb to about 300 kb, about 100 kb to about 200 kb, about 200 kb to about 1,000 kb, about 200 kb to about 900 kb, about 200 kb to about 800 kb, about 200 kb to about 700 kb, about 200 kb to about 600 kb, about 200 kb to about 500 kb, about 200 kb to about 400 kb, about 200 kb to about 300 kb, about 300 kb to about 1,000 kb, about 300 kb to about 900 kb, about 300 kb to about 800 kb, about 300 kb to about 700 kb, about 300 kb to about 600 kb, about 300 kb to about 500 kb, about 300 kb to about 400 kb, about 400 kb to about 1,000 kb, about 400 kb to about 900 kb, about 400 kb to about 800 kb, about 400 kb to about 700 kb, about 400 kb to about 600 kb, about 400 kb to about 500 kb, about 500 kb to about 1,000 kb, about 500 kb to about 900 kb, about 500 kb to about 800 kb, about 500 kb to about 700 kb, about 500 kb to about 600 kb, about 600 kb to about 1,000 kb, about 600 kb to about 900 kb, about 600 kb to about 800 kb, about 600 kb to about 700 kb, about 700 kb to about 1,000 kb, about 700 kb to about 900 kb, about 700 kb to about 800 kb, about 800 kb to about 1,000 kb, about 800 kb to about 900 kb, or about 900 kb to about 1,000 kb.

In some embodiments, the artificial chromosome(s) is a bacterial artificial chromosome (BAC) and can have a total number of nucleotides of up to 750 kb. In some embodiments, the artificial chromosome(s) is a BAC and can have a total number of nucleotides in the range of about 100 kb to about 750 kb, about 100 kb to about 700 kb, about 100 kb to about 600 kb, about 100 kb to about 500 kb, about 100 kb to about 400 kb, about 100 kb to about 300 kb, about 100 kb to about 200 kb, about 150 kb to about 750 kb, about 150 kb to about 700 kb, about 150 kb to about 600 kb, about 150 kb to about 500 kb, about 150 kb to about 400 kb, about 150 kb to about 300 kb, about 150 kb to about 200 kb, about 200 kb to about 750 kb, about 200 kb to about 700 kb, about 200 kb to about 600 kb, about 200 kb to about 500 kb, about 200 kb to about 400 kb, about 200 kb to about 300 kb, about 250 kb to about 750 kb, about 250 kb to about 700 kb, about 250 kb to about 600 kb, about 250 kb to about 500 kb, about 250 kb to about 400 kb, about 250 kb to about 300 kb, about 300 kb to about 750 kb, about 300 kb to about 700 kb, about 300 kb to about 600 kb, about 300 kb to about 500 kb, about 300 kb to about 400 kb, about 350 kb to about 750 kb, about 350 kb to about 700 kb, about 350 kb to about 600 kb, about 350 kb to about 500 kb, about 350 kb to about 400 kb, about 400 kb to about 750 kb, about 400 kb to about 700 kb, about 450 kb to about 600 kb, about 450 kb to about 500 kb, about 500 kb to about 750 kb, about 500 kb to about 700 kb, about 500 kb to about 600 kb, about 550 kb to about 750 kb, about 550 kb to about 700 kb, about 550 kb to about 600 kb, about 600 kb to about 750 kb, about 600 kb to about 700 kb, or about 650 kb to about 750 kb.

In some embodiments, the artificial chromosome(s) is a P1-derived artificial chromosome (PAC) and can have a total number of nucleotides of up to 300 kb. In some embodiments, the P1-derived artificial chromosome(s) can have a total number of nucleotides in the range of about 100 kb to about 300 kb, about 100 kb to about 200 kb, or about 200 kb to about 300 kb.

In some embodiments, the vector(s) is a viral vector and can have a total number of nucleotides of up to 10 kb. In some embodiments, the viral vector(s) can have a total number of nucleotides in the range of about 1 kb to about 2 kb, 1 kb to about 3 kb, about 1 kb to about 4 kb, about 1 kb to about 5 kb, about 1 kb to about 6 kb, about 1 kb to about 7 kb, about 1 kb to about 8 kb, about 1 kb to about 9 kb, about 1 kb to about 10 kb, about 2 kb to about 3 kb, about 2 kb to about 4 kb, about 2 kb to about 5 kb, about 2 kb to about 6 kb, about 2 kb to about 7 kb, about 2 kb to about 8 kb, about 2 kb to about 9 kb, about 2 kb to about 10 kb, about 3 kb to about 4 kb, about 3 kb to about 5 kb, about 3 kb to about 6 kb, about 3 kb to about 7 kb, about 3 kb to about 8 kb, about 3 kb to about 9 kb, about 3 kb to about 10 kb, about 4 kb to about 5 kb, about 4 kb to about 6 kb, about 4 kb to about 7 kb, about 4 kb to about 8 kb, about 4 kb to about 9 kb, about 4 kb to about 10 kb, about 5 kb to about 6 kb, about 5 kb to about 7 kb, about 5 kb to about 8 kb, about 5 kb to about 9 kb, about 5 kb to about 10 kb, about 6 kb to about 7 kb, about 6 kb to about 8 kb, about 6 kb to about 9 kb, about 6 kb to about 10 kb, about 7 kb to about 8 kb, about 7 kb to about 9 kb, about 7 kb to about 10 kb, about 8 kb to about 9 kb, about 8 kb to about 10 kb, or about 9 kb to about 10 kb.

In some embodiments, the vector(s) is a lentivirus and can have a total number of nucleotides of up to 8 kb. In some examples, the lentivirus(es) can have a total number of nucleotides of about 1 kb to about 2 kb, about 1 kb to about 3 kb, about 1 kb to about 4 kb, about 1 kb to about 5 kb, about 1 kb to about 6 kb, about 1 kb to about 7 kb, about 1 kb to about 8 kb, about 2 kb to about 3 kb, about 2 kb to about 4 kb, about 2 kb to about 5 kb, about 2 kb to about 6 kb, about 2 kb to about 7 kb, about 2 kb to about 8 kb, about 3 kb to about 4 kb, about 3 kb to about 5 kb, about 3 kb to about 6 kb, about 3 kb to about 7 kb, about 3 kb to about 8 kb, about 4 kb to about 5 kb, about 4 kb to about 6 kb, about 4 kb to about 7 kb, about 4 kb to about 8 kb, about 5 kb to about 6 kb, about 5 kb to about 7 kb, about 5 kb to about 8 kb, about 6 kb to about 8 kb, about 6 kb to about 7 kb, or about 7 kb to about 8 kb.

In some embodiments, the vector(s) is an adenovirus and can have a total number of nucleotides of up to 8 kb. In some embodiments, the adenovirus(es) can have a total number of nucleotides in the range of about 1 kb to about 2 kb, about 1 kb to about 3 kb, about 1 kb to about 4 kb, about 1 kb to about 5 kb, about 1 kb to about 6 kb, about 1 kb to about 7 kb, about 1 kb to about 8 kb, about 2 kb to about 3 kb, about 2 kb to about 4 kb, about 2 kb to about 5 kb, about 2 kb to about 6 kb, about 2 kb to about 7 kb, about 2 kb to about 8 kb, about 3 kb to about 4 kb, about 3 kb to about 5 kb, about 3 kb to about 6 kb, about 3 kb to about 7 kb, about 3 kb to about 8 kb, about 4 kb to about 5 kb, about 4 kb to about 6 kb, about 4 kb to about 7 kb, about 4 kb to about 8 kb, about 5 kb to about 6 kb, about 5 kb to about 7 kb, about 5 kb to about 8 kb, about 6 kb to about 7 kh, about 6 kb to about 8 kb, or about 7 kb to about 8 kb.

In some embodiments, the vector(s) is an adeno-associated virus (AAV vector) and can include a total number of nucleotides of up to 5 kb. In some embodiments, the AAV vector(s) can include a total number of nucleotides in the range of about 1 kb to about 2 kb, about 1 kb to about 3 kb, about 1 kb to about 4 kb, about 1 kb to about 5 kb, about 2 kb to about 3 kb, about 2 kb to about 4 kb, about 2 kb to about 5 kb, about 3 kb to about 4 kb, about 3 kb to about 5 kb, or about 4 kb to about 5 kb.

In some embodiments, the vector(s) is a Gateway® vector and can include a total number of nucleotides of up to 5 kb. In some embodiments, each Gateway® vector(s) includes a total number of nucleotides in the range of about 1 kb to about 2 kb, about 1 kb to about 3 kb, about 1 kb to about 4 kb, about 1 kb to about 5 kb, about 2 kb to about 3 kb, about 2 kb to about 4 kb, about 2 kb to about 5 kb, about 3 kb to about 4 kb, about 3 kb to about 5 kb, or about 4 kb to about 5 kb.

In some embodiments of any of the compositions, kits, and methods provided herein, the at least two different vectors can be substantially the same type of vector and may differ in size. In some embodiments, the at least two different vectors can be different types of vector, and may have substantially the same size or have different sizes.

In some embodiments, any of the at least two vectors can have a total number of nucleotides in the range of about 500 nucleotides to about 10,000 nucleotides, about 500 nucleotides to about 9,500 nucleotides, about 500 nucleotides to about 9,000 nucleotides, about 500 nucleotides to about 8,500 nucleotides, about 500 nucleotides to about 8,000 nucleotides, about 500 nucleotides to about 7,800 nucleotides, about 500 nucleotides to about 7,600 nucleotides, about 500 nucleotides to about 7,400 nucleotides, about 500 nucleotides to about 7,200 nucleotides, about 500 nucleotides to about 7,000 nucleotides, about 500 nucleotides to about 6,800 nucleotides, about 500 nucleotides to about 6,600 nucleotides, about 500 nucleotides to about 6,400 nucleotides, about 500 nucleotides to about 6,200 nucleotides, about 500 nucleotides to about 6,000 nucleotides, about 500 nucleotides to about 5,800 nucleotides, about 500 nucleotides to about 5,600 nucleotides, about 500 nucleotides to about 5,400 nucleotides, about 500 nucleotides to about 5,200 nucleotides, about 500 nucleotides to about 5,000 nucleotides, about 500 nucleotides to about 4,800 nucleotides, about 4,600 nucleotides, about 500 nucleotides to about 4,400 nucleotides, about 500 nucleotides to about 4,200 nucleotides, about 500 nucleotides to about 4,000 nucleotides, about 500 nucleotides to about 3,800 nucleotides, about 500 nucleotides to about 3,600 nucleotides, about 500 nucleotides to about 3,400 nucleotides, about 500 nucleotides to about 3,200 nucleotides, about 500 nucleotides to about 3,000 nucleotides, about 500 nucleotides to about 2,800 nucleotides, about 500 nucleotides to about 2,600 nucleotides, about 500 nucleotides to about 2,400 nucleotides, about 500 nucleotides to about 2,200 nucleotides, about 500 nucleotides to about 2,000 nucleotides, about 500 nucleotides to about 1,800 nucleotides, about 500 nucleotides to about 1,600 nucleotides, about 500 nucleotides to about 1,400 nucleotides, about 500 nucleotides to about 1,200 nucleotides, about 500 nucleotides to about 1,000 nucleotides, about 500 nucleotides to about 800 nucleotides, about 800 nucleotides to about 10,000 nucleotides, about 800 nucleotides to about 9,500 nucleotides, about 800 nucleotides to about 9,000 nucleotides, about 800 nucleotides to about 8,500 nucleotides, about 800 nucleotides to about 8,000 nucleotides, about 800 nucleotides to about 7,800 nucleotides, about 800 nucleotides to about 7,600 nucleotides, about 800 nucleotides to about 7,400 nucleotides, about 800 nucleotides to about 7,200 nucleotides, about 800 nucleotides to about 7,000 nucleotides, about 800 nucleotides to about 6,800 nucleotides, about 800 nucleotides to about 6,600 nucleotides, about 800 nucleotides to about 6,400 nucleotides, about 800 nucleotides to about 6,200 nucleotides, about 800 nucleotides to about 6,000 nucleotides, about 800 nucleotides to about 5,800 nucleotides, about 800 nucleotides to about 5,600 nucleotides, about 800 nucleotides to about 5,400 nucleotides, about 800 nucleotides to about 5,200 nucleotides, about 800 nucleotides to about 5,000 nucleotides, about 800 nucleotides to about 4,800 nucleotides, about 800 nucleotides to about 4,600 nucleotides, about 800 nucleotides to about 4,400 nucleotides, about 800 nucleotides to about 4,200 nucleotides, about 800 nucleotides to about 4,000 nucleotides, about 800 nucleotides to about 3,800 nucleotides, about 800 nucleotides to about 3,600 nucleotides, about 800 nucleotides to about 3,400 nucleotides, about 800 nucleotides to about 3,200 nucleotides, about 800 nucleotides to about 3,000 nucleotides, about 800 nucleotides to about 2,800 nucleotides, about 800 nucleotides to about 2,600 nucleotides, about 800 nucleotides to about 2,400 nucleotides, about 800 nucleotides to about 2,200 nucleotides, about 800 nucleotides to about 2,000 nucleotides, about 800 nucleotides to about 1,800 nucleotides, about 800 nucleotides to about 1,600 nucleotides, about 800 nucleotides to about 1,400 nucleotides, about 800 nucleotides to about 1,200 nucleotides, about 800 nucleotides to about 1,000 nucleotides, about 1,000 nucleotides to about 10,000 nucleotides, about 1,000 nucleotides to about 9,000 nucleotides, about 1,000 nucleotides to about 8,500 nucleotides, about 1,000 nucleotides to about 8,000 nucleotides, about 1,000 nucleotides to about 7,800 nucleotides, about 1,000 nucleotides to about 7,600 nucleotides, about 1,000 nucleotides to about 7,400 nucleotides, about 1,000 nucleotides to about 7,200 nucleotides, about 1,000 nucleotides to about 7,000 nucleotides, about 1,000 nucleotides to about 6,800 nucleotides, about 1,000 nucleotides to about 6,600 nucleotides, about 1,000 nucleotides to about 6,400 nucleotides, about 1,000 nucleotides to about 6,200 nucleotides, about 1,000 nucleotides to about 6,000 nucleotides, about 1,000 nucleotides to about 5,800 nucleotides, about 1,000 nucleotides to about 5,600 nucleotides, about 1,000 nucleotides to about 5,400 nucleotides, about 1,000 nucleotides to about 5,200 nucleotides, about 1,000 nucleotides to about 5,000 nucleotides, about 1,000 nucleotides to about 4,800 nucleotides, about 1,000 nucleotides to about 4,600 nucleotides, about 1,000 nucleotides to about 4,400 nucleotides, about 1,000 nucleotides to about 4,200 nucleotides, about 1,000 nucleotides to about 4,000 nucleotides, about 1,000 nucleotides to about 3,800 nucleotides, about 1,000 nucleotides to about 3,600 nucleotides, about 1,000 nucleotides to about 3,400 nucleotides, about 1,000 nucleotides to about 3,200 nucleotides, about 1,000 nucleotides to about 3,000 nucleotides, about 1,000 nucleotides to about 2,600 nucleotides, about 1,000 nucleotides to about 2,400 nucleotides, about 1,000 nucleotides to about 2,200 nucleotides, about 1,000 nucleotides to about 2,000 nucleotides, about 1,000 nucleotides to about 1,800 nucleotides, about 1,000 nucleotides to about 1,600 nucleotides, about 1,000 nucleotides to about 1,400 nucleotides, about 1,000 nucleotides to about 1,200 nucleotides, about 1,200 nucleotides to about 10,000 nucleotides, about 1,200 nucleotides to about 9,500 nucleotides, about 1,200 nucleotides to about 9,000 nucleotides, about 1,200 nucleotides to about 8,500 nucleotides, about 1,200 nucleotides to about 8,000 nucleotides, about 1,200 nucleotides to about 7,800 nucleotides, about 1,200 nucleotides to about 7,600 nucleotides, about 1,200 nucleotides to about 7,400 nucleotides, about 1,200 nucleotides to about 7,200 nucleotides, about 1,200 nucleotides to about 7,000 nucleotides, about 1,200 nucleotides to about 6,800 nucleotides, about 1,200 nucleotides to about 6,600 nucleotides, about 1,200 nucleotides to about 6,400 nucleotides, about 1,200 nucleotides to about 6,200 nucleotides, about 1,200 nucleotides to about 6,000 nucleotides, about 1,200 nucleotides to about 5,800 nucleotides, about 1,200 nucleotides to about 5,600 nucleotides, about 1,200 nucleotides to about 5,400 nucleotides, about 1,200 nucleotides to about 5,000 nucleotides, about 1,200 nucleotides to about 4,800 nucleotides, about 1,200 nucleotides to about 4,600 nucleotides, about 1,200 nucleotides to about 4,400 nucleotides, about 1,200 nucleotides to about 4,200 nucleotides, about 1,200 nucleotides to about 4,000 nucleotides, about 1,200 nucleotides to about 3,800 nucleotides, about 1,200 nucleotides to about 3,600 nucleotides, about 1,200 nucleotides to about 3,400 nucleotides, about 1,200 nucleotides to about 3,200 nucleotides, about 1,200 nucleotides to about 3,000 nucleotides, about 1,200 nucleotides to about 2,800 nucleotides, about 1,200 nucleotides to about 2,600 nucleotides, about 1,200 nucleotides to about 2,400 nucleotides, about 1,200 nucleotides to about 2,200 nucleotides, about 1,200 nucleotides to about 2,000 nucleotides, about 1,200 nucleotides to about 1,800 nucleotides, about 1,200 nucleotides to about 1,600 nucleotides, about 1,200 nucleotides to about 1,400 nucleotides, about 1,400 nucleotides to about 10,000 nucleotides, about 1,400 nucleotides to about 9,500 nucleotides, about 1,400 nucleotides to about 9,000 nucleotides, about 1,400 nucleotides to about 8,500 nucleotides, about 1,400 nucleotides to about 8,000 nucleotides, about 1,400 nucleotides to about 7,800 nucleotides, about 1,400 nucleotides to about 7,600 nucleotides, about 1,400 nucleotides to about 7,400 nucleotides, about 1,400 nucleotides to about 7,200 nucleotides, about 1,400 nucleotides to about 7,000 nucleotides, about 1,400 nucleotides to about 6,800 nucleotides, about 1,400 nucleotides to about 6,600 nucleotides, about 1,400 nucleotides to about 6,400 nucleotides, about 1,400 nucleotides to about 6,200 nucleotides, about 1,400 nucleotides to about 6,000 nucleotides, about 1,400 nucleotides to about 5,800 nucleotides, about 1,400 nucleotides to about 5,600 nucleotides, about 1,400 nucleotides to about 5,400 nucleotides, about 1,400 nucleotides to about 5,200 nucleotides, about 1,400 nucleotides to about 5,000 nucleotides, about 1,400 nucleotides to about 4,800 nucleotides, about 1,400 nucleotides to about 4,600 nucleotides, about 1,400 nucleotides to about 4,400 nucleotides, about 1,400 nucleotides to about 4,200 nucleotides, about 1,400 nucleotides to about 4,000 nucleotides, about 1,400 nucleotides to about 3,800 nucleotides, about 1,400 nucleotides to about 3,600 nucleotides, about 1,400 nucleotides to about 3,400 nucleotides, about 1,400 nucleotides to about 3,200 nucleotides, about 1,400 nucleotides to about 3,000 nucleotides, about 1,400 nucleotides to about 2,600 nucleotides, about 1,400 nucleotides to about 2,400 nucleotides, about 1,400 nucleotides to about 2,200 nucleotides, about 1,400 nucleotides to about 2,000 nucleotides, about 1,400 nucleotides to about 1,800 nucleotides, about 1,400 nucleotides to about 1,600 nucleotides, about 1,600 nucleotides to about 10,000 nucleotides, about 1,600 nucleotides to about 9,500 nucleotides, about 1,600 nucleotides to about 9,000 nucleotides, about 1,600 nucleotides to about 8,500 nucleotides, about 1,600 nucleotides to about 8,000 nucleotides, about 1,600 nucleotides to about 7,800 nucleotides, about 1,600 nucleotides to about 7,600 nucleotides, about 1,600 nucleotides to about 7,400 nucleotides, about 1,600 nucleotides to about 7,200 nucleotides, about 1,600 nucleotides to about 7,000 nucleotides, about 1,600 nucleotides to about 6,800 nucleotides, about 1,600 nucleotides to about 6,400 nucleotides, about 1,600 nucleotides to about 6,200 nucleotides, about 1,600 nucleotides to about 6,000 nucleotides, about 1,600 nucleotides to about 5,800 nucleotides, about 1,600 nucleotides to about 5,600 nucleotides, about 1,600 nucleotides to about 5,400 nucleotides, about 1,600 nucleotides to about 5,200 nucleotides, about 1,600 nucleotides to about 5,000 nucleotides, about 1,600 nucleotides to about 4,800 nucleotides, about 1,600 nucleotides to about 4,600 nucleotides, about 1,600 nucleotides to about 4,400 nucleotides, about 1,600 nucleotides to about 4,200 nucleotides, about 1,600 nucleotides to about 4,000 nucleotides, about 1,600 nucleotides to about 3,800 nucleotides, about 1,600 nucleotides to about 3,600 nucleotides, about 1,600 nucleotides to about 3,400 nucleotides, about 1,600 nucleotides to about 3,200 nucleotides, about 1,600 nucleotides to about 3,000 nucleotides, about 1,600 nucleotides to about 2,800 nucleotides, about 1,600 nucleotides to about 2,600 nucleotides, about 1,600 nucleotides to about 2,400 nucleotides, about 1,600 nucleotides to about 2,200 nucleotides, about 1,600 nucleotides to about 2,000 nucleotides, about 1,600 nucleotides to about 1,800 nucleotides, about 1,800 nucleotides to about 10,000 nucleotides, about 1,800 nucleotides to about 9,500 nucleotides, about 1,800 nucleotides to about 9,000 nucleotides, about 1,800 nucleotides to about 8,500 nucleotides, about 1,800 nucleotides to about 8,000 nucleotides, about 1,800 nucleotides to about 7,800 nucleotides, about 1,800 nucleotides to about 7,600 nucleotides, about 1,800 nucleotides to about 7,400 nucleotides, about 1,800 nucleotides to about 7,200 nucleotides, about 1,800 nucleotides to about 7,000 nucleotides, about 1,800 nucleotides to about 6,800 nucleotides, about 1,800 nucleotides to about 6,600 nucleotides, about 1,800 nucleotides to about 6,400 nucleotides, about 1,800 nucleotides to about 6,200 nucleotides, about 1,800 nucleotides to about 6,000 nucleotides, about 1,800 nucleotides to about 5,800 nucleotides, about 1,800 nucleotides to about 5,600 nucleotides, about 1,800 nucleotides to about 5,400 nucleotides, about 1,800 nucleotides to about 5,200 nucleotides, about 1,800 nucleotides to about 5,000 nucleotides, about 1,800 nucleotides to about 4,800 nucleotides, about 1,800 nucleotides to about 4,600 nucleotides, about 1,800 nucleotides to about 4,400 nucleotides, about 1,800 nucleotides to about 4,200 nucleotides, about 1,800 nucleotides to about 4,000 nucleotides, about 1,800 nucleotides to about 3,800 nucleotides, about 1,800 nucleotides to about 3,600 nucleotides, about 1,800 nucleotides to about 3,400 nucleotides, about 1,800 nucleotides to about 3,200 nucleotides, about 1,800 nucleotides to about 3,000 nucleotides, about 1,800 nucleotides to about 2,800 nucleotides, about 1,800 nucleotides to about 2,600 nucleotides, about 1,800 nucleotides to about 2,400 nucleotides, about 1,800 nucleotides to about 2,200 nucleotides, about 1,800 nucleotides to about 2,000 nucleotides, about 2,000 nucleotides to about 10,000 nucleotides, about 2,000 nucleotides to about 9,500 nucleotides, about 2,000 nucleotides to about 9,000 nucleotides, about 2,000 nucleotides to about 8,500 nucleotides, about 2,000 nucleotides to about 8,000 nucleotides, about 2,000 nucleotides to about 7,800 nucleotides, about 2,000 nucleotides to about 7,600 nucleotides, about 2,000 nucleotides to about 7,400 nucleotides, about 2,000 nucleotides to about 7,200 nucleotides, about 2,000 nucleotides to about 7,000 nucleotides, about 2,000 nucleotides to about 6,800 nucleotides, about 2,000 nucleotides to about 6,600 nucleotides, about 2,000 nucleotides to about 6,400 nucleotides, about 2,000 nucleotides to about 6,200 nucleotides, about 2,000 nucleotides to about 6,000 nucleotides, about 2,000 nucleotides to about 5,800 nucleotides, about 2,000 nucleotides to about 5,600 nucleotides, about 2,000 nucleotides to about 5,400 nucleotides, about 2,000 nucleotides to about 5,200 nucleotides, about 2,000 nucleotides to about 5,000 nucleotides, about 2,000 nucleotides to about 4,800 nucleotides, about 2,000 nucleotides to about 4,600 nucleotides, about 2,000 nucleotides to about 4,400 nucleotides, about 2,000 nucleotides to about 4,200 nucleotides, about 2,000 nucleotides to about 4,000 nucleotides, about 2,000 nucleotides to about 3,800 nucleotides, about 2,000 nucleotides to about 3,600 nucleotides, about 2,000 nucleotides to about 3,400 nucleotides, about 2,000 nucleotides to about 3,200 nucleotides, about 2,000 nucleotides to about 3,000 nucleotides, about 2,000 nucleotides to about 2,800 nucleotides, about 2,000 nucleotides to about 2,600 nucleotides, about 2,000 nucleotides to about 2,400 nucleotides, about 2,000 nucleotides to about 2,200 nucleotides, about 2,200 nucleotides to about 10,000 nucleotides, about 9,500 nucleotides, about 9,000 nucleotides, about 8,500 nucleotides, about 8,000 nucleotides, about 7,800 nucleotides, about 7,600 nucleotides, about 7,400 nucleotides, about 7,200 nucleotides, about 7,000 nucleotides, about 6,800 nucleotides, about 6,600 nucleotides, about 6,400 nucleotides, about 6,200 nucleotides, about 6,000 nucleotides, about 5,800 nucleotides, about 5,600 nucleotides, about 5,400 nucleotides, about 5,200 nucleotides, about 5,000 nucleotides, about 4,800 nucleotides, about 4,600 nucleotides, about 4,400 nucleotides, about 4,200 nucleotides, about 4,000 nucleotides, about 3,800 nucleotides, about 3,600 nucleotides, about 3,400 nucleotides, about 3,200 nucleotides, about 3,000 nucleotides, about 2,800 nucleotides, about 2,600 nucleotides, about 2,400 nucleotides, about 2,400 nucleotides to about 10,000 nucleotides, about 2,400 nucleotides to about 9,500 nucleotides, about 2,400 nucleotides to about 9,000 nucleotides, about 2,400 nucleotides to about 8,500 nucleotides, about 2,400 nucleotides to about 8,000 nucleotides, about 2,400 nucleotides to about 7,800 nucleotides, about 2,400 nucleotides to about 7,600 nucleotides, about 2,400 nucleotides to about 7,400 nucleotides, about 2,400 nucleotides to about 7,200 nucleotides, about 2,400 nucleotides to about 7,000 nucleotides, about 2,400 nucleotides to about 6,800 nucleotides, about 2,400 nucleotides to about 6,600 nucleotides, about 2,400 nucleotides to about 6,400 nucleotides, about 2,400 nucleotides to about 6,200 nucleotides, about 2,400 nucleotides to about 6,000 nucleotides, about 2,400 nucleotides to about 5,800 nucleotides, about 2,400 nucleotides to about 5,600 nucleotides, about 2,400 nucleotides to about 5,400 nucleotides, about 2,400 nucleotides to about 5,200 nucleotides, about 2,400 nucleotides to about 5,000 nucleotides, about 2,400 nucleotides to about 4,800 nucleotides, about 2,400 nucleotides to about 4,600 nucleotides, about 2,400 nucleotides to about 4,400 nucleotides, about 2,400 nucleotides to about 4,200 nucleotides, about 2,400 nucleotides to about 4,000 nucleotides, about 2,400 nucleotides to about 3,800 nucleotides, about 2,400 nucleotides to about 3,600 nucleotides, about 2,400 nucleotides to about 3,400 nucleotides, about 2,400 nucleotides to about 3,200 nucleotides, about 2,400 nucleotides to about 3,000 nucleotides, about 2,400 nucleotides to about 2,800 nucleotides, about 2,400 nucleotides to about 2,600 nucleotides, about 2,600 nucleotides to about 10,000 nucleotides, about 2,600 nucleotides to about 9,500 nucleotides, about 2,600 nucleotides to about 9,000 nucleotides, about 2,600 nucleotides to about 8,500 nucleotides, about 2,600 nucleotides to about 8,000 nucleotides, about 2,600 nucleotides to about 7,800 nucleotides, about 2,600 nucleotides to about 7,600 nucleotides, about 2,600 nucleotides to about 7,400 nucleotides, about 2,600 nucleotides to about 7,200 nucleotides, about 2,600 nucleotides to about 7,000 nucleotides, about 2,600 nucleotides to about 6,800 nucleotides, about 2,600 nucleotides to about 6,600 nucleotides, about 2,600 nucleotides to about 6,400 nucleotides, about 2,600 nucleotides to about 6,200 nucleotides, about 2,600 nucleotides to about 6,000 nucleotides, about 2,600 nucleotides to about 5,800 nucleotides, about 2,600 nucleotides to about 5,600 nucleotides, about 2,600 nucleotides to about 5,400 nucleotides, about 2,600 nucleotides to about 5,200 nucleotides, about 2,600 nucleotides to about 5,000 nucleotides, about 2,600 nucleotides to about 4,800 nucleotides, about 2,600 nucleotides to about 4,600 nucleotides, about 2,600 nucleotides to about 4,400 nucleotides, about 2,600 nucleotides to about 4,200 nucleotides, about 2,600 nucleotides to about 4,000 nucleotides, about 2,600 nucleotides to about 3,800 nucleotides, about 2,600 nucleotides to about 3,600 nucleotides, about 2,600 nucleotides to about 3,400 nucleotides, about 2,600 nucleotides to about 3,200 nucleotides, about 2,600 nucleotides to about 3,000 nucleotides, about 2,600 nucleotides to about 2,800 nucleotides, about 2,800 nucleotides to about 10,000 nucleotides, about 2,800 nucleotides to about 9,500 nucleotides, about 2,800 nucleotides to about 9,000 nucleotides, about 2,800 nucleotides to about 8,500 nucleotides, about 2,800 nucleotides to about 8,000 nucleotides, about 2,800 nucleotides to about 7,800 nucleotides, about 2,800 nucleotides to about 7,600 nucleotides, about 2,800 nucleotides to about 7,400 nucleotides, about 2,800 nucleotides to about 7,200 nucleotides, about 2,800 nucleotides to about 7,000 nucleotides, about 2,800 nucleotides to about 6,800 nucleotides, about 2,800 nucleotides to about 6,600 nucleotides, about 2,800 nucleotides to about 6,400 nucleotides, about 2,800 nucleotides to about 6,200 nucleotides, about 2,800 nucleotides to about 6,000 nucleotides, about 2,800 nucleotides to about 5,800 nucleotides, about 2,800 nucleotides to about 5,600 nucleotides, about 2,800 nucleotides to about 5,400 nucleotides, about 2,800 nucleotides to about 5,200 nucleotides, about 2,800 nucleotides to about 5,000 nucleotides, about 2,800 nucleotides to about 4,800 nucleotides, about 2,800 nucleotides to about 4,600 nucleotides, about 2,800 nucleotides to about 4,400 nucleotides, about 2,800 nucleotides to about 4,200 nucleotides, about 2,800 nucleotides to about 4,000 nucleotides, about 2,800 nucleotides to about 3,800 nucleotides, about 2,800 nucleotides to about 3,600 nucleotides, about 2,800 nucleotides to about 3,400 nucleotides, about 2,800 nucleotides to about 3,200 nucleotides, about 2,800 nucleotides to about 3,000 nucleotides, about 3,000 nucleotides to about 10,000 nucleotides, about 3,000 nucleotides to about 9,500 nucleotides, about 3,000 nucleotides to about 9,000 nucleotides, about 3,000 nucleotides to about 8,500 nucleotides, about 3,000 nucleotides to about 8,000 nucleotides, about 3,000 nucleotides to about 7,800 nucleotides, about 3,000 nucleotides to about 7,600 nucleotides, about 3,000 nucleotides to about 7,400 nucleotides, about 3,000 nucleotides to about 7,200 nucleotides, about 3,000 nucleotides to about 7,000 nucleotides, about 3,000 nucleotides to about 6,800 nucleotides, about 3,000 nucleotides to about 6,600 nucleotides, about 3,000 nucleotides to about 6,400 nucleotides, about 3,000 nucleotides to about 6,200 nucleotides, about 3,000 nucleotides to about 6,000 nucleotides, about 3,000 nucleotides to about 5,800 nucleotides, about 3,000 nucleotides to about 5,600 nucleotides, about 3,000 nucleotides to about 5,400 nucleotides, about 3,000 nucleotides to about 5,200 nucleotides, about 3,000 nucleotides to about 5,000 nucleotides, about 3,000 nucleotides to about 4,800 nucleotides, about 3,000 nucleotides to about 4,600 nucleotides, about 3,000 nucleotides to about 4,400 nucleotides, about 3,000 nucleotides to about 4,200 nucleotides, about 3,000 nucleotides to about 4,000 nucleotides, about 3,000 nucleotides to about 3,800 nucleotides, about 3,000 nucleotides to about 3,600 nucleotides, about 3,000 nucleotides to about 3,400 nucleotides, about 3,000 nucleotides to about 3,200 nucleotides, about 3,200 nucleotides to about 10,000 nucleotides, about 3,200 nucleotides to about 9,500 nucleotides, about 3,200 nucleotides to about 9,000 nucleotides, about 3,200 nucleotides to about 8,500 nucleotides, about 3,200 nucleotides to about 8,000 nucleotides, about 3,200 nucleotides to about 7,800 nucleotides, about 3,200 nucleotides to about 7,600 nucleotides, about 3,200 nucleotides to about 7,400 nucleotides, about 3,200 nucleotides to about 7,200 nucleotides, about 3,200 nucleotides to about 7,000 nucleotides, about 3,200 nucleotides to about 6,800 nucleotides, about 3,200 nucleotides to about 6,600 nucleotides, about 3,200 nucleotides to about 6,400 nucleotides, about 3,200 nucleotides to about 6,200 nucleotides, about 3,200 nucleotides to about 6,000 nucleotides, about 3,200 nucleotides to about 5,800 nucleotides, about 3,200 nucleotides to about 5,600 nucleotides, about 3,200 nucleotides to about 5,400 nucleotides, about 3,200 nucleotides to about 5,200 nucleotides, about 3,200 nucleotides to about 5,000 nucleotides, about 3,200 nucleotides to about 4,800 nucleotides, about 3,200 nucleotides to about 4,600 nucleotides, about 3,200 nucleotides to about 4,400 nucleotides, about 3,200 nucleotides to about 4,200 nucleotides, about 3,200 nucleotides to about 4,000 nucleotides, about 3,200 nucleotides to about 3,800 nucleotides, about 3,200 nucleotides to about 3,600 nucleotides, about 3,200 nucleotides to about 3,400 nucleotides, about 3,400 nucleotides to about 10,000 nucleotides, about 3,400 nucleotides to about 9,500 nucleotides, about 3,400 nucleotides to about 9,000 nucleotides, about 3,400 nucleotides to about 8,500 nucleotides, about 3,400 nucleotides to about 8,000 nucleotides, about 3,400 nucleotides to about 7,800 nucleotides, about 3,400 nucleotides to about 7,600 nucleotides, about 3,400 nucleotides to about 7,400 nucleotides, about 3,400 nucleotides to about 7,200 nucleotides, about 3,400 nucleotides to about 7,000 nucleotides, about 3,400 nucleotides to about 6,800 nucleotides, about 3,400 nucleotides to about 6,600 nucleotides, about 3,400 nucleotides to about 6,400 nucleotides, about 3,400 nucleotides to about 6,200 nucleotides, about 3,400 nucleotides to about 6,000 nucleotides, about 3,400 nucleotides to about 5,800 nucleotides, about 3,400 nucleotides to about 5,600 nucleotides, about 3,400 nucleotides to about 5,400 nucleotides, about 3,400 nucleotides to about 5,200 nucleotides, about 3,400 nucleotides to about 5,000 nucleotides, about 3,400 nucleotides to about 4,800 nucleotides, about 3,400 nucleotides to about 4,600 nucleotides, about 3,400 nucleotides to about 4,400 nucleotides, about 3,400 nucleotides to about 4,200 nucleotides, about 3,400 nucleotides to about 4,000 nucleotides, about 3,400 nucleotides to about 3,800 nucleotides, about 3,400 nucleotides to about 3,600 nucleotides, about 3,600 nucleotides to about 10,000 nucleotides, about 3,600 nucleotides to about 9,500 nucleotides, about 3,600 nucleotides to about 9,000 nucleotides, about 3,600 nucleotides to about 8,500 nucleotides, about 3,600 nucleotides to about 8,000 nucleotides, about 3,600 nucleotides to about 7,800 nucleotides, about 3,600 nucleotides to about 7,600 nucleotides, about 3,600 nucleotides to about 7,400 nucleotides, about 3,600 nucleotides to about 7,200 nucleotides, about 3,600 nucleotides to about 7,000 nucleotides, about 3,600 nucleotides to about 6,800 nucleotides, about 3,600 nucleotides to about 6,600 nucleotides, about 3,600 nucleotides to about 6,400 nucleotides, about 3,600 nucleotides to about 6,200 nucleotides, about 3,600 nucleotides to about 6,000 nucleotides, about 3,600 nucleotides to about 5,800 nucleotides, about 3,600 nucleotides to about 5,600 nucleotides, about 3,600 nucleotides to about 5,400 nucleotides, about 3,600 nucleotides to about 5,200 nucleotides, about 3,600 nucleotides to about 5,000 nucleotides, about 3,600 nucleotides to about 4,800 nucleotides, about 3,600 nucleotides to about 4,600 nucleotides, about 3,600 nucleotides to about 4,400 nucleotides, about 3,600 nucleotides to about 4,200 nucleotides, about 3,600 nucleotides to about 4,000 nucleotides, about 3,600 nucleotides to about 3,800 nucleotides, about 3,800 nucleotides to about 10,000 nucleotides, about 3,800 nucleotides to about 9,500 nucleotides, about 3,800 nucleotides to about 9,000 nucleotides, about 3,800 nucleotides to about 8,500 nucleotides, about 3,800 nucleotides to about 8,000 nucleotides, about 3,800 nucleotides to about 7,800 nucleotides, about 3,800 nucleotides to about 7,600 nucleotides, about 3,800 nucleotides to about 7,400 nucleotides, about 3,800 nucleotides to about 7,200 nucleotides, about 3,800 nucleotides to about 7,000 nucleotides, about 3,800 nucleotides to about 6,800 nucleotides, about 3,800 nucleotides to about 6,600 nucleotides, about 3,800 nucleotides to about 6,400 nucleotides, about 3,800 nucleotides to about 6,200 nucleotides, about 3,800 nucleotides to about 6,000 nucleotides, about 3,800 nucleotides to about 5,800 nucleotides, about 3,800 nucleotides to about 5,600 nucleotides, about 3,800 nucleotides to about 5,400 nucleotides, about 3,800 nucleotides to about 5,200 nucleotides, about 3,800 nucleotides to about 5,000 nucleotides, about 3,800 nucleotides to about 4,800 nucleotides, about 3,800 nucleotides to about 4,600 nucleotides, about 3,800 nucleotides to about 4,200 nucleotides, about 3,800 nucleotides to about 4,000 nucleotides, about 4,000 nucleotides to about 10,000 nucleotides, about 4,000 nucleotides to about 9,500 nucleotides, about 4,000 nucleotides to about 9,000 nucleotides, about 4,000 nucleotides to about 8,500 nucleotides, about 4,000 nucleotides to about 8,000 nucleotides, about 4,000 nucleotides to about 7,800 nucleotides, about 4,000 nucleotides to about 7,600 nucleotides, about 4,000 nucleotides to about 7,400 nucleotides, about 4,000 nucleotides to about 7,200 nucleotides, about 4,000 nucleotides to about 7,000 nucleotides, about 4,000 nucleotides to about 6,800 nucleotides, about 4,000 nucleotides to about 6,600 nucleotides, about 4,000 nucleotides to about 6,400 nucleotides, about 4,000 nucleotides to about 6,200 nucleotides, about 4,000 nucleotides to about 6,000 nucleotides, about 4,000 nucleotides to about 5,800 nucleotides, about 4,000 nucleotides to about 5,600 nucleotides, about 4,000 nucleotides to about 5,400 nucleotides, about 4,000 nucleotides to about 5,200 nucleotides, about 4,000 nucleotides to about 5,000 nucleotides, about 4,000 nucleotides to about 4,800 nucleotides, about 4,000 nucleotides to about 4,600 nucleotides, about 4,000 nucleotides to about 4,400 nucleotides, about 4,000 nucleotides to about 4,200 nucleotides, about 4,200 nucleotides to about 10,000 nucleotides, about 4,200 nucleotides to about 9,500 nucleotides, about 4,200 nucleotides to about 9,000 nucleotides, about 4,200 nucleotides to about 8,500 nucleotides, about 4,200 nucleotides to about 8,000 nucleotides, about 4,200 nucleotides to about 7,800 nucleotides, about 4,200 nucleotides to about 7,600 nucleotides, about 4,200 nucleotides to about 7,400 nucleotides, about 4,200 nucleotides to about 7,200 nucleotides, about 4,200 nucleotides to about 7,000 nucleotides, about 4,200 nucleotides to about 6,800 nucleotides, about 4,200 nucleotides to about 6,600 nucleotides, about 4,200 nucleotides to about 6,400 nucleotides, about 4,200 nucleotides to about 6,200 nucleotides, about 4,200 nucleotides to about 6,000 nucleotides, about 4,200 nucleotides to about 5,800 nucleotides, about 4,200 nucleotides to about 5,600 nucleotides, about 4,200 nucleotides to about 5,400 nucleotides, about 4,200 nucleotides to about 5,200 nucleotides, about 4,200 nucleotides to about 5,000 nucleotides, about 4,200 nucleotides to about 4,800 nucleotides, about 4,200 nucleotides to about 4,600 nucleotides, about 4,200 nucleotides to about 4,400 nucleotides, about 4,400 nucleotides to about 10,000 nucleotides, about 4,400 nucleotides to about 9,500 nucleotides, about 4,400 nucleotides to about 9,000 nucleotides, about 4,400 nucleotides to about 8,500 nucleotides, about 4,400 nucleotides to about 8,000 nucleotides, about 4,400 nucleotides to about 7,800 nucleotides, about 4,400 nucleotides to about 7,600 nucleotides, about 4,400 nucleotides to about 7,400 nucleotides, about 4,400 nucleotides to about 7,200 nucleotides, about 4,400 nucleotides to about 7,000 nucleotides, about 4,400 nucleotides to about 6,800 nucleotides, about 4,400 nucleotides to about 6,600 nucleotides, about 4,400 nucleotides to about 6,400 nucleotides, about 4,400 nucleotides to about 6,200 nucleotides, about 4,400 nucleotides to about 6,000 nucleotides, about 4,400 nucleotides to about 5,800 nucleotides, about 4,400 nucleotides to about 5,600 nucleotides, about 4,400 nucleotides to about 5,400 nucleotides, about 4,400 nucleotides to about 5,200 nucleotides, about 4,400 nucleotides to about 5,000 nucleotides, about 4,400 nucleotides to about 4,800 nucleotides, about 4,400 nucleotides to about 4,600 nucleotides, about 4,600 nucleotides to about 10,000 nucleotides, about 4,600 nucleotides to about 9,500 nucleotides, about 4,600 nucleotides to about 9,000 nucleotides, about 4,600 nucleotides to about 8,500 nucleotides, about 4,600 nucleotides to about 8,000 nucleotides, about 4,600 nucleotides to about 7,800 nucleotides, about 4,600 nucleotides to about 7,600 nucleotides, about 4,600 nucleotides to about 7,400 nucleotides, about 4,600 nucleotides to about 7,200 nucleotides, about 4,600 nucleotides to about 7,000 nucleotides, about 4,600 nucleotides to about 6,800 nucleotides, about 4,600 nucleotides to about 6,600 nucleotides, about 4,600 nucleotides to about 6,400 nucleotides, about 4,600 nucleotides to about 6,200 nucleotides, about 4,600 nucleotides to about 6,000 nucleotides, about 4,600 nucleotides to about 5,800 nucleotides, about 4,600 nucleotides to about 5,600 nucleotides, about 4,600 nucleotides to about 5,400 nucleotides, about 4,600 nucleotides to about 5,200 nucleotides, about 4,600 nucleotides to about 5,000 nucleotides, about 4,600 nucleotides to about 4,800 nucleotides, about 4,800 nucleotides to about 10,000 nucleotides, about 4,800 nucleotides to about 9,500 nucleotides, about 4,800 nucleotides to about 9,000 nucleotides, about 4,800 nucleotides to about 8,500 nucleotides, about 4,800 nucleotides to about 8,000 nucleotides, about 4,800 nucleotides to about 7,800 nucleotides, about 4,800 nucleotides to about 7,600 nucleotides, about 4,800 nucleotides to about 7,400 nucleotides, about 4,800 nucleotides to about 7,200 nucleotides, about 4,800 nucleotides to about 7,000 nucleotides, about 4,800 nucleotides to about 6,800 nucleotides, about 4,800 nucleotides to about 6,600 nucleotides, about 4,800 nucleotides to about 6,400 nucleotides, about 4,800 nucleotides to about 6,200 nucleotides, about 4,800 nucleotides to about 6,000 nucleotides, about 4,800 nucleotides to about 5,800 nucleotides, about 4,800 nucleotides to about 5,600 nucleotides, about 4,800 nucleotides to about 5,400 nucleotides, about 4,800 nucleotides to about 5,200 nucleotides, about 4,800 nucleotides to about 5,000 nucleotides, about 5,000 nucleotides to about 10,000 nucleotides, about 5,000 nucleotides to about 9,500 nucleotides, about 5,000 nucleotides to about 9,000 nucleotides, about 5,000 nucleotides to about 8,500 nucleotides, about 5,000 nucleotides to about 8,000 nucleotides, about 5,000 nucleotides to about 7,800 nucleotides, about 5,000 nucleotides to about 7,600 nucleotides, about 5,000 nucleotides to about 7,400 nucleotides, about 5,000 nucleotides to about 7,200 nucleotides, about 5,000 nucleotides to about 7,000 nucleotides, about 5,000 nucleotides to about 6,800 nucleotides, about 5,000 nucleotides to about 6,600 nucleotides, about 5,000 nucleotides to about 6,400 nucleotides, about 5,000 nucleotides to about 6,200 nucleotides, about 5,000 nucleotides to about 6,000 nucleotides, about 5,000 nucleotides to about 5,800 nucleotides, about 5,000 nucleotides to about 5,600 nucleotides, about 5,000 nucleotides to about 5,400 nucleotides, about 5,000 nucleotides to about 5,200 nucleotides, about 5,200 nucleotides to about 10,000 nucleotides, about 5,200 nucleotides to about 9,500 nucleotides, about 5,200 nucleotides to about 9,000 nucleotides, about 5,200 nucleotides to about 8,500 nucleotides, about 5,200 nucleotides to about 8,000 nucleotides, about 5,200 nucleotides to about 7,800 nucleotides, about 5,200 nucleotides to about 7,600 nucleotides, about 5,200 nucleotides to about 7,400 nucleotides, about 5,200 nucleotides to about 7,200 nucleotides, about 5,200 nucleotides to about 7,000 nucleotides, about 5,200 nucleotides to about 6,800 nucleotides, about 5,200 nucleotides to about 6,600 nucleotides, about 5,200 nucleotides to about 6,400 nucleotides, about 5,200 nucleotides to about 6,200 nucleotides, about 5,200 nucleotides to about 6,000 nucleotides, about 5,200 nucleotides to about 5,800 nucleotides, about 5,200 nucleotides to about 5,600 nucleotides, about 5,200 nucleotides to about 5,400 nucleotides, about 5,400 nucleotides to about 10,000 nucleotides, about 5,400 nucleotides to about 9,500 nucleotides, about 5,400 nucleotides to about 9,000 nucleotides, about 5,400 nucleotides to about 8,500 nucleotides, about 5,400 nucleotides to about 8,000 nucleotides, about 5,400 nucleotides to about 7,800 nucleotides, about 5,400 nucleotides to about 7,600 nucleotides, about 5,400 nucleotides to about 7,400 nucleotides, about 5,400 nucleotides to about 7,200 nucleotides, about 5,400 nucleotides to about 7,000 nucleotides, about 5,400 nucleotides to about 6,800 nucleotides, about 5,400 nucleotides to about 6,600 nucleotides, about 5,400 nucleotides to about 6,400 nucleotides, about 5,400 nucleotides to about 6,200 nucleotides, about 5,400 nucleotides to about 6,000 nucleotides, about 5,400 nucleotides to about 5,800 nucleotides, about 5,400 nucleotides to about 5,600 nucleotides, about 5,600 nucleotides to about 10,000 nucleotides, about 5,600 nucleotides to about 9,500 nucleotides, about 5,600 nucleotides to about 9,000 nucleotides, about 5,600 nucleotides to about 8,500 nucleotides, about 5,600 nucleotides to about 8,000 nucleotides, about 5,600 nucleotides to about 7,800 nucleotides, about 5,600 nucleotides to about 7,600 nucleotides, about 5,600 nucleotides to about 7,400 nucleotides, about 5,600 nucleotides to about 7,200 nucleotides, about 5,600 nucleotides to about 7,000 nucleotides, about 5,600 nucleotides to about 6,800 nucleotides, about 5,600 nucleotides to about 6,600 nucleotides, about 5,600 nucleotides to about 6,400 nucleotides, about 5,600 nucleotides to about 6,200 nucleotides, about 5,600 nucleotides to about 6,000 nucleotides, about 5,600 nucleotides to about 5,800 nucleotides, about 5,800 nucleotides to about 10,000 nucleotides, about 5,800 nucleotides to about 9,500 nucleotides, about 5,800 nucleotides to about 9,000 nucleotides, about 5,800 nucleotides to about 8,500 nucleotides, about 5,800 nucleotides to about 8,000 nucleotides, about 5,800 nucleotides to about 7,800 nucleotides, about 5,800 nucleotides to about 7,600 nucleotides, about 5,800 nucleotides to about 7,400 nucleotides, about 5,800 nucleotides to about 7,200 nucleotides, about 5,800 nucleotides to about 7,000 nucleotides, about 5,800 nucleotides to about 6,800 nucleotides, about 5,800 nucleotides to about 6,600 nucleotides, about 5,800 nucleotides to about 6,400 nucleotides, about 5,800 nucleotides to about 6,200 nucleotides, about 5,800 nucleotides to about 6,000 nucleotides, about 6,000 nucleotides to about 10,000 nucleotides, about 6,000 nucleotides to about 9,500 nucleotides, about 6,000 nucleotides to about 9,000 nucleotides, about 6,000 nucleotides to about 8,500 nucleotides, about 6,000 nucleotides to about 8,000 nucleotides, about 6,000 nucleotides to about 7,800 nucleotides, about 6,000 nucleotides to about 7,600 nucleotides, about 6,000 nucleotides to about 7,400 nucleotides, about 6,000 nucleotides to about 7,200 nucleotides, about 6,000 nucleotides to about 7,000 nucleotides, about 6,000 nucleotides to about 6,800 nucleotides, about 6,000 nucleotides to about 6,600 nucleotides, about 6,000 nucleotides to about 6,400 nucleotides, about 6,000 nucleotides to about 6,200 nucleotides, about 6,200 nucleotides to about 10,000 nucleotides, about 6,200 nucleotides to about 9,000 nucleotides, about 6,200 nucleotides to about 8,500 nucleotides, about 6,200 nucleotides to about 8,000 nucleotides, about 6,200 nucleotides to about 7,800 nucleotides, about 6,200 nucleotides to about 7,600 nucleotides, about 6,200 nucleotides to about 7,400 nucleotides, about 6,200 nucleotides to about 7,200 nucleotides, about 6,200 nucleotides to about 7,000 nucleotides, about 6,200 nucleotides to about 6,800 nucleotides, about 6,200 nucleotides to about 6,600 nucleotides, about 6,200 nucleotides to about 6,400 nucleotides, about 6,400 nucleotides to about 10,000 nucleotides, about 6,400 nucleotides to about 9,500 nucleotides, about 6,400 nucleotides to about 9,000 nucleotides, about 6,400 nucleotides to about 8,500 nucleotides, about 6,400 nucleotides to about 8,000 nucleotides, about 6,400 nucleotides to about 7,800 nucleotides, about 6,400 nucleotides to about 7,600 nucleotides, about 6,400 nucleotides to about 7,400 nucleotides, about 6,400 nucleotides to about 7,200 nucleotides, about 6,400 nucleotides to about 7,000 nucleotides, about 6,400 nucleotides to about 6,800 nucleotides, about 6,400 nucleotides to about 6,600 nucleotides, about 6,600 nucleotides to about 10,000 nucleotides, about 6,600 nucleotides to about 9,500 nucleotides, about 6,600 nucleotides to about 9,000 nucleotides, about 6,600 nucleotides to about 8,500 nucleotides, about 6,600 nucleotides to about 8,000 nucleotides, about 6,600 nucleotides to about 7,800 nucleotides, about 6,600 nucleotides to about 7,600 nucleotides, about 6,600 nucleotides to about 7,400 nucleotides, about 6,600 nucleotides to about 7,200 nucleotides, about 6,600 nucleotides to about 7,000 nucleotides, about 6,600 nucleotides to about 6,800 nucleotides, about 6,800 nucleotides to about 10,000 nucleotides, about 6,800 nucleotides to about 9,500 nucleotides, about 6,800 nucleotides to about 9,000 nucleotides, about 6,800 nucleotides to about 8,500 nucleotides, about 6,800 nucleotides to about 8,000 nucleotides, about 6,800 nucleotides to about 7,800 nucleotides, about 6,800 nucleotides to about 7,600 nucleotides, about 6,800 nucleotides to about 7,400 nucleotides, about 6,800 nucleotides to about 7,200 nucleotides, about 6,800 nucleotides to about 7,000 nucleotides, about 7,000 nucleotides to about 10,000 nucleotides, about 7,000 nucleotides to about 9,500 nucleotides, about 7,000 nucleotides to about 9,000 nucleotides, about 7,000 nucleotides to about 8,500 nucleotides, about 7,000 nucleotides to about 8,000 nucleotides, about 7,000 nucleotides to about 7,800 nucleotides, about 7,000 nucleotides to about 7,600 nucleotides, about 7,000 nucleotides to about 7,400 nucleotides, about 7,000 nucleotides to about 7,200 nucleotides, about 7,200 nucleotides to about 10,000 nucleotides, about 7,200 nucleotides to about 9,500 nucleotides, about 7,200 nucleotides to about 9,000 nucleotides, about 7,200 nucleotides to about 8,500 nucleotides, about 7,200 nucleotides to about 8,000 nucleotides, about 7,200 nucleotides to about 7,800 nucleotides, about 7,200 nucleotides to about 7,600 nucleotides, about 7,200 nucleotides to about 7,400 nucleotides, about 7,400 nucleotides to about 10,000 nucleotides, about 7,400 nucleotides to about 9,500 nucleotides, about 7,400 nucleotides to about 9,000 nucleotides, about 7,400 nucleotides to about 8,500 nucleotides, about 7,400 nucleotides to about 8,000 nucleotides, about 7,400 nucleotides to about 7,800 nucleotides, about 7,400 nucleotides to about 7,600 nucleotides, about 7,600 nucleotides to about 10,000 nucleotides, about 7,600 nucleotides to about 9,500 nucleotides, about 7,600 nucleotides to about 9,000 nucleotides, about 7,600 nucleotides to about 8,500 nucleotides, about 7,600 nucleotides to about 8,000 nucleotides, about 7,600 nucleotides to about 7,800 nucleotides, about 7,800 nucleotides to about 10,000 nucleotides, about 7,800 nucleotides to about 9,500 nucleotides, about 7,800 nucleotides to about 9,000 nucleotides, about 7,800 nucleotides to about 8,500 nucleotides, about 7,800 nucleotides to about 8,000 nucleotides, about 8,000 nucleotides to about 10,000 nucleotides, about 8,000 nucleotides to about 9,500 nucleotides, about 8,000 nucleotides to about 9,000 nucleotides, about 8,000 nucleotides to about 8,500 nucleotides, about 8,500 nucleotides to about 10,000 nucleotides, about 8,500 nucleotides to about 9,500 nucleotides, about 8,500 nucleotides to about 9,000 nucleotides, about 9,000 nucleotides to about 10,000 nucleotides, about 9,000 nucleotides to about 9,500 nucleotides, or about 9,500 nucleotides to about 10,000 nucleotides (inclusive).

Provided herein are exemplary vectors that can be used in any of the compositions and methods described herein. See, e.g., FIGS. 1-6.

A variety of different methods known in the art can be used to introduce any of vectors disclosed herein into a mammalian cell (e.g., a cochlear outer hair cell). Non-limiting examples of methods for introducing nucleic acid into a mammalian cell include: lipofection, transfection (e.g., calcium phosphate transfection, transfection using highly branched organic compounds, transfection using cationic polymers, dendrimer-based transfection, optical transfection, particle-based transfection (e.g., nanoparticle transfection), or transfection using liposomes (e.g., cationic liposomes)), microinjection, electroporation, cell squeezing, sonoporation, protoplast fusion, impalefection, hydrodynamic delivery, gene gun, magnetofection, viral transfection, and nucleofection.

Skilled practitioners will appreciate that any of the vectors described herein can be introduced into a mammalian cell by, for example, lipofection, and can be stably integrated into an endogenous gene locus (e.g., a stereocilin gene locus or a stereocilin pseudogene 1 gene locus). In some embodiments, the vectors provided herein stably integrate into an endogenous defective stereocilin gene locus, and thereby replace the defective stereocilin gene with a nucleic acid encoding a functioning (e.g., wildtype) stereocilin protein.

Various molecular biology techniques that can be used to introduce a mutation(s) and/or a deletion(s) into an endogenous gene are also known in the art. Non-limiting examples of such techniques include site-directed mutagenesis, CRISPR (e.g., CRISPR/Cas9-induced knock-in mutations and CRISPR/Cas9-induced knockout mutations), and TALENs. These methods can be used to correct the sequence of a defective endogenous gene present in a chromosome of a target cell.

Any of the vectors described herein can further include a control sequence, e.g., a control sequence selected from the group of a transcription initiation sequence, a transcription termination sequence, a promoter sequence, an enhancer sequence, an RNA splicing sequence, a polyadenylation (polyA) sequence, and a Kozak consensus sequence. Non-limiting examples of these control sequences are described herein. In some embodiments, a promoter can be a native promoter, a constitutive promoter, an inducible promoter, and/or a tissue-specific promoter.

Promoters

The term "promoter" means a DNA sequence recognized by enzymes/proteins in a mammalian cell required to initiate the transcription of a specific gene (e.g., a stereocilin gene). A promoter typically refers to, e.g., a nucleotide sequence to which an RNA polymerase and/or any associated factor binds and at which transcription is initiated. Non-limiting examples of promoters are described herein. Additional examples of promoters are known in the art.

In some embodiments, a vector encoding an N-terminal portion of a stereocilin protein (e.g., a human stereocilin protein) can include a promoter and/or an enhancer. The vector encoding the N-terminal portion of the stereocilin protein can include any of the promoters and/or enhancers described herein or known in the art.

In some embodiments, the promoter is an inducible promoter, a constitutive promoter, a mammalian cell promoter, a viral promoter, a chimeric promoter, an engineered promoter, a tissue-specific promoter, or any other type of promoter known in the art. In some embodiments, the promoter is a RNA polymerase II promoter, such as a mammalian RNA polymerase II promoter. In some embodiments, the promoter is a RNA polymerase III promoter, including, but not limited to, a H1 promoter, a human U6 promoter, a mouse U6 promoter, or a swine U6 promoter. The promoter will generally be one that is able to promote transcription in cochlear cells such as hair cells. In some examples, the promoter is a cochlea-specific promoter or a cochlea-oriented promoter.

A variety of promoters are known in the art that can be used herein. Non-limiting examples of promoters that can be used herein include: human EF1a, human cytomegalovirus (CMV) (U.S. Pat. No. 5,168,062), human ubiquitin C (UBC), mouse phosphoglycerate kinase 1, polyoma adenovirus, simian virus 40 (SV40), β-globin, β-actin, α-fetoprotein, γ-globin, β-interferon, γ-glutamyl transferase, mouse mammary tumor virus (MMTV), Rous sarcoma virus, rat insulin, glyceraldehyde-3-phosphate dehydrogenase, metallothionein II (MT II), amylase, cathepsin, MI muscarinic receptor, retroviral LTR (e.g. human T-cell leukemia virus HTLV), AAV ITR, interleukin-2, collagenase, platelet-derived growth factor, adenovirus 5 E2, stromelysin, murine MX gene, glucose regulated proteins (GRP78 and GRP94), α-2-macroglobulin, vimentin, MHC class I gene H-2κb, HSP70, proliferin, tumor necrosis factor, thyroid stimulating hormone a gene, immunoglobulin light chain, T-cell receptor, HLA DQα and DQβ, interleukin-2 receptor, MHC class II, MHC class II HLA-DRα, muscle creatine kinase, prealbumin (transthyretin), elastase I, albumin gene, c-fos, c-HA-ras, neural cell adhesion molecule (NCAM), H2B (TH2B) histone, rat growth hormone, human serum amyloid (SAA), troponin I (TN I), duchenne muscular dystrophy, human immunodeficiency virus, and Gibbon Ape Leukemia Virus (GALV) promoters. Additional examples of promoters are known in the art. See, e.g., Lodish, Molecular Cell Biology, Freeman and Company, New York 2007. In some embodiments, the promoter is the CMV immediate early promoter. In some embodiments, the promoter is a CMV promoter, e.g., a CMV promoter comprising or consisting of SEQ ID NO: 21. In some embodiments, the promoter is a CAG promoter or a CAG/CBA promoter. In some embodiments, the promoter is a CBA promoter, e.g., a CBA promoter comprising or consisting of SEQ ID NO: 22.

The term "constitutive" promoter refers to a nucleotide sequence that, when operably linked with a nucleic acid encoding a protein (e.g., a stereocilin protein), causes RNA to be transcribed from the nucleic acid in a mammalian cell under most or all physiological conditions.

Examples of constitutive promoters include, without limitation, the retroviral Rous sarcoma virus (RSV) LTR promoter, the cytomegalovirus (CMV) promoter (see, e.g., Boshart et al, Cell 41:521-530, 1985), the SV40 promoter, the dihydrofolate reductase promoter, the beta-actin promoter, the phosphoglycerol kinase (PGK) promoter, and the EF1-alpha promoter (Invitrogen).

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen®, Clontech®, and Ariad®. Additional examples of inducible promoters are known in the art.

Examples of inducible promoters regulated by exogenously supplied compounds include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, *Proc. Natl. Acad. Sci. U.S.A.* 93:3346-3351, 1996), the tetracycline-repressible system (Gossen et al, *Proc. Natl. Acad. Sci. U.S.A.* 89:5547-5551, 1992), the tetracycline-inducible system (Gossen et al, *Science* 268:1766-1769, 1995, see also Harvey et al, *Curr. Opin. Chem. Biol.* 2:512-518, 1998), the RU486-inducible system (Wang et al, *Nat. Biotech.* 15:239-243, 1997) and Wang et al, *Gene Ther.* 4:432-441, 1997), and the rapamycin-inducible system (Magari et al. *J. Clin. Invest.* 100:2865-2872, 1997).

The term "tissue-specific" promoter refers to a promoter that is active only in certain specific cell types and/or tissues (e.g., transcription of a specific gene occurs only within cells expressing transcription regulatory proteins that bind to the tissue-specific promoter).

In some embodiments, the regulatory sequences impart tissue-specific gene expression capabilities. In some cases, the tissue-specific regulatory sequences bind tissue-specific transcription factors that induce transcription in a tissue-specific manner.

Exemplary tissue-specific promoters include but are not limited to the following: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, an alpha-myosin heavy chain (a-MHC) promoter, and a cardiac Troponin T (cTnT) promoter. Additional exemplary promoters include Beta-actin promoter, hepatitis B virus core promoter (Sandig et al., *Gene Ther.* 3:1002-1009, 1996), alpha-fetoprotein (AFP) promoter (Arbuthnot et al., *Hum. Gene Ther.* 7:1503-1514, 1996), bone osteocalcin promoter (Stein et al., *Mol. Biol. Rep.* 24:185-196, 1997); bone sialoprotein promoter (Chen et al., *J. Bone Miner. Res.* 11:654-664, 1996), CD2 promoter (Hansal et al., *J. Immunol.* 161:1063-1068, 1998); immunoglobulin heavy chain promoter; T cell receptor alpha-chain promoter, neuronal such as neuron-specific enolase (NSE) promoter (Andersen et al., *Cell. Mol. Neurobiol.* 13:503-515, 1993), neurofilament light-chain gene promoter (Piccioli et al., *Proc. Natl. Acad. Sci. U.S.A.* 88:5611-5615, 1991), and the neuron-specific vgf gene promoter (Piccioli et al., *Neuron* 15:373-384, 1995).

In some embodiments, the tissue-specific promoter is a cochlea-specific promoter. In some embodiments, the tissue-specific promoter is a cochlear hair cell-specific promoter. Non-limiting examples of cochlear hair cell-specific promoters include but are not limited to: a ATOH1 promoter, a POU4F3 promoter, a LHX3 promoter, a MYO7A promoter, a MYO6 promoter, a α9ACHR promoter, and a α10ACHR promoter. In some embodiments, the promoter is an outer hair cell-specific promoter such as a PRESTIN promoter or an ONCOMOD promoter. See, e.g., Zheng et al., *Nature* 405:149-155, 2000; Tian et al. *Dev. Dyn.* 231:199-203, 2004; and Ryan et al., *Adv. Otorhinolaryngol.* 66:99-115, 2009.

Enhancers and 5' Cap

In some instances, a vector can include a promoter sequence and/or an enhancer sequence. The term "enhancer" refers to a nucleotide sequence that can increase the level of transcription of a nucleic acid encoding a protein of interest (e.g., a stereocilin protein). Enhancer sequences (50-1500 basepairs in length) generally increase the level of transcription by providing additional binding sites for transcription-associated proteins (e.g., transcription factors). In some embodiments, an enhancer sequence is found within an intronic sequence. Unlike promoter sequences, enhancer sequences can act at much larger distance away from the transcription start site (e.g., as compared to a promoter). Non-limiting examples of enhancers include a RSV enhancer, a CMV enhancer, and a SV40 enhancer. In some embodiments, the CMV enhancer sequence comprises or consists of SEQ ID NO: 20.

Poly(A) Sequences

In some embodiments, any of the vectors provided herein can include a poly(A) sequence. Most nascent eukaryotic mRNAs possess a poly(A) tail at their 3' end which is added during a complex process that includes cleavage of the primary transcript and a coupled polyadenylation reaction (see, e.g., Proudfoot et al., *Cell* 108:501-512, 2002). The poly(A) tail confers mRNA stability and transferability (Molecular Biology of the Cell, Third Edition by B. Alberts et al., Garland Publishing, 1994). In some embodiments, the poly(A) sequence is positioned 3' to the nucleic acid sequence encoding the C-terminus of the stereocilin protein.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (e.g., 50, 60, 70, 100, 200, 500, 1000, 2000, 3000, 4000, or 5000) added to the pre-mRNA through the action of an enzyme, polyadenylate polymerase. In higher eukaryotes, the poly(A) tail is added onto transcripts that contain a specific sequence, the polyadenylation signal or "poly(A) sequence." The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, a "poly(A) sequence" is a sequence that triggers the endonuclease cleavage of an mRNA and the additional of a series of adenosines to the 3' end of the cleaved mRNA.

There are several poly(A) sequences that can be used, including those derived from bovine growth hormone (bgh) (Woychik et al., *Proc. Natl. Acad. Sci. U.S.A.* 81 (13): 3944-3948, 1984; U.S. Pat. No. 5,122,458), mouse-β-globin, mouse-α-globin (Orkin et al., *EMBO J.* 4 (2): 453-456, 1985; Thein et al., *Blood* 71 (2): 313-319, 1988), human collagen, polyoma virus (Batt et al., *Mol. Cell Biol.* 15 (9): 4783-4790, 1995), the Herpes simplex virus thymidine kinase gene (HSV TK), IgG heavy-chain gene polyadenylation signal (US 2006/0040354), human growth hormone (hGH) (Szymanski et al., *Mol. Therapy* 15 (7): 1340-1347, 2007), the group consisting of SV40 poly(A) site, such as the SV40 late and early poly(A) site (Schek et al., *Mol. Cell Biol.* 12 (12): 5386-5393, 1992). In some embodiments, the bGH polyA sequence comprises or consists of SEQ ID NO: 34.

The poly(A) sequence can a sequence of AATAAA. The AATAAA sequence may be substituted with other hexanucleotide sequences with homology to AATAAA which are capable of signaling polyadenylation, including ATTAAA, AGTAAA, CATAAA, TATAAA, GATAAA, ACTAAA, AATATA, AAGAAA, AATAAT, AAAAAA, AATGAA, AATCAA, AACAAA, AATCAA, AATAAC, AATAGA, AATTAA, or AATAAG (see, e.g., WO 06/12414).

In some embodiments, the poly(A) sequence can be a synthetic polyadenylation site (see, e.g., the pCI-neo expression vector of Promega which is based on Levitt el al, *Genes Dev.* 3 (7): 1019-1025, 1989). In some embodiments, the poly(A) sequence is the polyadenylation signal of soluble neuropilin-1 (sNRP) (AAATAAAATACGAAATG, SEQ ID NO: 38) (see, e.g., WO 05/073384). Additional examples of poly(A) sequences are known in the art.

Internal Ribosome Entry Site (IRES)

In some embodiments, a vector encoding the C-terminus of the stereocilin protein can include a polynucleotide internal ribosome entry site (IRES). An IRES sequence is used to produce more than one polypeptide from a single gene transcript. An IRES forms a complex secondary structure that allows translation initiation to occur from any position with an mRNA immediately downstream from where the IRES is located (see, e.g., Pelletier and Sonenberg, *Mol. Cell. Biol.* 8 (3): 1103-1112, 1988).

There are several IRES sequences known to those in skilled in the art, including those from, e.g., foot and mouth disease virus (FMDV), encephalomyocarditis virus (EMCV), human rhinovirus (HRV), cricket paralysis virus, human immunodeficiency virus (HIV), hepatitis A virus (HAV), hepatitis C virus (HCV), and poliovirus (PV). See e.g., Alberts, Molecular Biology of the Cell, Garland Science, 2002; and Hellen et al., *Genes Dev.* 15 (13): 1593-612, 2001.

In some embodiments, the IRES sequence that is incorporated into the vector that encodes the C-terminus of a stereocilin protein is the foot and mouth disease virus (FMDV). The Foot and Mouth Disease Virus 2A sequence is a small peptide (approximately 18 amino acids in length) that has been shown to mediate the cleavage of polyproteins (Ryan, M D et al., *EMBO* 4:928-933, 1994; Mattion et al., *J. Virology* 70:8124-8127, 1996; Furler et al., *Gene Therapy* 8:864-873, 2001; and Halpin et al., *Plant Journal* 4:453-459, 1999). The cleavage activity of the 2A sequence has previously been demonstrated in artificial systems including plasmids and gene therapy vectors (AAV and retroviruses) (Ryan et al., *EMBO* 4:928-933, 1994; Mattion et al., *J. Virology* 70:8124-8127, 1996; Furler et al., *Gene Therapy* 8:864-873, 2001; and Halpin et al., *Plant Journal* 4:453-459, 1999; de Felipe et al., *Gene Therapy* 6:198-208, 1999; de Felipe et al., Human *Gene Therapy* 11:1921-1931, 2000; and Klump et al., *Gene Therapy* 8:811-817, 2001).

Reporter Sequences

Any of the vectors provided herein can optionally include a sequence encoding a reporter protein ("a reporter sequence"). Non-limiting examples of reporter sequences include DNA sequences encoding: a beta-lactamase, a beta-galactosidase (LacZ), an alkaline phosphatase, a thymidine kinase, a green fluorescent protein (GFP), a red fluorescent protein, an mCherry fluorescent protein, a yellow fluorescent protein, a chloramphenicol acetyltransferase (CAT), and a luciferase. Additional examples of reporter sequences are known in the art. When associated with regulatory elements which drive their expression, the reporter sequence can provide signals detectable by conventional means, including enzymatic, radiographic, colorimetric, fluorescence, or other spectrographic assays; fluorescent activating cell sorting (FACS) assays; immunological assays (e.g., enzyme linked immunosorbent assay (ELISA), radioimmunoassay (RIA), and immunohistochemistry).

In some embodiments, the reporter sequence is turbo green fluorescent protein (tGFP) (SEQ ID NO: 31).

tGFP cDNA (SEQ ID NO: 31)
ATGGAGAGCGACGAGAGCGGCCTGCCCGCCATGGAGATCGAGTGCCGCAT

CACCGGCACCCTGAACGGCGTGGAGTTCGAGCTGGTGGGCGGCGGAGAGG

GCACCCCCGAGCAGGGCCGCATGACCAACAAGATGAAGAGCACCAAAGGC

GCCCTGACCTTCAGCCCCTACCTGCTGAGCCACGTGATGGGCTACGGCTT

CTACCACTTCGGCACCTACCCCAGCGGCTACGAGAACCCCTTCCTGCACG

CCATCAACAACGGCGGCTACACCAACACCCGCATCGAGAAGTACGAGGAC

GGCGGCGTGCTGCACGTGAGCTTCAGCTACCGCTACGAGGCCGGCCGCGT

GATCGGCGACTTCAAGGTGATGGGCACCGGCTTCCCCGAGGACAGCGTGA

TCTTCACCGACAAGATCATCCGCAGCAACGCCACCGTGGAGCACCTGCAC

CCCATGGGCGATAACGATCTGGATGGCAGCTTCACCCGCACCTTCAGCCT

GCGCGACGGCGGCTACTACAGCTCCGTGGTGGACAGCCACATGCACTTCA

AGAGCGCCATCCACCCCAGCATCCTGCAGAACGGGGGCCCCATGTTCGCC

TTCCGCCGCGTGGAGGAGGATCACAGCAACACCGAGCTGGGCATCGTGGA

GTACCAGCACGCCTTCAAGACCCCGGATGCAGATGCCGGTGAAGAA tGFP Protein (SEQ ID NO: 32)
MESDESGLPAMEIECRITGTLNGVEFELVGGGEGTPEQGRMTNKMKSTKG

ALTFSPYLLSHVMGYGFYHFGTYPSGYENPFLHAINNGGYTNTRIEKYED

GGVLHVSFSYRYEAGRVIGDFKVMGTGFPEDSVIFTDKIIRSNATVEHLH

PMGDNDLDGSFTRTFSLRDGGYYSSVVDSHMHFKSAIHPSILQNGGPMFA

FRRVEEDHSNTELGIVEYQHAFKTPDADAGEE

In some embodiments, the reporter sequence is the LacZ gene, and the presence of a vector carrying the LacZ gene in a mammalian cell (e.g., a cochlear outer hair cell) is detected by assays for beta-galactosidase activity. In other embodiments, the reporter is a fluorescent protein (e.g., green fluorescent protein) or luciferase, the presence of a vector carrying the fluorescent protein or luciferase in a mammalian cell (e.g., a cochlear outer hair cell) may be measured by fluorescent techniques (e.g., fluorescent microscopy or FACS) or light production in a luminometer (e.g., a spectrophotometer or an IVIS imaging instrument). In some embodiments, the reporter sequence can be used to verify the tissue-specific targeting capabilities and tissue-specific promoter regulatory activity of any of the vectors described herein.

Flanking Regions Untranslated Regions (UTRs)

In some embodiments, any of the vectors described herein (e.g., any of the at least two different vectors) can include an untranslated region. In some embodiments, a vector can includes a 5' UTR or a 3' UTR.

Untranslated regions (UTRs) of a gene are transcribed but not translated. The 5' UTR starts at the transcription start site and continues to the start codon but does not include the start codon. The 3' UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into any of the vectors, compositions, kits, or methods as described herein to enhance the stability of a stereocilin protein.

Natural 5' UTRs include a sequence that plays a role in translation initiation. They harbor signatures like Kozak sequences, which are commonly known to be involved in the process by which the ribosome initiates translation of many genes. Kozak sequences have the consensus sequence CCR (A/G)CCAUGG, where R is a purine (A or G) three bases upstream of the start codon (AUG), which is followed by another "G". The 5' UTR have also been known, e.g., to form secondary structures that are involved in elongation factor binding.

For example, in some embodiments, a 5' UTR is included in any of the vectors described herein. Non-limiting examples of 5' UTRs including those from the following genes: albumin, serum amyloid A, Apolipoprotein A/B/E, transferrin, alpha fetoprotein, erythropoietin, and Factor VIII, can be used to enhance expression of a nucleic acid molecule, such as a mRNA.

In some embodiments, a 5' UTR from a mRNA that is transcribed by a cell in the cochlea can be included in any of the vectors, compositions, kits, and methods described herein.

3' UTRs are known to have stretches of adenosines and uridines embedded in them. These AU-rich signatures are particularly prevalent in genes with high rates of turnover. Based on their sequence features and functional properties, the AU-rich elements (AREs) can be separated into three classes (Chen et al., *Mol. Cell. Biol.* 15:5777-5788, 1995; Chen et al., *Mol. Cell Biol.* 15:2010-2018, 1995): Class I AREs contain several dispersed copies of an AUUUA motif within U-rich regions. For example, c-Myc and MyOD mRNAs contain class I AREs. Class II AREs possess two or more overlapping UUAUUUA(U/A)(U/A) nonamers. GM-CSF and TNF-alpha mRNAs are examples that contain class II AREs. Class III AREs are less well defined. These U-rich regions do not contain an AUUUA motif. Two well-studied examples of this class are c-Jun and myogenin mRNAs.

Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

An exemplary human wildtype 5' UTR is or includes the sequence of SEQ ID NO: 24. An exemplary human wildtype 3' UTR is or includes the sequence of SEQ ID NO: 33.

In some embodiments of any of the compositions described herein, a 5' UTR, a 3' UTR, or both are included in a vector (e.g., any of the vectors described herein). For example, any of the 5' UTRs described herein can be operatively linked to the start codon in any of the coding sequences described herein. For example, any of the 3' UTRs can be operatively linked to the 3'-terminal codon (last codon) in any of the coding sequences described herein.

In some embodiments of any of the compositions described herein, the 5' UTR comprises at least 10 contiguous (e.g., at least 15 contiguous, at least 20 contiguous, at least 25 contiguous, at least 30 contiguous, at least 35 contiguous, at least 40 contiguous, at least 45 contiguous, at least 50 contiguous, at least 55 contiguous, at least 60 contiguous, at least 65 contiguous, or at least 70 contiguous) nucleotides from anywhere within SEQ ID NO: 24.

For example, a 5' UTR can include or consist of one or more of: nucleotide positions 1 to 70, nucleotide positions 1 to 60, nucleotide positions 1 to 50, nucleotide positions 1 to 40, nucleotide positions 1 to 30, nucleotide positions 1 to 20, nucleotide positions 1 to 10, nucleotide positions 10 to 70, nucleotide positions 10 to 60, nucleotide positions 10 to 50, nucleotide positions 10 to 40, nucleotide positions 10 to 30, nucleotide positions 10 to 20, nucleotide positions 20 to 70, nucleotide positions 20 to 60, nucleotide positions 20 to 50, nucleotide positions 20 to 40, nucleotide positions 20 to 30, nucleotide positions 30 to 70, nucleotide positions 30 to 60, nucleotide positions 30 to 50, nucleotide positions 30 to 40, nucleotide positions 40 to 70, nucleotide positions 40 to 60, nucleotide positions 40 to 50, nucleotide positions 50 to 70, nucleotide positions 50 to 60, nucleotide positions 60 to 70, nucleotide positions 100 to 105, of SEQ ID NO: 24.

In some embodiments of any of the compositions described herein, the 5' UTR comprises a sequence that is at least 70% (e.g., at least 75%, at least 80%, at least 90%, at least 91%, at least 92%, at least 93%, at least 94%, at least 95%, at least 96%, at least 97%, at least 98%, or at least 99%) identical to SEQ ID NO: 24.

In some embodiments of any of the compositions described herein, the 3' UTR comprises at least 10 contiguous (e.g., at least 15 contiguous, at least 20 contiguous, at least 25 contiguous, at least 30 contiguous, at least 35 contiguous, at least 40 contiguous, at least 45 contiguous, at least 50 contiguous, at least 55 contiguous, at least 60 contiguous, at least 65 contiguous, at least 70 contiguous, at least 75 contiguous, at least 80 contiguous, at least 85 contiguous, at least 90 contiguous, at least 95 contiguous, at least 100 contiguous, or at least 105 contiguous) nucleotides from anywhere within SEQ ID NO: 33.

For example, a 3' UTR can include or consist of one or more of: nucleotide positions 1 to 107, nucleotide positions 1 to 105, nucleotide positions 1 to 100, nucleotide positions 1 to 90, nucleotide positions 1 to 80, nucleotide positions 1 to 70, nucleotide positions 1 to 60, nucleotide positions 1 to 50, nucleotide positions 1 to 40, nucleotide positions 1 to 30, nucleotide positions 1 to 20, nucleotide positions 1 to 10, nucleotide positions 10 to 107, nucleotide positions 10 to 105, nucleotide positions 10 to 100, nucleotide positions 10 to 90, nucleotide positions 10 to 80, nucleotide positions 10 to 70, nucleotide positions 10 to 60, nucleotide positions 10 to 50, nucleotide positions 10 to 40, nucleotide positions 10 to 30, nucleotide positions 10 to 20, nucleotide positions 20 to 107, nucleotide positions 20 to 105, nucleotide positions 20 to 100, nucleotide positions 20 to 90, nucleotide positions 20 to 80, nucleotide positions 20 to 70, nucleotide positions 20 to 60, nucleotide positions 20 to 50, nucleotide positions 20 to 40, nucleotide positions 20 to 30, nucleotide positions 30 to 107, nucleotide positions 30 to 105, nucleotide positions 30 to 100, nucleotide positions 30 to 90, nucleotide positions 30 to 80, nucleotide positions 30 to 70, nucleotide positions 30 to 60, nucleotide positions 30 to 50, nucleotide positions 30 to 40, nucleotide positions 40 to 107, nucleotide positions 40 to 105, nucleotide positions 40 to 100, nucleotide positions 40 to 90, nucleotide positions 40 to 80, nucleotide positions 40 to 70, nucleotide positions 40 to 60, nucleotide positions 40 to 50, nucleotide positions 50 to 107, nucleotide positions 50 to 105, nucleotide positions 50 to 100, nucleotide positions 50 to 90, nucleotide positions 50 to 80, nucleotide positions 50 to 70, nucleotide positions 50 to 60, nucleotide positions 60 to, nucleotide positions 60 to 107, nucleotide positions 60 to 105, nucleotide positions 60 to 100, nucleotide positions 60 to 90, nucleotide positions 60 to 80, nucleotide positions 60 to 70, nucleotide positions 70 to 107, nucleotide positions 70 to 105, nucleotide positions 70 to 100, nucleotide positions 70 to 90, nucleotide positions 70 to 80, nucleotide positions 80 to 107, nucleotide positions 80 to 105, nucleotide positions 80 to 100, nucleotide positions 80 to 90, nucleotide positions 90 to 107, nucleotide positions 90 to 105, nucleotide positions 90 to 100, nucleotide positions 100 to 107, nucleotide positions 100 to 105, of SEQ ID NO: 33.

In some embodiments of any of the compositions described herein, the 3' UTR comprises a sequence that is at least 70% (e.g., at least 75%, at least 80%, at least 90%, at least 91%, at least 92%, at least 93%, at least 94%, at least 95%, at least 96%, at least 97%, at least 98%, or at least 99%) identical to SEQ ID NO: 33.

Human 5' UTR of STRC
(SEQ ID NO: 24)
GCCCTGCCCTCACCTGGCTATCCCACACAGGTGAGAATAACCAGAACTCA

CCTCCGGTACCAGTGTTCACTTG

Human 3' UTR of STRC
(SEQ ID NO: 33)
GCCTGTCTCTACAGTAGAAGGAGATTGTGGGGAGAGAAATCTTAAGTCAT

AATGAATAAAGTGCAAACAGAAGTGCATCCTGATTATTTTCAGAAGCTGA

TGAGGAATA

In some embodiments, the introduction, removal, or modification of 3' UTR AREs can be used to modulate the stability of an mRNA encoding a stereocilin protein. In other embodiments, AREs can be removed or mutated to increase the intracellular stability and thus increase translation and production of a stereocilin protein.

In other embodiments, non-UTR sequences may be incorporated into the 5' or 3' UTRs. In some embodiments, introns or portions of intron sequences may be incorporated into the flanking regions of the polynucleotides in any of the vectors, compositions, kits, and methods provided herein. Incorporation of intronic sequences may increase protein production as well as mRNA levels. An intron can be an intron from a stereocilin gene or can be an intron from a heterologous gene, e.g., a hybrid adenovirus/mouse immunoglobulin intron (Yew et al., *Human Gene Ter.* 8 (5): 575-584, 1997), an SV40 intron (Ostedgaard et al., *Proc. Natl. Acad. Sci. U.S.A.* 102 (8): 2952-2957, 2005) an MVM intron (Wu et al., *Mol. Ther.* 16 (2): 280-289, 2008), a factor IX truncated intron 1 (Wu et al., *Mol. Ther.* 16 (2): 280-289, 2008; Kurachi et al., *J. Biol. Chem.* 270 (10): 5276-5281, 1995), a chimeric β-globulin splice donor/immunoglobulin heavy chain spice acceptor intron (Wu et al., *Mol. Ther.* 16 (2): 280-289, 2008; Choi et al., *Mol. Brain* 7:17, 2014) a SV40 late splice donor/splice acceptor intron (19S/16S) (Yew et al., *Human Gene Ther.* 8 (5): 575-584, 1997), a hybrid adenovirus spice donor/Igg splice acceptor (Choi et al., *Mol. Brain* 7:17, 1991; Huang and Gorman, *Mol. Cell Biol.* 10 (4): 1805-1810, 1990).

Non-limiting examples of a splice donor and splice acceptor sequences are SEQ ID NOs: 6 and 7, respectively.

In some embodiments of any of the vectors described herein, the vector includes a chimeric intron sequence (SEQ ID NO: 23).

In some embodiments of any of the vectors described herein, the vector includes a T2A sequence (SEQ ID NO: 29).

T2A cDNA sequence
(SEQ ID NO: 29)
GAGGGCAGAGGAAGTCTGCTAACATGCGGTGACGTCGAGGAGAATCCTGG

CCCA

T2A Protein
(SEQ ID NO: 30)
GSGEGRGSLLTCGDVEENPGP

Additional Sequences

Any of the vectors provided herein can optionally include additional nucleotide sequences ("a stuffer sequence") in order to optimize the total number of basepairs in the vector. For example, in order to optimize packaging, each vector can be designed to contain a total of about 4,000 base pairs to about 4,700 base pairs, e.g., about 4,000 base pairs to about 4,650 base pairs, about 4,000 base pairs to about 4,600 base pairs, about 4,000 base pairs to about 4,550 base pairs, about 4,000 base pairs to about 4,500 base pairs, about 4,000 base pairs to about 4,450 base pairs, about 4,000 base pairs to about 4,400 base pairs, about 4,000 base pairs to about 4,350 base pairs, about 4,000 base pairs to about 4,300 base pairs, about 4,000 base pairs to about 4,250 base pairs, about 4,000 base pairs to about 4,200 base pairs, about 4,000 base pairs to about 4,150 base pairs, about 4,000 base pairs to about 4,100 base pairs, about 4,000 base pairs to about 4,050 base pairs, about 4,050 base pairs to about 4,700 base pairs, about 4,050 base pairs to about 4,650 base pairs, about 4,050 base pairs to about 4,600 base pairs, about 4,050 base pairs to about 4,550 base pairs, about 4,050 base pairs to about 4,500 base pairs, about 4,050 base pairs to about 4,450 base pairs, about 4,050 base pairs to about 4,400 base pairs, about 4,050 base pairs to about 4,350 base pairs, about 4,050 base pairs to about 4,300 base pairs, about 4,050 base pairs to about 4,250 base pairs, about 4,050 base pairs to about 4,200 base pairs, about 4,050 base pairs to about 4,150 base pairs, about 4,050 base pairs to about 4,100 base pairs, about 4,100 base pairs to about 4,700 base pairs, about 4,100 base pairs to about 4,650 base pairs, about 4,100 base pairs to about 4,600 base pairs, about 4,100 base pairs to about 4,550 base pairs, about 4,100 base pairs to about 4,500 base pairs, about 4,100 base pairs to about 4,450 base pairs, about 4,100 base pairs to about 4,400 base pairs, about 4,100 base pairs to about 4,350 base pairs, about 4,100 base pairs to about 4,300 base pairs, about 4,100 base pairs to about 4,250 base pairs, about 4,100 base pairs to about 4,200 base pairs, about 4,100 base pairs to about 4,150 base pairs, about 4,150 base pairs to about 4,700 base pairs, about 4,150 base pairs to about 4,650 base pairs, about 4,150 base pairs to about 4,600 base pairs, about 4,150 base pairs to about 4,550 base pairs, about 4,150 base pairs to about 4,500 base pairs, about 4,150 base pairs to about 4,450 base pairs, about 4,150 base pairs to about 4,400 base pairs, about 4,150 base pairs to about 4,350 base pairs, about 4,150 base pairs to about 4,300 base pairs, about 4,150 base pairs to about 4,250 base pairs, about 4,150 base pairs to about 4,200 base pairs, about 4,200 base pairs to about 4,700 base pairs, about 4,200 base pairs to about 4,650 base pairs, about 4,200 base pairs to about 4,600 base pairs, about 4,200 base pairs to about 4,550 base pairs, about 4,200 base pairs to about 4,500 base pairs, about 4,200 base pairs to about 4,450 base pairs, about 4,200 base pairs to about 4,400 base pairs, about 4,200 base pairs to about 4,350 base pairs, about 4,200 base pairs to about 4,300 base pairs, about 4,200 base pairs to about 4,250 base pairs, about 4,250 base pairs to about 4,700 base pairs, about 4,250 base pairs to about 4,650 base pairs, about 4,250 base pairs to about 4,600 base pairs, about 4,250 base pairs to about 4,550 base pairs, about 4,250 base pairs to about 4,500 base pairs, about 4,250 base pairs to about 4,450 base pairs, about 4,250 base pairs to about 4,400 base pairs, about 4,250 base pairs to about 4,350 base pairs, about 4,250 base pairs to about 4,300 base pairs, about 4,300 base pairs to about 4,700 base pairs, about 4,300 base pairs to about 4,650 base pairs, about 4,300 base pairs to about 4,600 base pairs, about 4,300 base pairs to about 4,550 base pairs, about 4,300 base pairs to about 4,500 base pairs, about 4,300 base pairs to about 4,450 base pairs, about 4,300 base pairs to about 4,400 base pairs, about 4,300 base pairs to about 4,350 base pairs, about 4,350 base pairs to about 4,700 base pairs, about 4,350 base pairs to about 4,650 base pairs, about 4,350 base pairs to about 4,600 base pairs, about 4,350 base pairs to about 4,550 base pairs, about 4,350 base pairs to about 4,500 base pairs, about 4,350 base pairs to about 4,450 base pairs, about 4,350 base pairs to about 4,400 base pairs, about 4,400 base pairs to about 4,700 base pairs, about 4,400 base pairs to about 4,650 base pairs, about 4,400 base pairs to about 4,600 base pairs, about 4,400 base pairs to about 4,550 base pairs, about 4,400 base pairs to about 4,500 base pairs, about 4,400 base pairs to about 4,450 base pairs, about 4,450 base pairs to about 4,700 base pairs, about 4,450 base pairs to about 4,650 base pairs, about 4,450 base pairs to about 4,600 base pairs, about 4,450 base pairs to about 4,550 base pairs, about 4,450 base pairs to about 4,500 base pairs, about 4,500 base pairs to about 4,700 base pairs, about 4,500 base pairs to about 4,650 base pairs, about 4,500 base pairs to about 4,600 base pairs, about 4,500 base pairs to about 4,550 base pairs, about 4,550 base pairs to about 4,700 base pairs, about 4,550 base pairs to about 4,650 base pairs, about 4,550 base pairs to about 4,600 base pairs, about 4,600 base pairs to about 4,700 base pairs, about 4,600 base pairs to about 4,650 base pairs, or about 4,650 base pairs to about 4,700 base pairs (inclusive).

Figure 2:
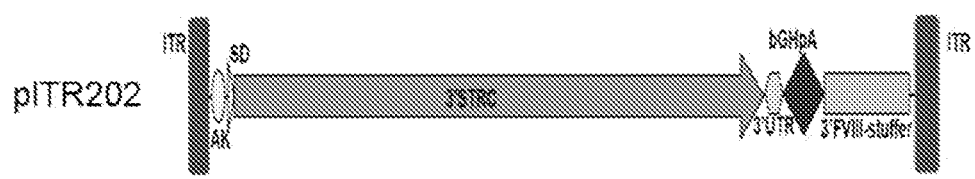
FIG. 2 is an exemplary schematic representation of a genetic map of a STRC vector (pITR-202; SEQ ID NO: 13; 4434 bp) that can be used in any of the present methods described herein. The vector includes an ITR sequence (SEQ ID NO: 18), an AK sequence (SEQ ID NO: 26), a SD sequence (SEQ ID NO: 6), a 3' STRC coding sequence (SEQ ID NO: 28), a 3' UTR sequence (SEQ ID NO: 33), a bovine growth hormone poly-adenylation signal (bGHpA) (SEQ ID NO: 34), a 3' FVIII stuffer sequence (SEQ ID NO: 35), and an ITR sequence (SEQ ID NO: 36).
Figure 3:
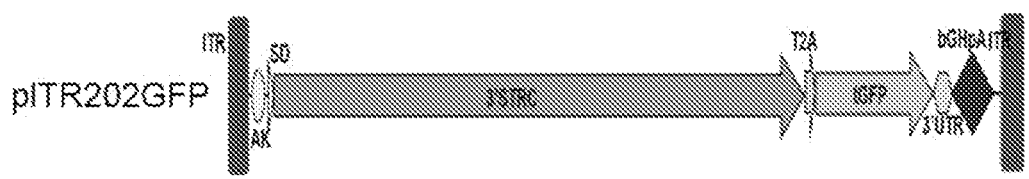
FIG. 3 is an exemplary schematic representation of a genetic map of a STRC vector (pITR-202GFP; SEQ ID NO: 14; 4693 bp) that can be used in any of the present methods described herein. The vector includes an ITR sequence (SEQ ID NO: 18), an AK sequence (SEQ ID NO: 26), a SD sequence (SEQ ID NO: 6), a 3' STRC coding sequence (SEQ ID NO: 28), a T2A sequence (SEQ ID NO: 29), a tGFP sequence (SEQ ID NO: 31), a 3' UTR sequence (SEQ ID NO: 33), a bGHpA sequence (SEQ ID NO: 34), and an ITR sequence (SEQ ID NO: 36).
Figure 4:
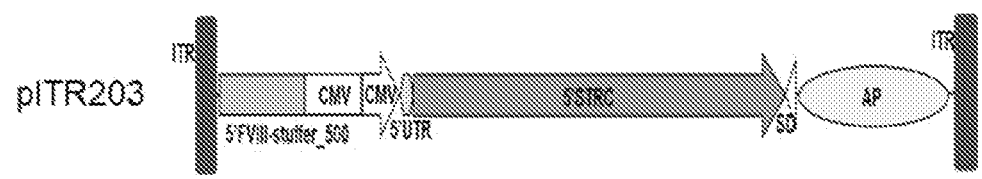
FIG. 4 is an exemplary schematic representation of a genetic map of a STRC vector (pITR-203; SEQ ID NO: 15; 4619 bp) that can be used in any of the present methods described herein. The vector includes an ITR sequence (SEQ ID NO: 18), a 5' FVIII stuffer_500 sequence (SEQ ID NO: 37), a CMV enhancer (SEQ ID NO: 20), a CMV promoter sequence (SEQ ID NO: 21), a 5' UTR sequence (SEQ ID NO: 24), a 5' STRC coding sequence (SEQ ID NO: 25), a SD sequence (SEQ ID NO: 6), an AP sequence (AP) (SEQ ID NO: 27), and an ITR sequence (SEQ ID NO: 36).
Figure 5:
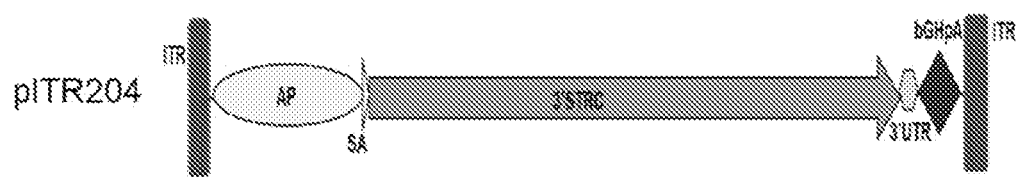
FIG. 5 is an exemplary schematic representation of a genetic map of a STRC vector (pITR-204; SEQ ID NO: 16; 4729 bp) that can be used in any of the present methods described herein. The vector includes an ITR sequence (SEQ ID NO: 18), an AP sequence (SEQ ID NO: 27), a splicing acceptor signal (SA) sequence (SEQ ID NO: 7), a 3' STRC coding sequence (SEQ ID NO: 28), a 3' UTR sequence (SEQ ID NO: 33), a bGHpA sequence (SEQ ID NO: 34), and an ITR sequence (SEQ ID NO: 36).
Figure 6:
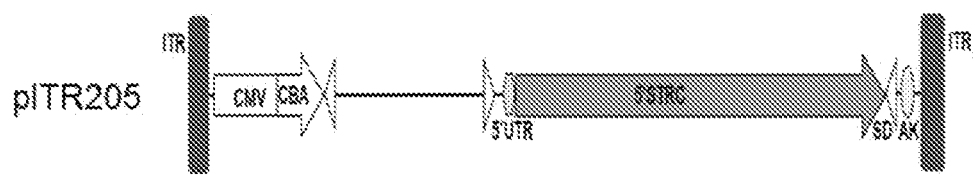
FIG. 6 is an exemplary schematic representation of a genetic map of a STRC vector (pITR-205; SEQ ID NO: 17; 4460 bp) that can be used in any of the present methods described herein. The vector includes an ITR sequence (SEQ ID NO: 18), a CMV enhancer (SEQ ID NO: 20), a chicken β-actin (CBA) promoter (SEQ ID NO: 22), a chimeric intron sequence (SEQ ID NO: 23), a 5' UTR sequence (SEQ ID NO: 24), a 5' STRC coding sequence (SEQ ID NO: 25), a SD sequence (SEQ ID NO: 6), an AK sequence (SEQ ID NO: 26), and an ITR sequence (SEQ ID NO: 36).

A stuffer sequence can be any nucleotide sequence, e.g., up to 1000 bp, that can be included in any of the vectors described herein that is not transcribed and that does not serve a regulatory function in order to achieve a desirable vector size (e.g., a vector size of about 4 kb to about 5 kb, or any of the vector sizes provided herein). For example, a stuffer sequence can by any nucleotide sequences of about 100 bp to about 1000 bp (e.g., about 100 bp to about 900 bp, about 100 bp to about 850 bp, about 100 bp to about 800 bp, about 100 bp to about 750 bp, about 100 bp to about 700 bp, about 100 bp to about 650 bp, about 100 bp to about 600 bp, about 100 bp to about 550 bp, about 100 bp to about 500 bp, about 100 bp to about 450 bp, about 100 bp to about 400 bp, about 100 bp to about 350 bp, about 100 bp to about 300 bp, about 100 bp to about 250 bp, about 100 bp to about 200 bp, about 100 bp to about 150 bp, about 150 bp to about 1000 bp, about 150 bp to about 900 bp, about 150 bp to about 850 bp, about 150 bp to about 800 bp, about 150 bp to about 750 bp, about 150 bp to about 700 bp, about 150 bp to about 650 bp, about 150 bp to about 600 bp, about 150 bp to about 550 bp, about 150 bp to about 500 bp, about 150 bp to about 450 bp, about 150 bp to about 400 bp, about 150 bp to about 350 bp, about 150 bp to about 300 bp, about 150 bp to about 250 bp, about 150 bp to about 200 bp, about 200 bp to about 1000 bp, about 200 bp to about 900 bp, about 200 bp to about 850 bp, about 200 bp to about 800 bp, about 200 bp to about 750 bp, about 200 bp to about 700 bp, about 200 bp to about 650 bp, about 200 bp to about 600 bp, about 200 bp to about 550 bp, about 200 bp to about 500 bp, about 200 bp to about 450 bp, about 200 bp to about 400 bp, about 200 bp to about 350 bp, about 200 bp to about 300 bp, about 200 bp to about 250 bp, about 250 bp to about 1000 bp, about 250 bp to about 900 bp, about 250 bp to about 850 bp, about 250 bp to about 800 bp, about 250 bp to about 750 bp, about 250 bp to about 700 bp, about 250 bp to about 650 bp, about 250 bp to about 600 bp, about 250 bp to about 550 bp, about 250 bp to about 500 bp, about 250 bp to about 450 bp, about 250 bp to about 400 bp, about 250 bp to about 350 bp, about 250 bp to about 300 bp, about 300 bp to about 1000 bp, about 300 bp to about 900 bp, about 300 bp to about 850 bp, about 300 bp to about 800 bp, about 300 bp to about 750 bp, about 300 bp to about 700 bp, about 300 bp to about 650 bp, about 300 bp to about 600 bp, about 300 bp to about 550 bp, about 300 bp to about 500 bp, about 300 bp to about 450 bp, about 300 bp to about 400 bp, about 300 bp to about 350 bp, about 350 bp to about 1000 bp, about 350 bp to about 900 bp, about 350 bp to about 850 bp, about 350 bp to about 800 bp, about 350 bp to about 750 bp, about 350 bp to about 700 bp, about 350 bp to about 650 bp, about 350 bp to about 600 bp, about 350 bp to about 550 bp, about 350 bp to about 500 bp, about 350 bp to about 450 bp, about 350 bp to about 400 bp, about 400 bp to about 1000 bp, about 400 bp to about 900 bp, about 400 bp to about 850 bp, about 400 bp to about 800 bp, about 400 bp to about 750 bp, about 400 bp to about 700 bp, about 400 bp to about 650 bp, about 400 bp to about 600 bp, about 400 bp to about 550 bp, about 400 bp to about 500 bp, about 400 bp to about 450 bp, about 450 bp to about 1000 bp, about 450 bp to about 900 bp, about 450 bp to about 850 bp, about 450 bp to about 800 bp, about 450 bp to about 750 bp, about 450 bp to about 700 bp, about 450 bp to about 650 bp, about 450 bp to about 600 bp, about 450 bp to about 550 bp, about 450 bp to about 500 bp, about 500 bp to about 1000 bp, about 500 bp to about 900 bp, about 500 bp to about 850 bp, about 500 bp to about 800 bp, about 500 bp to about 750 bp, about 500 bp to about 700 bp, about 500 bp to about 650 bp, about 500 bp to about 600 bp, about 500 bp to about 550 bp, about 550 bp to about 1000 bp, about 550 bp to about 900 bp, about 550 bp to about 850 bp, about 550 bp to about 800 bp, about 550 bp to about 750 bp, about 550 bp to about 700 bp, about 550 bp to about 650 bp, about 550 bp to about 600 bp, about 600 bp to about 1000 bp, about 600 bp to about 900 bp, about 600 bp to about 850 bp, about 600 bp to about 800 bp, about 600 bp to about 750 bp, about 600 bp to about 700 bp, about 600 bp to about 650 bp, about 650 bp to about 1000 bp, about 650 bp to about 900 bp, about 650 bp to about 850 bp, about 650 bp to about 800 bp, about 650 bp to about 750 bp, about 650 bp to about 700 bp, about 700 bp to about 1000 bp, about 700 bp to about 900 bp, about 700 bp to about 850 bp, about 700 bp to about 800 bp, about 700 bp to about 750 bp, about 750 bp to about 1000 bp, about 750 bp to about 900 bp, about 750 bp to about 850 bp, about 750 bp to about 800 bp, about 800 bp to about 1000 bp, about 800 bp to about 900 bp, about 800 bp to about 850 bp, about 850 bp to about 1000 bp, about 850 bp to about 900 bp, about 900 bp to about 1000 bp, about 900 to about 950 bp, or about 950 bp to about 1000 bp). SEQ ID NOs. 19, 35 and 37 are exemplary human factor FVIII stuffer sequences that can be used in any of the vectors described herein. Additional stuffer sequences are known in the art. Exemplary vectors that include stuffer sequences are shown in FIGS. 1, 2 and 4.

Mammalian Cells

Also provided herein is a cell (e.g., a mammalian cell) that includes any of the nucleic acids, vectors (e.g., at least two different vectors described herein), or compositions described herein. Skilled practitioners will appreciate that the nucleic acids and vectors described herein can be introduced into any mammalian cell. Non-limiting examples of vectors and methods for introducing vectors into mammalian cells are described herein.

In some embodiments, the cell is a human cell, a mouse cell, a porcine cell, a rabbit cell, a dog cell, a cat cell, a rat cell, or a non-human primate cell. In some embodiments, the cell is a specialized cell of the cochlea. In some embodiments, the cell is a cochlear inner hair cell or a cochlear outer hair cell. In some embodiments, the cell is a cochlear inner hair cell. In some embodiments, the cell is a cochlear outer hair cell.

In some embodiments, the mammalian cell is in vitro. In some embodiments, the mammalian cell is present in a mammal. In some embodiments, the mammalian cell is autologous cell obtained from a subject and cultured ex vivo.

Methods

Also provided herein is a method of introducing into a cochlea of a mammal (e.g., a human) a therapeutically effective amount of any of the compositions described herein. Also provided are methods of increasing expression of an active stereocilin protein (e.g., a full-length stereocilin protein) in an outer hair cell in a cochlea of a mammal (e.g., a human) that include introducing into the cochlea of the mammal a therapeutically effective amount of any of the compositions described herein. Also provided are methods of treating non-symptomatic sensorineural hearing loss in a subject (e.g., a human) identified as having a defective stereocilin gene, where the methods include administering a therapeutically effective amount of any of the compositions described herein into the cochlea of a subject.

In some embodiments of any of these methods, the mammal has been previously identified as having a defective stereocilin gene (e.g., a stereocilin gene having a mutation that results in a decrease in the expression and/or activity of a stereocilin protein encoded by the gene). Some embodiments of any of these methods further include, prior to the introducing or administering step, determining that the subject has a defective stereocilin gene. Some embodiments of any of these methods can further include detecting a mutation in a stereocilin gene in a subject. Some embodiments of any of the methods can further include identifying or diagnosing a subject as having non-symptomatic sensorineural hearing loss.

In some embodiments of any of these methods, two or more doses of any of the compositions described herein are introduced or administered into the cochlea of the mammal or subject. Some embodiments of any of these methods can include introducing or administering a first dose of the composition into the cochlea of the mammal or subject, assessing hearing function of the mammal or subject following the introducing or the administering of the first dose, and administering an additional dose of the composition into the cochlea of the mammal or subject found not to have a hearing function within a normal range (e.g., as determined using any test for hearing known in the art).

In some embodiments of any of the methods described herein, the composition can be formulated for intra-cochlear administration. In some embodiments of any of the methods described herein, the compositions described herein can be administered via intra-cochlear administration or local administration. In some embodiments of any of the methods described herein, the compositions are administered through the use of a medical device (e.g., any of the exemplary medical devices described herein).

In some embodiments, intra-cochlear administration can be performed using any of the methods described herein or known in the art. For example, a composition can be administered or introduced into the cochlea using the following surgical technique: first using visualization with a 0 degree, 2.5-mm rigid endoscope, the external auditory canal is cleared and a round knife is used to sharply delineate an approximately 5-mm tympanomeatal flap. The tympanomeatal flap is then elevated and the middle car is entered posteriorly. The chorda tympani nerve is identified and divided, and a currette is used to remove the scutal bone, exposing the round window membrane. To enhance apical distribution of the administered or introduced composition, a surgical laser may be used to make a small 2-mm fenestration in the oval window to allow for perilymph displacement during trans-round window membrane infusion of the composition. The microinfusion device is then primed and brought into the surgical field. The device is maneuvered to the round window, and the tip is seated within the bony round window overhang to allow for penetration of the membrane by the microneedle(s). The footpedal is engaged to allow for a measured, steady infusion of the composition. The device is then withdrawn and the round window and stapes foot plate are sealed with a gelfoam patch.

In some embodiments of any of the methods described herein, the subject or mammal is a rodent, a non-human primate, or a human. In some embodiments of any of the methods described herein, the subject or mammal is an adult, a teenager, a juvenile, a child, a toddler, an infant, or a newborn. In some embodiments of any of the methods described herein, the subject or mammal is 1-5, 1-10, 1-20, 1-30, 1-40, 1-50, 1-60, 1-70, 1-80, 1-90, 1-100, 1-110, 2-5, 2-10, 10-20, 20-30, 30-40, 40-50, 50-60, 60-70, 70-80, 80-90, 90-100, 100-110, 10-30, 10-40, 10-50, 10-60, 10-70, 10-80, 10-90, 10-100, 10-110, 20-40, 20-50, 20-60, 20-70, 20-80, 20-90, 20-100, 20-110, 30-50, 30-60, 30-70, 30-80, 30-90, 30-100, 40-60, 40-70, 40-80, 40-90, 40-100, 50-70, 50-80, 50-90, 50-100, 60-80, 60-90, 60-100, 70-90, 70-100, 70-110, 80-100, 80-110, or 90-110 years of age. In some embodiments of any of the methods described herein, the subject or mammal is 1, 2, 3, 4, 5, 6, 7, 8, 9, 10, or 11 months of age.

In some embodiments of any of the methods described herein, the subject or mammal has or is at risk of developing non-syndromic sensorineural hearing loss. In some embodiments of any of the methods described herein, the subject or mammal has been previously identified as having a mutation in a stereocilin gene. (All references here to "stereocilin gene" refer to the gene that is not the stereocilin pseudogene.) In some embodiments of any of the methods described herein, the subject or mammal has any of the mutations in a stereocilin gene that are described herein or are known in the art to be associated with non-symptomatic sensorineural hearing loss.

In some embodiments of any of the methods described herein, the subject or mammal has been identified as being a carrier of a mutation in a stereocilin gene (e.g., via genetic testing). In some embodiments of any of the methods described herein, the subject or human has been identified as having a mutation in a stereocilin gene and has been diagnosed with non-symptomatic sensorineural hearing loss. In some embodiments of any of the methods described herein, the subject or human has been identified as having non-symptomatic sensorineural hearing loss.

In some embodiments, successful treatment of non-symptomatic sensorineural hearing loss can be determined in a subject using any of the conventional functional hearing tests known in the art. Non-limiting examples of functional hearing tests are various types of audiometric assays (e.g., pure-tone testing, speech testing, test of the middle ear, auditory brainstem response, and otoacoustic emissions).

Also provided herein are methods of increasing expression of an active stereocilin protein (e.g., a full-length stereocilin protein) in a mammalian cell that include introducing any of the compositions described herein into the mammalian cell. In some embodiments of these methods, the mammalian cell is a cochlear outer hair cell. In some embodiments of these methods, the mammalian cell is a human cell (e.g., a human cochlear outer hair cell). In some embodiments of these methods, the mammalian cell is in vitro. In some embodiments of these methods, the mammalian cell is in a mammal. In some embodiments of these methods, the mammalian cell is originally obtained from a mammal and is cultured ex vivo. In some embodiments, the mammalian cell has previously been determined to have a defective stereocilin gene.

Methods for introducing any of the compositions described herein into a mammalian cell are known in the art (e.g., via lipofection or through the use of a viral vector, e.g., any of the viral vectors described herein).

An increase in expression of an active stereocilin protein (e.g., a full-length stereocilin protein) as described herein is, e.g., as compared to a control or to the level of expression of an active stereocilin protein (e.g., a full-length stereocilin protein) prior to the introduction of the vector(s).

Methods of detecting expression and/or activity of stereocilin are known in the art. In some embodiments, the level of expression of a stereocilin protein can be detected directly (e.g., detecting stereocilin protein or detecting stereocilin mRNA). Non-limiting examples of techniques that can be used to detect expression and/or activity of stereocilin directly include: real-time PCR, Western blotting, immunoprecipitation, immunohistochemistry, or immunofluorescence. In some embodiments, expression of a stereocilin protein can be detected indirectly (e.g., through functional hearing tests).

Pharmaceutical Compositions and Kits

In some embodiments, any of the compositions described herein can further include one or more agents that promote the entry of a nucleic acid or any of the vectors described herein into a mammalian cell (e.g., a liposome or cationic lipid). In some embodiments, any of the vectors described herein can be formulated using natural and/or synthetic polymers. Non-limiting examples of polymers that may be included in any of the compositions described herein can include, but are not limited to, DYNAMIC POLYCONJUGATE® (Arrowhead Research Corp., Pasadena, Calif.), formulations from Mirus Bio® (Madison, Wis.) and Roche® Madison (Madison, Wis.), PhaseRX® polymer formulations such as, without limitation, SMARTT POLYMER TECHNOLOGY® (PhaseRX, Seattle, Wash.), DMRI/DOPE, poloxamer, VAXFECTIN® adjuvant from Vical (San Diego, Calif.), chitosan, cyclodextrin from Calando Pharmaceuticals (Pasadena, Calif.), dendrimers and poly (lactic-co-glycolic acid) (PLGA) polymers, RONDEL™ (RNAi/Oligonucleotide Nanoparticle Delivery) polymers (Arrowhead Research Corporation®, Pasadena, Calif.), and pH responsive co-block polymers, such as, but not limited to, those produced by PhaseRX® (Seattle, Wash.). Many of these polymers have demonstrated efficacy in delivering oligonucleotides in vivo into a mammalian cell (see, e.g., deFougerolles, *Human Gene Ther.* 19:125-132, 2008; Rozema et al., *Proc. Natl. Acad. Sci. U.S.A.* 104:12982-12887, 2007; Rozema et al., *Proc. Natl. Acad. Sci. U.S.A.* 104:12982-12887, 2007; Hu-Lieskovan et al., *Cancer Res.* 65:8984-8982, 2005; Heidel et al., *Proc. Natl. Acad. Sci. U.S.A.* 104:5715-5721, 2007).

Any of the compositions described herein can be, e.g., a pharmaceutical composition. A pharmaceutical composition can include any of the compositions described herein and one or more pharmaceutically or physiologically acceptable carriers, diluents, or excipients. Such compositions may comprise one or more buffers, such as neutral-buffered saline, phosphate-buffered saline, and the like; one or more carbohydrates, such as glucose, mannose, sucrose, and dextran; mannitol; one or more proteins, polypeptides, or amino acids, such as glycine; one or more antioxidants; one or more chelating agents, such as EDTA or glutathione; and/or one or more preservatives.

In some embodiments, the composition includes a pharmaceutically acceptable carrier (e.g., phosphate buffered saline, saline, or bacteriostatic water). Upon formulation, solutions will be administered in a manner compatible with the dosage formulation and in such amount as is therapeutically effective. The formulations are easily administered in a variety of dosage forms such as injectable solutions, injectable gels, drug-release capsules, and the like.

As used herein, the term "pharmaceutically acceptable carrier" includes solvents, dispersion media, coatings, antibacterial agents, antifungal agents, and the like that are compatible with pharmaceutical administration. Supplementary active compounds can also be incorporated into any of the compositions described herein.

In some embodiments, a single dose of any of the compositions described herein can include a total sum amount of the at least two different vectors of at least 1 ng, at least 2 ng, at least 4 ng, about 6 ng, about 8 ng, at least 10 ng, at least 20 ng, at least 30 ng, at least 40 ng, at least 50 ng, at least 60 ng, at least 70 ng, at least 80 ng, at least 90 ng, at least 100 ng, at least 200 ng, at least 300 ng, at least 400 ng, at least 500 ng, at least 1 µg, at least 2 µg, at least 4 µg, at least 6 µg, at least 8 µg, at least 10 µg, at least 12 µg, at least 14 µg, at least 16 µg, at least 18 µg, at least 20 µg, at least 22 µg, at least 24 µg, at least 26 µg, at least 28 µg, at least 30 µg at least 32 µg, at least 34 µg, at least 36 µg, at least 38 µg, at least 40 µg, at least 42 µg, at least 44 µg, at least 46 µg, at least 48 µg, at least 50 µg, at least 52 µg, at least 54 µg, at least 56 µg, at least 58µ, at least 60µ, at least 62µ, at least 64µ, at least 66 µg, at least 68µ g, at least 70 µg, at least 72 µg, at least 74 µg, at least 76 µg, at least 78 µg, at least 80 µg, at least 82 µg, at least 84 µg, at least 86 µg, at least 88 µg, at least 90 µg, at least 92 µg, at least 94 µg, at least 96 µg, at least 98 µg, at least 100 µg, at least 102 µg, at least 104 µg, at least 106 µg, at least 108 µg, at least 110 µg, at least 112 µg, at least 114 µg, at least 116 µg, at least 118 µg, at least 120 µg, at least 122 µg, at least 124 µg, at least 126 µg, at least 128 µg, at least 130 µg at least 132 µg, at least 134 µg, at least 136 µg, at least 138 µg, at least 140 µg, at least 142 µg, at least 144 µg, at least 146 µg, at least 148 µg, at least 150 µg, at least 152 µg, at least 154 µg, at least 156 µg, at least 158 µg, at least 160 µg, at least 162 µg, at least 164 µg, at least 166 µg, at least 168 µg, at least 170 µg, at least 172 µg, at least 174 µg, at least 176 µg, at least 178 µg, at least 180 µg, at least 182 µg, at least 184 µg, at least 186 µg, at least 188µ, at least 190µ, at least 192µ, at least 194µ, at least 196 µg, at least 198µ, or at least 200 µg, e.g., in a buffered solution.

The compositions provided herein can be, e.g., formulated to be compatible with their intended route of administration. A non-limiting example of an intended route of administration is local administration (e.g., intra-cochlear administration).

In some embodiments, the therapeutic compositions are formulated to include a lipid nanoparticle. In some embodiments, the therapeutic compositions are formulated to include a polymeric nanoparticle. In some embodiments, the therapeutic compositions are formulated to comprise a minicircle DNA. In some embodiments, the therapeutic compositions are formulated to comprise a CELiD DNA. In some embodiments, the therapeutic compositions are formulated to comprise a synthetic perilymph solution. An exemplary synthetic perilymph solution includes 20-200 mM NaCl; 1-5 mM KCl; 0.1-10 mM $CaCl_2$); 1-10 mM glucose; 2-50 mM HEPES, having a pH of between about 6 and about 9.

Also provided are kits including any of the compositions described herein. In some embodiments, a kit can include a solid composition (e.g., a lyophilized composition including the at least two different vectors described herein) and a liquid for solubilizing the lyophilized composition. In some embodiments, a kit can include a pre-loaded syringe including any of the compositions described herein.

In some embodiments, the kit includes a vial comprising any of the compositions described herein (e.g., formulated as an aqueous composition, e.g., an aqueous pharmaceutical composition).

In some embodiments, the kits can include instructions for performing any of the methods described herein.

Routes of Administration

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active AAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Any of the compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present invention into suitable host cells. In particular, the vector delivered trangenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or any of the vectors disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trails examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 Tm. Sonication of MLVs results in the formation of small unilamellar vesicles (SUVs) with diameters in the range of 200 to 500.ANG., containing an aqueous solution in the core.

Alternatively, nanocapsule formulations of any of the vectors described herein may be used. Nanocapsules can generally entrap substances in a stable and reproducible way. To avoid side effects due to intracellular polymeric overloading, such ultrafine particles (sized around 0.1 Tm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering any of the compositions described herein to a host. Sonophoresis (ie., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intranodally, intramedullary, intramuscularly, by intravenous (i.v.) injection, or intraperitoneally. In one aspect, the nucleic acid compositions of the present invention are administered to a patient by intradermal or subcutaneous injection. In one aspect, the nucleic compositions of the present invention are administered by i.v. injection.

Devices and Surgical Methods

Provided herein are therapeutic delivery systems for treating non-symptomatic sensorineural hearing loss. In one aspect, the therapeutic delivery systems include i) a medical device capable of creating one or a plurality of incisions in a round window membrane of an inner ear of a human subject in need thereof, and ii) an effective dose of a composition (e.g., any of the compositions described herein). In some embodiments, the medical device includes a plurality of micro-needles.

Also provided herein are surgical methods for treatment of hearing loss (e.g., non-symptomatic sensorineural hearing loss). In some embodiments, the methods include the steps of: introducing into a cochlea of a human subject a first incision at a first incision point; and administering intracochlearly a therapeutically effective amount of any of the compositions provided herein. In some embodiments, the composition is administered to the subject at the first incision point. In some embodiments, the composition is administered to the subject into or through the first incision.

In some embodiments of any of the methods described herein, any of the compositions described herein is administered to the subject into or through the cochlea oval window membrane. In some embodiments of any of the methods described herein, any of the compositions described herein is administered to the subject into or through the cochlea round window membrane. In some embodiments of any of the methods described herein, the composition is administered using a medical device capable of creating a plurality of incisions in the round window membrane. In some embodiments, the medical device includes a plurality of micro-needles. In some embodiments, the medical device includes a plurality of micro-needles including a generally circular first aspect, where each micro-needle has a diameter of at least about 10 microns. In some embodiments, the medical device includes a base and/or a reservoir capable of holding the composition. In some embodiments, the medical device includes a plurality of hollow micro-needles individually including a lumen capable of transferring the composition. In some embodiments, the medical device includes a means for generating at least a partial vacuum.

The invention is further described in detail by reference to the following experimental examples. These examples are provided for purposes of illustration only, and are not intended to be limiting unless otherwise specified. Thus, the invention should in no way be construed as being limited to the following examples, but rather should be construed to encompass any and all variations that become evident as a result of the teaching provided herein.

Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

Examples

Example 1: Construction of Viral Vectors

Recombinant AAV is generated by transfection with an adenovirus-free method as used by Xiao et al. *J. Virol.* 73 (5): 3994-4003, 1999. The cis plasmids with AAV ITRs, the trans plasmid with AAV Rep and Cap genes, and a helper plasmid with an essential region from an adenovirus genome are co-transfected in 293 cells in a ratio of 1:1:2. The AAV vectors used here express human stereocilin or mouse stereocilin under multiple dual vector strategies using the constructs described below. AAV serotypes 1, 2, 3, 4, 5, 6, 7, 8, 9, rh8, rh10, rh39, rh43, and Anc80 are each prepared to encapsulate three sets of stereocilin constructs to test (i) a concatemerization-transplicing strategy, (ii) a hybrid intronic-homologous recombination-transplicing strategy, and (iii) an exonic homologous recombination strategy, as summarized by Pryadkina et al., *Meth. Clin. Devel.* 2:15009, 2015.

Example 2: Generating and Purifying Viral Particles

Recombinant AAV-1 is produced using a triple transfection protocol and purified by two sequential cesium chloride (CsCl) density gradients, as described by Pryadkina et al., *Mol. Ther.* 2:15009, 2015. At the end of second centrifugation, 11 fractions of 500 µl are recovered from the CsCl density gradient tube and purified through dialysis in 1× PBS. The fractions are analyzed by dot blot to determine those containing rAAV genomes. The viral genome number (vg) of each preparation is determined by a quantitative real-time PCR-based titration method using primers and probe corresponding to the ITR region of the AAV vector genome (Bartoli et al. *Gene. Ther.* 13:20-28, 2006).

Example 3: Formulation of Viral Particles

AAV produced at a titer of 1e14 vg/mL is prepared at dilutions of 3.2e13, 1.0e13, 3.2e12, 1.0e12 vg/mL in artificial perilymph. Artificial perilymph is prepared by combining the following reagents: NaCl, 120 mM; KCl, 3.5 mM; $CaCl_2$), 1.5 mM; glucose, 5.5 mM; HEPES, 20 mM. The artificial perilymph is titrated with NaOH to adjust its pH to 7.5 (total $Na^+$ concentration of 130 mM) (Chen et al., *J. Controlled Rel.* 110:1-19, 2005).

Example 4: Device Description

The AAV-STRC formulation is delivered to the cochlea using a specialized microcatheter designed for consistent and safe penetration of the round window membrane (RWM). The microcatheter is shaped such that the surgeon performing the delivery procedure can enter the middle ear cavity via the external auditory canal and contact the end of the microcatheter with the RWM. The distal end of the microcatheter is comprised of at least one microneedle with diameter between 10 and 1,000 microns, which produces perforations in the RWM that are sufficient to allow AAV-STRC to enter the cochlear perilymph of the scala tympani at a rate of approximately 1 uL/min, but small enough to heal without surgical repair. The remaining portion of the microcatheter, proximal to the microneedle(s), is loaded with the AAV-STRC/artificial perilymph formulation at a titer of approximately 1e13 vg/mL. The proximal end of the microcatheter is connected to a micromanipulator that allows for precise, low volume infusions of approximately 1 uL/min.

Example 5: Animal Model 1A: Surgical Method in Aged Mice

AAV-STRC prepared in artificial perilymph is administered to the scala tympani in mice as described by Shu et al. (*Human Gene Therapy*, doi: 10.1089/hum.2016.053. June 2016.3. Six-week-old male mice are anesthetized using an intraperitoneal injection of xylazine (20 mg/kg) and ketamine (100 mg/kg). Body temperature is maintained at 37° C. using an electric heating pad. An incision is made from the right post-auricular region and the tympanic bulla is exposed. The bulla is perforated with a surgical needle and the small hole is expanded to provide access to the cochlea. The bone of the cochlear lateral wall of the scala tympani is thinned with a dental drill so that the membranous lateral wall is left intact. A Nanoliter Microinjection System in conjunction with glass micropipette is used to deliver a total of approximately 300 nL of AAV-STRC in artificial perilymph to the scala tympani at a rate of 2 nL/second. The glass micropipette is left in place for 5 minutes post-injection. Following cochleostomy and injection, the opening in the tympanic bulla is sealed with dental cement, and the muscle and skin are sutured. The mice are allowed to awaken from anesthesia and their pain is controlled with 0.15 mg/kg buprenorphine hydrochloride for 3 days.

Example 6: Animal Model 2: Reciprocating Micropump in Guinea Pig

Surgical Procedure

AAV-STRC prepared in artificial perilymph is administered to guinea pigs to assess distribution and toxicity following intracochlear delivery with a reciprocating micropump as described by Tandon et al., *Lab Chip*, DOI: 10.1039/c51c01396h, 2015. Male guinea pigs weighing approximately 350 g each (n=16) are anesthetized with a combination of pentobarbital sodium (Nembutal; 25 mg kg-1, injected intraperitoneally), fentanyl (0.2 mg kg-1, intramuscularly), and haloperidol (10 mg kg-1, intramuscularly). Lidocaine with epinephrine is given subcutaneously at the incision site as a topical anesthetic. Using a dorsal approach, a 5 mm diameter hole is made in the bulla and a cochleostomy is created approximately 0.5 mm distal to the round window membrane. The cannula of the micropump (described below) is inserted into the cochleostomy, threaded into the cochlea 3 mm apically, and glued to the bulla with a common cyanoacrylate glue. For compound action potential (CAP) measurements, a perfluoroalkoxyalkane-insulated silver wire electrode (203 µm uncoated diameter) is inserted near the round window niche and glued to the bulla.

Procedures for measurement of distortion product otoacoustic emissions (DPOAEs) and CAPs are performed as previously described in Tandon et al. *Biomed Microdevices* 17:3-21, 2015. DPOAEs are measured before and after the cochleostomy procedure at the characteristic frequencies: 32, 24, 16, 12, 8, 5.6, 4, and 2.78 kHz in order to monitor any damage that occurs as a result of the surgery.

AAV-STRC at a maximum titer of 1e14 vg/mL is administered to the guinea pig using a micropump as described by Tandon et al. *Lab Chip*, DOI: 10.1039/c51c01396h, 2015. The micropump system has 4 selectable ports. These ports are connected to: (i) a large fluidic capacitor used for artificial perilymph storage; (ii) an outlet that connects to the cochlea; (iii) the outlet from an integrated AAV-STRC reservoir; (iv) the inlet to the integrated AAV-STRC reservoir. Each port is fluidically connected to a central pump chamber, and each is individually addressed with a valve. The sequence of events for reciprocating AAV-STRC delivery is as follows: (i) an internal AAV-STRC-refresh loop is run, transferring AAV-STRC from the AAV-STRC reservoir into the main infuse-withdraw line; (ii) AAV-STRC is infused into the cochlea and some artificial perilymph is drained from the artificial perilymph storage capacitor; (iii) the first two steps can be repeated several times for additional doses; (iv) after the AAV-STRC has been allowed to diffuse for some time, a volume of perilymph is withdrawn from the cochlea that is equal to the volume infused in steps (i)-(iii), refilling the artificial perilymph storage capacitor. This process results in net delivery of drug with zero net fluid volume added to the cochlea.

The fluidic capacitors in the micropump are cylindrical chambers whose ceilings are a thin (25.4 µm), flexible, polyimide membrane. The pump chamber has a diameter of 3.5 mm, the fluidic storage capacitor has a diameter of 14 mm, and all of the remaining capacitors have diameters of 4 mm. The same membrane is deflected to block flow at each of the valves. The valve chambers have diameters of 3.1 mm. The serpentine channel that comprises the drug reservoir has a square cross section of width 762 µm and a length of 410 mm for a total volume of 238 µL. All of the other microchannels in the pump have a width of 400 µm and a height of 254 µm. Acute drug delivery in guinea pigs The micropump is loaded with AAV-STRC and artificial perilymph, and the cannula inserted into a cochleostomy made in the region of the cochlea between the locations with characteristic frequency sensitivity of 24 and 32 kHz, and threaded apically 3 mm, terminating in the 12-16 kHz region. Baseline DPOAE and CAP hearing tests are performed prior to the start of AAV-STRC/artificial perilymph infusion. The pump is then activated and approximately 1 µL of artificial perilymph is infused every 5 min until a total of approximately 10 µL of artificial perilymph is delivered to the cochlea. After a 20 min wait time, approximately 10 µL of perilymph is withdrawn from the cochlea. AAV-STRC delivery is then initiated at a rate of approximately 1 µL every 5 min until a total of approximately 10 µL of fluid delivered.

Animals are sacrificed at 1 week, 1 month, 3 months, and 6 months post-treatment (n=4 per group) and their *cochleae* extracted. Extent of AAV transduction and STRC expression along the organ of *Corti* is assessed via immunostaining with anti-STRC antibodies. Antibodies against markers for hair cells (Myo7a) and supporting cells (Sox2) are used to quantify IHCs, OHCs, supporting cells and stereocilia morphology. Annexin V staining is used to assess evidence of apoptosis in cells along the cochlear sensory epithelium.

Example 7: Animal Model 3: Sheep

AAV-STRC prepared in artificial perilymph is administered to juvenile sheep to assess distribution and toxicity following delivery to the cochlea via trans-RWM infusion. Baseline auditory brainstem response (ABR) and distortion product optoacoustic emissions (DPOAEs) are measured in female sheep at 3 months of age (n=40), bilaterally, to assess pre-treatment inner hair cell (IHC) and outer hair cell (OHC) function. Following baseline ABR and DPOAE measurements, 20 µL of AAV1-STRC at titers of 1.0e14, 3.2e13, 1.0e13 and 3.2e12 vg/mL is injected into the left scala tympani of the sheep (n=10 per group). Each animal's right ear is left as an untreated control. ABR and DPOAE measurements are taken again bilaterally 1, 5 and 10 days following the surgical procedure. At 6 months post-procedure, additional bilateral ABR and DPOAE measurements are taken from all animals, and the animals are subsequently sacrificed and their *cochleae* removed.

In half of the sacrificed animals (n=5 from each of the dose cohorts), immunostaining is performed to identify hair cell structures and to assess STRC protein expression along the cochlear sensory epithelium. Antibodies against markers for hair cells (Myo7a), supporting cells (Sox2) and stereocilin are used as described previously (Duncker et al. 2013, *J Neurosci* 33 (22): 9508-9519). At the basal, middle and apical turns of the organ of *corti*, total numbers of hair cells and those hair cells expressing STRC are counted within 200 µm regions.

In the remaining half of the sacrificed animals (remaining 5 animals from each dose cohort), cochlear tissue samples are collected from the same basal, middle and apical regions as described above, and assayed for stereocilin mRNA transcript.

Example 8: Animal Model 3A: CRISPR Generated Transgenic Large Animal Model (Sheep Generation of Plasmid Co-Expressing Cas9 and sgRNA The pX330-U6-Chimeric_BB-CBh-hSpCas9 plasmid (Addgene plasmid #42230) is digested with BsbI, dephosphorylated using Antartic Phosphatase, and the linearized vector is gel purified. To generate the bicistronic vector (pX330-cas9-STRC) expressing Cas9 and sgRNA against STRC, a pair of oligos for targeting stereocilin exon 1 is annealed, phosphorylated and ligated to a linearized vector (Cong et al., *Science* 339 (6121): 819-23, 2013).

Genome Editing Assay in Cells

The A15 astroglial sheep cell line (Vilette et al., 2000 *In Vitro Cell Dev Biol Anim* 36 (1): 45-9) is maintained in DMEM in 10% Fetal Bovine Serum, 2 mM glutamine, 1% sodium pyruvate and 1% penicillin/streptomycin. Cells are transfected in 24-well plates with 2 µg of pX330-cas9-STRC co-expressing Cas9 and sgRNA against stereocilin using Lipofectamine® LTX reagent. Three days later, genomic DNA from transfected cells is extracted and quantified using a NanoDrop™ 2000 spectrophotometer, measuring A260/A280 and A260/A230 ratios to account for sample purity.

Gene mutation activity of sgRNA sequence at the target locus of STRC exon 1 is quantified using the T7EI mismatch detection assay. DNA sequence of interest is PCR-amplified with a high-fidelity polymerase (Herculase II fusion polymerase) using specific primers. The resultant PCR product is then denatured and slowly re-annealed (95° C., 2 min; 95° C. to 85° C., −2° C./see; 85° C. to 25° C., −1° C./sec) to produce a homoduplex/heteroduplex mix. This is then digested by 5U of T7EI restriction enzyme at 37° C. for 30 minutes. Digestion products are separated by 2% agarose gel electrophoresis. The ratio of cleaved to uncleaved products is used to calculate NHEJ frequency as previously described using Image J software (Menoret et al. 2011 *Advanced protocols for Animal Transgenesis. An ISTT Manual*. Heidelberg: Springer. p117-36). NHEJ frequency is calculated as % gene modification=100×(1-(1-fraction cleaved) $\wedge(½)$.

Production of sgRNA and Cas9 mRNA

As described previously (Bellec et al., *Current Gene Ther.*, 2015), T7 promoter is added to sgRNA template by PCR amplification of the pX330-cas9-STRC plasmid. The PCR product is purified using NucleoSpin® Gel and PCR Clean-up. It is used as the template for in vitro transcription using MEGAshortscript™ T7 kit according to the manufacturer's manual. Following completion of transcription, DNase I treatment is performed.

The Cas9 mRNA is transcribed using a Pmel-digested Cas9 expression JDS246 plasmid (Addgene plasmid #43861) and the mMESSAGE mMACHINE® T7 ULTRA Transcription Kit according to the manufacturer's manual. Following completion of transcription, the poly(A) tailing reaction and DNase I treatment are performed. Both the Cas9 mRNA and the sgRNAs are purified using a MEGAclear™ kit and eluted in elution buffer.

In Vitro Production of Embryos

The sheep embryos are produced by in vitro fertilization according to routine procedure as described previously (Crispo et al. 2014 *Transgenic Res,* 24 (1): 31-41). Briefly, sheep ovaries from a slaughterhouse are transported to the laboratory and cumulus oocyte complexes (COCs) are aspirated in recovery medium. The selected COCs are placed in maturation medium for 24 h in 5% CO2 in humidified air atmosphere at 39° C. Then, expanded COCs are inseminated in 100 µl drops with 1×106 dose of frozen-thawed semen selected by ascendant migration on a swim up method. Fertilization is carried out in 5% CO2 with humidified atmosphere at 39° C. for 22 h.

Microinjection into Zygotes

Soon after fertilization, 600 presumptive zygotes are randomly assigned to three experimental groups to be microinjected (CRISPR group, n=200; and Buffer group, n=200) or not (Control group, n=200). Microinjection of the CRISPR group is performed by microinjection into the cytoplasm with 5 ng/µl of sgRNA and 20 ng/µl of Cas9 mRNA diluted in injection buffer (10 mM Tris pH 7.5, 0.1 mM EDTA), while the Buffer group is injected with the same procedure but with buffer alone. Lastly, injected and non-injected embryos are transferred to culture medium under mineral oil, in 5% CO2, 5% O2 and 90% N2 in humidified atmosphere at 39° C. Cleavage rate on Day 2 (cleaved zygotes per total oocytes) and development rate on Day 6 (morulae and blastocysts per total oocytes) are recorded for all experimental groups. After Day 6, DNA from 20 CRISPR group embryos are analyzed by Sanger sequencing to detect the mutation at the STRC gene level.

To determine the in vivo efficiency of the system, blastocysts produced by CRISPR/Cas9 zygote microinjection are transferred to recipient females. Only early blastocysts, blastocysts and expanded blastocysts classified as excellent or good (i.e. Grade 1 as defined in Stringfellow et al. 2010, *Manual of the International Embryo Transfer Society*) are transferred on Day 6 after fertilization. Embryo transfer is performed by minimally invasive surgery assisted by laparoscopy to place the embryos into the cranial side of the ipsilateral uterine horn to the corpus *luteum*. Recipient ewes are previously synchronized to be on Day 6 of the estrous cycle using a standard protocol to control ovulation described previously, as described by Menchaca et al. 2004, *Reprod Fertil Dev.* 16 (4): 403-413.

Monitoring of Fetuses and Lambs

Pregnancy diagnosis and fetal development are performed on Day 30 and 105, respectively, by using β-mode ultrasonography equipped with a 5 and 3.5 MHz probe. Day 0 of the experiment is defined as the moment of embryo fertilization. Several parameters are measured to study the development of fetuses at Day 105 of gestation: thoracic diameter, biparietal diameter, occipitonasal length and heart rate. At delivery, length of gestation, gender, rectal temperature, heart and respiratory rates, body weight, thoracic perimeter, biparietal diameter, crown-rump and occipitonasal length, height at withers, height at hips, width at hips and width at chest were recorded. Body weight and morphometric variables are determined at birth, and 15, 30 and 60 days later.

Identification and Genotyping of Transgenic Animals

Samples from skin and limb muscle of the lambs are taken seven days after birth and T7EI assay, western blot test and histology examinations are performed in order to identify and characterize KO founders and off-target sites. Total DNA is isolated from skin biopsies for all animals and from muscle for some animals. Samples are analyzed using capillary electrophoresis. Genotyping of STRC exon 1 is performed by direct sequencing of PCR amplicons and in muscle biopsies by additional sequencing of isolated bacterial clones with individual amplicon sequences.

Analysis of Stereocilin Expression

Western blotting is performed to determine the presence of myostatin in the muscle fiber. Equal amounts of total proteins are run on 12% (v/v) gel electrophoresis and electrophoretically transferred to a PVDF membrane. Monoclonal mouse anti-stereocilin antibody is used in the western blotting. The washed membranes are incubated with 1:50000 dilution of secondary antibody linked to horseradish peroxidase (HPR). HPR activity is detected using western blot chemiluminescence.

AAV-STRC Rescue Therapy in Transgenic Sheep Model

AAV-STRC prepared in artificial perilymph is administered to STRC knockout transgenic sheep to assess the ability to restore normal hearing function following delivery to the cochlea via trans-RWM infusion. Baseline auditory brainstem response (ABR) and distortion product optoacoustic emissions (DPOAEs) are measured in female sheep at 3 months of age (n=30), bilaterally, to assess pre-treatment inner hair cell (IHC) and outer hair cell (OHC) function. Following baseline ABR and DPOAE measurements, 20 µL of AAV1-STRC at titers of 1.0e14, 3.2e13, and 1.0e13 vg/mL is injected into the left scala tympani of the sheep (n=10 per group). Each animal's right ear is left as an untreated control. ABR and DPOAE measurements are taken again bilaterally 1, 5 and 10 days following the surgical procedure. At 6 months post-procedure, additional bilateral ABR and DPOAE measurements are taken from all animals, and the animals are subsequently sacrificed and their *cochleae* removed.

In half of the sacrificed animals (n=5 from each of the dose cohorts), immunostaining is performed to identify hair cell structures and to assess STRC protein expression along the cochlear sensory epithelium. Antibodies against markers for hair cells (Myo7a), supporting cells (Sox2) and stereocilin are used as described previously (Duncker et al., *J Neurosci* 33 (22): 9508-9519, 2013). At the basal, middle and apical turns of the organ of *corti*, total numbers of hair cells and those hair cells expressing STRC are counted within 200 µm regions.

In the remaining half of the sacrificed animals (remaining 5 animals from each dose cohort), cochlear tissue samples are collected from the same basal, middle and apical regions as described above, and assayed for stereocilin mRNA transcript as described previously (Duncker et al. 2013, *J Neurosci* 33 (22): 9508-9519, 2013; Heidrych et al., *Hum. Mol. Genet.* 17:3814-3821, 2008; Heidrych et al., *Hum. Mol. Genet.* 18:2779-2790, 2009).

Example 9: Human Clinical Example (Pediatric Treatment

The patient is put under general anesthesia. The surgeon approaches the tympanic membrane from external auditory canal, makes a small incision at the inferior edge of the external auditory canal where it meets the tympani membrane, and lifts the tympanic membrane as a flap to expose the middle ear space. A surgical laser is used to make a small opening (approximately 2 mm) in the stapes footplate. The surgeon then penetrates the round window membrane with a microcatheter loaded with a solution of AAV-STRC prepared in artificial perilymph at a titer of 1e13 vg/mL. The microcatheter is connected to a micromanipulator that infuses approximately 20 µL of the AAV-STRC solution at a rate of approximately 1 µL/min. At the conclusion of the AAV-STRC infusion, the surgeon withdraws the microcatheter and patches the holes in the stapes foot plate and RWM with a gel foam patch. The procedure concludes with replacement of the tympanic membrane flap.

Example 10: Non-Invasive Prenatal Testing of Maternal Blood to Detect STRC Mutation Maternal blood samples (20-40 mL) are collected into Cell-free DNA tubes. At least 7 mL of plasma is isolated from each sample via a double centrifugation protocol of 2,000 g for 20 minutes, followed by 3,220 g for 30 minutes, with supernatant transfer following the first spin. cfDNA is isolated from 7-20 mL plasma using a QIAGEN QIAmp®

Circulating Nuclei Acid kit and eluted in 45 μL TE buffer. Pure maternal genomic DNA is isolated from the buffy coat obtained following the first centrifugation.

By combining thermodynamic modeling of the assays to select probes with minimized likelihood of probe-probe interaction with amplification approaches described previously (Stiller et al., Genome Res. 19 (10): 1843-1848, 2009), multiplexing of 11,000 assays can be achieved. Maternal cfDNA and maternal genomic DNA samples are pre-amplified for 15 cycles using 11,000 target-specific assays and an aliquot is transferred to a second PCR reaction of 15 cycles using nested primers. Samples are prepared for sequencing by adding barcoded tags in a third 12-cycle round of PCR. The targets include a genomic sequence in chromosome 15 known to be the site of a stereocilin loss-of-function mutation (Mandelker et al., *J. Mol. Diagnostics* 16 (6): 639-647, 2014). The amplicons are then sequenced using an Illumina HiSeq™ sequencer. Genome sequence alignment is performed using commercially available software.

Example 11: Adenovirus (AAV) Trans-Splicing Strategy

At least two different nucleic acid vectors (e.g., AAV vectors) can be to reconstitute an active stereocilin gene (e.g., a full-length stereocilin gene) within a cell following intermolecular concatemerization and trans-splicing. See, e.g., Yan et al., *Proc. Natl. Acad. Sci. U.S.A.* 97:12; 6716-6721, 2000, incorporated in its entirety herein.

In some examples, two different nucleic acid vectors will be used. A first nucleic acid vector can include a promoter (e.g., any of the promoters described herein), a first coding sequence that encodes an N-terminal portion of a stereocilin protein positioned 3' of the promoter (e.g., any of the sizes of a portion of a stereocilin protein described herein and/or any of the N-terminal portions of a stereocilin protein described herein), and a splicing donor signal sequence positioned at the 3' end of the first coding sequence. A second nucleic acid vector can include a splicing acceptor signal sequence, a second coding sequence that encodes a C-terminal portion of a stereocilin protein (i.e., the entire portion of the stereocilin protein that is not included in the N-terminal portion) positioned at the 3' end of the splicing acceptor signal sequence (e.g., any of the sizes of a portion of a stereocilin protein described herein and/or any of the C-terminal portions of a stereocilin protein described herein), and a polyadenylation sequence at the 3' end of the second coding sequence (e.g., any of the polyadenylation sequences described herein). In some embodiments, each of the encoded portions is at least 30 amino acid residues in length (e.g., at least 50 amino acids, at least 75 amino acids, or at least 100 amino acids in length), the amino acid sequence of each of the encoded portions does not overlap with the sequence of the other encoded portion, and no single vector of the two different vectors encodes an active stereocilin protein (e.g., a full-length stereocilin protein). When introduced into a mammalian cell (e.g., any of the mammalian cells described herein) splicing occurs between the splicing donor signal sequence and the splicing acceptor signal sequence, thereby forming a recombined nucleic acid that encodes an active stereocilin protein (e.g., a full-length stereocilin protein).

In another example, three different nucleic acid vectors can be used. A first nucleic acid vector can include a portion of a promoter sequence (e.g., any of the promoter sequences described herein), a first coding sequence of a stereocilin gene that encodes a first portion of a stereocilin protein (e.g., any of the stereocilin coding sequences described herein) positioned 3' of the promoter, and a first splicing donor signal sequence positioned at the 3' end of the first coding sequence. A second nucleic acid vector can include a first splicing acceptor signal sequence, a second coding sequence of a stereocilin gene that encodes a second portion of a stereocilin protein positioned at the 3' end of the first splicing acceptor signal sequence, and a second splicing donor signal sequence positioned at the 3' end of the second coding sequence (e.g., any of the splicing donor signals described herein). A feature of the second nucleic acid vector will be that self-splicing cannot occur (i.e., splicing will not occur between the second splicing donor signal sequence and the first splicing acceptor signal sequence of the second nucleic acid vector). In some embodiments, the splicing donor signal sequence of the first nucleic acid vector and the second splicing donor signal of the second nucleic acid vector are the same (e.g., any of the splicing donor signals described herein or known in the art). In some embodiments, the first splicing donor signal sequence of the first nucleic acid vector and the second splicing donor signal sequence of the second nucleic acid vector are different (e.g., any of the splicing donor signal sequences described herein or known in the art). A third nucleic acid vector will include a second splicing acceptor signal sequence, a third coding sequence of a stereocilin gene that encodes a third portion of a stereocilin protein positioned at the 3' end of the second splicing acceptor signal sequence, and a polyadenylation sequence positioned at the 3' end of the third coding sequence (e.g., any of the polyadenylation sequences described herein). In such methods where three nucleic acid vectors are used, the first splicing donor sequence and the first splicing acceptor sequence can assemble together (recombine) and the second slicing donor sequence and the second slicing acceptor sequence can assemble together (recombine), and the portion of stereocilin protein encoded by the first, second, and third coding sequences do not overlap, and when introduced into a mammalian cell (e.g., any of the mammalian cells described herein), splicing occurs between the first splicing donor sequence and the first splicing acceptor sequence, and between the second splicing donor sequence and the second splicing acceptor sequence, to form a recombined nucleic acid that encodes an active stereocilin protein (e.g., a full-length stereocilin protein). Based on the strategies provided above, one skilled in the art would understand how to develop a strategy using four, five, or six different nucleic acid vectors.

In any of the examples of these methods, the amino acid sequence of each of the encoded portions do not overlap, and no single vector encodes an active stereocilin protein (e.g., a full-length stereocilin protein).

Each of the at least two different vectors includes a coding sequence that encodes a different portion of a stereocilin protein, each of the encoded portions can be at least 30 amino acids (e.g., between about 30 amino acids to about 1600 amino acids, or any of the other subranges of this range described herein).

In some embodiments, each of the coding sequences can include at least one exon and at least one intron of SEQ ID NO: 4 (e.g., at least two exons and at least one intron, at least two exons and at least two introns, at least three exons and at least one intron, at least three exons and at least two introns, or at least three exons and at least three introns). In some embodiments, each of the at least two different vectors includes a coding sequence that encodes a different portion of a stereocilin protein, each of the encoded portions can encode up to 80% of the amino acid sequence of SEQ ID NO: 1 (e.g., up to 10%, up to 20%, up to 30%, up to 40%, up to 50%, up to 60%, or up to 70% of SEQ ID NO: 1) such that each of the encoded portions is non-overlapping. In some embodiments, each of the at least two different vectors includes a coding sequence that encodes a different portion of a stereocilin protein, each of the encoded portions encoding up to 80% of the amino acid sequence of SEQ ID NO: 1 (e.g., up to 10%, up to 20%, up to 30%, up to 40%, up to 50%, up to 60%, or up to 70% of SEQ ID NO: 1), such that each of the encoded portions is non-overlapping.

Each of the at least two nucleic acid vectors may further include an inverted terminal repeat (ITR) to allow head-to-tail recombination. The ITR will be subsequently removed via splicing. For example, the ITR could be a palindromic double-D ITR as described in Yan et al., *Proc. Natl. Acad. Sci. U.S.A.* 97 (12): 6716-6721, 2000, incorporated in its entirety herein. For example, the ITR could be a AAV serotype-2 ITR as described in Gosh et al., *Mol. Ther.* 16:124-130, 2008, and Gosh et al., *Human Gene Ther.* 22:77-83, 2011. In some embodiments of any of the vectors described herein, the vector can include a 5' ITR and/or a 3' ITR. In some embodiments, the 5' ITR includes or consists of SEQ ID NO: 18. In some embodiments, the 3' ITR includes or consists of SEQ ID NO: 36.

Non-limiting examples of splicing acceptor and/or donor signal sequences are known in the art. Sec, e.g., Reich et al., *Human Gene Ther.* 14 (1): 37-44, 2003, and Lai et al. (2005) *Nat. Biotechnol.* 23 (11): 1435-1439, 2005, 2005. The splicing donor and acceptor signal sequences can be any endogenous intron splicing signal of a gene (e.g., a stereocilin gene). For example, the splicing donor signal sequence can be: 5'-GTAAGTATCAAGGTTACAAGACAGGTTTAA-GGAGACCAATAGA AACTGGGCTTGTCGAGACA-GAGAAGACTCTTGCGTTTCT-3' (SEQ ID NO: 6) and the splicing acceptor signal can be 5'-GATAGGCACCTAT-TGGTCTTACTG ACATCCACTTTGCCTTTCTCTC-CACAG-3' (SEQ ID NO: 7) (see, e.g., Trapani et al., *EMBO Mol. Med.* 6 (2): 194-211, 2014). Methods of evaluating splicing and splicing efficiency are known in the art (see, e.g., Lai et al., *Nat. Biotechnol.* 23 (11): 1435-1439, 2005).

Example 12: Hybrid Vector Trans-Splicing Strategy Using an Alkaline Phosphatase (AP) Highly Recombinogenic Exogenous Gene Region At least two (e.g., two, three, four, five, or six) different nucleic acid vectors (e.g., AAV vectors) can also be used in any of the methods described herein to reconstitute an active stereocilin gene (e.g., a full-length stereocilin gene) within a cell following intermolecular concatemerization, marker gene-mediated recombination, and trans-splicing. This strategy is a hybrid strategy as it will include homologous recombination and/or trans-splicing. See, e.g., Gosh et al., *Mol. Ther.* 16:124-130, 2008; Gosh et al., *Human Gene Ther.* 22:77-83, 2011; and Duan et al., *Mol. Ther.* 4:383-391, 2001, each incorporated in its entirety herein. As used herein, a detectable marker gene can be a highly recombinogenic DNA sequence that will allow for coding sequence-independent recombination. An non-limiting example of a detectable marker gene is an alkaline phosphatase (AP) gene. For example, the detectable marker gene can be the middle one-third of the human placental AP complementary DNA, which is 872 bp in length (see, e.g., Gosh et al., 2008). At least two different nucleic acid vectors will contain a detectable marker gene (e.g., any of the detectable marker genes described herein). Since the hybrid vector will be constructed based on a trans-splicing vector as described in Example 10, an active stereocilin gene (e.g., a full-length stereocilin gene) may be reconstituted using either ITR-mediated recombination and trans-splicing or detectable marker gene-mediated (e.g., AP-gene mediated) recombination and trans-splicing. After trans-splicing, an active stereocilin gene (e.g., a full-length stereocilin gene) will be reconstituted in the genomic DNA of a mammalian cell (e.g., any mammalian cell described herein).

In one example, two different nucleic acid vectors will be used. A first nucleic acid vector can include a promoter (e.g., any of the promoters described herein), a first coding sequence that encodes an N-terminal portion of a stereocilin protein positioned 3' of the promoter (e.g., any of the sizes of a portion of a stereocilin protein described herein and/or any of the N-terminal portions of a stereocilin protein described herein), a splicing donor signal sequence positioned at the 3' end of the first coding sequence, and a first detectable marker gene positioned 3' of the splicing donor signal sequence. A second nucleic acid vector can include a second detectable marker gene, a splicing acceptor signal sequence positioned 3' of the second detectable marker gene, a second coding sequence that encodes a C-terminal portion of a stereocilin protein positioned at the 3' end of the splicing acceptor signal sequence (e.g., any of the sizes of a portion of a stereocilin protein described herein and/or any of the C-terminal portions of a stereocilin protein described herein), and a polyadenylation sequence at the 3' end of the second coding sequence (e.g., any of the polyadenylation sequences described herein). In some embodiments, each of the encoded portions is at least 30 amino acid residues in length (e.g., at least 50 amino acids, at least 75 amino acids, or at least 100 amino acids in length), the amino acid sequence of each of the encoded portions do not overlap, and no single vector of the two different vectors encodes an active stereocilin protein (e.g., a full-length stereocilin protein). When introduced into a mammalian cell (e.g., any of the mammalian cells described herein) splicing occurs between the splicing donor signal sequence and the splicing acceptor signal sequence, thereby forming a recombined nucleic acid that encodes an active stereocilin protein (e.g., a full-length stereocilin protein).

In another example, three different nucleic acid vectors can be used. A first nucleic acid vector can include a portion of promoter sequence (e.g., any of the promoter sequences described herein), a first coding sequence of a stereocilin gene that encodes a first portion of a stereocilin protein (e.g., any of the stereocilin coding sequences described herein) positioned 3' of the promoter, a first splicing donor signal sequence positioned at the 3' end of the first coding sequence, and a first detectable marker gene. A second nucleic acid vector can include a second detectable marker gene, a first splicing acceptor signal sequence positioned 3' of the second detectable marker gene, a second coding sequence of a stereocilin gene that encodes a second portion of a stereocilin protein positioned at the 3' end of the first splicing acceptor signal sequence, a second splicing donor signal sequence positioned at the 3' end of the second coding sequence (e.g., any of the splicing donor signals described herein), and a third detectable marker gene. A feature of the second nucleic acid vector will be that self-splicing cannot occur (i.e., splicing will not occur between the second splicing donor signal sequence and the first splicing acceptor signal sequence of the second nucleic acid vector). In some embodiments, the splicing donor signal sequence of the first nucleic acid vector and the second splicing donor signal of the second nucleic acid vector are the same (e.g., any of the splicing donor signals described herein or known in the art).

In some embodiments, the first splicing donor signal sequence of the first nucleic acid vector and the second splicing donor signal sequence of the second nucleic acid vector are different (e.g., any of the splicing donor signal sequences described herein or known in the art). A third nucleic acid vector can include a fourth detectable marker gene, a second splicing acceptor signal sequence positioned 3' of the fourth detectable marker gene, a third coding sequence of a stereocilin gene that encodes a third portion of a stereocilin protein positioned at the 3' end of the second splicing acceptor signal sequence, and a polyadenylation sequence positioned at the 3' end of the third coding sequence (e.g., any of the polyadenylation sequences described herein). In such methods where three nucleic acid vectors are used, the first splicing donor sequence and the first splicing acceptor sequence can assemble together (recombine) and the second slicing donor sequence and the second slicing acceptor sequence can assemble together (recombine), and the portion of stereocilin protein encoded by the first, second, and third coding sequences do not overlap, and when introduced into a mammalian cell (e.g., any of the mammalian cells described herein), splicing occurs between the first splicing donor sequence and the first splicing acceptor sequence, and between the second splicing donor sequence and the second splicing acceptor sequence, to form a recombined nucleic acid that encodes an active stereocilin protein (e.g., a full-length stereocilin protein). As can be appreciated in the art when three nucleic acid vectors are used, two of the at least two different nucleic acid vectors can include a detectable marker gene (e.g., an AP marker gene) and one of the at least two different nucleic acid vectors may include a splicing acceptor signal sequence that is complementary to a splicing donor signal sequence in a nucleic acid vector that includes a detectable marker gene. For example, in some embodiments, the first and second nucleic acid vectors can include a detectable marker gene (e.g., an AP marker gene), and the third nucleic acid vector will include a splicing acceptor signal sequence that is complementary to the splicing donor signal sequence in the second nucleic acid vector, and the third nucleic acid vector will not include a detectable marker gene (e.g., an AP marker gene). In other examples, the second and third nucleic acid vector can include a detectable marker gene (e.g., an AP marker gene), and the first nucleic acid vector will include a splicing donor signal sequence that is complementary to the splicing acceptor signal sequence in the second nucleic acid vector and the first nucleic acid vector will not include a detectable marker gene (e.g., an AP marker gene).

Based on the strategies provided above, one skilled in the art would understand how to develop a strategy using four, five, or six vectors.

The coding sequences provided in the at least two nucleic acid vectors (e.g., two, three, four, five or six) will not be overlapping. Each of the at least two different vectors can include a coding sequence that encodes a different portion of a stereocilin protein, each of the encoded portions being, e.g., at least 30 amino acids (e.g., about 30 amino acids to about 1600 amino acids, or any of the other subranges of this range described herein).

In some embodiments, each of the at least two different vectors includes a coding sequence that encodes a different portion of a stereocilin protein, each of the encoded portions encoding at least one exon and at least one intron of SEQ ID NO: 4 (e.g., at least two exons and at least one intron, at least two exons and at least two introns, at least three exons at least one intron, at least three exons and at least two introns, or at least three exons and at least three introns). In some embodiments, each of the at least two different vectors include a coding sequence that encodes a different portion of a stereocilin protein, each of the encoded portions encoding up to 80% of SEQ ID NO: 1 (e.g., up to 10%, up to 20%, up to 30%, up to 40%, up to 50%, up to 60%, up to 70% of SEQ ID NO: 1) such that each of the encoded portions is non-overlapping. In some embodiments, each of the at least two different vectors include a coding sequence that encodes a different portion of a stereocilin protein, each of the encoded portions encoding up to 80% of SEQ ID NO: 1 (e.g., up to 10%, up to 20%, up to 30%, up to 40%, up to 50%, up to 60%, or up to 70% of SEQ ID NO:1), such that each of the encoded portions is non-overlapping.

As described in Example 10, each of the at least two nucleic acid vectors may further include an inverted terminal repeat (ITR) to allow head-to-tail recombination. The ITR will be subsequently removed via splicing. Examples of ITRs and splicing acceptor and/or donor signal sequences are known in the art and have been described in Example 10.

Example 13: Hybrid Vector Trans-Splicing Strategy Using a F1 Phage Highly Recombinogenic Exogenous Gene Region (AK)

At least two (e.g., two, three, four, five, or six) different nucleic acid vectors (e.g., AAV vectors) can also be used in any of the methods described herein to reconstitute an active stereocilin gene (e.g., a full-length stereocilin gene) within a cell following intermolecular concatemerization, marker gene-mediated recombination, and trans-splicing. This strategy is a hybrid strategy as it will include homologous recombination and/or trans-splicing. Sec, e.g., Trapani et al., *EMBO Mol. Med.* 6 (2): 194-211, 2014, incorporated in its entirety herein. As used herein, an F1 phage recombinogenic region (AK) will be used to allow coding sequence-independent recombination. The F1 phage recombinogenic region may be a 77 bp recombinogenic region from the F1 phage genome as described in Trapani et al. (2014). At least two different nucleic acid vectors will contain an F1 phage recombinogenic region. Since the hybrid vector will be constructed based on a trans-splicing vector as described in Example 10, a nucleic acid encoding an active stereocilin protein (e.g., a full-length stereocilin protein) may be generated using either ITR-mediated recombination and trans-splicing or F1 phage recombinogenic region-induced recombination and trans-splicing. After trans-splicing, a nucleic acid encoding an active stereocilin protein (e.g., a full-length stereocilin protein) will be generated in a mammalian cell (e.g., any of the mammalian cells described herein).

In one example, two different nucleic acid vectors will be used. A first nucleic acid vector can include a promoter (e.g., any of the promoters described herein), a first coding sequence that encodes an N-terminal portion of a stereocilin protein positioned 3' of the promoter (e.g., any of the sizes of a portion of a stereocilin protein described herein and/or any of the N-terminal portions of a stereocilin protein described herein), a splicing donor signal sequence positioned at the 3' end of the first coding sequence, and an F1 phage recombinogenic region positioned 3' of the splicing donor signal sequence. A second nucleic acid vector can include an F1 phage recombinogenic region, a splicing acceptor signal sequence positioned 3' of the F1 phage recombinogenic region, a second coding sequence that encodes a C-terminal portion of a stereocilin protein positioned at the 3' end of the splicing acceptor signal sequence (e.g., any of the sizes of a portion of a stereocilin protein described herein and/or any of the C-terminal portions of a stereocilin protein described herein), and a polyadenylation sequence at the 3' end of the second coding sequence (e.g., any of the polyadenylation sequences described herein). In some embodiments, each of the encoded portions is at least 30 amino acid residues in length (e.g., at least 50 amino acids, at least 75 amino acids, or at least 100 amino acids in length), the amino acid sequence of each of the encoded portions do not overlap, and no single vector of the two different vectors encodes an active stereocilin protein (e.g., a full-length stereocilin protein). When introduced into a mammalian cell (e.g., any of the mammalian cells described herein) splicing occurs between the splicing donor signal sequence and the splicing acceptor signal sequence, thereby forming a recombined nucleic acid that encodes an active stereocilin protein (e.g., a full-length stereocilin protein).

In another example, three different nucleic acid vectors will be used. A first nucleic acid vector can include a portion of promoter sequence (e.g., any of the promoter sequences described herein), a first coding sequence of a stereocilin gene that encodes a first portion of a stereocilin protein (e.g., any of the stereocilin coding sequences described herein) positioned 5' of the promoter, a first splicing donor signal sequence positioned at the 3' end of the first coding sequence, and an F1 phage recombinogenic region. A second nucleic acid vector can include an F1 phage recombinogenic region, a first splicing acceptor signal sequence positioned 3' of the F1 phage recombinogenic region, a second coding sequence of a stereocilin gene that encodes a second portion of a stereocilin protein positioned at the 3' end of the first splicing acceptor signal sequence, a second splicing donor signal sequence positioned at the 3' end of the second coding sequence (e.g., any of the splicing donor signals described herein), and an F1 phage recombinogenic region. A feature of the second nucleic acid vector will be that self-splicing cannot occur (i.e., splicing will not occur between the second splicing donor signal sequence and the first splicing acceptor signal sequence of the second nucleic acid vector). In some embodiments, the splicing donor signal sequence of the first nucleic acid vector and the second splicing donor signal of the second nucleic acid vector are the same (e.g., any of the splicing donor signals described herein or known in the art). In some embodiments, the first splicing donor signal sequence of the first nucleic acid vector and the second splicing donor signal sequence of the second nucleic acid vector are different (e.g., any of the splicing donor signal sequences described herein or known in the art). A third nucleic acid vector can include an F1 phage recombinogenic region, a second splicing acceptor signal sequence positioned 3' of the F1 phage recombinogenic region, a third coding sequence of a stereocilin gene that encodes a third portion of a stereocilin protein positioned at the 3' end of the second splicing acceptor signal sequence, and a polyadenylation sequence positioned at the 3' end of the third coding sequence (e.g., any of the polyadenylation sequences described herein). In such methods where three nucleic acid vectors are used, the first splicing donor sequence and the first splicing acceptor sequence can assemble together (recombine) and the second slicing donor sequence and the second slicing acceptor sequence can assemble together (recombine), and the portion of stereocilin protein encoded by the first, second, and third coding sequences do not overlap, and when introduced into a mammalian cell (e.g., any of the mammalian cells described herein), splicing occurs between the first splicing donor sequence and the first splicing acceptor sequence, and between the second splicing donor sequence and the second splicing acceptor sequence, to form a recombined nucleic acid that encodes an active stereocilin protein (e.g., a full-length stereocilin protein). As can be appreciated in the art when three nucleic acid vectors are used, two of the different nucleic acid vectors can include an F1 phage recombinogenic region and one of the different nucleic acid vectors may include a splicing acceptor signal sequence that is complementary to a splicing donor signal sequence in a nucleic acid vector that includes an F1 phage recombinogenic region. For example, in some embodiments, the first and second nucleic acid vectors can include an F1 phage recombinogenic region, and the third nucleic acid vector will include a splicing acceptor signal that is complementary to the splicing donor signal sequence in the second nucleic acid vector, and the third nucleic acid vector will not include an F1 phage recombinogenic region (e.g., an AP marker gene). In other examples, the second and third nucleic acid vector can include an F1 phage recombinogenic region and the first nucleic acid vector will include a splicing donor signal sequence that is complementary to the splicing acceptor signal sequence in the second nucleic acid vector and the first nucleic acid vector will not include an F1 phage recombinogenic region. Based on the strategies provided above, one skilled in the art would understand how to develop a strategy using four, five, or six vectors.

The coding sequences provided in each of the at least two nucleic acid vectors (e.g., two, three, four, five or six) will not be overlapping. Each of the at least two different vectors include a coding sequence that encodes a different portion of a stereocilin protein, each of the encoded portions being at least 30 amino acids (e.g., about 30 amino acids to about 1600 amino acids, or any of the subranges of this range described herein).

In some embodiments, each of the at least two different vectors include a coding sequence that encodes a different portion of a stereocilin protein, each of the encoded portions encoding at least one exon and at least one intron of SEQ ID NO: 4 (e.g., at least two exons and at least one intron, at least two exons and at least two introns, at least three exons at least one intron, at least three exons and at least two introns, or at least three exons and at least three introns). In some embodiments, each of the at least two different vectors includes a coding sequence that encodes a different portion of a stereocilin protein, each of the encoded portions encoding up to 80% of SEQ ID NO: 1 (e.g., up to 10%, up to 20%, up to 30%, up to 40%, up to 50%, up to 60%, or up to 70% of SEQ ID NO: 1) such that each of the encoded portions is non-overlapping. In some embodiments, each of the at least two different vectors include a coding sequence that encodes a different portion of a stereocilin protein, each of the encoded portions encoding up to 80% of SEQ ID NO: 1 (e.g., up to 10%, up to 20%, up to 30%, up to 40%, up to 50%, up to 60%, or up to 70% of SEQ ID NO: 1), such that each of the encoded portions is non-overlapping.

As described in Example 10, each of the at least two nucleic acid vectors may further include an inverted terminal repeat (ITR) to allow head-to-tail recombination. The ITR will be subsequently removed via splicing. Examples of ITRs and splicing acceptor and/or donor signals are known in the art and have been described in Example 10.

Example 14: CRISPR-Cas9-Mediated Knockin STRC Pseudogene Lacking Undesired Residues The genomic sequences of the functional STRC gene and the STRC pseudogene are 98.9% identical and the coding regions are 99.6% homologous (Francey et al., *Am. J. Med. Genet. A.* 158A (2): 298-308, 2012). Francey et al. determined that 56 bp between exons 16 and 28 were divergent.

Verpy et al. determined that a nonsense mutation in exon 20 of the STRC pseudogene rendered the protein expressed from the pseudogene inactive (Verpy et al., *Nat. Genet.* 29:345-349, 2001). Expression of a functional STRC gene may be obtained using a composition including a CRISPR-Cas9 vector to correct (e.g., modify, replace) the nonsense mutation in exon 20 of the STRC pseudogene (SEQ ID NO: 5) to generate a sequence encoding an active stereocilin protein (e.g., a full-length stereocilin protein) in a mammalian cell, and thereby treat non-syndromic sensorineural hearing loss in a subject in need thereof. Various CRISRP-Cas9 techniques that can be used to introduce a mutation into an endogenous gene are also known in the art. See, e.g., Merkle et al., *Cell Rep.* 11 (6): 875-883, 2015; He et al., *Nucleic Acids Res.* 44 (9):e85, 2016; Wang et al., *Mol. Ther. Nucleic Acids* 5:e396, 2016, and Verma et al., *Methods Mol. Biol.* 1513:119-140, 2017. For example, a composition including a Cas9 nuclease (e.g., *Streptococcus pyogenes*) and a guide RNA that includes at the 5' end of the guide RNA a complementary region consisting of about 20 nucleotides (e.g., 20, 21 or 22) that is complementary to about 20 (e.g., 20, 21 or 22) consecutive nucleotides within positions 13955-14151 of SEQ ID NO:5 can be used in CRISPR/Cas9 RNA-guided genome editing to remove a nonsense mutation at a predetermined site in an endogenous stereocilin pseudogene sequence of SEQ ID NO: 5; and when introduced into a mammalian cell, a nucleic acid encoding an active stereocilin protein (e.g., a full-length stereocilin protein) is reconstituted at the locus of the stereocilin pseudogene.

Example 15: AAV-mediated Antisense Oligonucleotide Delivery

An additional approach to generate a functional STRC transcript from the STRC pseudogene will include using AAV-mediated antisense oligonucleotide delivery via exon skipping. See, e.g., Chamorro et al., *Mol. Ther. Nucleic Acids* 5: c307, 2016; Kawecka et al., *Curr. Gene Ther.* 15 (4): 395-415, 2015; Bremer et al., *Mol. Ther.* 5:e3379, 2016; Tei et al., *Biochem. Biophys. Res. Commun.* 461 (3): 481-486, 2015; and Jirka et al., *Nucleic Acid Ther.* 24 (1): 25-36, 2014. As shown in Bremer et al., antisense oligonucleotides can be designed to bind to a particular exon of interest and lead to in-frame exon skipping at the RNA level, thereby restoring gene function.

In the case of a stereocilin gene, a study can be conducted to determine the eligibility of exon 20 of the STRC pseudogene as a target for exon skipping, using techniques such as those used in Bremer et al. (2016). Upon determination of the eligibility of exon 20 of the STRC pseudogene, antisense oligonucleotides with sequences corresponding to 17-23 base pairs in exon 20 can be generated and analyzed for their melting temperature, GC-content, off-target binding and binding energy. In some embodiments, the oligonucleotides will be synthesized as 2'—O— methyl phosphorothioate antisense oligonucleotides and analyzed for exon skipping by RT-PCR. To determine de novo expression of the corrected STRC pseudogene in a cell, cells (e.g., a mammalian cell, a human cell, or any cell described herein) will be transfected within a nucleic acid vector (e.g., an AAV vector) including an antisense oligonucleotide of a stereocilin gene (e.g., an antisense oligonucleotide corresponding to part of exon 20 of a STRC pseudogene) using known transfection methods in the art, and expression of the corrected STRC pseudogene will be determined using methods such as RT-PCR, immunofluorescence, or Western blot, as well as functional biochemical assays for a stereocilin protein. For example, in some embodiments, a composition including a nucleic acid vector that includes an antisense oligonucleotide that is complementary to at least a portion (e.g., at least 5 contiguous nucleotides, at least 10 contiguous nucleotides, at least 15 contiguous nucleotides, at least 20 contiguous nucleotides, at least 25 contiguous nucleotides, at least 30 contiguous nucleotides, at least 35 contiguous nucleotides, at least 40 contiguous nucleotides, at least 45 contiguous nucleotides, at least 50 contiguous nucleotides, at least 55 contiguous nucleotides, at least 60 contiguous nucleotides, at least 65 contiguous nucleotides, at least 70 contiguous nucleotides, at least 75 contiguous nucleotides, at least 80 contiguous nucleotides, at least 85 contiguous nucleotides, at least 90 contiguous nucleotides, at least 95 contiguous nucleotides, at least 100 contiguous nucleotides, at least 105 contiguous nucleotides, at least 110 contiguous nucleotides, at least 115 contiguous nucleotides, at least 120 contiguous nucleotides, at least 125 contiguous nucleotides, at least 130 contiguous nucleotides, at least 135 contiguous nucleotides, at least 140 contiguous nucleotides, at least 145 contiguous nucleotides, at least 150 contiguous nucleotides, at least 155 contiguous nucleotides, at least 160 contiguous nucleotides, at least 165 contiguous nucleotides, at least 170 contiguous nucleotides, at least 175 contiguous nucleotides, at least 180 contiguous nucleotides, at least 185 contiguous nucleotides, or at least 190 contiguous nucleotides) of the nucleotide sequence of SEQ ID NO: 5 within positions 13955-14151 will be introduced into a mammalian cell and a functional stereocilin protein will be generated. One skilled in the art will appreciate that an exon 20 antisense oligonucleotide (e.g., an antisense oligonucleotide of SEQ ID NO: 5 complementary to sequence within the region defined by positions 13955-14141) will be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range of numbers having one of those numbers at the low end and a higher number at the high end. In some embodiments, the antisense oligonucleotides of exon 20 will be 20 nucleotides in length. In some embodiments, the antisense oligonucleotides of exon 20 (e.g., an antisense oligonucleotide of SEQ ID NO: 5 complementary to sequence comprising of positions 13955-14141) will be 15 to 30 nucleotides in length. In some embodiments, the antisense oligonucleotides of exon 20 (e.g., an antisense oligonucleotide of SEQ ID NO: 5) will be at least 80% identical (e.g., at least 85%, at least 90%, at least 95%, at least 97%, at least 98%, at least 99%, 80%, 81%, 82%, 83%, 84%, 85%, 86%, 87%, 88%, 89%, 90%, 91%, 92%, 93%, 94%, 95%, 96%, 97%, 98%, or 99%) to the complement of a portion of the region defined by positions 13955-14151 of SEQ ID NO: 5.

Example 16. STRC Expression in HEK293FT Cells

HEK293FT cells were seeded overnight at 7E4 cells/well in a 24-well format and were transfected with exemplary single or dual STRC vectors using jetprime reagent. 72 hours post-transfection, HEK293FT cells were harvested with 200 μL RIPA buffer/well. Thirty microliters of samples were loaded into each well onto a 4-12% Bis-Tris protein gel. STRC protein expression was determined using a STRC polyclonal antibody. Beta-actin (ACTB) was used as a loading control.

Figure 7:
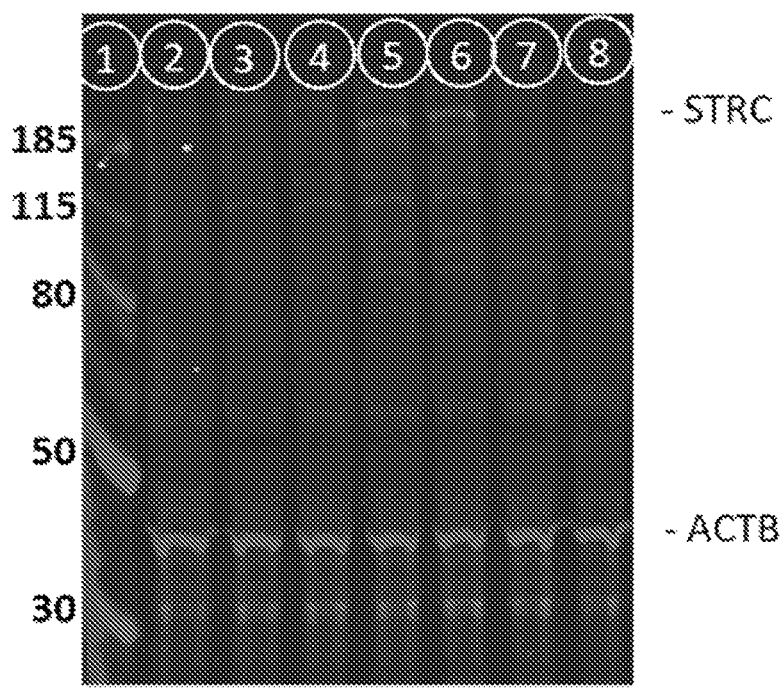
FIG. 7 is an image of an immunoblot of STRC protein levels from transfected HEK293FT cells with single or dual STRC vectors 72-hours post-transfection using a polyclonal STRC antibody. β-actin (ACTB) was used as a loading control. Lane 1—Prestrained Page Rule; Lane 2—400 ng pITR-201 plus 400 ng pITR-202; Lane 3—400 ng pITR-201 plus 400 ng pITR-202GFP; Lane 4—400 ng pITR-203 plus 400 ng pITR-204; Lane 5—400 ng pITR-205 plus 400 ng pITR-202; Lane 6—400 ng pITR-205 plus 400 ng pITR-202GFP; Lane 7—800 ng pITR-202GFP; and Lane 8—untransfected control cell lysate.

As shown in FIG. 7, the dual STRC vectors using CBA/CAG promoter (pITR-205 plus pITR-202 and pITR-205 plus pITR-202GFP) resulted in more intense full-length STRC protein in HEK293FT cells. This result confirmed that STRC protein can be expressed by exemplary STRC vectors described herein.

Figure 8:
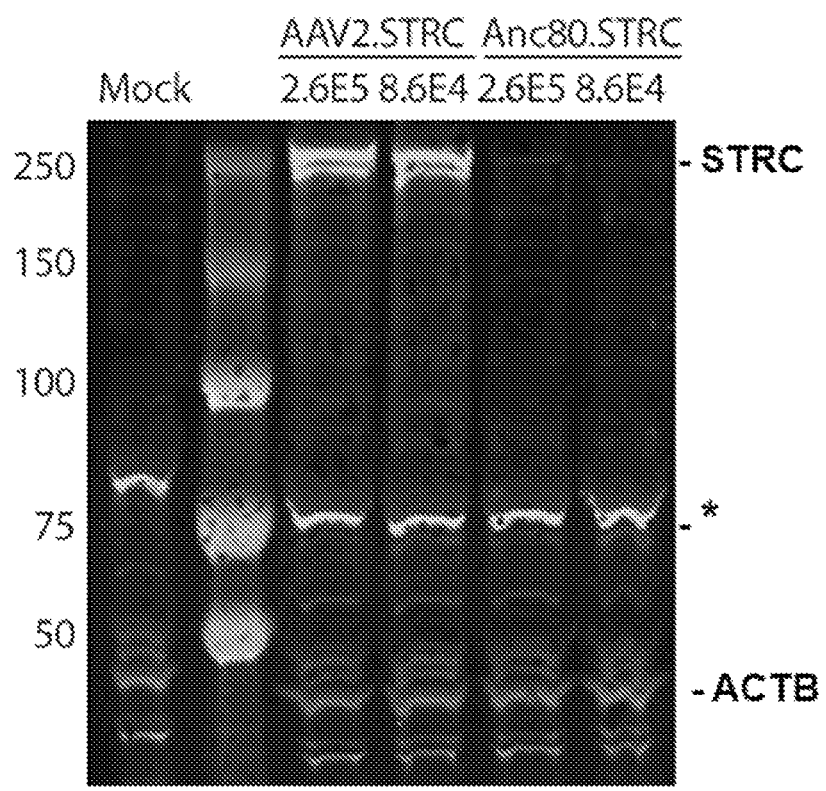
FIG. 8 is an image of an immunoblot of STRC protein levels from transduced HEK293FT cells with dual STRC vectors (AAV2.STRC and Anc80.STRC) at different MOIs (2.6E5, 8.6E4, 2.6E5, and 8.6E4) 72-hours post-transfection using a polyclonal STRC antibody. β-actin (ACTB) was used as a loading control.

Next, HEK293FT cells were transduced with dual STRC vectors at different MOIs and were seeded overnight at 1.2E5 cells/well in a 24-well format with etoposide reagent. HEK293FT cells were harvested 72 hours post-infection with 200 μL RIPA buffer/well. As shown in FIG. 8, HEK293FT cells transduced with AAV2 vectors showed higher expression of full-length STRC protein as compared to HEK293FT cells transduced with AAV·Anc80 vector.

Figure 9:
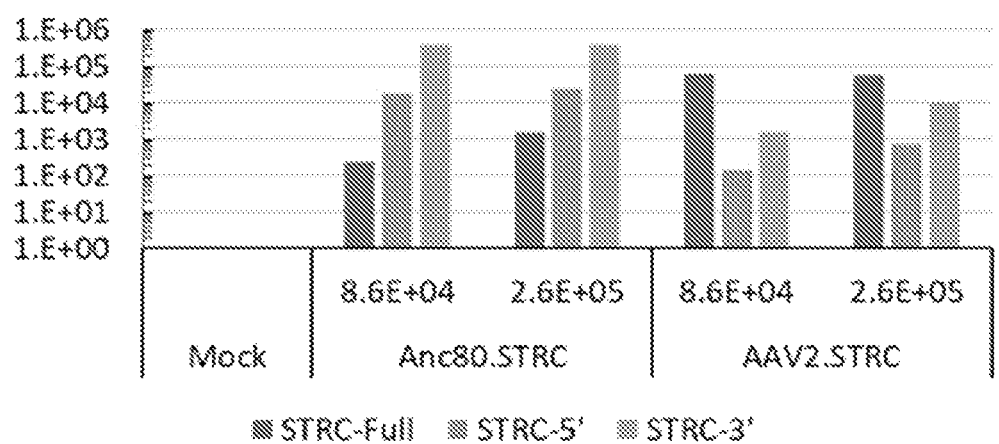
FIG. 9 is a bar graph showing the relative RNA expression of STRC (5' STRC, 3' STRC and full-length STRC) relative to GAPDH in HEK293FT cells transduced with AAV2.STRC (at MOI 8.6E4 and MOI 2.6E5) and Anc80.STRC (at MOI 8.6E4 and 2.6E5), respectively.

FIG. 9 showed high levels of STRC RNA expression relative to GAPDH in HEK293FT cells infected with either Anc80.STRC (at MOI 8.6E4 and MOI 2.6E5) or AAV2.STRC (at MOI 8.6E4 and MOI 2.6E5).

Example 17. STRC Expression in P1-3 Cochlear Mouse Explants

Figure 10:
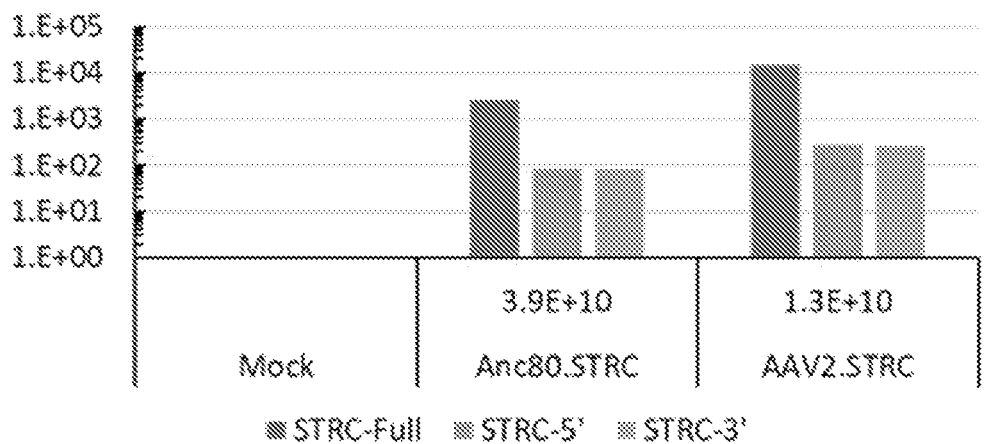
FIG. 10 is a bar graph showing the relative RNA expression of STRC (5' STRC, 3' STRC and full-length STRC) relative to GAPDH in P1-3 cochlear explants from WT mice infected 16-hours with AAV2.STRC (at MOI 1.3E10) and Anc80.STRC (at MOI 3.9E10), respectively.

P2 cochlear from WT mice were infected after plating and were harvested for RNA and immunofluorescence 72 hours after infection. As shown in FIG. 10, full-length STRC was efficiently expressed in cochlear explants infected with Anc80.STRC at MOI 3.9E10 and AAV2.STRC at MOI 1.3E10, respectively.

Figures 11A, 11B:
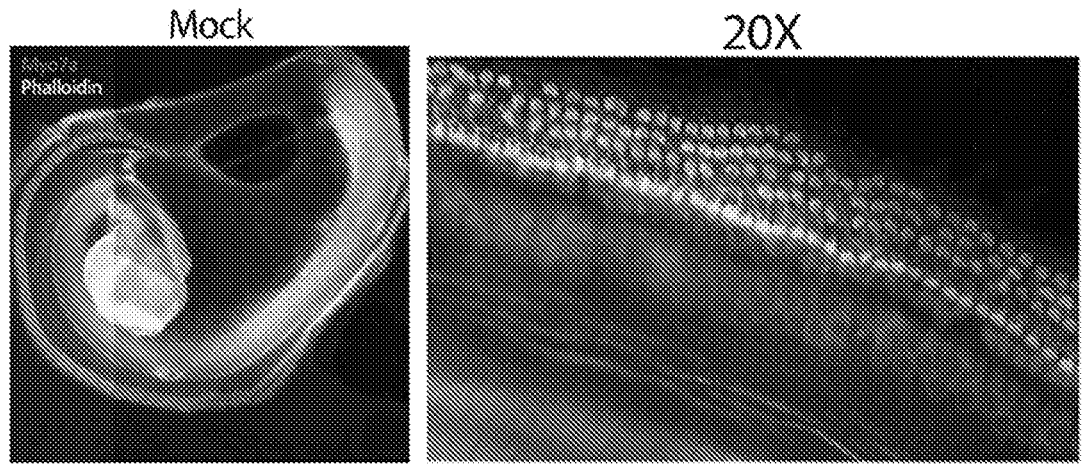
FIG. 11A is an exemplary fluorescent image of P1-3 cochlear explants from mock-infected WT mice showing Myo7a and phalloidin staining.
FIG. 11B is an exemplary fluorescent image of P1-3 cochlear explants from mock-infected WT mice showing Myo7a and phalloidin staining. Magnification 20×.
Figures 11C, 11D:
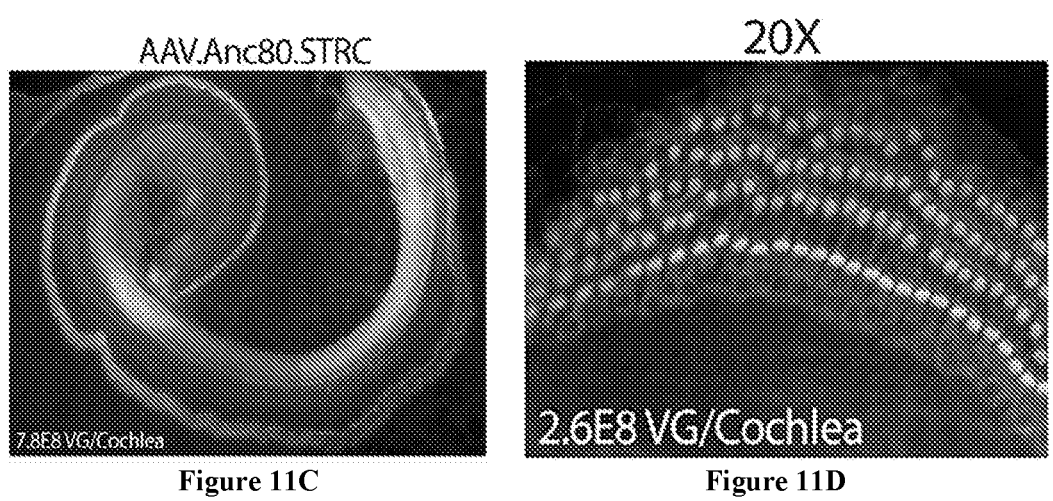
FIG. 11C is an exemplary fluorescent image of P1-3 cochlear explants from AAV·Anc80·STRC-infected (at MOI 7.8E8 VG/cochlea) WT mice showing Myo7a and phalloidin staining.
FIG. 11D is an exemplary fluorescent image of P1-3 cochlear explants from AAVanc80·dSTRC-infected (at MOI 2.6E8 VG/cochlea) WT mice showing Myo7a and phalloidin staining. Magnification 20×.
Figure 11E:
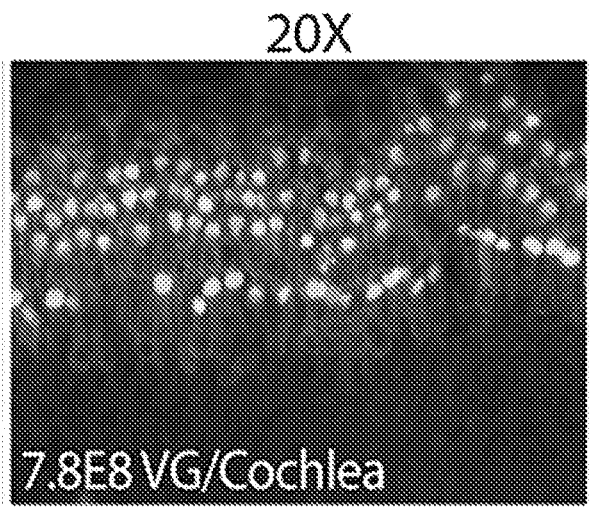
FIG. 11E is an exemplary fluorescent image of P1-3 cochlear explants from AAV·Anc80·STRC-infected (at MOI 7.8E8 VG/cochlea) WT mice showing Myo7a and phalloidin staining. Magnification 20×.
Figure 12A:
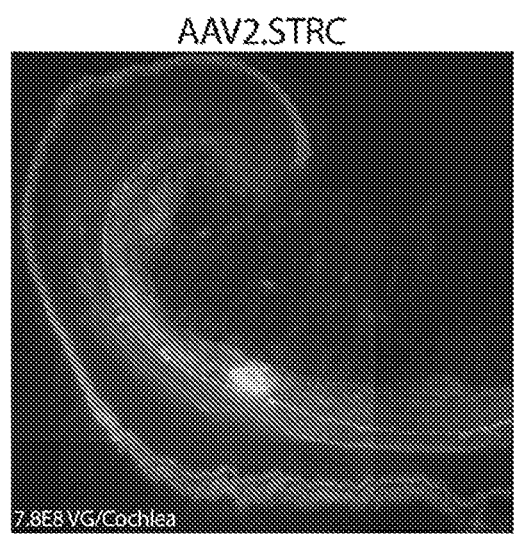
FIG. 12A is an exemplary fluorescent image of P1-3 cochlear explants from AAV2.STRC-infected (at MOI 7.8E8 VG/cochlea) WT mice showing Myo7a and phalloidin staining.
Figure 12B:
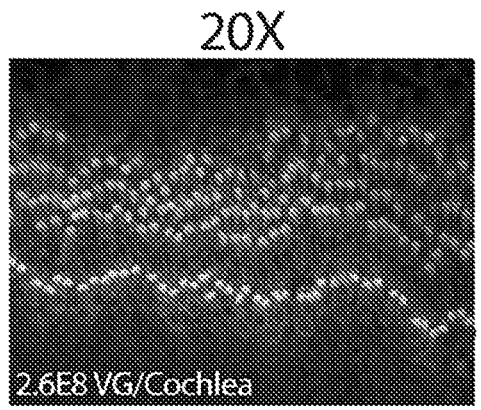
FIG. 12B is an exemplary fluorescent image of P1-3 cochlear explants from AAV2.STRC-infected (at MOI 2.6E8 VG/cochlea) WT mice showing Myo7a and phalloidin staining. Magnification 20×.
Figure 12C:
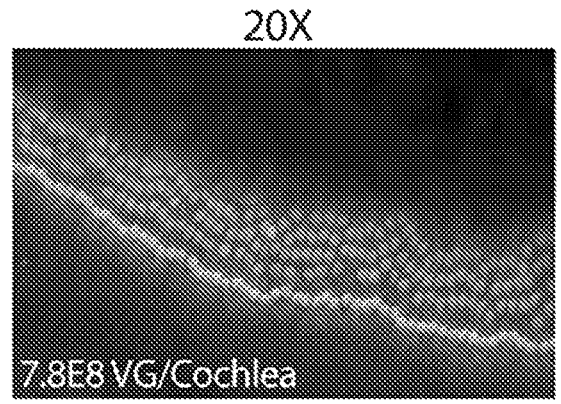
FIG. 12C is an exemplary fluorescent image of P1-3 cochlear explants from AAV2.STRC-infected (at MOI 7.8E8 VG/cochlea) WT mice showing Myo7a and phalloidin staining. Magnification 20×.

As shown in FIGS. 11A-E and 12A-C, outer hair cells and inner cells of P1-3 cochlear explants expressed Myo7a and phalloidin when transduced with AAV·Anc80·dSTRC (7.8E VG/cochlea, 2.6E8 VG/cochlea) and AAV2·dSTRC (7.8E8 VG/cochlea and 2.6E8 VG/cochlea). FIGS. 11A and 11B showed the natural cochlear structure, in which Myo7a is expressed in both outer and inner hair cells, while phalloidin is expressed exclusively in the inner hair cells. A similar staining pattern was observed in P1-3 cochlear explants transduced with AAV·Anc80·STRC (FIGS. 11C-E), and in P1-3 cochlear explants transduced with AAV2.STRC (FIGS. 12A-C).

Transfection with either vector did not disrupt the structural integrity of outer hair cells or inner hair cells of the cochlea. Comparison between non-infected with AAV2·dSTRC and AAV·Anc80·dSTRC infected explants showed robust numbers of living hair cells suggesting the relative safety of the vectors. Thus, FIGS. 11A-E and 12A-C showed lack of toxicity of STRC vectors with viable and organized outer hair cells, inner hair cells, and stereociliary bundles.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

---

What is claimed is:

1. A composition comprising a first nucleic acid vector and a second nucleic acid vector, wherein:
   the first nucleic acid vector comprises (i) a promoter and (ii) a 5' coding sequence of a stereocilin protein according to SEQ ID NO: 25, and
   the second nucleic acid vector comprises a 3' coding sequence of a stereocilin protein according to SEQ ID NO: 28.

2. The composition of claim 1, wherein each of the first nucleic acid vector and the second nucleic acid vector is a plasmid, a transposon, a cosmid, or a viral vector.

3. The composition of claim 1, wherein each of the first nucleic acid vector and the second nucleic acid vector is a viral vector selected from an adeno-associated virus (AAV) vector, an adenovirus vector, a lentivirus vector, or a retrovirus vector.

4. The composition of claim 3, wherein the viral vector is an AAV vector.

5. The composition of claim 1, wherein the first nucleic acid vector further comprises a Kozak sequence.

6. The composition of claim 1, wherein the first nucleic acid vector comprises a promoter that is an inducible promoter, a constitutive promoter, or a tissue-specific promoter.

7. The composition of claim 1, wherein the second nucleic acid vector further comprises a poly(dA) sequence.

8. The composition of claim 1, further comprising a pharmaceutically acceptable excipient.

9. The composition of claim 1, wherein:
   the first nucleic acid vector and a splicing donor signal sequence positioned at the 3' end of the 5' coding sequence; and
   the second nucleic acid vector comprises a splicing acceptor signal sequence, and a polyadenylation sequence at the 3' end of the second coding sequence; and
   when introduced into a mammalian cell, splicing occurs between the splicing donor signal sequence and the splicing acceptor signal sequence, thereby forming a recombined nucleic acid that encodes a full-length stereocilin protein.

10. The composition of claim 1, wherein:
    the first nucleic acid vector comprises a splicing donor signal sequence positioned at the 3' end of the first coding sequence, and a F1 phage recombinogenic region positioned 3' to the splicing donor signal sequence; and
    the second nucleic acid vector comprises a F1 phage recombinogenic region, a splicing acceptor signal sequence positioned 3' of the F1 phage recombinogenic region, and a polyadenylation sequence positioned at the 3' end of the second coding sequence; and
    when introduced into a mammalian cell, splicing occurs between the splicing donor signal and the splicing acceptor signal, thereby forming a recombined nucleic acid that encodes a full-length stereocilin protein.

11. The composition of claim 1, wherein at least one of the 5' or 3' coding sequences includes a nucleotide sequence spanning two neighboring exons of a stereocilin gene and lacks an intronic sequence between the two neighboring exons.

12. A kit comprising a composition of any one of claims 1, 9, 10, and 11.

13. A method comprising:
    introducing into a cochlea of a mammal a therapeutically effective amount of the composition of any one of claims 9, 10 and 11.

14. A method of increasing expression of a full-length stereocilin protein in an outer hair cell in a cochlea of a mammal, the method comprising:
    introducing into the cochlea of the mammal a therapeutically effective amount of the composition of any one of claims 9, 10 and 11.

15. A method of treating non-symptomatic sensorineural hearing loss in a subject identified as having a defective stereocilin gene, the method comprising:
    administering a therapeutically effective amount of a composition of any one of claims 9, 10 and 11 into the cochlea of the subject.

* * * * *